(12) United States Patent
Dellinger et al.

(10) Patent No.: US 10,767,175 B2
(45) Date of Patent: Sep. 8, 2020

(54) HIGH SPECIFICITY GENOME EDITING USING CHEMICALLY MODIFIED GUIDE RNAS

(71) Applicant: Agilent Technologies, Inc., Santa Clara, CA (US)

(72) Inventors: Douglas J Dellinger, Boulder, CO (US); Daniel E Ryan, San Francisco, CA (US); Subhadeep Roy, Lafayette, CO (US); Jeffrey R Sampson, San Jose, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 0 days.

(21) Appl. No.: 15/493,129

(22) Filed: Apr. 20, 2017

(65) Prior Publication Data
US 2017/0355985 A1 Dec. 14, 2017

Related U.S. Application Data

(60) Provisional application No. 62/347,553, filed on Jun. 8, 2016.

(51) Int. Cl.
*C12N 15/11* (2006.01)
*C12N 15/90* (2006.01)

(52) U.S. Cl.
CPC ............ *C12N 15/11* (2013.01); *C12N 15/111* (2013.01); *C12N 15/907* (2013.01); *C12N 2310/20* (2017.05); *C12N 2310/312* (2013.01); *C12N 2310/315* (2013.01); *C12N 2310/3125* (2013.01); *C12N 2310/321* (2013.01); *C12N 2310/346* (2013.01); *C12N 2320/10* (2013.01); *C12N 2320/50* (2013.01)

(58) Field of Classification Search
None
See application file for complete search history.

(56) References Cited

U.S. PATENT DOCUMENTS

| | | | |
|---|---|---|---|
| 5,032,401 A | 7/1991 | Jamas et al. | |
| 5,607,677 A | 3/1997 | Jamas et al. | |
| 7,371,580 B2 | 5/2008 | Yakhini et al. | |
| 8,202,983 B2 | 6/2012 | Dellinger et al. | |
| 9,650,617 B2 | 5/2017 | May et al. | |
| 9,822,407 B2 | 11/2017 | Joung et al. | |
| 2005/0281781 A1 | 12/2005 | Ostroff | |
| 2010/0076183 A1 | 3/2010 | Dellinger et al. | |
| 2014/0068797 A1* | 3/2014 | Doudna | C12N 15/102 800/18 |
| 2014/0090113 A1 | 3/2014 | Cogan et al. | |
| 2014/0090116 A1 | 3/2014 | Ainley et al. | |
| 2014/0170753 A1 | 6/2014 | Zhang | |
| 2014/0273037 A1 | 9/2014 | Wu | |
| 2014/0273226 A1 | 9/2014 | Wu | |
| 2014/0273232 A1 | 9/2014 | Zhang et al. | |
| 2014/0273233 A1 | 9/2014 | Chen et al. | |
| 2014/0273235 A1 | 9/2014 | Voytas et al. | |
| 2014/0294773 A1 | 10/2014 | Brouns et al. | |
| 2014/0309487 A1 | 10/2014 | Lee et al. | |
| 2014/0310828 A1 | 10/2014 | Lee et al. | |
| 2014/0349400 A1 | 11/2014 | Jakimo et al. | |
| 2014/0357523 A1 | 12/2014 | Zeiner et al. | |
| 2014/0364333 A1 | 12/2014 | Wu et al. | |
| 2015/0044191 A1 | 2/2015 | Liu et al. | |
| 2015/0044192 A1 | 2/2015 | Liu et al. | |
| 2015/0044772 A1 | 2/2015 | Zhao | |
| 2015/0064149 A1 | 3/2015 | West et al. | |
| 2015/0064708 A1 | 3/2015 | Sastry-Dent et al. | |
| 2015/0067921 A1 | 3/2015 | Cogan et al. | |
| 2015/0071906 A1 | 3/2015 | Liu et al. | |
| 2015/0071946 A1 | 3/2015 | Solyom et al. | |
| 2015/0079680 A1 | 3/2015 | Bradley et al. | |
| 2015/0098954 A1 | 4/2015 | Hyde et al. | |
| 2015/0118216 A1 | 4/2015 | Liu et al. | |
| 2015/0128307 A1 | 5/2015 | Sastry-Dent et al. | |
| 2015/0128308 A1 | 5/2015 | Sastry-Dent et al. | |
| 2015/0128309 A1 | 5/2015 | Sastry-Dent et al. | |
| 2015/0133315 A1 | 5/2015 | Jacobson et al. | |
| 2015/0140664 A1 | 5/2015 | Byrne et al. | |
| 2015/0156996 A1 | 6/2015 | Fahrenkrug et al. | |
| 2015/0315252 A1 | 11/2015 | Haugwitz et al. | |
| 2015/0315576 A1 | 11/2015 | Caliando et al. | |

(Continued)

FOREIGN PATENT DOCUMENTS

| | | |
|---|---|---|
| EP | 2800811 A1 | 11/2014 |
| EP | 2892321 A2 | 7/2015 |

(Continued)

OTHER PUBLICATIONS

Barrangou et al., Nucleic Acids Research, Apr. 2015; 43(7)3407-3419 (Year: 2015).*
Randar et al., PNAS, Nov. 2015; E7110-E7117 (Year: 2015).*
Guilinger et al., "Fusion of catalytically inactive Cas9 to FokI nuclease improves the specificity of genome modification," Nat. Biotechnol. 32, 577-582 (2014).
Haeussler et al., "Evaluation of off-target and on-target scoring algorithms and integration into the guide RNA selection tool CRISPOR," Genome Biol. 17, 148 (2016).
Havlicek et al., "Re-engineered RNA-guided FokI-nucleases for improved genome editing in human cells," Mol. Ther. 25, 342-355 (2017).

(Continued)

*Primary Examiner* — James D Schultz
(74) *Attorney, Agent, or Firm* — Faegre Drinker Biddle & Reath LLP

(57) ABSTRACT

The present invention relates to guide RNAs having chemical modifications and their use in CRISPR-Cas systems. The chemically modified guide RNAs have enhanced specificity for target polynucleotide sequences. The present invention also relates to methods of using chemically modified guide RNAs for cleaving or nicking polynucleotides, and for high specificity genome editing.

23 Claims, 24 Drawing Sheets

Specification includes a Sequence Listing.

(56) References Cited

U.S. PATENT DOCUMENTS

| | | |
|---|---|---|
| 2015/0322432 A1 | 11/2015 | Anderson et al. |
| 2015/0344836 A1 | 12/2015 | Finer et al. |
| 2016/0030477 A1 | 2/2016 | Conway et al. |
| 2016/0040189 A1 | 2/2016 | Kennedy et al. |
| 2016/0046959 A1 | 2/2016 | Landel et al. |
| 2016/0090622 A1 | 3/2016 | Liu et al. |
| 2016/0138027 A1 | 5/2016 | Gan et al. |
| 2016/0168592 A1 | 6/2016 | Church et al. |
| 2016/0206566 A1 | 7/2016 | Lu et al. |
| 2016/0257974 A1 | 9/2016 | Bradley et al. |
| 2016/0298097 A1 | 10/2016 | Chavez et al. |
| 2016/0339064 A1 | 11/2016 | Kovarik et al. |
| 2017/0051296 A1 | 2/2017 | Beetham et al. |
| 2017/0298383 A1 | 10/2017 | Albertsen et al. |

FOREIGN PATENT DOCUMENTS

| | | |
|---|---|---|
| EP | 2893006 A1 | 7/2015 |
| EP | 3241902 B1 | 2/2018 |
| WO | 2013126794 A1 | 8/2013 |
| WO | 2013141680 A1 | 9/2013 |
| WO | 2013142578 A1 | 9/2013 |
| WO | 2013176772 | 11/2013 |
| WO | WO2013176772 | 11/2013 |
| WO | WO2013176844 | 11/2013 |
| WO | 2014039684 | 3/2014 |
| WO | 2014039702 | 3/2014 |
| WO | 2014065596 A1 | 5/2014 |
| WO | 2014071219 A1 | 5/2014 |
| WO | 2014089290 A1 | 6/2014 |
| WO | 2014089513 A1 | 6/2014 |
| WO | 2014089533 A2 | 6/2014 |
| WO | 2014093595 A1 | 6/2014 |
| WO | 2014093622 A2 | 6/2014 |
| WO | 2014093635 A1 | 6/2014 |
| WO | 2014093655 A2 | 6/2014 |
| WO | 2014093661 A2 | 6/2014 |
| WO | 2014093688 A1 | 6/2014 |
| WO | 2014093694 A1 | 6/2014 |
| WO | 2014093701 A1 | 6/2014 |
| WO | 2014093709 A1 | 6/2014 |
| WO | 2014093712 A1 | 6/2014 |
| WO | 2014093718 A1 | 6/2014 |
| WO | 2014099744 A1 | 6/2014 |
| WO | 2014099750 A2 | 6/2014 |
| WO | 2014144288 A1 | 9/2014 |
| WO | 2014145599 A2 | 9/2014 |
| WO | 2014150624 A1 | 9/2014 |
| WO | 2014152432 A2 | 9/2014 |
| WO | 2014153118 A1 | 9/2014 |
| WO | WO2014144592 | 9/2014 |
| WO | WO2014144761 | 9/2014 |
| WO | 2014039970 A9 | 10/2014 |
| WO | 2014159719 A1 | 10/2014 |
| WO | 2014165349 A1 | 10/2014 |
| WO | 2014165825 A2 | 10/2014 |
| WO | 2014172458 A1 | 10/2014 |
| WO | 2014172470 A2 | 10/2014 |
| WO | 2014186585 A2 | 11/2014 |
| WO | 2014191128 A1 | 12/2014 |
| WO | 2014191518 A1 | 12/2014 |
| WO | 2014191521 A2 | 12/2014 |
| WO | 2014197568 A2 | 12/2014 |
| WO | 2014201015 A2 | 12/2014 |
| WO | 2014204725 A1 | 12/2014 |
| WO | 2014204726 A1 | 12/2014 |
| WO | 2015006294 A2 | 1/2015 |
| WO | 2015006437 A1 | 1/2015 |
| WO | 2015006498 A2 | 1/2015 |
| WO | 2015013583 A2 | 1/2015 |
| WO | 2015026883 A1 | 2/2015 |
| WO | 2015026885 A1 | 2/2015 |
| WO | 2015026886 A1 | 2/2015 |
| WO | 2015030881 A1 | 3/2015 |
| WO | 2015033293 A1 | 3/2015 |
| WO | 2015035136 A2 | 3/2015 |
| WO | 2015035139 A2 | 3/2015 |
| WO | 2015035162 A2 | 3/2015 |
| WO | 2015040075 A1 | 3/2015 |
| WO | 2015052133 A1 | 4/2015 |
| WO | 2015052231 A2 | 4/2015 |
| WO | 2015053995 A1 | 4/2015 |
| WO | 2015054253 A1 | 4/2015 |
| WO | 2015054375 A2 | 4/2015 |
| WO | 2015066636 A2 | 5/2015 |
| WO | 2015066637 A1 | 5/2015 |
| WO | 2015070083 A1 | 5/2015 |
| WO | 2015075056 A1 | 5/2015 |
| WO | 2015089277 A1 | 6/2015 |
| WO | 2015089351 A1 | 6/2015 |
| WO | 2015089354 A1 | 6/2015 |
| WO | 2015089406 A1 | 6/2015 |
| WO | 2015089419 A2 | 6/2015 |
| WO | 2015089427 A1 | 6/2015 |
| WO | 2015089462 A1 | 6/2015 |
| WO | 2015089465 A1 | 6/2015 |
| WO | 2015089473 A1 | 6/2015 |
| WO | 2015089486 A2 | 6/2015 |
| WO | 2014204728 A8 | 7/2015 |
| WO | 2015139139 A1 | 9/2015 |
| WO | 2015184259 A1 | 12/2015 |
| WO | 2015184262 A1 | 12/2015 |
| WO | 2015184268 A1 | 12/2015 |
| WO | 2015200334 A1 | 12/2015 |
| WO | 2015200378 A1 | 12/2015 |
| WO | 2015200555 A2 | 12/2015 |
| WO | 2015200725 A1 | 12/2015 |
| WO | 2014204723 A9 | 2/2016 |
| WO | 2016022363 A2 | 2/2016 |
| WO | 2014204724 A9 | 3/2016 |
| WO | 2016033246 A1 | 3/2016 |
| WO | 2016033315 A2 | 3/2016 |
| WO | 2016046288 A1 | 3/2016 |
| WO | 2016049024 A2 | 3/2016 |
| WO | 2016049163 A2 | 3/2016 |
| WO | 2016049251 A1 | 3/2016 |
| WO | 2016049657 A1 | 3/2016 |
| WO | 2016057755 A1 | 4/2016 |
| WO | 2016057800 A1 | 4/2016 |
| WO | 2016057821 A2 | 4/2016 |
| WO | 2016057835 A2 | 4/2016 |
| WO | 2016057951 A2 | 4/2016 |
| WO | 2016069282 A1 | 5/2016 |
| WO | 2016069283 A1 | 5/2016 |
| WO | 2016070037 A2 | 5/2016 |
| WO | 2016073079 A2 | 5/2016 |
| WO | WO-2016/089433 A1 | 6/2016 |
| WO | WO-2016/100951 A2 | 6/2016 |
| WO | WO-2017/004261 A1 | 1/2017 |
| WO | WO-2017/068377 A1 | 4/2017 |
| WO | 2017104404 A1 | 6/2017 |
| WO | 2017105991 A1 | 6/2017 |
| WO | 2017106414 A1 | 6/2017 |
| WO | 2017106569 A1 | 6/2017 |
| WO | 2017106657 A1 | 6/2017 |
| WO | 2017106767 A1 | 6/2017 |
| WO | WO-2017/136794 A1 | 8/2017 |
| WO | WO-2018/107028 A1 | 6/2018 |

OTHER PUBLICATIONS

Hendel et al., "Quantifying genome-editing outcomes at endogenous loci with SMRT sequencing," Cell Rep. 7, 293-305 (2014).
Hendel et al., "Chemically modified guide RNAs enhance CRISPR-Cas genome editing in human primary cells," Nat. Biotechnol. 33, 985-989 (2015).
Hruscha et al., "Efficient CRISPR/Cas9 genome editing with low off-target effects in zebrafish," Development 140, 4982-4987 (2013).
Hsu et al., "DNA targeting specificity of RNA-guided Cas9 nucleases," Nat. Biotechnol. 31, 827-832 (2013).
Hu et al., "Detecting DNA double-stranded breaks in mammalian genomes by linear amplification-mediated high-throughput genome-wide translocation sequencing," Nat Protoc. 11, 853-871 (2016).

(56) References Cited

OTHER PUBLICATIONS

Iyer et al. "Off-target mutations are rare in Cas9-modified mice," Nat. Methods 12, 479 (2015).
Jiang et al., "A Cas9-guide RNA complex preorganized for target DNA recognition," Science 348, 1477-1481 (2015).
Kim et al., "Highly Efficient RNA-guided genome editing in human cells via delivery of purified Cas9 ribonucleoproteins," Genome Res. 24, 1012-1019 (2014).
Kim et al., "Digenome-seq: genome-wide profiling of CRISPR-Cas9 off-target effects in human cells," Nat. Methods 12, 237-243 (2015).
Kim et al., "Genome-wide target specificities of CRISPR-Cas9 nucleases revealed by multiplex Digenome-seq," Genome Res. 26,406-415 (2016).
Kim et al., "Genome-wide analysis reveals specificities of Cpf1 endonucleases in human cells," Nat. Biotechnol. 34, 863-868 (2016).
Kleinstiver et al., "High-fidelity CRISPR-Cas9 nucleases with no detectable genome-wide off-target effects," Nature 529, 490-495 (2016).
Kleinstiver et al., "Genome-wide specificities of CRISPR-Cas Cpf1 nucleases in human cells," Nat. Biotechnol. 34, 869-874 (2016).
Knight et al. "Dynamics of CRISPR-Cas9 genome interrogation in living cells," Science 350, 823-826 (2015).
Komor et al., "Programmable editing of a target base in genomic DNA without double-stranded DNA cleavage," Nature 533, 420-424 (2016).
Koo et al., "Measuring and reducing off-target activities of programmable nucleases including CRISPR-Cas9," Mol. Cells 38, 475-481 (2015).
Kuscu et al., "Genome-wide analysis reveals characteristics of off-target sites bound by Cas9 endonuclease," Nat. Biotechnol. 32, 677-683 (2014).
Lee et al., "Nuclease target site selection for maximizing on-target activity and minimizing off-target effects in genome editing," Mol. Ther. 24, 475-487 (2016).
Ledford, "CRISPR, the Disruptor," Nature 522, 20-24 (2015).
Lim et al., "Structural roles of guide RNAs in the nuclease activity of Cas9 endonuclease," Nat. Commun. 7, 13350 (2016).
Lin et al., "CRISPR/Cas9 systems have off-target activity with insertions or deletions between target DNA and guide RNA sequences," Nucleic Acids Res. 42, 7473-7485 (2014).
Ma et al., "CRISPR-Cas9 nuclear dynamics and target recognition in living cells," J. Cell Biol. 214, 529-537 (2016).
Pattanayak et al., "High-throughput profiling of off-target DNA cleavage reveals RNA-programmed Cas9 nuclease specificity," Nat Biotechnol. 31, 839-843 (2013).
Peterson et al., "Genome-wide assessment of efficiency and specificity in CRISPR/Cas9 mediated multiple site targeting in Arabidopsis," PLoS ONE 11, e0162169 (2016).
Polstein et al., "Genome-wide specificity of DNA binding, gene regulation, and chromatin remodeling by TALE- and CRISPR/Cas9-based transcriptional activators," Genome Res. 25, 1158-1169 (2015).
Qiu et al., "Mutation detection using Surveyor™ nuclease," Biotechniques 36, 702-707 (2004).
Ran et al., "Double nicking by RNA-guided CRISPR Cas9 for enhanced genome editing specificity," Cell 154, 1380-1389 (2013).
Ren et al., "Enhanced specificity and efficiency of the CRISPR/Cas9 system with optimized sgRNA parameters in *Drosophila*," Cell Rep. 9, 1151-1162 (2014).
Semenova et al., "Interference by clustered regularly interspaced short palindromic repeat (CRISPR) RNA is governed by a seed sequence," Proc. Natl. Acad. Sci. USA 108, 10098-10103 (2011).
Shen et al., "Efficient genome modification by CRISPR-Cas9 nickase with minimal off-target effects," Nat. Methods 11, 399-402 (2014).
Singh et al., "Cas9-chromatin binding information enables more accurate CRISPR off-target prediction," Nucleic Acids Res. 43, e118 (2015).
Singh et al., "Real-time observation of DNA recognition and rejection by the RNA-guided endonuclease Cas9," Nat. Commun. 7, 12778 (2016).
Slaymaker et al., "Rationally engineered Cas9 nucleases with improved specificity", Science 351, 84-88 (2016).
Smith et al., "Whole-genome sequencing analysis reveals high specificity of CRISPR/Cas9 and TALEN-based genome aditing in human iPSCs," Cell Stem Cell. 15, 12-13 (2014).
Tsai et al., "Dimeric CRISPR RNA-guided FokI nucleases for highly specific genome editing," Nat. Biotechnol. 32, 569-576 (2014).
Tsai et al., "GUIDE-seq enables genome-wide profiling of off-target cleavage by CRISPR-Cas nucleases," Nat. Biotechnol. 33, 187-197 (2015).
Tsai & Joung, "Defining and improving the genome-wide specificities of CRISPR-Cas9 nucleases," Nat. Rev. Genet. 17, 300-312 (2016).
Tycko et al., "Methods for optimizing CRISPR-Cas9 genome editing specificity," Mol. Cell 63, 355-370 (2016).
Wang et al., "Unbiased detection of off-target cleavage by CRISPR-Cas9 and TALENs using integrase-defective lentiviral vectors," Nat. Biotechnol. 33, 175-178 (2015).
Wu et al., "Genome-wide binding of the CRISPR endonuclease Cas9 in mammalian cells," Nat. Biotechnol. 32, 670-676 (2014).
Wu et al., "Target specificity of the CRISPR-Cas9 system," Quant. Biol. 2, 59-70 (2014).
Wyvekens et al., "Dimeric CRISPR RNA-guided FokI-dCas9 nucleases directed by truncated gRNAs for highly specific genome editing," Hum. Gene Ther. 26, 425-431 (2015).
Yang et al., "Targeted and genome-wide sequencing reveal single nucleotide variations impacting specificity of Cas9 in human stem cells," Nat. Commun. 5, 5507 (2014).
Zetsche et al., "Cpf1 is a single RNA-guided endonuclease of a Class 2 CRISPR-Cas system," Cell,163, 759-771 (2015).
Zischewski et al. "Detection of on-target and off-target mutations generated by CRISPR/Cas9 and other sequence-specific nucleases," Biotech. Adv. 35, 95-104 (2017).
Zheng et al. "Profiling single-guide RNA specificity reveals a mismatch sensitive core sequence," Sci. Rep. 7, 40638 (2017).
http://crispr.mit.edu, Accessed Apr. 18, 2017.
http://www.rgenome.net/Cas-OFF-Finder, Accessed Apr. 18, 2017.
https://cm.jefferson.edu/Off-Spotter, Accessed Apr. 18, 2017.
New England Biolabs Catalog, 1996.
WIPO, et al., International Search Report and Written Opinion dated Sep. 12, 2017, Application No. PCT/US17/036648, 12 pages.
Bisaria et al., "Lessons from enzyme kinetics reveal specificity principles for RNA-guided nucleases in RNA interference and CRISPR-based genome editing," Cell Syst., 4:21-29, (2017).
Belfort et al., "Homing Endonucleases: Keeping the House in Order", Nucleic Acids Res., vol. 25, pp. 3379-3388, (1997).
Cho et al., "Targeted Genome Engineering in Human Cells with the cas( ma-guided endonuclease", Nat. Biotechnol. Mar. 2013.
Cho et al., "Analysis of off-target effects of CRISPR/Cas-derived RNA-guided endonucleases and nickases," Genome Res., vol. 24, pp. 0132-0141, (2014).
Dellinger et al., "Solid-Phase Chemical Synthesis of Phosphonoacetate and Thiophosphonoacetate Oligodeoxynucleotides", J. Am. Chem. Soc., vol. 125, pp. 940-950, (2003).
Dellinger et al., "Streamlined Process for the Chemical Synthesis of RNA Using 2'-O-Thionocarbamate-Protected Nucleoside Phosphoramidites in the Solid Phase", J. Am. Chem. Soc., vol. 133, pp. 11540-11556, (2011).
Doyon et al., "Enhancing Zinc-Finger-Nuclease Activity with Improved Obligate Heterodimeric Architectures", Nat. Methods, vol. 8, pp. 74-81, (2011).
El-Sagheer, A.H., et al. "Click chemistry with DNA", Chem. Soc. Rev., vol. 39, pp. 1388-1405, (2010).
Frock et al., "Genome-wide detection of DNA double-stranded breaks induced by engineered nucleases," Nat. Biotechnol., vol. 33, pp. 179-186, (2015).
Gao et al., "Single Cas9 nickase induced generation of NRAMP1 knockin cattle with reduced off-target effects," Genome Biol., vol. 18, p. 13, (2017).
Gasiunas et al., "Cas9—crRNA ribonucleoprotein complex mediates specific DNA cleavage for adaptive immunity in bacteria", Proc. Natl. Acad. Sci. USA, 109:39, (2012).

(56) References Cited

OTHER PUBLICATIONS

Fu et al., "High-frequency off-target mutagenesis induced by CRISPR-Cas nucleases in human cells," Nat. Biotechnol., vol. 31, pp. 822-826, (2013).
http://crispr.mit.edu.
http://www.rgenome.net/Cas-OFFinder.
https://cm.jefferson.edu/Off-Spotter.
Piccirilli, J. A., et al., "Enzymatic Incorporation of a New Base pair into DNA and RNA Extends the Genetic Alphabet." Nature, vol. 343, p. 33, (1990).
Schneider et al. "Information Content of Binding Sites on Nucleotide Sequences" J. Mol. Biol., 188, 415-431 (1986).
Jinek et al., "A Programmable Dual-RNA-Guided DNA Endonuclease in Adaptive Bacterial Immunity", Science, vol. 337, pp. 816-821, (2012).
Krueger et al., "Synthesis and Properties of Size-Expanded DNAs: Toward Designed, Functional Genetic Systems", Acc. Chem. Res., vol. 40, pp. 141-150, (2007).
Lahoud et al., "Enzymatic Synthesis of Structure-Free DNA with Pseudo-Complementary Properties", Nucl. Acids Res. vol. 36, 3409-3419 (2008).
Lange et al., "Classical Nuclear Localization Signals: Definition, Function, and Interaction with Importin $\alpha^*$", J. Biol. Chem., vol. 282, pp. 5101-5105, (2007).
Kuznetsova, S.A., "Synthesis and properties of DNA duplexes containing hydrocarbon bridges instead of a nucleoside residue", Bioorganicheskaia khimiia/Akademiia nauk SSSR, vol. 14:12, pp. 1656-1662, (1988).
Lujambio et al., "Genetic Unmasking of an Epigenetically Silenced microRNA in Human Cancer Cells", Cancer Res., (2007).
Miller et al., "An improved zinc-finger nuclease architecture for highly specific genome editing", Nat. Biotechnol. vol. 25, pp. 778-785, (2007).
Mojibul, H.M., et al., "DNA-associated click chemistry", Sci. China Chem., vol. 57:2, pp. 215-231, 2014.
New England Biolabs Catalog.
Kumar et al., "Template-Directed Oligonucleotide Strand Ligation, Covalent Intramolecular DNA Circularization and Catenation Using Click Chemistry", J. Am. Chem. Soc., vol. 129, pp. 6859-6864, (2007).
Ran et al., "In vivo genome editing using Staphylococcus aureus Cas9", Nature, vol. 520, pp. 186-191, (2015).
Rappaport, H. P., "Replication of the Base Pair 6-Thioguanine/S-Methyl-2-pyrimidinonweith the Large Klenow Fragment of *Escherichia coli* DNA Polymerase I", Biochemistry, vol. 32, p. 3047, (1993).
Shabarova, "Synthesis and properties of DNA duplexes containing hydrocarbon bridges instead of a nucleoside residue", Bioorg. Khim., vol. 14:12, pp. 1656-1662, (1988).
Gori et al., "Delivery and specificity of CRISPR/Cas9 genome editing technologies for human gene therapy," Hum. Gene Ther., vol. 26, pp. 443-451, (2015).
Szczpek et al., "Structure-based redesign of the dimerization interface reduces the toxicity of zinc-finger nucleases", Nat. Biotechnol., vol. 25, pp. 786-793, (2007).
Threlfall et al., "Synthesis and biological activity of phosphonoacetate- and thiophosphonoacetate-modified 2¢-O-methyl oligoribonucleotides", Org. Biomol. Chem., vol. 10, pp. 746-754, (2012).
Tietze et al., "Squaric Acid Diethyl Ester: A New Coupling Reagent for the formation of Drug Biopolymer Conjugates. Synthesis of Squaric Acid Ester Amides and Diamides", Chem. Ber., vol. 124, pp. 1215-1221, (1991).
Fu et al., "Distinct patterns of Cas9 mismatch tolerance in vitro and in vivo," Nucleic Acids Res., vol. 44, pp. 5365-5377, (2016).
Yamada, Dellinger, et al., "Synthesis and Biochemical Evaluation of Phosphonoformate Oligodeoxyribonucleotides", J Am. Chem. Soc., vol. 128:15, pp. 5251-5261, (2006).
Fu et al., "Improving CRISPR-Cas nuclease specificity using truncated guide RNAs," Nat. Biotechnol., vol. 32, pp. 279-284, (2014).
Cradick et al., "CRISPR/Cas9 systems targeting p-globin and CCR5 genes have substantial off-target activity," Nucleic Acids Res., vol. 41, pp. 9584-9592, (2013).
Davis et al., "Small molecule-triggered Cas9 protein with improved genome-editing specificity," Nat. Chem. Biol., vol. 11, pp. 316-318, (2013).
Doench et al., "Optimized sgRNA design to maximize activity and minimize off-target effects of CRISPR-Cas9," Nat. Biotechnol., vol. 34, pp. 184-191 (2016).
Mark Behlke: "Optimized, chemically-modified crRNA:tracrRNA complexes for CRISPR gene editing," Feb. 24, 2016 (Feb. 24, 2016), pp. 1-31, XP055287706 Retrieved from the Internet: URL:http://crispr-congress.com/wp-content/uploads/sites/76/2015/10/mark-behike-final-presentation.pdf [retrieved Jul. 12, 2016].
Extended European Search Report dated Jan. 3, 2020 in European Patent Application No. 17811048.2.
Ryan, D., et al., "Improving CRISPR-Cas specificity with chemical modifications in single-guide RNAs," *Nucleic Acids Research*, 2018, 46(2): 792-803.

\* cited by examiner

| Entry | Guide Sequence for CLTA1 target | ON:OFF1 Ratio | Specificity Score | ON:OFF3 Ratio | Specificity Score |
|---|---|---|---|---|---|
| 1 | AGUCCUCAUCUCCCUCAAGC- | 1.07 | 0.93 | 0.95 | 0.83 |
| 2 | AsGsUsCCUCAUCUCCCUCAAGC- | 1.00 | 0.84 | 0.93 | 0.78 |
| 3 | A*sG*sU*sCCUCAUCUCCCUCAAGC- | 1.09 | 0.92 | 1.01 | 0.85 |
| 4 | A*sGUCCUCAUCUCCCUCAAGC- | 1.04 | 0.95 | 0.97 | 0.89 |
| 5 | UCCUCAUCUCCCUCAAGC- | 1.20 | 0.94 | 0.96 | 0.75 |
| 6 | CCUCAUCUCCCUCAAGC- | 2.63 | 2.24 | 1.02 | 0.87 |
| 7 | G₀AGUCCUCAUCUCCCUCAAGC- | 1.03 | 0.93 | 0.98 | 0.89 |
| 8 | G₀G₀AGUCCUCAUCUCCCUCAAGC- | 0.98 | 0.86 | 0.99 | 0.87 |
| 9 | A*GUCCUCAUCUCCCUCAAGC- | 1.06 | 0.87 | 0.98 | 0.81 |
| 10 | A*G*UCCUCAUCUCCCUCAAGC- | 0.99 | 0.90 | 0.99 | 0.90 |
| 11 | A*G*U*CCUCAUCUCCCUCAAGC- | 1.11 | 0.95 | 1.05 | 0.90 |
| 12 | A*G*U*C*CUCAUCUCCCUCAAGC- | 3.56 | 2.50 | 2.04 | 1.43 |
| 13 | A*G*U*C*C*UCAUCUCCCUCAAGC- | 5.75 | 2.32 | 2.49 | 1.01 |
| 14 | AGUCCUCAUCUCCCUCAAGC- | 1.00 | 0.84 | 0.91 | 0.76 |
| 15 | AGUCCUCAUCUCCCUCAAGC- | 1.05 | 0.90 | 0.95 | 0.81 |
| 16 | C₀*A*G*UCCUCAUCUCCCUCAAGC- | 0.99 | 0.82 | 0.99 | 0.81 |
| 17 | G₀*A*G*UCCUCAUCUCCCUCAAGC- | 1.06 | 0.75 | 1.02 | 0.73 |
| 18 | U₀*C₀*A*G*U*CCUCAUCUCCCUCAAGC- | 1.59 | 0.89 | 1.09 | 0.61 |
| 19 | A₀*G₀*A*G*U*CCUCAUCUCCCUCAAGC- | 1.27 | 0.74 | 1.08 | 0.63 |
| 20 | C₀*U₀*C₀*A*G*U*C*CUCAUCUCCCUCAAGC- | 4.70 | 1.84 | 4.32 | 1.69 |
| 21 | G₀*A₀*G₀*A*G*U*C*CUCAUCUCCCUCAAGC- | 3.69 | 1.33 | 3.50 | 1.26 |
| 22 | AGUCCUCAUCUCCCUCAAGC*- | 1.05 | 0.88 | 0.99 | 0.83 |
| 23 | AGUCCUCAUCUCCCUCAAG*C- | 1.04 | 0.87 | 0.99 | 0.83 |
| 24 | AGUCCUCAUCUCCCUCAA*GC- | 1.07 | 0.91 | 1.02 | 0.86 |
| 25 | AGUCCUCAUCUCCCUCA*AGC- | 1.01 | 0.90 | 0.96 | 0.86 |
| 26 | AGUCCUCAUCUCCCUCA*A*GC- | 0.93 | 0.78 | 0.91 | 0.77 |
| 27 | AGUCCUCAUCUCCCUCAAGC- | 1.01 | 0.86 | 0.97 | 0.83 |
| 28 | AGUCCUCAUCUCCCUCAAGC- | 1.00 | 0.83 | 0.98 | 0.82 |
| 29 | AGUCCUCAUCUCCCUCAAGC- | 1.04 | 0.90 | 0.98 | 0.84 |
| 30 | AGUCCUCAUCUCCCUCAAGC- | 1.01 | 0.85 | 0.97 | 0.82 |
| 31 | AGUCCUCAUCUCCCUCAAGC- | 1.76 | 0.39 | 4.11 | 0.90 |
| 32 | AGUCCUCAUCUCCCUCAAGC- | 1.06 | 0.95 | 0.96 | 0.86 |

On- vs. Off-target Cleavage Ratios & Specificity Scores for in vitro cleavage of CLTA1

FIG. 8B

| Entry | Internal MP position(s) | Guide Sequence for CLTA4 target | ON : OFF1 Ratio | Specificity Score | ON : OFF2 Ratio | Specificity Score | ON : OFF3 Ratio | Specificity Score |
|---|---|---|---|---|---|---|---|---|
| 1 | 4 | G*CAG*AUGUAGUGUUUCCACA- | 1.3 | 1.1 | 1.9 | 1.7 | 34.5 | 30.0 |
| 2 | 5 | G*CAGA*UGUAGUGUUUCCACA- | 1.1 | 0.9 | 2.3 | 2.0 | large | 165.9 |
| 3 | 6 | G*CAGAU*GUAGUGUUUCCACA- | 1.0 | 0.8 | 0.9 | 0.8 | 1.0 | 0.9 |
| 4 | 7 | G*CAGAUG*UAGUGUUUCCACA- | 1.1 | 0.8 | 1.1 | 0.8 | 9.7 | 7.1 |
| 5 | 8 | G*CAGAUGU*AGUGUUUCCACA- | 1.0 | 0.8 | 0.9 | 0.7 | 1.1 | 0.9 |
| 6 | 9 | G*CAGAUGUA*GUGUUUCCACA- | 1.0 | 0.9 | 0.8 | 0.7 | 1.7 | 1.4 |
| 7 | 10 | G*CAGAUGUAG*UGUUUCCACA- | 1.0 | 0.8 | 1.2 | 1.0 | 1.0 | 0.8 |
| 8 | 11 | G*CAGAUGUAGU*GUUUCCACA- | 1.2 | 0.9 | 1.1 | 0.8 | 1.7 | 1.2 |
| 9 | 12 | G*CAGAUGUAGUG*UUUCCACA- | 1.0 | 0.9 | 1.1 | 1.0 | 2.1 | 1.9 |
| 10 | 13 | G*CAGAUGUAGUGU*UUCCACA- | 1.0 | 0.9 | 0.9 | 0.9 | 1.1 | 1.0 |
| 11 | 14 | G*CAGAUGUAGUGUU*UCCACA- | 1.0 | 0.9 | 1.2 | 1.2 | 2.9 | 2.8 |
| 12 | 15 | G*CAGAUGUAGUGUUU*CCACA- | 1.1 | 0.2 | 3.7 | 0.6 | large | 6.0 |
| 13 | 16 | G*CAGAUGUAGUGUUUC*CACA- | 1.0 | 0.9 | 1.0 | 0.9 | 2.0 | 1.8 |
| 14 | 17 | G*CAGAUGUAGUGUUUCC*ACA- | 0.9 | 0.9 | 0.9 | 0.8 | 1.0 | 0.9 |
| 15 | 18 | G*CAGAUGUAGUGUUUCCA*CA- | 1.0 | 0.9 | 0.9 | 0.8 | 1.2 | 1.0 |
| 16 | 19 | G*CAGAUGUAGUGUUUCCAC*A- | 1.0 | 0.9 | 0.9 | 0.8 | 1.1 | 1.0 |
| 17 | 20 | G*CAGAUGUAGUGUUUCCACA*- | 1.0 | 0.9 | 0.9 | 0.8 | 1.0 | 0.9 |
| 18 | control | GCAGAUGUAGUGUUUCCACA- | 1.0 | 0.9 | 0.9 | 0.8 | 1.4 | 1.2 |
| 19 | 5-7 | G*CAGA*U*G*UAGUGUUUCCACA- | large | 2.8 | large | 2.8 | large | 2.8 |
| 20 | 6-8 | G*CAGAU*G*U*AGUGUUUCCACA- | 1.4 | 0.6 | 6.4 | 2.6 | large | 33.5 |
| 21 | 7-9 | G*CAGAUG*U*A*GUGUUUCCACA- | 2.5 | 0.1 | large | 0.1 | large | 0.1 |
| 22 | 8-10 | G*CAGAUGU*A*G*UGUUUCCACA- | 2.3 | 0.6 | large | 14.9 | 12.4 | 3.3 |
| 23 | 9-11 | G*CAGAUGUA*G*U*GUUUCCACA- | 2.1 | 0.6 | large | 14.3 | large | 14.3 |
| 24 | 10-12 | G*CAGAUGUAG*U*G*UUUCCACA- | 1.2 | 0.3 | large | 11.1 | large | 11.1 |
| 25 | 11-13 | G*CAGAUGUAGU*G*U*UUCCACA- | 7.6 | 1.5 | large | 7.8 | 8.3 | 1.6 |
| 26 | 12-14 | G*CAGAUGUAGUG*U*U*UCCACA- | 20.8 | 5.8 | large | 15.6 | large | 15.6 |
| 27 | 13-15 | G*CAGAUGUAGUGU*U*U*CCACA- | large | 0.1 | large | 0.1 | large | 0.1 |
| 28 | 14-16 | G*CAGAUGUAGUGUU*U*C*CACA- | large | 0.2 | 1.4 | 0.0 | large | 0.2 |

FIG. 9B

| Entry | Internal MP position(s) | Guide Sequence for IL2RG target | % Target Cleaved | | Ratio | Specificity Score |
|---|---|---|---|---|---|---|
| | | | ON | OFF3 | ON : OFF3 | |
| 1 | 2 | U*G*GUAAUGAUGGCUUCAACA- | 80% | 75% | 1.1 | 0.9 |
| 2 | 3 | U*GG*UAAUGAUGGCUUCAACA- | 85% | 62% | 1.4 | 1.2 |
| 3 | 4 | U*GGU*AAUGAUGGCUUCAACA- | 63% | 8% | 8.4 | 5.2 |
| 4 | 5 | U*GGUA*AUGAUGGCUUCAACA- | 76% | 31% | 2.5 | 1.9 |
| 5 | 6 | U*GGUAA*UGAUGGCUUCAACA- | 75% | 69% | 1.1 | 0.8 |
| 6 | 7 | U*GGUAAU*GAUGGCUUCAACA- | 65% | 3% | 18.8 | 12.3 |
| 7 | 8 | U*GGUAAUG*AUGGCUUCAACA- | 73% | 53% | 1.4 | 1.0 |
| 8 | 9 | U*GGUAAUGA*UGGCUUCAACA- | 73% | 32% | 2.3 | 1.6 |
| 9 | 10 | U*GGUAAUGAU*GGCUUCAACA- | 64% | 48% | 1.3 | 0.9 |
| 10 | 11 | U*GGUAAUGAUG*GCUUCAACA- | 65% | 18% | 3.7 | 2.4 |
| 11 | 12 | U*GGUAAUGAUGG*CUUCAACA- | 84% | 10% | 8.3 | 7.0 |
| 12 | 13 | U*GGUAAUGAUGGC*UUCAACA- | 95% | 21% | 4.5 | 4.2 |
| 13 | 14 | U*GGUAAUGAUGGCU*UCAACA- | 96% | 10% | 9.7 | 9.3 |
| 14 | 15 | U*GGUAAUGAUGGCUU*CAACA- | 29% | 8% | 3.8 | 1.1 |
| 15 | 16 | U*GGUAAUGAUGGCUUC*AACA- | 96% | 9% | 10.7 | 10.2 |
| 16 | 17 | U*GGUAAUGAUGGCUUCA*ACA- | 95% | 12% | 7.7 | 7.3 |
| 17 | 18 | U*GGUAAUGAUGGCUUCAA*CA- | 92% | 17% | 5.4 | 4.9 |
| 18 | 19 | U*GGUAAUGAUGGCUUCAAC*A- | 92% | 25% | 3.6 | 3.3 |
| 19 | 20 | U*GGUAAUGAUGGCUUCAACA*- | 87% | 61% | 1.4 | 1.2 |
| 20 | control | U*GGUAAUGAUGGCUUCAACA- | 84% | 68% | 1.2 | 1.0 |
| 21 | 4-6 | U*GGU*A*A*UGAUGGCUUCAACA- | 19% | | | |
| 22 | 5-7 | U*GGUA*A*U*GAUGGCUUCAACA- | 11% | | | |
| 23 | 6-8 | U*GGUAA*U*G*AUGGCUUCAACA- | 4% | | | |
| 24 | 7-9 | U*GGUAAU*G*A*UGGCUUCAACA- | 2% | 3% | 0.5 | 0.0 |
| 25 | 8-10 | U*GGUAAUG*A*U*GGCUUCAACA- | 23% | 4% | 5.7 | 1.3 |
| 26 | 9-11 | U*GGUAAUGA*U*G*GCUUCAACA- | 50% | 4% | 12.1 | 6.0 |
| 27 | 10-12 | U*GGUAAUGAU*G*G*CUUCAACA- | 39% | 6% | 6.6 | 2.6 |
| 28 | 11-13 | U*GGUAAUGAUG*G*C*UUCAACA- | 35% | 3% | 10.7 | 3.7 |
| 29 | 12-14 | U*GGUAAUGAUGG*C*U*UCAACA- | 19% | 3% | 5.6 | 1.1 |
| 30 | 13-15 | U*GGUAAUGAUGGC*U*U*CAACA- | 4% | 4% | 1.1 | 0.0 |

On- vs. Off-target Cleavage Ratios & Specificity Scores for in vitro cleavage of IL2RG

FIG. 10

| Entry | Internal MP position(s) | Guide Sequence for HBB target | % Target Cleaved ON | % Target Cleaved OFF1 | Ratio ON : OFF1 | Specificity Score |
|---|---|---|---|---|---|---|
| 1 | 4 | C*UUG*CCCCACAGGGCAGUAA- | 30% | 3% | 10.1 | 3.0 |
| 2 | 5 | C*UUGC*CCCACAGGGCAGUAA- | 53% | 3% | 16.7 | 8.9 |
| 3 | 6 | C*UUGCC*CCACAGGGCAGUAA- | 73% | 37% | 2.0 | 1.4 |
| 4 | 7 | C*UUGCCC*CACAGGGCAGUAA- | 39% | 3% | 14.1 | 5.5 |
| 5 | 8 | C*UUGCCCC*ACAGGGCAGUAA- | 40% | 7% | 6.1 | 2.4 |
| 6 | 9 | C*UUGCCCCA*CAGGGCAGUAA- | 59% | 5% | 11.9 | 7.0 |
| 7 | 10 | C*UUGCCCCAC*AGGGCAGUAA- | 58% | 6% | 10.1 | 5.9 |
| 8 | 11 | C*UUGCCCCACA*GGGCAGUAA- | 53% | 3% | 20.3 | 10.9 |
| 9 | 12 | C*UUGCCCCACAG*GGCAGUAA- | 75% | 21% | 3.6 | 2.7 |
| 10 | 13 | C*UUGCCCCACAGG*GCAGUAA- | 66% | 20% | 3.3 | 2.2 |
| 11 | 14 | C*UUGCCCCACAGGG*CAGUAA- | 76% | 19% | 3.9 | 3.0 |
| 12 | 15 | C*UUGCCCCACAGGGC*AGUAA- | 0% | 2% | 0.0 | 0.0 |
| 13 | 16 | C*UUGCCCCACAGGGCA*GUAA- | 65% | 27% | 2.4 | 1.6 |
| 14 | 17 | C*UUGCCCCACAGGGCAG*UAA- | 81% | 47% | 1.7 | 1.4 |
| 15 | 18 | C*UUGCCCCACAGGGCAGU*AA- | 76% | 34% | 2.2 | 1.7 |
| 16 | 19 | C*UUGCCCCACAGGGCAGUA*A- | 62% | 23% | 2.7 | 1.7 |
| 17 | control | C*UUGCCCCACAGGGCAGUAA- | 75% | 38% | 2.0 | 1.5 |

On- vs. Off-target Cleavage Ratios & Specificity Scores for in vitro cleavage of HBB

FIG. 11A

| Entry | sgRNA Name | ON target | OFF1 target | ON:OFF1 ratio | Specificity Score |
|---|---|---|---|---|---|
| 1 | HBB_11MP_1xMP | 53% | 3% | 20.3 | 10.9 |
| 2 | HBB_5MP_1xMP | 53% | 3% | 16.7 | 8.9 |
| 3 | HBB_9MP_1xMP | 59% | 5% | 11.9 | 7.0 |
| 4 | HBB_10MP_1xMP | 58% | 6% | 10.1 | 5.9 |
| 5 | HBB_7MP_1xMP | 39% | 3% | 14.1 | 5.5 |
| 6 | HBB_14MP_1xMP | 76% | 19% | 3.9 | 3.0 |
| 7 | HBB_4MP_1xMP | 30% | 3% | 10.1 | 3.0 |
| 8 | HBB_12MP_1xMP | 75% | 21% | 3.6 | 2.7 |
| 9 | HBB_8MP_1xMP | 40% | 7% | 6.1 | 2.4 |
| 10 | HBB_13MP_1xMP | 66% | 20% | 3.3 | 2.2 |
| 11 | HBB_18MP_1xMP | 76% | 34% | 2.2 | 1.7 |
| 12 | HBB_19MP_1xMP | 62% | 23% | 2.7 | 1.7 |
| 13 | HBB_16MP_1xMP | 65% | 27% | 2.4 | 1.6 |
| 14 | HBB_1xMP (control) | 75% | 38% | 2.0 | 1.5 |
| 15 | HBB_6MP_1xMP | 73% | 37% | 2.0 | 1.4 |
| 16 | HBB_17MP_1xMP | 81% | 47% | 1.7 | 1.4 |
| 17 | HBB_15MP_1xMP | 0% | 2% | 0.0 | 0.0 |
| 18 | HBB_6,7MP_1xMP | 50% | 1% | 50.0 | 25.0 |
| 19 | HBB_10,17MP_1xMP | 50% | 1% | 49.5 | 24.5 |
| 20 | HBB_5,17MP_1xMP | 46% | 1% | 46.1 | 21.3 |
| 21 | HBB_5,16MP_1xMP | 45% | 1% | 45.1 | 20.4 |
| 22 | HBB_6,10MP_1xMP | 61% | 2% | 34.5 | 20.9 |
| 23 | HBB_10,16MP_1xMP | 40% | 1% | 39.6 | 15.7 |
| 24 | HBB_5,9MP_1xMP | 65% | 3% | 23.5 | 15.3 |
| 25 | HBB_9,16MP_1xMP | 38% | 1% | 38.1 | 14.6 |
| 26 | HBB_6,17MP_1xMP | 37% | 1% | 37.5 | 14.0 |
| 27 | HBB_6,8MP_1xMP | 45% | 2% | 26.7 | 12.0 |
| 28 | HBB_9,10MP_1xMP | 50% | 2% | 24.0 | 12.0 |
| 29 | HBB_10,13MP_1xMP | 51% | 2% | 22.2 | 11.4 |
| 30 | HBB_9,14MP_1xMP | 34% | 1% | 33.5 | 11.3 |
| 31 | HBB_9,17MP_1xMP | 54% | 3% | 20.4 | 11.1 |
| 32 | HBB_13,17MP_1xMP | 32% | 1% | 31.9 | 10.2 |
| 33 | HBB_7,14MP_1xMP | 48% | 2% | 20.7 | 9.8 |
| 34 | HBB_5,14MP_1xMP | 46% | 2% | 19.8 | 9.2 |
| 35 | HBB_5,6MP_1xMP | 58% | 4% | 13.5 | 7.9 |
| 36 | HBB_6,11MP_1xMP | 46% | 3% | 17.3 | 7.9 |
| 37 | HBB_9,13MP_1xMP | 54% | 4% | 12.8 | 7.0 |
| 38 | HBB_13,14MP_1xMP | 75% | 8% | 9.6 | 7.2 |
| 39 | HBB_6,9MP_1xMP | 61% | 6% | 10.2 | 6.2 |
| 40 | HBB_14,17MP_1xMP | 23% | 1% | 23.3 | 5.4 |
| 41 | HBB_7,17MP_1xMP | 53% | 6% | 9.3 | 4.9 |
| 42 | HBB_16,17MP_1xMP | 21% | 1% | 20.9 | 4.4 |
| 43 | HBB_8,14MP_1xMP | 36% | 2% | 16.0 | 5.7 |
| 44 | HBB_8,9MP_1xMP | 27% | 2% | 17.5 | 4.7 |
| 45 | HBB_8,13MP_1xMP | 42% | 4% | 9.4 | 3.9 |
| 46 | HBB_7,13MP_1xMP | 39% | 4% | 10.2 | 3.9 |
| 47 | HBB_8,16MP_1xMP | 32% | 3% | 11.8 | 3.8 |
| 48 | HBB_10,14MP_1xMP | 26% | 2% | 14.0 | 3.7 |
| 49 | HBB_7,16MP_1xMP | 37% | 4% | 9.0 | 3.3 |
| 50 | HBB_7,9MP_1xMP | 32% | 3% | 10.1 | 3.3 |
| 51 | HBB_5,8MP_1xMP | 17% | 1% | 18.9 | 2.9 |
| 52 | HBB_6,14MP_1xMP | 64% | 14% | 4.5 | 2.9 |
| 53 | HBB_6,13MP_1xMP | 69% | 16% | 4.2 | 2.9 |
| 54 | HBB_5,13MP_1xMP | 35% | 5% | 7.7 | 2.7 |
| 55 | HBB_6,16MP_1xMP | 62% | 17% | 3.6 | 2.2 |
| 56 | HBB_7,10MP_1xMP | 21% | 2% | 8.4 | 1.7 |
| 57 | HBB_6,17MP_1xMP | 68% | 37% | 1.8 | 1.3 |
| 58 | HBB_8,10MP_1xMP | 16% | 2% | 7.8 | 1.2 |
| 59 | HBB_1xMP (control) | 69% | 44% | 1.6 | 1.1 |
| 60 | HBB_13,16MP_1xMP | 10% | 1% | 9.9 | 1.0 |
| 61 | HBB_14,16MP_1xMP | 9% | 1% | 9.0 | 0.8 |
| 62 | HBB_9,10MP_1xMP | 16% | 3% | 5.1 | 0.8 |
| 63 | HBB_5,7MP_1xMP | 18% | 6% | 2.9 | 0.5 |
| 64 | HBB_5,11MP_1xMP | 4% | 2% | 1.8 | 0.1 |

FIG. 12A

In K562 cells:

| Entry | sgRNA Name or Type of Control | ON target | OFF1 target | ON:OFF1 ratio | Specificity Score |
|---|---|---|---|---|---|
| 1 | HBB_11MP_1xMP | 69.6% | 0.9% | 80.2 | 55.8 |
| 2 | HBB_8MP_1xMP | 81.2% | 3.0% | 26.9 | 21.8 |
| 3 | HBB_7MP_1xMP | 53.5% | 3.1% | 17.2 | 9.2 |
| 4 | HBB_10MP_1xMP | 66.7% | 9.1% | 7.3 | 4.9 |
| 5 | HBB_9MP_1xMP | 65.0% | 9.0% | 7.2 | 4.7 |
| 6 | HBB_13MP_1xMP | 61.5% | 19.6% | 3.1 | 1.9 |
| 7 | HBB_3xMS (control) | 92.3% | 52.6% | 1.8 | 1.6 |
| 8 | HBB_unmodif (control) | 84.3% | 46.5% | 1.8 | 1.5 |
| 9 | HBB_1xMP (control) | 78.5% | 44.4% | 1.8 | 1.4 |
| 10 | HBB_14MP_1xMP | 34.3% | 12.3% | 2.8 | 1.0 |
| 11 | HBB_17MP_1xMP | 34.4% | 22.0% | 1.6 | 0.5 |
| 12 | HBB_16MP_1xMP | 9.1% | 5.5% | 1.7 | 0.2 |
| 13 | HBB_6,10MP_1xMP | 64.4% | 4.4% | 14.6 | 9.4 |
| 14 | HBB_5,17MP_1xMP | 25.8% | 1.5% | 17.4 | 4.5 |
| 15 | HBB_6,7MP_1xMP | 29.5% | 2.7% | 10.8 | 3.2 |
| 16 | HBB_10,17MP_1xMP | 24.9% | 3.0% | 8.3 | 2.1 |
| 17 | HBB_5,16MP_1xMP | 6.5% | 0.2% | 27.6 | 1.8 |
| 18 | HBB_5,9MP_1xMP | 17.6% | 2.8% | 6.3 | 0.8 |
| 19 | HBB_9,17MP_1xMP | 6.5% | 0.8% | 7.8 | 0.5 |
| 20 | GFP transfection control | 0.1% | 0.1% | | |
| 21 | Mock transfection control | 0.2% | 0.0% | | |

In iPS cells:

| Entry | sgRNA Name or Type of Control | ON target | OFF1 target | ON:OFF1 ratio | Specificity Score |
|---|---|---|---|---|---|
| 22 | HBB_11MP_1xMP | 45.1% | 0.5% | 96.1 | 43.3 |
| 23 | HBB_8MP_1xMP | 51.8% | 1.8% | 29.3 | 15.2 |
| 24 | HBB_7MP_1xMP | 38.2% | 2.0% | 19.9 | 7.8 |
| 25 | HBB_10MP_1xMP | 37.9% | 6.1% | 6.3 | 2.4 |
| 26 | HBB_9MP_1xMP | 32.5% | 4.9% | 6.6 | 2.1 |
| 27 | HBB_13MP_1xMP | 37.1% | 19.7% | 1.9 | 0.7 |
| 28 | HBB_14MP_1xMP | 25.2% | 14.3% | 1.8 | 0.4 |
| 29 | HBB_3xMS (control) | 31.3% | 22.6% | 1.4 | 0.4 |
| 30 | HBB_1xMP (control) | 34.0% | 31.8% | 1.1 | 0.4 |
| 31 | HBB_unmodif (control) | 25.3% | 19.6% | 1.3 | 0.3 |
| 32 | HBB_16MP_1xMP | 7.8% | 6.2% | 1.3 | 0.1 |
| 33 | HBB_17MP_1xMP | 16.4% | 17.3% | 1.0 | 0.2 |
| 34 | HBB_6,10MP_1xMP | 35.7% | 2.0% | 17.4 | 6.2 |
| 35 | HBB_5,17MP_1xMP | 16.2% | 0.6% | 29.1 | 4.7 |
| 36 | HBB_5,16MP_1xMP | 6.3% | 0.1% | 59.1 | 3.7 |
| 37 | HBB_6,7MP_1xMP | 21.2% | 2.1% | 10.0 | 2.1 |
| 38 | HBB_10,17MP_1xMP | 11.4% | 1.1% | 10.1 | 1.1 |
| 39 | HBB_5,9MP_1xMP | 9.0% | 1.4% | 6.5 | 0.6 |
| 40 | HBB_9,17MP_1xMP | 3.3% | 0.6% | 5.2 | 0.2 |
| 41 | GFP transfection control | 0.0% | 0.0% | | |
| 42 | Mock transfection control | 0.0% | 0.0% | | |

FIG. 12B

In K562 cells:

| Entry | sgRNA Name or Type of Control | ON target | OFF1 target | ON : OFF1 ratio | Specificity Score |
|---|---|---|---|---|---|
| 1 | HBB_11MP_1xMP | 69.6% | 0.9% | 88.2 | 55.8 |
| 2 | HBB_5MP_1xMP | 81.2% | 3.0% | 26.9 | 21.8 |
| 3 | HBB_7MP_1xMP | 53.5% | 3.1% | 17.2 | 9.2 |
| 4 | HBB_10MP_1xMP | 66.7% | 9.1% | 7.3 | 4.9 |
| 5 | HBB_9MP_1xMP | 65.0% | 9.0% | 7.2 | 4.7 |
| 6 | HBB_13MP_1xMP | 61.5% | 19.6% | 3.1 | 1.9 |
| 7 | HBB_14MP_1xMP | 34.9% | 12.3% | 2.8 | 1.0 |
| 8 | HBB_3xMS (control) | 92.3% | 52.6% | 1.8 | 1.6 |
| 9 | HBB_unmodif (control) | 84.3% | 46.5% | 1.8 | 1.5 |
| 10 | HBB_1xMP (control) | 78.5% | 44.4% | 1.8 | 1.4 |
| 11 | HBB_16MP_1xMP | 9.1% | 5.5% | 1.7 | 0.2 |
| 12 | HBB_17MP_1xMP | 34.4% | 22.0% | 1.6 | 0.5 |
| 13 | HBB_5,16MP_1xMP | 6.5% | 0.2% | 27.6 | 1.8 |
| 14 | HBB_5,17MP_1xMP | 25.8% | 1.5% | 17.4 | 4.5 |
| 15 | HBB_6,10MP_1xMP | 64.4% | 4.4% | 14.6 | 9.4 |
| 16 | HBB_6,7MP_1xMP | 29.5% | 2.7% | 10.8 | 3.2 |
| 17 | HBB_10,17MP_1xMP | 24.9% | 3.0% | 8.3 | 2.1 |
| 18 | HBB_9,17MP_1xMP | 6.5% | 0.8% | 7.8 | 0.9 |
| 19 | HBB_9,9MP_1xMP | 12.6% | 2.0% | 6.3 | 0.8 |
| 20 | GFP transfection control | 0.1% | 0.1% | | |
| 21 | Mock transfection control | 0.2% | 0.0% | | |

In iPS cells:

| Entry | sgRNA Name or Type of Control | ON target | OFF1 target | ON : OFF1 ratio | Specificity Score |
|---|---|---|---|---|---|
| 22 | HBB_11MP_1xMP | 45.1% | 0.5% | 98.1 | 43.3 |
| 23 | HBB_5MP_1xMP | 51.8% | 1.8% | 29.3 | 15.2 |
| 24 | HBB_7MP_1xMP | 39.2% | 2.0% | 19.9 | 7.8 |
| 25 | HBB_9MP_1xMP | 32.5% | 4.9% | 6.6 | 2.1 |
| 26 | HBB_10MP_1xMP | 37.9% | 6.1% | 6.3 | 2.4 |
| 27 | HBB_13MP_1xMP | 37.1% | 19.7% | 1.9 | 0.7 |
| 28 | HBB_14MP_1xMP | 25.3% | 14.3% | 1.8 | 0.4 |
| 29 | HBB_3xMS (control) | 31.3% | 22.6% | 1.4 | 0.4 |
| 30 | HBB_unmodif (control) | 25.3% | 19.6% | 1.3 | 0.3 |
| 31 | HBB_16MP_1xMP | 7.8% | 6.2% | 1.3 | 0.1 |
| 32 | HBB_1xMP (control) | 34.0% | 31.8% | 1.1 | 0.4 |
| 33 | HBB_17MP_1xMP | 16.4% | 17.3% | 1.0 | 0.2 |
| 34 | HBB_5,16MP_1xMP | 6.3% | 0.1% | 59.1 | 3.7 |
| 35 | HBB_5,17MP_1xMP | 16.2% | 0.6% | 29.1 | 4.7 |
| 36 | HBB_6,10MP_1xMP | 35.7% | 2.0% | 17.4 | 6.2 |
| 37 | HBB_10,17MP_1xMP | 11.4% | 1.1% | 10.1 | 1.1 |
| 38 | HBB_6,7MP_1xMP | 21.2% | 2.1% | 10.0 | 2.1 |
| 39 | HBB_5,9MP_1xMP | 9.0% | 1.4% | 6.5 | 0.6 |
| 40 | HBB_9,17MP_1xMP | 3.3% | 0.6% | 5.2 | 0.2 |
| 41 | GFP transfection control | 0.0% | 0.0% | | |
| 42 | Mock transfection control | 0.0% | 0.0% | | |

| Entry | Target Gene | sgRNA Name or Type of Control | ON target | OFF2 target | ON : OFF2 ratio | Specificity Score |
|---|---|---|---|---|---|---|
| 1 | IL2RG | IL2RG_unmodif (control) | 98.5% | 5.228% | 18.8 | 18.6 |
| 2 | IL2RG | IL2RG_1xMP | 97.8% | 0.094% | 1,040 | 1,020 |
| 3 | IL2RG | IL2RG_5MP_1xMP | 93.2% | 0.005% | 18,600 | 17,400 |
| 4 | IL2RG | IL2RG_11MP_1xMP | 87.1% | 0.008% | 10,900 | 9,500 |
| 5 | VEGFA | VEGFA_1xMP | 74.1% | 10.82% | 6.8 | 5.1 |
| 6 | VEGFA | VEGFA_5MP_1xMP | 75.7% | 0.19% | 398 | 302 |
| 7 | VEGFA | VEGFA_7MP_1xMP | 16.5% | 0.02% | 825 | 136 |
| 8 | VEGFA | VEGFA_9MP_1xMP | 42.0% | 0.22% | 191 | 80 |
| 9 | VEGFA | VEGFA_10MP_1xMP | 23.7% | 0.08% | 296 | 70 |
| 10 | VEGFA | VEGFA_11MP_1xMP | 23.9% | 0.11% | 217 | 52 |

FIG. 14

HIGH SPECIFICITY GENOME EDITING USING CHEMICALLY MODIFIED GUIDE RNAS

CROSS REFERENCE TO RELATED APPLICATIONS

This application claims the benefit of U.S. Provisional Application No. 62/347,553, filed Jun. 8, 2016, the contents of which is incorporated by reference in its entirety.

FIELD OF THE INVENTION

The present invention relates to the field of molecular biology. In particular, the present invention relates to the clusters of regularly interspaced short palindromic repeats (CRISPR) technology.

BACKGROUND OF THE INVENTION

The native prokaryotic CRISPR-Cas system comprises an array of short repeats with intervening variable sequences of constant length (i.e., clusters of regularly interspaced short palindromic repeats, or "CRISPR"), and CRISPR-associated ("Cas") proteins. The RNA of the transcribed CRISPR array is processed by a subset of the Cas proteins into small guide RNAs, which generally have two components as discussed below. There are at least six different systems: Type I, Type II, Type III, Type IV, Type V and Type VI. The enzymes involved in the processing of the RNA into mature crRNA are different in the six systems. In the native prokaryotic Type II system, the guide RNA ("gRNA") comprises two short, non-coding RNA species referred to as CRISPR RNA ("crRNA") and trans-acting RNA ("tracrRNA"). In an exemplary system, the gRNA forms a complex with a Cas nuclease. The gRNA:Cas nuclease complex binds a target polynucleotide sequence having a protospacer adjacent motif ("PAM") and a protospacer, which is a sequence complementary to a portion of the gRNA. The recognition and binding of the target polynucleotide by the gRNA:Cas nuclease complex induces cleavage of the target polynucleotide. The native CRISPR-Cas system functions as an immune system in prokaryotes, where gRNA:Cas nuclease complexes recognize and silence exogenous genetic elements in a manner analogous to RNAi in eukaryotic organisms, thereby conferring resistance to exogenous genetic elements such as plasmids and phages.

It has been demonstrated that a single-guide RNA ("sgRNA") where the crRNA and tracrRNA are covenlently linked can replace the complex formed between the naturally-existing crRNA and tracrRNA.

Considerations relevant to developing a gRNA, including a sgRNA, include specificity, stability, and functionality. Specificity refers to the ability of a particular gRNA:Cas nuclease complex to bind, nick, and/or cleave a desired target sequence, whereas less or no binding, nicking, and/or cleavage of polynucleotides different in sequence and/or location from the desired target occurs. Thus, specificity refers to minimizing off-target effects of the gRNA:Cas nuclease complex. There is a need for providing gRNA, including sgRNA, having desired binding affinity for the target polynucleotide with reduced off-target effects while, nonetheless, having desired gRNA functionality. There is also a need for improved ways to make and use gRNA, including sgRNA, having enhanced specificity, with desired binding affinity for the target polynucleotide and/or reduced off-target binding.

BRIEF DESCRIPTION OF THE DRAWINGS

FIG. 3 is not intended to be limiting and many other modifications as described herein can be employed.

FIG. 5C also illustrates chemical modification in the sampling region.

FIG. 8B is derived from the cleavage results in FIG. 8A by calculating a ratio of cleaved target polynucleotide versus cleaved off-target polynucleotide for each synthetic sgRNA assayed. Also calculated is a "Specificity Score" obtained by multiplying each ratio by the respective ON-target cleavage percentage per guide RNA assayed. The shaded ratios and Specificity Scores are notable for their larger values with respect to the others shown in FIG. 8B.

FIG. 9B is derived from the cleavage results in FIG. 9A by calculating a ratio of cleaved target polynucleotide versus cleaved off-target polynucleotide for each synthetic sgRNA assayed. Specificity Scores are calculated as described for FIG. 8B, and the scores greater than or equal to 1.5 are shaded. The three highest scores per off-target polynucleotide are indicated by darker shading.

FIG. 10 shows the impact of MP modifications at various locations in gRNAs targeted to a sequence in the human IL2RG gene with regard to in vitro cleavage of target polynucleotide called "ON" and separately assayed cleavage of an off-target polynucleotide called "OFF3" in this figure representing IL2RG ON-target and IL2RG OFF3-target, respectively. A ratio is calculated for cleaved target polynucleotide versus cleaved off-target polynucleotide for each synthetic sgRNA assayed. Specificity Scores are calculated as described for FIG. 8B, and the scores greater than 2.0 are shaded. The three highest scores are indicated by darker shading.

FIG. 11A shows the impact of MP modifications at various locations in gRNAs targeted to a sequence in the human HBB gene with regard to in vitro cleavage of target polynucleotide called "ON" and separately assayed cleavage of an off-target polynucleotide called "OFF1" in this figure representing HBB ON-target and HBB OFF1-target, respectively. A ratio is calculated for cleaved target polynucleotide versus cleaved off-target polynucleotide for each synthetic sgRNA assayed. Specificity Scores are calculated as described for FIG. 8B, and the scores greater than 2.0 are shaded. The three highest scores are indicated by darker shading.

FIG. 12A shows the same results in entries 1-17 as shown in FIG. 11A, with the entries ranked according to Specificity Score from highest to lowest. Entries 18-64 show the impact of additional MP modifications at various locations in gRNAs targeted to a sequence in the human HBB gene with regard to in vitro cleavage of target polynucleotide called "ON" and separately assayed cleavage of an off-target polynucleotide called "OFF1," representing HBB ON-target and HBB OFF1-target, respectively. "1xMP" indicates that the terminal nucleotides at both the 5' and 3' ends have been modified with MP. A ratio is calculated for cleaved target polynucleotide versus cleaved off-target polynucleotide for each synthetic sgRNA assayed. Specificity Scores are calculated as described for FIG. 8B. The highest scores are shaded.

FIG. 12B shows the impact of MP modifications at various locations in gRNAs targeted to a sequence in the human HBB gene in transfected cells with regard to cleavage of a target genomic locus called "ON" and concurrent cleavage of an off-target genomic locus called "OFF1" in this figure representing endogenous HBB ON-target and HBB OFF1-target sites respectively. The percentage of cleavage yielded at either or both sites in cultured cells transfected with a complex of synthetic sgRNA and recombinant Cas9 protein is determined 48 hours post-transfection by PCR amplification of the on-target and off-target loci in split samples of purified genomic DNA, followed by next-generation sequencing of pooled amplicons and bioinformatic partitioning of the sequence reads according to the presence versus absence of an indel near the on-target or off-target cleavage site being evaluated. Indels generated in each sample of transfected cells are normalized relative to a control sample of mock-transfected cells treated with buffer instead of sgRNA:Cas9 complex. A ratio is calculated for the number of sequence reads showing a target site indel versus the number of reads showing an off-target site indel for each sgRNA transfected separately. Specificity Scores are calculated as described for FIG. 8B. "1xMP" indicates that the terminal nucleotides at both the 5' and 3' ends have been modified with MP. Entries 1-21 show results obtained by transfecting and culturing K562 cells, whereas entries 22-42 show results obtained by transfecting and culturing induced pluripotent stem cells (also known as iPS cells or iPSCs). Entries 1-12 are ranked according to Specificity Score from highest to lowest. Likewise entries 13-19, entries 22-33, and entries 34-40 are ranked by Specificity Score per grouping. Specificity Scores greater than 2.0 are shaded.

FIG. 12C shows an alternative organization of the results in FIG. 12B according to the measured ratios, sorted from highest to lowest ratio per grouping.

FIG. 13 shows a comparison of the results presented in FIGS. 9A, 9B, 10 and 11A. FIG. 13 shows several trends from studies of chemically modified guide RNAs with respect to target specificity when used in a Cas system for cleaving target polynucleotides. The concepts supported by the trends are especially useful when off-target polynucleotides are also present in the Cas system.

FIG. 14 shows the impact of various types of modifications in IL2RG sgRNAs and VEGFA sgRNAs in K562 cells.

DETAILED DESCRIPTION OF THE INVENTION

Figure 1:
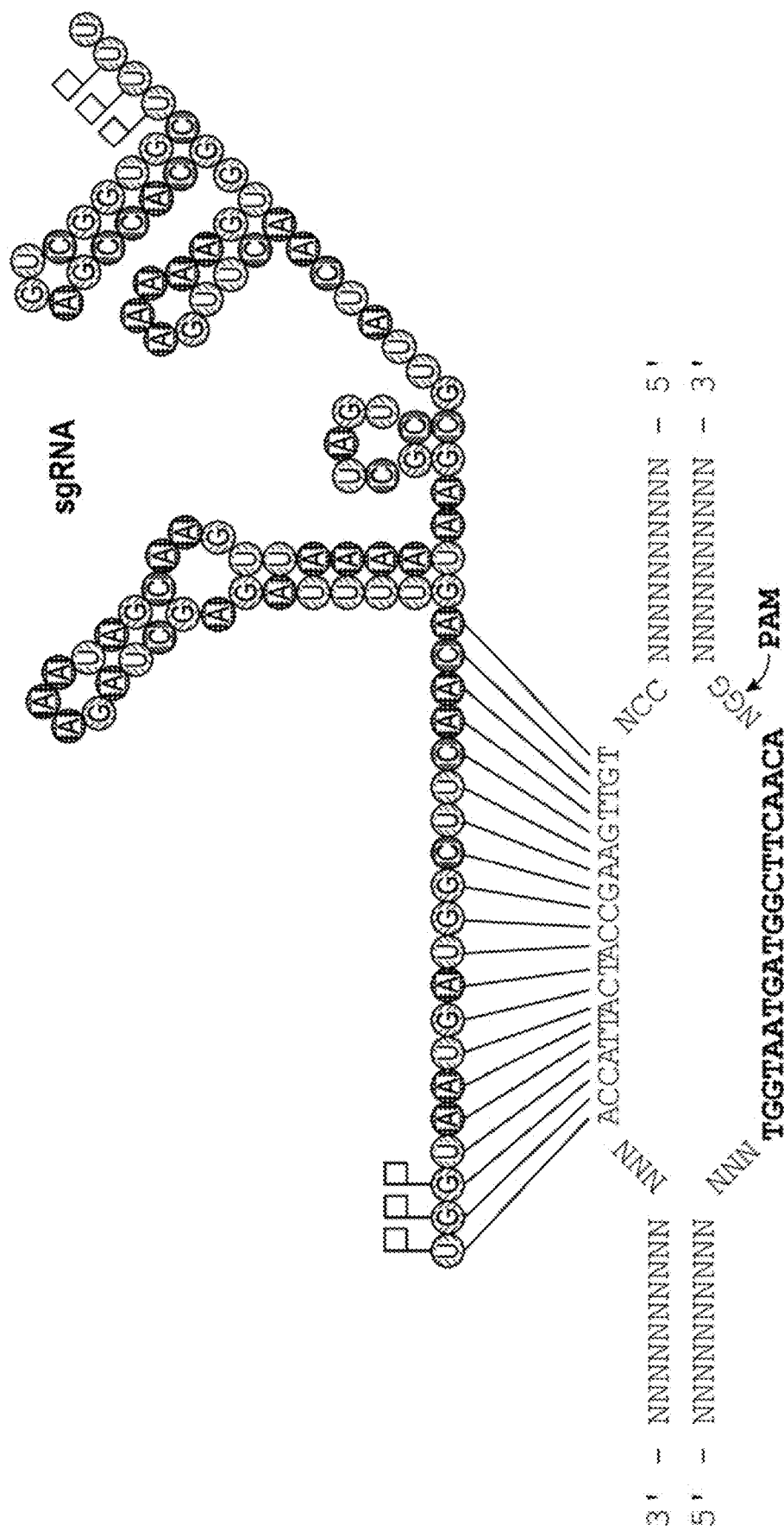
FIG. 1 is an illustration of an exemplary CRISPR-Cas system. A complex is formed by a single-guide RNA and a Cas protein, and the complex recognizes and binds a target polynucleotide. The Cas nuclease is the *S. pyrogenes* Cas9 nuclease. The *S. pyrogenes* Cas9 nuclease recognizes a PAM sequence (here, the PAM sequence is a 3-nucleotide sequence of NGG, where N is A, G, C or T, but other PAM sequences are known to exist, such as NAG and others). The sgRNA includes a guide sequence, a crRNA sequence or segment, and tracrRNA sequence or segment. The guide sequence of the sgRNA hybridizes with the DNA target directly upstream of the PAM sequence.

This invention is based, at least in part, on an unexpected discovery that certain chemical modifications to gRNAs are tolerated by the CRISPR-Cas system and decrease the off-target effects of Cas:gRNA complexation without substantially compromising the efficacy of Cas:gRNA binding to, nicking of, and/or cleavage of the target polynucleotide.

This invention provides synthetic guide RNAs comprising at least one specificity-enhancing modification. In certain embodiments, the at least one specificity-enhancing modification weakens or strengthens the association of at least one nucleotide pair between the synthetic guide RNA and the target polynucleotide and/or weakens the association of at least one nucleotide pair between the synthetic guide RNA and at least one off-target polynucleotide such that at least one of the off-target weakenings is greater than the on-target weakening if present. The synthetic guide RNA has gRNA functionality. The specificity-enhancing modification(s) can be located in the guide sequence, for example, in the locking region, sampling region, and/or seed region. In certain embodiments, the specificity-enhancing modification(s) lowers melting temperatures of duplexes formed by the gRNA and a target polynucleotide sequence and off-target polynucleotide sequence(s), or raises melting temperature of the gRNA/target duplex and lowers melting temperature of at least one gRNA/off-target duplex. This invention also provides gRNA:Cas protein complex comprising these synthetic guide RNAs, methods for cleaving, nicking or binding target polynucleotides using the synthetic guide RNAs, and sets, libraries, kits and arrays comprising the synthetic guide RNAs. This invention also provides method of preparing synthetic guide RNAs.

I. Definitions

As used herein, the term "guide RNA" generally refers to an RNA molecule (or a group of RNA molecules collectively) that can bind to a Cas protein and aid in targeting the Cas protein to a specific location within a target polynucleotide (e.g., a DNA or an mRNA molecule). A guide RNA can comprise a crRNA segment and a tracrRNA segment. As used herein, the term "crRNA" or "crRNA segment" refers to an RNA molecule or portion thereof that includes a polynucleotide-targeting guide sequence, a stem sequence (for additional clarity: the stem sequence encompasses a stem-forming sequence which, in a single guide RNA, forms a stem with a corresponding part of tracrRNA), and, optionally, a 5'-overhang sequence. As used herein, the term "tracrRNA" or "tracrRNA segment" refers to an RNA molecule or portion thereof that includes a protein-binding segment (e.g., the protein-binding segment is capable of interacting with a CRISPR-associated protein, such as a Cas9). The tracrRNA also includes a segment that hybridizes partially or completely to the crRNA. The term "guide RNA" encompasses a single-guide RNA (sgRNA), where the crRNA segment and the tracrRNA segment are located in the same RNA molecule or strand. The term "guide RNA" also encompasses, collectively, a group of two or more RNA molecules, where the crRNA segment and the tracrRNA segment are located in separate RNA molecules. The term "guide RNA" also encompasses an RNA molecule or suitable group of molecular segments that binds a Cas protein other than Cas9 (e.g., Cpf1 protein) and that possesses a guide sequence within the single or segmented strand of RNA comprising the functions of a guide RNA which include Cas protein binding to form a gRNA:Cas protein complex capable of binding, nicking and/or cleaving a complementary sequence (or "target sequence") in a target polynucleotide.

The term "guide sequence" refers to a contiguous sequence of nucleotides in a guide RNA which has partial or complete complementarity to a target sequence in a target polynucleotide and can hybridize to the target sequence by base pairing facilitated by a Cas protein. As illustrated in the example shown in FIG. 1, a target sequence is adjacent to a PAM site (the PAM sequence, and its complementary sequence on the other strand, together constitute a PAM site). Immediately upstream of the PAM sequence (NGG for cas9) is a sequence (bolded, bottom strand in FIG. 1) complementary to the target sequence. The target sequence, which hybridizes to the guide sequence, is immediately downstream from the complement (CCN for cas9) of the PAM sequence. Nucleotide 1 of the guide sequence (first nucleotide at the 5') is complementary to the last nucleotide of the target sequence, while the last nucleotide of the guide sequence (nucleotide 20 of the guide sequence in FIG. 1) is complementary to the first nucleotide of the target sequence, which is next to the PAM site (and immediately downstream from the complement of the PAM sequence). In other examples such as Cpf1, the location of the target sequence, which hybridizes to the guide sequence, may be upstream from the complement of the PAM sequence.

A guide sequence can be as short as about 10 nucleotides and as long as about 30 nucleotides. Typical guide sequences are 15, 16, 17, 18, 19, 20, 21, 22, 23 and 24 nucleotides long. Synthetic guide sequences are usually 20 nucleotides long, but can be longer or shorter. When a guide sequence is shorter than 20 nucleotides, it is typically a deletion from the 5'-end compared to a 20-nucleotide guide sequence. By way of example, a guide sequence may consist of 20 nucleotides complementary to a target sequence. In other words, the guide sequence is identical to the 20 nucleotides upstream of the PAM sequence, except the A/U difference between DNA and RNA. If this guide sequence is truncated by 3 nucleotides from the 5'-end, nucleotide 4 of the 20-nucleotide guide sequence now becomes nucleotide 1 in the 17-mer, nucleotide 5 of the 20-nucleotide guide sequence now becomes nucleotide 2 in the 17-mer, etc. The new position is the original position minus 3. Similarly, a guide sequence may hybridize to more than 20 nucleotides at the target site, and the additional nucleotides are located at the 5'-end of the guide sequence, because the 3'-end of the guide sequence is complementary to the target next to the PAM site. Again by way of example, in a 22-nucleotide guide sequence, the original nucleotide 1 in the 20-mer now becomes nucleotide 3, the original nucleotide 2 in the 20-mer becomes nucleotide 4, etc. The new position is the original position plus 2, or minus (−2). Thus, a guide sequence consists of nucleotides 1 through "20 minus N" (20-N) counting from the 5'-end, wherein N is a positive or negative integer between −10 and 10 (optionally between −10 and 6). A given nucleotide position within the guide sequence will be noted as "Position Number Minus N" (number-N). For example, the nucleotide at position 5 will be noted as "5-N" (5 minus N), to indicate the shift of position 5 from the reference position obtained from a 20 nucleotides guide sequence that occurs when the guide sequence is truncated or extended by N nucleotides at the 5'-end. Nucleotide positions are positive integers. Thus, any (Number-N) position that is negative or zero is moot, and should be ignored. A guide sequence can be positioned anywhere within the strand or strands that constitute a gRNA. Typical guide sequences are located at or near the 5' end or the 3' end of a gRNA strand.

The term "scaffold" refers to the portions of guide RNA molecules comprising sequences which are substantially identical or are highly conserved across natural biological species. Scaffolds include the tracrRNA segment and the portion of the crRNA segment other than the polynucleotide-targeting guide sequence (repeat portion) at or near the 3' end of the crRNA segment.

The term "nucleic acid", "polynucleotide" or "oligonucleotide" refer to a DNA molecule, an RNA molecule, or analogs thereof. As used herein, the terms "nucleic acid", "polynucleotide" and "oligonucleotide" include, but are not limited to DNA molecules such as cDNA, genomic DNA, plasmid or vector DNA or synthetic DNA and RNA molecules such as a guide RNA, messenger RNA or synthetic RNA. Moreover, as used herein, the terms "nucleic acid" and "polynucleotide" include single-stranded and double-stranded forms. A standard convention in the art is that oligonucleotides, polynucleotides, RNA molecules, distinct strands of DNA molecules, and various nucleic acids comprising 2 or more nucleotides are generally numbered from their 5' ends, and this convention is used throughout, including instances of 5' extensions or "overhangs" covalently linked to such molecules.

As used herein, "modification" or "chemical modification" refers to a chemical moiety, or portion of a chemical structure, which differs from that found in the four most common natural ribonucleotides: adenosine, guanosine, cytidine, and uridine ribonucleotides. Thus the term "modification" refers to a molecular change in, or on, the most common natural molecular structure of adenosine, guanosine, cytidine, or uridine ribonucleotide. The term "modification" may refer to a change in or on a nucleobase, in or on a sugar, and/or in an internucleotide phosphodiester linkage. The term "modification" may refer to a chemical structural change in a ribonucleotide that occurs in nature such as a chemical modification that occurs in natural transfer RNAs (tRNAs), for example but not limited to 2'-O-Methyl, 1-Methyladenosine, 2-Methyladenosine, I-Methylguanosine, 7-Methylguanosine, 2-Thiocytosine, 5-Methylcytosine, 5-Formylcytosine, Pseudouridine, Dihydrouridine, Ribothymidine, or the like. The term "modification" may refer to a chemical modification that is not typically found in nature, for example but not limited to 2'-Fluoro, 2'-O-Methoxyethyl, 2'-O-Phenyl, or the like. The term "same modification" refers to the same type of chemical modification in or on a sugar, or in an internucleotide linkage; for example, a 2'-O-Methyl may be attached to the 2' position of an adenosine, guanosine, cytidine, and/or uridine ribonucleotide, and such modifications may be referred to as the same type of modification or the "same modification." Conversely, modifications to nucleobases would only be identified as the "same modification" if the modified nucleobases were composed of the same molecular structure. To illustrate the distinction by example, 1-Methylguanosine and 7-Methylguanosine both have a methyl group modification of the most common natural guanosine but they are not the "same modification" because the modified nucleobases have different molecular structures. In further examples, a strand of RNA may comprise three modified nucleotides, for example a guanosine and two cytidines, each modified by 2'-O-Methyl-3'-Phosphonoacetate, and such nucleotides may accurately be described as modified in an identical manner or modified with the same modification. Conversely, a different strand of RNA may comprise a 5-Methylcytidine as well as a cytidine that lacks a 5-methyl substituent, and both cytidine nucleotides may be modified by 2'-O-Methyl-3'-Phosphonoacetate, nonetheless these two cytidine nucleotides comprise different modifications and would not be referred to as modified in an identical manner.

The term "modification" in the context of an oligonucleotide or polynucleotide includes but is not limited to (a) end modifications, e.g., 5' end modifications or 3' end modifications, (b) nucleobase (or "base") modifications, including replacement or removal of bases, (c) sugar modifications, including modifications at the 2', 3', and/or 4' positions, and (d) backbone modifications, including modification or replacement of the phosphodiester linkages. The term "modified nucleotide" generally refers to a nucleotide having a modification to the chemical structure of one or more of the base, the sugar, and the phosphodiester linkage or backbone portions, including nucleotide phosphates. Chemical modifications to guide RNA are disclosed in U.S. patent application Ser. No. 14/757,204, filed Dec. 3, 2015, the entire contents of which are incorporated by reference herein.

The terms "xA", "xG", "xC", "xT", "xU", or "x(A,G,C,T,U)" and "yA", "yG", "yC", "yT", "yU", or "y(A,G,C,T,U)" refer to nucleotides, nucleobases, or nucleobase analogs as described by Krueger et al., "Synthesis and Properties of Size-Expanded DNAs: Toward Designed, Functional Genetic Systems", (2007) *Acc. Chem. Res.* 40, 141-50, the contents of which is hereby incorporated by reference in its entirety.

The term "Unstructured Nucleic Acid" or "UNA" refers to nucleotides, nucleobases, or nucleobase analogs as described in U.S. Pat. No. 7,371,580, the contents of which is hereby incorporated by reference in its entirety. An unstructured nucleic acid, or UNA, modification is also referred to as a "pseudo-complementary" nucleotide, nucleobase or nucleobase analog (see e.g., Lahoud et al. (1991) *Nucl. Acids Res.* 36:10, 3409-19).

The terms "PACE" and "thioPACE" refer to internucleotide phosphodiester linkage analogs containing phosphonoacetate or thiophosphonoacetate groups, respectively. These modifications belong to a broad class of compounds comprising phosphonocarboxylate moiety, phosphonocarboxylate ester moiety, thiophosphonocarboxylate moiety and thiophosphonocarboxylate ester moiety. These linkages can be described respectively by the general formulae $P(CR^1R^2)_n COOR$ and $(S)-P(CR^1R^2)_n COOR$ wherein n is an integer from 0 to 6 and each of $R^1$ and $R^2$ is independently selected from the group consisting of H, an alkyl and substituted alkyl. Some of these modifications are described by Yamada, Dellinger, et al., "Synthesis and Biochemical Evaluation of Phosphonoformate Oligodeoxyribonucleotides" (2006) *J. Am. Chem. Soc.* 128:15, 5251-61, the contents of which is hereby incorporated by reference in its entirety.

In some places of the present disclosure, particularly in figures disclosing structures and sequences of synthetic guide RNAs and experimental results with such synthetic guide RNAs certain abbreviations are used to indicate certain modifications. "M" is used herein to indicate a 2'-O-methyl modification; "S" is used herein to indicate a 3'-phosphorothioate internucleotide linkage modification; "P" is used herein to indicate a 3'-phosphonoacetate (or PACE) internucleotide linkage modification; "MS" is used herein to indicate a 2'-O-methyl-3'-phosphorothioate internucleotide linkage modification; "MP" is used herein to indicate an 2'-O-methyl-3'-phosphonoacetate (or 2'-O-methyl-3'-PACE) internucleotide linkage modification; and "MSP" is used herein to indicate a 2'-O-methyl-3'-thiophosphonoacetate internucleotide linkage modification.

"Sugar pucker" refers to a sugar ring that is non-planar due to steric forces causing one or two atoms of a 5-membered sugar ring to be out of plane. In ribofuranose, the plane C1'-O4'-C4' is fixed. Endo-pucker means that C2' or C3' are turned out of this plane into the direction of O5'. Exo-pucker describes a shift in the opposite direction. C2'-endo and C3'-endo are naturally in equilibrium, but chemical modification can drive the sugar to a preferred pucker. In RNA C3'-endo conformation is predominant. DNA may adjust and is able to take on both conformations.

The term "seed region" refers to the region of the guide sequence that is complementary to a target nucleic acid sequence which initiates hybridization of the guide sequence to the target nucleic acid sequence. In some cases, the seed region forms a quasi-stable duplex that is aided by a protein, peptide, or protein complex. In general, the term seed region in a guide sequence of a gRNA consists of nucleotides 11 through 20 in a 20-nucleotide guide sequence, counted from the 5' end of the guide sequence, but the region can run shorter or longer depending on the nucleotide sequence and on chemical modifications on the RNA nucleotides in this region or through modification of the associated peptides, proteins or protein complexes.

The term "sampling region" refers to the region adjacent to the seed region, and the binding of these nucleotides proceeds until the binding energy of the duplex is equivalent to the temperature at which the binding is occurring. In general, the term sampling region in a gRNA consists of nucleotides 5 through 10 in a 20-nucleotide guide sequence, counted from the 5' end of the guide sequence, unless otherwise indicated, as may be the case when one or more modifications functionally extend the sampling region, thereby encompassing nucleotides 1 through 10, alternatively 2 through 10, alternatively 3 through 10, alternatively 4 through 10, alternatively 1 through 11, alternatively 2 through 11, alternatively 3 through 11, alternatively 4 through 11, alternatively 5 through 11, alternatively 1 through 12, alternatively 2 through 12, alternatively 3 through 12, in the guide sequence.

The term "locking region" refers to the region adjacent to the sampling region in which the binding energy of the duplex formed is above the temperature at which the binding is occurring. In general, the term locking region in a gRNA consists of nucleotides 1 through 4 in a 20-nucleotide guide sequence, counted from the 5' end of the guide sequence, unless otherwise indicated, as may be the case when one or more modifications functionally shorten the locking region to nucleotide 1, alternatively nucleotides 1 through 2, alternatively nucleotides 1 through 3, at the 5' end of a guide sequence. The locking region can extend beyond the 20-nucleotide length of typical guide sequences of CRISPR-Cas9 systems if one or more nucleotides are covalently linked to the 5' end to extend the guide sequence from the typical 20 nucleotides to 21 nucleotides, alternatively to 22 nucleotides, alternatively to 23 nucleotides, alternatively to 24 nucleotides, alternatively to 25 nucleotides or more.

As used herein, the term "target polynucleotide" or "target" refers to a polynucleotide containing a target nucleic acid sequence. A target polynucleotide may be single-stranded or double-stranded, and, in certain embodiments, is double-stranded DNA. In certain embodiments, the target polynucleotide is single-stranded RNA. A "target nucleic acid sequence" or "target sequence," as used herein, means a specific sequence or the complement thereof that one wishes to bind to, nick, or cleave using a CRISPR system.

In certain embodiments, two or more target sequences may be selected to be bound, nicked or cleaved in the same reaction, for example to replace the sequence between two particular target sequences for homologous recombination purposes. Alternatively, two or more target sequences are also useful when multiple targets are to be bound and enriched at the same time. Thus, where two mor more target sequences are used, the respective target polynucleotides may or may not be in the same gene, depending on the purpose.

An "off-target polynucleotide" or "off-target" refers to a polynucleotide containing a partially homologous acid sequence to the intended target nucleic acid. An off-target polynucleotide may be single-stranded or double-stranded, and, in certain embodiments, is double-stranded DNA. An "off-target nucleic acid sequence" or "off-target sequence," as used herein, means a specific sequence or the complement thereof that one does not wish to bind to, nick, or cleave using a CRISPR system and that has substantial sequence identity with, but is not identical to, a target nucleic acid sequence. For example, an off-target nucleic acid sequence has substantial sequence identity with a target nucleic acid sequence when it has at least about 60%, at least about 75%, at least about 85%, at least about 90%, at least about 90-95%, at least about 97%, or more nucleotide (or amino acid) sequence identity.

The terms "HBB polynucleotide, "VEGFA polynucleotide," "IL2RG polynucleotide," "CLTA1 "polynucleotide," and "CLTA4 polynucleotide" refer to any polynucleotide that comprises at least a portion of the genes HBB, VEGFA, IL2RG, CLTA1 or CLTA4, respectively. Such polynucleotides include naturally occurring, recombinant, or synthetic polynucleotides. Such polynucleotides may include polynucleotide sequences found at the locus in the genome associated with such genes, and accordingly encompasses alleles and variants of such genes.

The term "specificity" refers to how well a guide RNA is able to distinguish between ON target polynucleotides and one or more OFF target polynucleotides. The specificity of a guide RNA can be determined by, for example, calculating an ON target cleaving, binding, or nicking percentage as well as an OFF target cleaving, binding, or nicking percentage; calculating an ON:OFF ratio; and/or a specificity score derived from comparable ON and OFF target percentages (see Examples of this disclosure). The term "ON target percentage" refers to the percentage of cleaving, nicking or binding of a target polynucleotide within an assay; by way of example, a guide RNA having a 90% ON target percentage if it leads to the cleavage, nicking or binding of 90% of the target polynucleotides present in an assay. The term "ON:OFF ratio" refers to the ratio of ON target percentage and OFF target percentage per guide RNA assayed; by way of example, a guide RNA having a 80% ON target percentage and a 8% OFF target percentage has an ON:OFF ratio of 10. The term "specificity score" refers to a number obtained by multiplying an ON:OFF ratio by its respective ON-target percentage per guide RNA assayed; by way of example, a guide RNA having a 80% ON target percentage and a 8% OFF target percentage yields an ON:OFF ratio of 10 and has a specificity score of 8. In some assays, binding or nicking is assessed using cleaving as a surrogate; for example, in an assay where indel formation at a target site is quantified by sequencing to assess cleavage, such assay can be used to assess binding or nicking activity of the gRNA as well.

The term "consecutive specificity-enhancing modifications" refers to two or more specificity-enhancing modifications in a guide RNA that are adjacent to each other. The guide RNA may comprise 1, 2, 3, 4, 5, 6, 7, 8, 9, 10, 11, 12, 13, 14, 15, 16, 17, 18, 19, 20, 21, 22, 23 or 24 consecutive specificity-enhancing modifications. In widely used CRISPR-Cas9 systems, the guide RNA comprises a guide sequence comprising nucleotides 1 through 20, counted from the 5' end of the guide sequence. The one or more consecutive specificity-enhancing modifications may comprise modification at, for example, nucleotides 1 and 2, nucleotides 1 through 3, nucleotides 1 through 4, nucleotides 1 through 5, nucleotides 1 through 6, nucleotides 1 through 7, nucleotides 1 through 8, nucleotides 1 through 9, nucleotides 1 through 10, nucleotides 2 and 3, nucleotides 2 through 4, nucleotides 2 through 5, nucleotides 2 through 6, nucleotides 2 through 7, nucleotides 2 through 8, nucleotides 2 through 9, nucleotides 2 through 10, nucleotides 3 and 4, nucleotides 3 through 5, nucleotides 3 through 6, nucleotides 3 through 7, nucleotides 3 through 8, nucleotides 3 through 9, nucleotides 3 through 10, and so on.

The term "hybridization" or "hybridizing" refers to a process where completely or partially complementary polynucleotide strands come together under suitable hybridization conditions to form a double-stranded structure or region in which the two constituent strands are joined by hydrogen bonds. As used herein, the term "partial hybridization" includes where the double-stranded structure or region contains one or more bulges or mismatches. Although hydrogen bonds typically form between adenine and thymine or adenine and uracil (A and T or A and U) or cytosine and guanine (C and G), other noncanonical base pairs may form (see, e.g., Adams et al., "The Biochemistry of the Nucleic Acids," 11th ed., 1992). It is contemplated that modified nucleotides may form hydrogen bonds that allow or promote hybridization in a non-cannonical way.

The term "cleavage" or "cleaving" refers to breaking of the covalent phosphodiester linkage in the phosphodiester backbone of a polynucleotide. The terms "cleavage" or "cleaving" encompass both single-stranded breaks and double-stranded breaks. Double-stranded cleavage can occur as a result of two distinct single-stranded cleavage events. Cleavage can result in the production of either blunt ends or staggered ends.

The term "CRISPR-associated protein" or "Cas protein" refers to a wild type Cas protein, a fragment thereof, or a mutant or variant thereof. The term "Cas mutant" or "Cas variant" refers to a protein or polypeptide derivative of a wild type Cas protein, e.g., a protein having one or more point mutations, insertions, deletions, truncations, a fusion protein, or a combination thereof. In certain embodiments, the "Cas mutant" or "Cas variant" substantially retains the nuclease activity of the Cas protein. In certain embodiments, the "Cas mutant" or "Cas variant" is mutated such that one or both nuclease domains are inactive. In certain embodiments, the "Cas mutant" or "Cas variant" has nuclease activity. In certain embodiments, the "Cas mutant" or "Cas variant" lacks some or all of the nuclease activity of its wild-type counterpart. The term "CRISPR-associated protein" or "Cas protein" also includes a wild type Cpf1 protein of various species of prokaryotes (and named for Clustered Regularly Interspaced Short Palindromic Repeats from *Prevotella* and *Francisella* 1 ribonucleoproteins or CRISPR/Cpf1 ribonucleoproteins), a fragment thereof, or a mutant or variant thereof.

The term "nuclease domain" of a Cas protein refers to the polypeptide sequence or domain within the protein which possesses the catalytic activity for DNA cleavage. Cas9 typically catalyzes a double-stranded break upstream of the PAM sequence. A nuclease domain can be contained in a single polypeptide chain, or cleavage activity can result from the association of two (or more) polypeptides. A single nuclease domain may consist of more than one isolated stretch of amino acids within a given polypeptide. Examples of these domains include RuvC-like motifs (amino acids 7-22, 759-766 and 982-989 in SEQ ID NO: 1) and HNH motif (amino acids 837-863); see Gasiunas et al. (2012) *Proc. Natl. Acad. Sci. USA* 109:39, E2579-E2586 and WO2013176772.

A synthetic guide RNA that has "gRNA functionality" is one that has one or more of the functions of naturally occurring guide RNA, such as associating with a Cas protein, or a function performed by the guide RNA in association with a Cas protein. In certain embodiments, the functionality includes binding a target polynucleotide. In certain embodiments, the functionality includes targeting a Cas protein or a gRNA:Cas protein complex to a target polynucleotide. In certain embodiments, the functionality includes nicking a target polynucleotide. In certain embodiments, the functionality includes cleaving a target polynucleotide. In certain embodiments, the functionality includes associating with or binding to a Cas protein. For example, the Cas protein may be engineered to be a "dead" Cas protein (dCas) fused to one or more proteins or portions thereof, such as a transcription factor enhancer or repressor a deaminase protein etc., such that the one or more functions is/are performed by the fused protein(s) or portion(s) thereof. In certain embodiments, the functionality is any other known function of a guide RNA in a CRISPR-Cas system with a Cas protein, including an artificial CRISPR-Cas system with an engineered Cas protein. In certain embodiments, the functionality is any other function of natural guide RNA. The synthetic guide RNA may have gRNA functionality to a greater or lesser extent than a naturally occurring guide RNA. In certain embodiments, a synthetic guide RNA may have greater functionality as to one property and lesser functionality as to another property in comparison to a similar naturally occurring guide RNA.

A Cas protein having a single-strand "nicking" activity refers to a Cas protein, including a Cas mutant or Cas variant, that has reduced ability to cleave one of two strands of a dsDNA as compared to a wild type Cas protein. For example, in certain embodiments, a Cas protein having a single-strand nicking activity has a mutation (e.g., amino acid substitution) that reduces the function of the RuvC domain (or the HNH domain) and as a result reduces the ability to cleave one strand of the target DNA. Examples of such variants include the D10A, H839A/H840A, and/or N863A substitutions in *S. pyogenes* Cas9, and also include the same or similar substitutions at equivalent sites in Cas9 enzymes of other species.

A Cas protein having "binding" activity or that "binds" a target polynucleotide refers to a Cas protein which forms a complex with a guide RNA and, when in such a complex, the guide RNA hybridizes with another polynucleotide, such as a target polynucleotide sequence, via hydrogen bonding between the bases of the guide RNA and the other polynucleotide to form base pairs. The hydrogen bonding may occur by Watson Crick base pairing or in any other sequence specific manner. The hybrid may comprise two strands forming a duplex, three or more strands forming a multi-stranded triplex, or any combination of these.

A "CRISPR function" means any function or effect that can be achieved by a CRISPR system, including but not limited to gene editing, DNA cleavage, DNA nicking, DNA binding, regulation of gene expression, CRISPR activation (CRISPRa), CRISPR interference (CRISPRi), and any other function that can be achieved by linking a cas protein to another effector, thereby achieving the effector function on a target sequence recognized by the cas protein. For example, a nuclease-free cas protein can be fused to a transcription factor, a deaminase, a methylase, etc. The resulting fusion protein, in the presence of a guide RNA for the target, can be used to regulate the transcription of, deaminate, or methylate, the target.

As used herein, the term "portion" or "fragment" of a sequence refers to any portion of the sequence (e.g., a nucleotide subsequence or an amino acid subsequence) that is smaller than the complete sequence. Portions of polynucleotides can be any length, for example, at least 5, 10, 15, 20, 25, 30, 40, 50, 75, 100, 150, 200, 300 or 500 or more nucleotides in length. A portion of a guide sequence can be about 50%, 40%, 30%, 20%, 10% of the guide sequence, e.g., one-third of the guide sequence or shorter, e.g., 7, 6, 5, 4, 3, or 2 nucleotides in length.

The term "derived from" in the context of a molecule refers to a molecule isolated or made using a parent molecule or information from that parent molecule. For example, a Cas9 single-mutant nickase and a Cas9 double-mutant null-nuclease (also known as deactivated Cas9, "dead Cas9", or dCas9) are derived from a wild-type Cas9 protein.

The term "substantially identical" in the context of two or more polynucleotides (or two or more polypeptides) refers to sequences or subsequences that have at least about 60%, at least about 70%, at least about 80%, at least about 90%, about 90-95%, at least about 95%, at least about 98%, at least about 99% or more nucleotide (or amino acid) sequence identity, when compared and aligned for maximum correspondence using a sequence comparison algorithm or by visual inspection. Preferably, the "substantial identity" between polynucleotides exists over a region of the polynucleotide at least about 20 nucleotides in length, at least about 50 nucleotides in length, at least about 100 nucleotides in length, at least about 200 nucleotides in length, at least about 300 nucleotides in length, at least about 500 nucleotides in length, or over the entire length of the polynucleotide. Preferably, the "substantial identity" between polypeptides exists over a region of the polypeptide at least about 50 amino acid residues in length, at least about 100 amino acid residues in length, or over the entire length of the polypeptide.

As disclosed herein, a number of ranges of values are provided. It is understood that each intervening value, to the tenth of the unit of the lower limit, between the upper and lower limits of that range is also specifically contemplated. Each smaller range or intervening value encompassed by a stated range is also specifically contemplated. The term "about" generally refers to plus or minus 10% of the indicated number. For example, "about 10%" may indicate a range of 9% to 11%, and "about 20" may mean from 18-22. Other meanings of "about" may be apparent from the context, such as rounding off, so, for example "about 1" may also mean from 0.5 to 1.4.

II. CRISPR-Mediated Sequence-Specific Binding and/or Cleavage or Nicking

Shown in FIG. 1 is a diagram of CRISPR-Cas9-mediated sequence-specific cleavage of DNA. The guide RNA is depicted as sgRNA with an exemplary 20-nucleotide (or 20-nt; nucleotide is often abbreviated as "nt") guide sequence (other guide sequences may be, for example, from about 15 to about 30 nts in length) within the 5' domain, an internally positioned base-paired stem, and a 3' domain. The guide sequence is complementary to an exemplary 20-nt target sequence in a DNA target. The stem corresponds to a repeat sequence in crRNA and is complementary to a sequence in the tracrRNA. The 3' domain of the guide RNA corresponds to the 3' domain of the tracrRNA that binds a Cas9 nuclease. The Cas9:gRNA complex binds and cleaves a target DNA sequence or protospacer directly upstream of a PAM sequence recognized by Cas9. In FIG. 1, a 3-nt PAM sequence is exemplified; however, other PAM sequences including 4-nt, 5-nt and even longer PAM sequences are known.

Guide RNAs, for CRISPR-Cas genome editing, function in RNA-protein complexes where the RNA acts both as a scaffold for the protein and as sequence recognition for the duplex DNA target. The complex recognizes genomic DNA through first scanning for the nucleotide PAM sequence. Once a PAM sequence is identified the RNA-protein complex attempts to form an RNA/DNA duplex between the genomic DNA target and the guide sequence of the guide RNA. This duplex is first initiated by a Cas protein-mediated base pairing of the "seed region" of the gRNA, in which the seed region is thought to be around ten nucleotides in length. After the binding of the seed region, a stable RNA/DNA duplex is formed by the hybridization of the remaining nucleotides on the 5' end of the guide RNA; this typically results in a 20-nucleotide DNA/RNA duplex and proceeds to a double-stranded cleavage of the target DNA by the protein complex.

An important aspect to enable the utility of CRISPR-Cas RNA-protein complexes for genome editing is sequence specificity. CRISPR-Cas RNA-protein complexes cleave genomic DNA as a first step in the process to inactivate or modify a gene through repair or recombination. In this process the cleavage of genomic DNA at unintentional "off-target" sites can have unwanted consequences, such as the creation of sequence mutations elsewhere in the genome. Currently, these off-target cleavage events are either being detected by screening techniques, removed by breeding techniques, or ignored. CRISPR-Cas RNA-protein complexes evolved as an adaptive immune system in prokaryotes; an improvement in sequence specificity of these complexes would constitute a significant advance and innovation toward CRISPR-Cas RNA-protein complexes having wide utility as a tool in eukaryotic genomics.

Sequence specificity starts by a gRNA:Cas protein complex being able to scan, detect, and bind to a target site, or string of contiguous nucleotides within the entire genome of an organism. In order to do this the target sequence needs to be long enough that its string or sequence of contiguous nucleotides exists only once in the entire genome of the organism of interest and is located at the site of the desired genome editing. The length of the string of contiguous nucleotides, or polynucleotide, necessary to impart uniqueness within a genome is determined by the "information content" of that particular polynucleotide. For most eukaryotic cells and organisms, the target polynucleotide needs to be in the range of 18 to 22 nucleotides in length to have enough information content to be unique (J. Mol. Biol. (1986), 188, 415-431) in the entire genome. In general, the longer the target polynucleotide the more information content and the more likely its sequence will exist only once in a genome; a 19-nucleotide sequence has more information content than an 18-nucleotide sequence, a 20-nucleotide sequence has more information content than a 19-nucleotide sequence and so on. However, a unique 20-nucleotide sequence could match the sequence of all but 1 nucleotide in a different 20-nt sequence elsewhere in the genome, and the sequence containing a single mismatch comprises an off-target site. The relative binding of a guide sequence to the off-target sequence versus the 20-nucleotide target sequence is controlled by the respective binding energies and kinetic equilibria between the guide sequence and the on-target sequence as well as the off-target sequence.

The differential binding energies of oligonucleotides are controlled and can be maximized by the cooperative effect of DNA and RNA binding. Cooperativity has been defined for DNA and RNA binding during hybridization in two ways. First, when an oligonucleotide begins to bind its individual nucleotide subunits, the binding of nucleotide subunits to complementary nucleobases has a positive effect on the subsequent binding of the next adjacent nucleotide in the oligonucleotide sequence. At the same time the unbinding of an individual nucleotide has a negative effect on the binding of the next adjacent nucleotide. When a mismatch attempts to base pair, the unbinding of that mismatched pair has a negative effect on the binding of the adjacent nucleotide pair and likewise when a matched nucleotide pair binds successfully it has a positive effect on the binding of the adjacent nucleotide pair. From an overall energy perspective when an oligonucleotide begins to bind as individual nucleotide subunits that bind and unbind in multiple incremental steps, the intermediate states are statistically underrepresented relative to a system where the steps occur independently of each other. In other words, there are limited degrees of freedom and a limited number of kinetic states other than bound or unbound. From a molecular perspective the string of nucleotides is somewhat rigid and once a nucleotide binds, the adjacent nucleotide has very limited energetic confirmations it can adopt other than the one that leads to binding. The need for molecular rigidity to retain DNA and RNA cooperative binding was first demonstrated almost 30 years ago by Z. A. Shabarova (1988) Bioorg. Khim. 14:12, 1656-62. DNA oligonucleotides comprising 14 nucleotides in length were constructed from two oligonucleotides, each 7 nucleotides in length, which were covalently connected by 1,3-diaminopropane or 1,3-propanediol linkages by using chemical ligation. The flexible oligonucleotide was bound to a complementary 14-nucleotide DNA oligonucleotide and the binding energy measured. Without the rigidity of the natural DNA backbone the flexible 14-nucleotide DNA single strand bound with a significantly lower binding energy, as if it were two independent 7-nucleotide DNA oligonucleotides lacking cooperativity. The observed phenomenon known as cooperativity allows a higher degree of match verses mismatch distinction than would be seen in a non-cooperative system and is an important component for increasing the specificity of nucleotide sequences. The Cas protein has been shown by crystal structure to pre-order the 10 nucleotides of the seed region into a single-stranded portion of an A-form helix. The preordering of the RNA into an A-form helix limits the number of kinetic states that the guide sequence of the gRNA can adopt, thus increasing the cooperativity of the DNA/RNA hybridization in the seed region.

The overall binding energy of a string of nucleotides to a complementary string of nucleotides is typically defined by the melting temperature (Tm). The melting temperature is the temperature required to dissociate two bound nucleotide strings or strands (i.e., bound by base pairing or hybridization) to the point that they are 50% bound and 50% unbound. The melting temperature is measured by a phenomenon known as hyperchromicity. The UV absorption is increased when the two bound oligonucleotide strands are being separated by heat. Heat denaturation of oligonucleotides causes the double helix structure to unwind to form single-stranded oligonucleotides. When two bound oligonucleotides in solution are heated above their melting temperature, the duplex unwinds to form two single strands that absorb more light than the duplex. When the UV absorbance is graphed as a function of the temperature, a sigmoidal curve is obtained at the point where the duplex begins to dissociate and the center of the sigmoidal curve is defined as the Tm.

Figure 4:
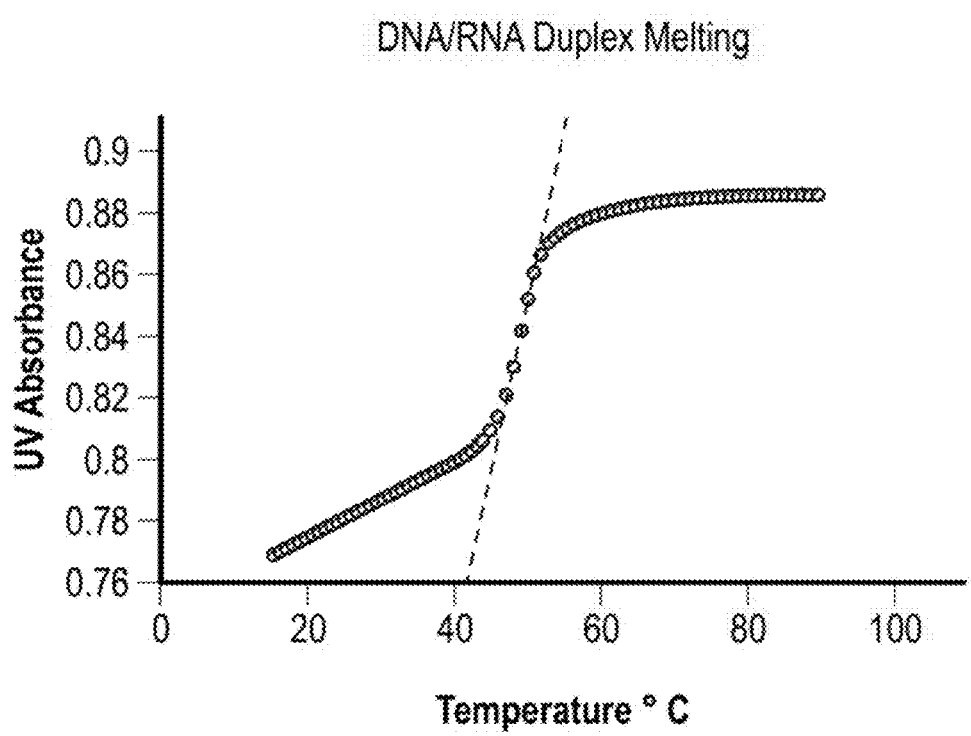
FIG. 4 is a graph demonstrating how ultraviolet light (UV) absorbance increases as an oligonucleotide duplex separates into separate strands by heating. A sigmoidal curve reflects the dissociation of the duplex into separate strands, and the center of the sigmoidal curve is the $T_m$ of the duplex. The curve indicates that the melting temperature of a 20-nucleotide RNA/DNA duplex at physiological salt concentrations is around 50° C.

FIG. 4 is a graph demonstrating how UV absorbance increases as an oligonucleotide duplex separates into separate strands by heating. A sigmoidal curve reflects the dissociate of the duplex into separate strands, and the center of the sigmoidal curve is the $T_m$ of the duplex. This curve indicates that the melting temperature of a 20-nucleotide DNA/RNA duplex at physiological salt concentrations is around 50° C.

An oligonucleotide duplex has the greatest match verses mismatch specificity at the melting temperature where only 50% of the duplex is formed. At this temperature a single mismatch at an off-target polynucleotide will block hybridization of the oligonucleotide if the binding and unbinding of the duplex has a high degree of cooperativity or shows a steep sigmoidal curve. If a gene editing experiment is performed at 37° C., then the best discrimination of match verses mismatch would be obtained using a guide RNA whose binding to its target would have a Tm of 37° C. The issue here is that this aspect is based only on the thermodynamics of single-stranded nucleic acids, and by contrast a guide RNA with a 37° C. Tm would only partially bind to its double-stranded target, thereby giving low overall activity or gene editing. Nonetheless, lowering the overall Tm of the guide RNA to its target incrementally while monitoring activity should increase the specificity. This principle was demonstrated by Yanfang et al. (2014) Nat. Biotechnol. 32, 279-284, by truncating the guide RNA from 20 nucleotides to 17 nucleotides in length; they claimed a 5,000-fold increase in specificity at certain off-target sites without sacrificing on-target genome editing efficiencies. At physiological salt conditions, truncation of an RNA in a RNA/DNA duplex decreases the Tm of that duplex by about 2° C. per base pair. Truncation of the guide sequence in a gRNA to 17 nucleotides would decrease the binding energy by around 6° C. resulting in a duplex Tm of around 42° C. However, when the guide sequence is truncated from 20 nucleotides to 17 nucleotides, significant information content is lost such that it can more readily find an increased number of off-target sites identical or similar to the 17-nt guide sequence across the entire genome. A more useful approach would be to decrease the binding energy of the 20-nucleotide RNA/DNA duplex through chemical modification while retaining cooperativity of binding and unbinding.

Figure 5A:
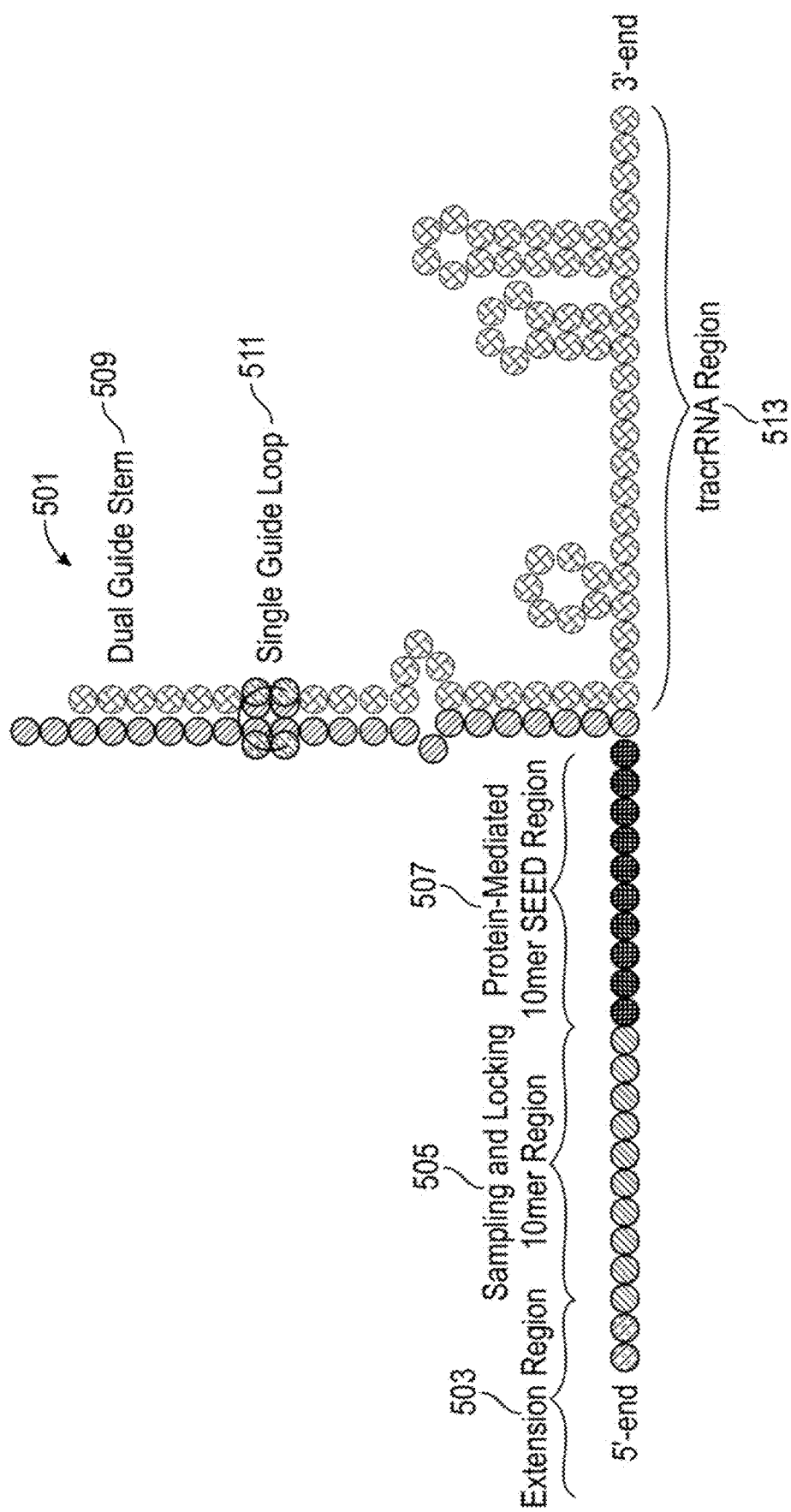
FIG. 5A illustrates a single-guide RNA (sgRNA) or a two-piece dual-guide RNA ("dgRNA") wherein a crRNA segment and a tracrRNA segment form a hybridized duplex and shows the guide RNA's extension region, locking region, sampling region, seed region (typically a 10-mer), a dual-guide stem or a single-guide stem-loop, and a tracrRNA region.

Guide RNAs for CRISPR-Cas genome editing, or for target polynucleotide cleaving or nicking, exist as either single-guide RNAs or two-piece dual-guide RNAs where the two pieces are referred to as the crRNA (clustered repeat RNA) and the tracrRNA (trans-activating clustered repeat RNA). See FIGS. 2A and 2B above. FIG. 5A also illustrates a single-guide RNA or two-piece dual-guide RNA 501 (wherein a crRNA segment and a tracrRNA segment form a hybridized duplex). Moving from left to right (i.e., from the 5' end to the 3' end of the guide RNA), FIG. 5A generally shows an extension 503 (sometimes referred to as an overhang) on the guide RNA, a sampling and locking region 505, a Cas protein-binding seed region 507 (typically a 10-nt portion), a dual-guide stem 509 or a single-guide stem-loop 511, and a tracrRNA region 513. Cas9 protein can bind any or all of these gRNA regions except perhaps 503. The guide sequence comprises the locking, sampling, and seed regions. For both the single-guide RNA and the dual-guide RNA, the guide sequence of about 20 nucleotides on the 5' end of the guide RNA is what binds and forms a stable duplex with the target DNA. This hybridization binding relative to competing hybridization with other sites of similar sequence determines the overall specificity of the gRNA for the target and thus the specificity of genome editing or gene inactivation by a gRNA:Cas protein complex.

The binding of guide RNAs to their target polynucleotides occurs via Cas9-mediated formation of a seed RNA/DNA duplex initiated by the 3' end of the guide sequence. Once the initial seed duplex is formed, the gRNA should continue to hybridize toward its 5' end like a zipper.

Figure 5B:
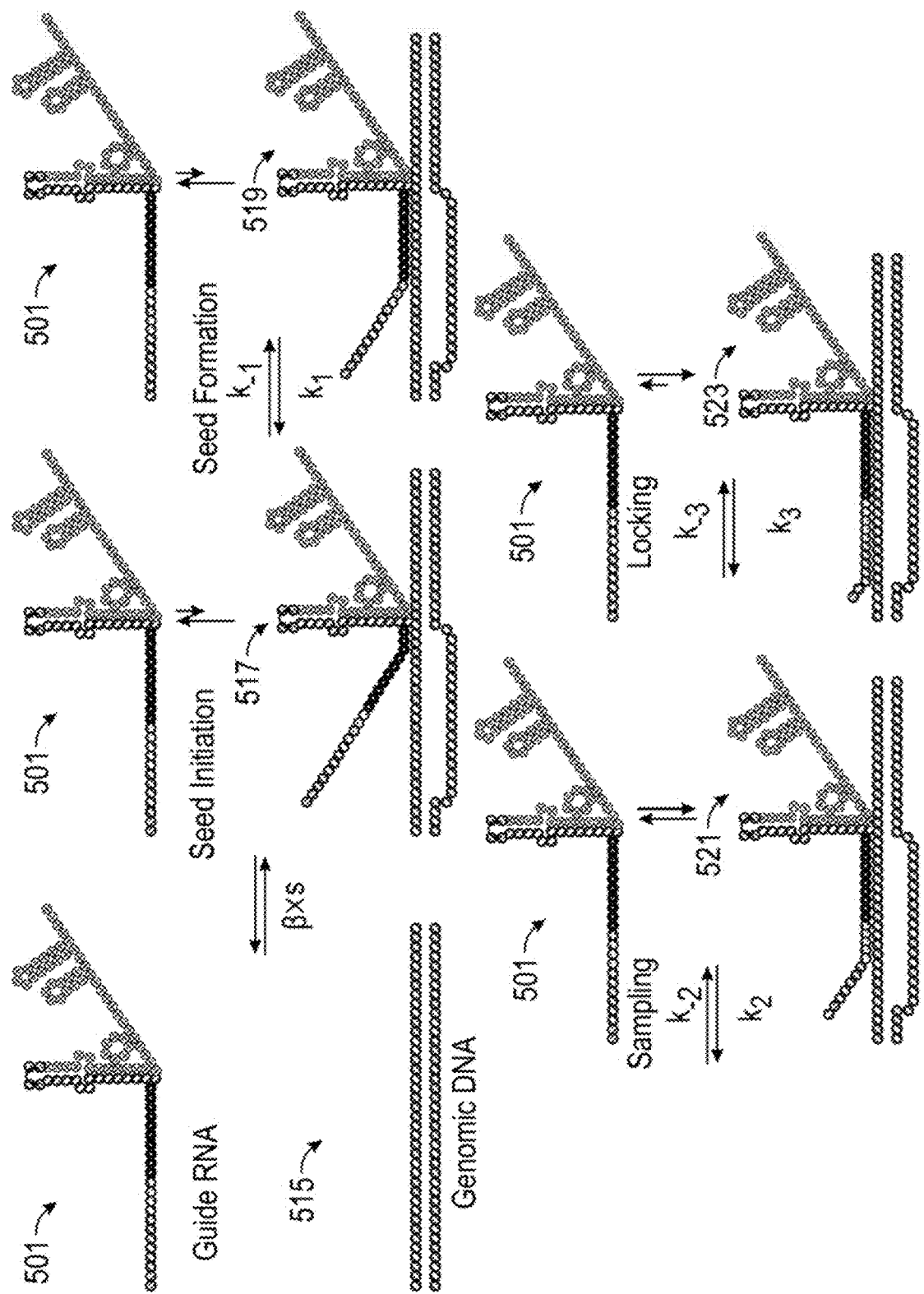
FIG. 5B illustrates how, after the initial formation of a seed duplex between the seed portion of a guide sequence and a complementary DNA sequence, the binding of the nucleotides proceeds sequentially through the sampling region and locking region to form a RNA/DNA duplex having a melting temperature.

FIG. 5B illustrates how, after the initial formation of a seed duplex 517 from gRNA 501 and genomic DNA 515, the binding of the nucleotides proceeds sequentially through the sampling region. The sampling region is the region adjacent to the seed region, and the hybridization binding of these nucleotides proceeds until the point where the binding energy of the duplex is approximately equivalent to the temperature at which the binding is occurring. The rate of binding and unbinding in this region is controlled by the larger equilibrium of the bound versus unbound RNA (e.g., 501 versus 519 or 501 versus 521) which is also controlled by interaction of the Cas9 protein. In the case of guide RNAs forming an RNA/DNA duplex with genomic DNA at physiological salt concentrations and at 37° C., the typical sampling region spans the 5 to 6 nucleotides just 5' of the 10-nucleotide seed region, based on the fact that a 15- to 16-nucleotide RNA/DNA duplex has a Tm of approximately 37° C. Once the number of bound nucleotides surpasses the Tm threshold, the binding continues in a sequential fashion through the locking region to the point where 20 nucleotides of the guide sequence are bound, and the binding may proceed farther if a target-complementary extension or 5' overhang is present on the 5' end of the guide sequence. Once the binding reaches the locking region, the equilibrium between bound RNA versus unbound RNA (e.g., 501 versus 523) changes such that its unbinding or release of a target polynucleotide is negatively impacted by the overall equilibrium of the bound versus unbound RNA which now lies significantly in the direction of the bound or hybridized state. The effect that the larger equilibrium of the bound versus unbound RNA has on specificity was shown by Slaymaker et al. (2016), "Rationally engineered Cas9 nucleases with improved specificity", Science 351, 84-8. Slaymaker et al. reported that a Cas9 protein was engineered that decreased off-target indel formation by converting positively charged amino acids in the nucleic acid-binding groove (or nt groove) of the protein to neutrally charged alanine residues. These changes decrease the overall Cas9-mediated affinity of the guide RNA for the double-stranded target DNA and force the affinity to depend more on the RNA/DNA hybridization including base-pair recognition.

Figure 5C:
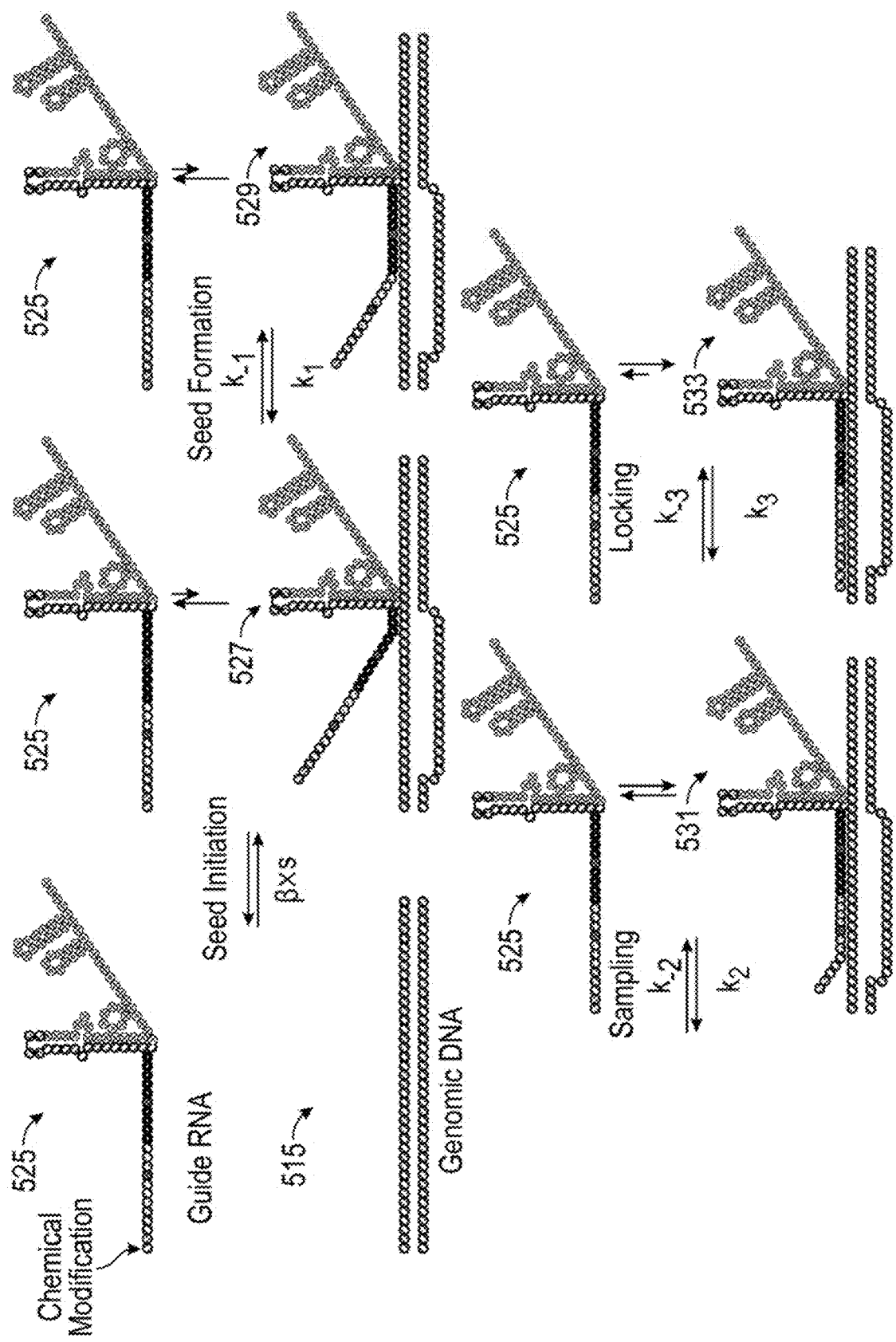
FIG. 5C illustrates that chemical modifications in nucleotides of the seed region can decrease the binding energy of individual base pairs while retaining a high level of cooperativity, thereby extending the sampling region and lowering the melting temperature of the RNA/DNA duplex.

FIG. 5C illustrates how chemical modifications of nucleotides that decrease the binding energy of individual base pairs yet retain a high level of cooperativity can be utilized in the seed and sampling regions of a gRNA 525 to extend the sampling region beyond 5 or 6 nucleotides. This effect can significantly increase the specificity of binding of a guide RNA 525 to genomic DNA 515, as the chemical modifications increase the number of nucleotides required to achieve a hybridization binding energy equivalent to the temperature at which the binding is occurring. In a similar effect, the overall number of nucleotides required to shift the larger equilibrium of the bound versus unbound RNA (525 versus 527, 531, or 533) is increased, and this is calculated to result in an overall increase in sequence specificity.

It was surprising and unexpected to find that nucleotide modifications can be used to decrease the activity of gRNA:Cas protein complexes toward partially complementary off-target polynucleotides through any of three different motifs in the guide sequence portion: the heterocyclic nucleobase, the sugar, and the internucleotide phosphate linkage. In gRNAs having chemical modification(s), it is important that the modification does not significantly increase non-specific binding or significantly decrease the cooperativity of hybridization, as either or both can promote off-target binding, nicking or cleaving by the Cas protein, which is undesirable.

Among the nucleobases in a guide sequence, it is possible to decrease the number of atoms accessible for base pairing and thus decrease the hydrogen-bonding potential that drives hybridization. However, decreasing the hydrogen bonding potential can also increase recognition of off-target polynucleotide sequences through alternative base pairing. To avoid this, it is important to utilize high-specificity base pairing in a guide sequence. An example of modifying the nucleobase to promote high specificity is to install a 2-thio-uridine in place of a uridine in a guide sequence. Uridine nucleotides, which normally bind to adenosine nucleotides by two hydrogen bonds, can alternatively bind to guanosine nucleotides to yield a rather weak base pair often referred to as a G-U wobble pair. If 2-thiouridine is used instead of uridine, the 2-thiouridine can form only a less stable G-U wobble pair if any, because the sulfur substituent on the C2 position of the uracil base cannot serve as a hydrogen bond acceptor.

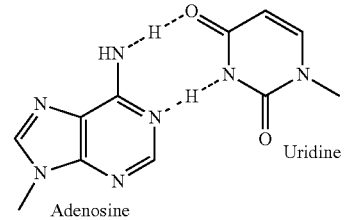

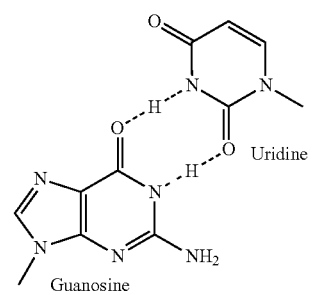

Wobble Base Pair

-continued

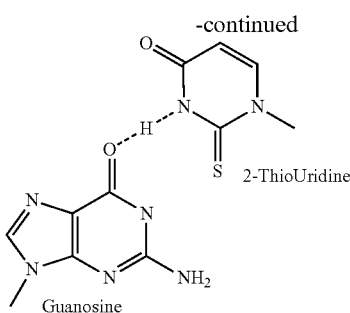

2-ThioUridine

Guanosine

This same strategy can be used to decrease the hydrogen bonding potential of a typical Guanosine/Cytidine base pair by reducing the number of potential hydrogen bonds from three to two, for example by using either 2-thiocytidine or 4-thioguanosine. Their diminished potential for forming hydrogen bonds in modified G-C base pairs is illustrated here.

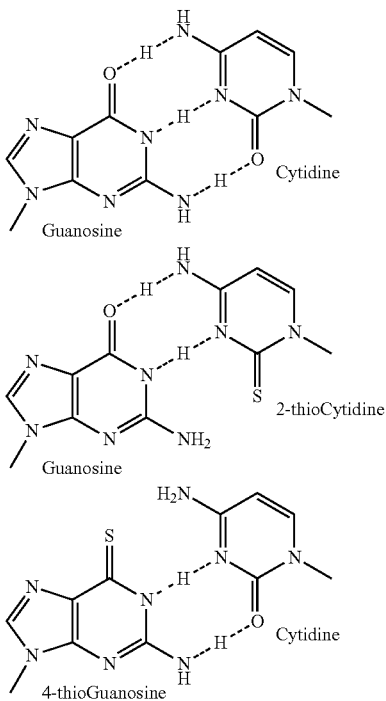

Modifications of the sugar moiety of a ribonucleotide can also be used to decrease the affinity of a guide sequence to a complementary DNA strand. This can be done in two ways, the first is to alter the sugar pucker, and the second is to deform the RNA/DNA duplex by steric crowding. Generally, the sugar pucker is described to be in either one of two states: the 2'-endo (south, DNA-like) sugar pucker, or the 3'-endo (north, RNA-like) sugar pucker. The 2'-endo pucker is thought to have a destabilizing effect on base pairing, and this is thought result from changes in the torsional angle of the glycosidic bond, thus preventing formation of the highest-affinity base-stacking geometry. Examples of modifications to RNA that can result in a 2'-endo conformation are deoxyribose, 2'-deoxy-2'-fluoro-arabinofuranosyl, 2'-deoxy-2'-fluororibofuranosyl, 2'-O-phenyl, 2'-thiophenyl, 2'-S-thiophenyl, 2'-methyl, 2'-ethyl, 2'-propyl, 2'-allyl, 2'-allylphenyl, 2'-methylhydroxy, 2'-methyloxymethyl, 2'-O-carbamate, 2'-O-ethylamino, 2'-O-allylamino, 2'-O-propylamino and 2'-O-substituted phenyl substituents.

Modification of an internucleotide bond can also decrease the binding affinity of nucleotides while maintaining the cooperativity of base pair hybridization. Examples of these are phosphonoacetates, thiophosphonoacetates, phosphonocarboxylates, thiophosphonocarboxylates, phosphonopropionates, phosphonothiopropionates, methylphosphonates, methylphosphonothioates, and boranophosphonates.

In certain embodiments, a sugar modification or nucleobase modification that increases or decreases the binding energy of the overall guide RNA can be added to modulate or further tune the binding energy from incorporation of other modifications to the guide RNA. As an example, incorporation of a 2'-O-methyl-thiophosphonoacetate (MSP) will decrease the binding energy of the guide RNA by ≅1.5 degrees as compared to the unmodified guide RNA. If a 2'-O-methyl nucleotide is incorporated elsewhere in the guide sequence it will increase the overall binding energy by ≅0.2 degrees and the resulting guide RNA will have a decreased overall binding energy of ≅1.3 degrees as compared to the unmodified guide RNA. In certain embodiments, the sugar modification comprises 2'-O—$C_{1-3}$alkyl-O—$C_{1-3}$alkyl, such as 2'-methoxyethoxy (2'-O—$CH_2CH_2OCH_3$) also known as 2'-O-(2-methoxyethyl) or 2'-MOE. In certain embodiments, the sugar modification comprises 2'-halo, such as 2'-F, 2'-Br, 2'-Cl, or 2'-I. In certain embodiments, the sugar modification comprises 2'-$NH_2$. In certain embodiments, the sugar modification comprises 2'-H (e.g., a 2'-deoxynucleotide). In certain embodiments, the sugar modification comprises 2'-arabino or 2'-F-arabino. In certain embodiments, the sugar modification comprises 2'-LNA or 2'-ULNA. In certain embodiments, the sugar comprises a 4'-thioribosyl.

In certain embodiments, a nucleotide sugar modification or nucleobase modification that increases or decreases the binding energy of the overall guide RNA can be incorporated on the same nucleotide where a phosphodiester linkage is modified to modulate the binding energy of the modified nucleotide. As an example, 3'-phosphonocarboxylate linkages can be used with sugar modifications such as 2'-O-methyl, 2'-F, or 2'-O-(2-methoxyethyl). In certain embodiments, the sugar comprises 2'-O—$C_{1-3}$alkyl-O—$C_{1-3}$alkyl, such as 2'-methoxyethoxy (2'-O—$CH_2CH_2OCH_3$) also known as 2'-O-(2-methoxyethyl) or 2'-MOE. In certain embodiments, the sugar comprises 2'-halo, such as 2'-F, 2'-Br, 2'-Cl, or 2'-I. In certain embodiments, the sugar comprises 2'-$NH_2$. In certain embodiments, the sugar comprises 2'-H (e.g., a 2'-deoxynucleotide). In certain embodiments, the sugar comprises 2'-arabino or 2'-F-arabino. In certain embodiments, the sugar comprises 2'-LNA or 2'-ULNA. In certain embodiments, the sugar comprises a 4'-thioribosyl.

III. Guide RNAs

In at least one aspect, the present invention comprises a chemically modified guide RNA that has guide RNA functionality. The chemically modified guide RNA comprises at least one specificity-enhancing modification and may comprise other chemical modifications having more functions or different functions than specificity enhancement.

A guide RNA that comprises any nucleotide other than the four canonical ribonucleotides, namely A, C, G, and U, whether unnatural or natural (e.g., a pseudouridine, inosine or a deoxynucleotide), is a chemically modified guide RNA. Likewise, a guide RNA that comprises any backbone or internucleotide linkage other than a natural phosphodiester internucleotide linkage possesses a chemical modification and therefore is a chemically modified guide RNA. In certain embodiments, the retained functionality includes binding a Cas protein. In certain embodiments, the retained functionality includes binding a target polynucleotide. In certain embodiments, the retained functionality includes targeting a Cas protein or a gRNA:Cas protein complex to a target polynucleotide. In certain embodiments, the retained functionality includes nicking a target polynucleotide by a gRNA:Cas protein complex. In certain embodiments, the retained functionality includes cleaving a target polynucleotide by a gRNA:Cas protein complex. In certain embodiments, the retained functionality is any other known function of a guide RNA in a CRISPR-Cas system with a Cas protein, including an artificial CRISPR-Cas system with an engineered Cas protein. In certain embodiments, the retained functionality is any other function of a natural guide RNA.

A. Exemplary Modifications

In certain embodiments, the specificity-enhancing modification is a deoxyribose nucleotide, a 2'-deoxy-2'-fluoroarabinofuranosyl nucleotide, a 2'-deoxy-2'-fluororibofuranosyl nucleotide, a sugar having a 2'-O-phenyl, 2'-S-thiophenyl, 2'-methyl, 2'-ethyl, 2'-propyl, 2'-allyl, 2'-allylphenyl, 2'-methylhydroxy, 2'-methyloxymethyl, 2'-O-carbamate, 2'-O-ethylamino, 2'-O-allylamino, 2'-O-propylamino, or 2'-O-substituted phenyl, or combinations thereof. In certain embodiments, the specificity-enhancing modification is a phosphonoacetate, thiophosphonoacetate, phosphonopropionate, phosphonothiopropionate, methylphosphonate, methylphosphonothioate, or boranophosphonate; or combinations of any of the foregoing.

In certain embodiments, a nucleotide sugar modification incorporated into the guide RNA is selected from the group consisting of deoxyribose, 2'-deoxy-2'-fluoroarabinofuranosyl, 2'-deoxy-2'-fluororibofuranosyl, and sugars having 2'-O-phenyl, 2'-S-thiophenyl, 2'-methyl, 2'-ethyl, 2'-propyl, 2'-allyl, 2'-allylphenyl, 2'-methylhydroxy, 2'-methyloxymethyl, 2'-O-carbamate, 2'-O-ethylamino, 2'-O-allylamino, 2'-O-propylamino, and 2'-O-substituted phenyl. In certain embodiments, an internucleotide linkage modification incorporated into the guide RNA is selected from the group consisting of: phosphorothioate "P(S)" (P(S)), phosphonocarboxylate $(P(CH_2)_n COOR)$ such as phosphonoacetate "PACE" $(P(CH_2COO^-))$, thiophosphonocarboxylate $((S)P(CH_2)_n COOR)$ such as thiophosphonoacetate "thioPACE" $((S)P(CH_2COO^-))$, alkylphosphonate $(P(C_{1-3}alkyl))$ such as methylphosphonate —$P(CH_3)$, boranophosphonate $(P(BH_3))$, and phosphorodithioate $(P(S)_2)$. In certain embodiments, an internucleotide linkage modification incorporated into the guide RNA is selected from the group consisting of phosphonoacetates, thiophosphonoacetates, phosphonopropionates, phosphonothiopropionates, methylphosphonates, methylphosphonothioates, and boranophosphonates.

In certain embodiments, a nucleobase ("base") modification incorporated into the guide RNA is selected from the group consisting of: 2-thiouracil ("2-thioU"), 2-thiocytosine ("2-thioC"), 4-thiouracil ("4-thioU"), 6-thioguanine ("6-thioG"), 2-aminopurine, pseudouracil, hypoxanthine, 7-deazaguanine, 7-deaza-8-azaguanine, 7-deazaadenine, 7-deaza-8-azaadenine, 5-methylcytosine ("5-methylC"), 5-methyluracil ("5-methylU"), 5-hydroxymethylcytosine, 5-hydroxymethyluracil, 5,6-dehydrouracil, 5-ethynylcytosine, 5-aminoallyluracil ("5-aminoallylU"), 5-aminoallyl-cytosine ("5-aminoallylC"), an abasic nucleotide, Unstructured Nucleic Acid ("UNA"), isoguanine ("isoG"), isocytosine ("isoC") [as described in "Enzymatic Incorporation of a New Base pair into DNA and RNA Extends the Genetic Alphabet." Piccirilli, J. A.; Krauch, T.; Moroney, S. E.; Benner, S. A. (1990) *Nature,* 343, 33], 5-methyl-2-pyrimidine (as described in Rappaport, H. P. (1993) *Biochemistry,* 32, 3047), x(A,G,C,T,U) and y(A,G,C,T,U).

In certain embodiments, one or more isotopic modifications are introduced on the nucleotide sugar, the nucleobase, the phosphodiester linkage and/or the nucleotide phosphates. Such modifications include nucleotides comprising one or more $^{15}N$, $^{13}C$, $^{14}C$, Deuterium, $^3H$, $^{32}P$, $^{131}I$ atoms or other atoms or elements used as tracers.

In certain embodiments, an "end" modification incorporated into the guide RNA is selected from the group consisting of: PEG (polyethyleneglycol), hydrocarbon linkers (including: heteroatom (O,S,N)-substituted hydrocarbon spacers; halo-substituted hydrocarbon spacers; keto-, carboxyl-, amido-, thionyl-, carbamoyl-, thionocarbamaoyl-containing hydrocarbon spacers), spermine linkers, dyes including fluorescent dyes (for example fluoresceins, rhodamines, cyanines) attached to linkers such as for example 6-fluorescein-hexyl, quenchers (for example dabcyl, BHQ) and other labels (for example biotin, digoxigenin, acridine, streptavidin, avidin, peptides and/or proteins). In certain embodiments, an "end" modification comprises a conjugation (or ligation) of the guide RNA to another molecule comprising an oligonucleotide (comprising deoxynucleotides and/or ribonucleotides), a peptide, a protein, a sugar, an oligosaccharide, a steroid, a lipid, a folic acid, a vitamin and/or other molecule. In certain embodiments, an "end" modification incorporated into the guide RNA is located internally in the guide RNA sequence via a linker such as for example 2-(4-butylamidofluorescein)propane-1,3-diol bis(phosphodiester) linker (depicted below), which is incorporated as a phosphodiester linkage and can be incorporated anywhere between two nucleotides in the guide RNA.

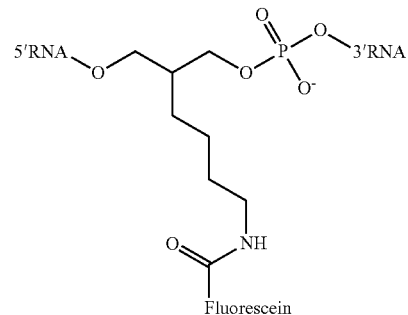

2-(4-butylamidofluorescein)propane-1,3-diol bis(phosphodiester) Linker

Other linkers include for example by way of illustration, but are not limited to:

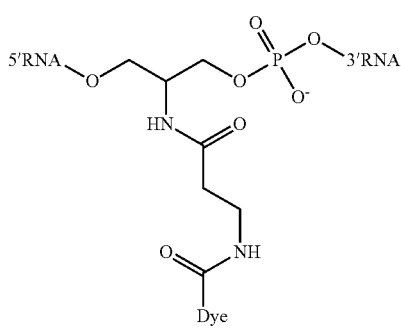

2-(3-(dye-amido)propanamido)propane-1,3-diol bis (phosphodiester) Linker

In certain embodiments, the end modification comprises a terminal functional group such as an amine, a thiol (or sulfhydryl), a hydroxyl, a carboxyl, carbonyl, thionyl, thiocarbonyl, a carbamoyl, a thiocarbamoyl, a phosphoryl, an alkene, an alkyne, an halogen or a functional group-terminated linker, either of which can be subsequently conjugated to a desired moiety, for example a fluorescent dye or a non-fluorescent label or tag or any other molecule such as for example an oligonucleotide (comprising deoxynucleotides and/or ribonucleotides, including an aptamer), an amino acid, a peptide, a protein, a sugar, an oligosaccharide, a steroid, a lipid, a folic acid, a vitamin. The conjugation employs standard chemistry well-known in the art, including but not limited to coupling via N-hydroxysuccinimide, isothiocyanate, DCC (or DCI), and/or any other standard method.

In certain embodiments, the label or dye is attached or conjugated to a modified nucleotide in the gRNA. The conjugation of a fluorescent dye or other moiety such as a non-fluorescent label or tag (for example biotin, avidin, streptavidin, or moiety containing an isotopic label such as $^{15}$N, $^{13}$C, $^{14}$C, Deuterium, $^{3}$H, $^{32}$P, $^{125}$I and the like) or any other molecule such as for example an oligonucleotide (comprising deoxynucleotides and/or ribonucleotides including an aptamer), an amino acid, a peptide, a protein, a sugar, an oligosaccharide, a steroid, a lipid, a folic acid, a vitamin or other molecule can be effectuated using the so-called "click" chemistry or the so-called "squarate" conjugation chemistry. The "click" chemistry refers to the [3+2] cycloaddition of an alkyne moiety with an azide moiety, leading to a triazolo linkage between the two moieties as shown in the following scheme:

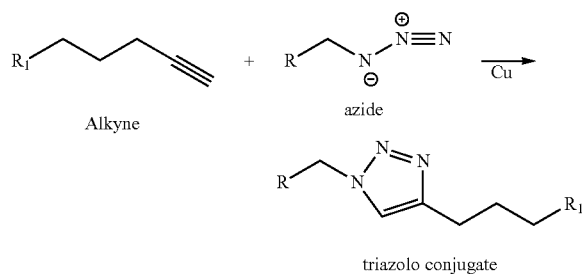

as described for example in El-Sagheer, A. H. and Brown, T. "Click chemistry with DNA", *Chem. Soc. Rev.*, 2010, 39, 1388-1405 and Mojibul, H. M. and XiaoHua, P., DNA-associated click chemistry, *Sci. China Chem.*, 2014, 57:2, 215-31, the contents of which are hereby incorporated by reference in their entirety.

In certain embodiments, the conjugation can be effectuated by alternative cycloaddition such as Diels-Alder [4+2] cycloaddition of a n-conjugated diene moiety with an alkene moiety.

The "squarate" conjugation chemistry links two moieties each having an amine via a squarate derivative to result in a squarate conjugate that contains a squarate moiety (see e.g., Tietze et al. (1991) *Chem. Ber.*, 124, 1215-21, the contents of which are hereby incorporated by reference in their entirety). For example, a fluorescein containing a linker amine is conjugated to an oligoribonucleotide containing an amine through a squarate linker as described in the scheme below. An example of the squarate linker is depicted in the following scheme:

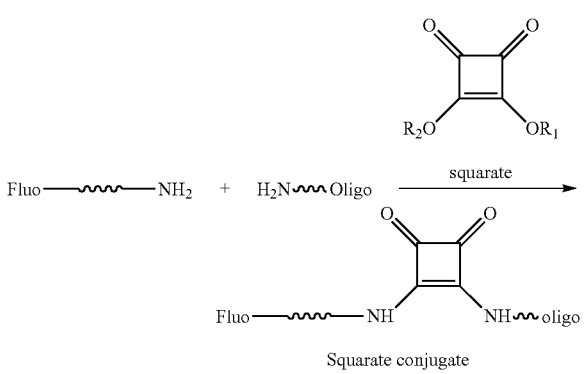

B. Guide RNA with at Least One Specificity-Enhancing Modification

In one aspect, the present technology provides a guide RNA having at least one specificity-enhancing modification, constituting a modified gRNA and optionally a stability-enhancing modification.

In certain embodiments, at least one specificity-enhancing modification is within the guide sequence or crRNA segment of the guide RNA. In certain embodiments, the modification is within the guide sequence of the crRNA. In certain embodiments, the modification is within the first five (5) nucleotides of the 5' end of the guide sequence or crRNA segment. In certain embodiments, the modification is within the first four (4) nucleotides of the guide sequence or crRNA segment. In certain embodiments, the modification is within the first three (3) nucleotides of the guide sequence or crRNA segment. In certain embodiments, the modification is also within a 5'-overhang on the crRNA segment. In certain embodiments, where the guide sequence consists of nucleotides 1 through 20-N, counted from the 5' end of the guide sequence, where N is a positive or negative integer between −10 and 10 (optionally between −10 and 6), at least one specificity-enhancing modification is within nucleotides 4-N to 20-N, alternatively within nucleotides 5-N to 20-N, alternatively within nucleotides 10-N to 20-N, alternatively within nucleotides 13-N to 20-N, alternatively within nucleotides 13-N to 14-N or 16-N to 19-N, alternatively within nucleotides 13-N to 14-N or 16-N to 18-N. In certain embodiments, the modification is at nucleotides 4-N, 5-N, 7-N, 9-N, 10-N, 11-N, or any combination thereof.

In certain embodiments, a modified gRNA comprises 1, 2, 3, 4, 5, 6, 7, 8, 9, 10, 11, 12, 13, 14, 15, 16, 17, 18, 19 or 20 specificity-enhancing modified nucleotides in the guide sequence portion of the gRNA and up to 100 additional modified nucleotides in the other portions or segments of the gRNA. In other embodiments, the modified gRNA comprises a 5' extension or overhang on the guide sequence portion, and the extension is 1 to 20 nucleotides in length comprising 1, 2, 3, 4, 5, 6, 7, 8, 9, 10, 11, 12, 13, 14, 15, 16, 17, 18, 19 or 20 specificity-enhancing modified nucleotides in addition to the 1, 2, 3, 4, 5, 6, 7, 8, 9, 10, 11, 12, 13, 14, 15, 16, 17, 18, 19 or 20 specificity-enhancing modified nucleotides in the guide sequence portion of the gRNA and optionally comprising up to 100 additional modified nucleotides in the other portions of the gRNA. In certain embodiments, all nucleotides in a gRNA are modified. In certain embodiments, all the modifications are the same. In certain embodiments, all the modified nucleotides have the same type of modification. In certain embodiments, the modified gRNA comprises a combination of differently modified nucleotides. In certain embodiments, the modified gRNA comprises two or more modified nucleotides. In certain embodiments, the modified gRNA comprises three or more modified nucleotides. In certain embodiments, the modified nucleotides are arranged contiguously. In certain embodiments, the modified gRNA comprises at least one contiguous stretch of modified nucleotides. In certain embodiments, the modified gRNA comprises a contiguous stretch of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified nucleotides. Each modified nucleotide may independently comprise one or more types of modifications. In certain embodiments, no modified nucleotides are contiguous, or some but not all are contiguous, in the sequence of the modified gRNA.

In certain embodiments, a chemical modification is within the 5' portion of the guide RNA. When a guide RNA is a dual guide RNA, a chemical modification within a 5' portion refers to a modification within the 5' portion of the crRNA segment of the guide RNA, and not to a modification within a 5' portion of a tracrRNA segment. When a guide RNA is a single guide RNA, it has one 5' portion, located in the crRNA segment. In certain embodiments, the modification is within the first five (5) nucleotides of the 5' portion of the guide RNA. In certain embodiments, the modification is within the first three (3) nucleotides of the 5' portion of the guide RNA. In certain embodiments, the modification is within the 3' portion of the guide RNA. In certain embodiments, the modification is within the last five (5) nucleotides of the 3' portion of the guide RNA. In certain embodiments, the modification is within the last three (3) nucleotides of the 3' portion of the guide RNA. In certain embodiments, the modification is within the internal region (i.e., between the 5' end and the 3' end) of the guide RNA.

In certain embodiments, a chemical modification is incorporated in the 5' portion or the 3' portion of the guide RNA, particularly within the first 5 or 10 nucleotides of the 5' portion or within the last 5 or 10 nucleotides of the 3' portion to, for example, protect the RNA from degradation by nucleases or for other purposes. In some other embodiments, the modification is in both the 5' portion and the 3' portion of the guide RNA, particularly within the first 5 or 10 nucleotides of the 5' portion and within the last 5 or 10 nucleotides of the 3' portion to, for example, protect the RNA from degradation by nucleases or for other purposes. In certain embodiments, more than one type of modification is present in both the 5' portion and the 3' portion of the guide RNA. In certain embodiments, the modifications are located at the 5' end, at the 3' end, and within the internal sequence of the guide RNA. In certain embodiments, a guide RNA comprises 40 or fewer, alternatively 20 or fewer, alternatively 15 or fewer, alternatively 10 or fewer, alternatively 5 or fewer, alternatively 3 or fewer deoxyribonucleotide residues in the 5' or 3' portion of the guide RNA. Where the guide RNA is a dual guide, each RNA molecule may comprise modification(s) at the 5'-end, 3'-end, or both. In certain embodiments, consecutive nucleotides at the end (5', 3', or both) are modified, such as 2, 3, 4, 5 or more consecutive nucleotides.

In general, the guide sequence consists of 20-N nucleotides, where N is an integer between −10 and 10 (optionally between −10 and 6). N can be selected from −10, −9, −8, −7, −6, −5, −4, −3, −2, −1, 0, 1, 2, 3, 4, 5, 6, 7, 8, 9, and 10. For example, the guide sequence may be 20 nucleotides long (N=0), 19 nucleotides long (N=1), 21 nucleotides long (N=−1), or the like. In certain embodiments, the guide sequence comprises at least one specificity-enhancing modification at nucleotide position (starting from the 5'-end of the guide sequence) 4-N, 5-N, 7-N, 9-N or 11-N, or a combination thereof. A few examples are described below.

In certain embodiments, the guide sequence consists of nucleotides 1 through 20, counted from the 5' end of the guide sequence, and comprises a chemical modification at at least one nucleotide selected from positions 4, 5, 7, 9, 10, and 11. In certain embodiments, the chemical modification is at nucleotide 11 of the guide sequence. In certain embodiments, the chemical modification is at nucleotide 5 of the guide sequence. In certain embodiments, the chemical modification is at nucleotide 7 of the guide sequence. In certain embodiments, the chemical modification is at nucleotide 10 of the guide sequence. In certain embodiments, the chemical modification is at nucleotide 9 of the guide sequence. In certain embodiments, the chemical modification is at nucleotide 4 of the guide sequence. In certain embodiments, the guide RNA comprises at least one end modification. In certain embodiments, the guide RNA comprises a 5' extension or overhang upstream of the guide sequence.

In certain embodiments, the guide sequence consists of nucleotides 1 through 19, counted from the 5' end of the guide sequence, and comprises a chemical modification at at least one nucleotide selected from positions 3, 4, 6, 8, 9, and 10. In certain embodiments, the chemical modification is at nucleotide 4 of the guide sequence. In certain embodiments, the chemical modification is at nucleotide 6 of the guide sequence. In certain embodiments, the chemical modification is at nucleotide 8 of the guide sequence. In certain embodiments, the chemical modification is at nucleotide 9 of the guide sequence. In certain embodiments, the chemical modification is at nucleotide 10 of the guide sequence. In certain embodiments, the chemical modification is at nucleotide 3 of the guide sequence. In certain embodiments, the guide RNA comprises at least one end modification. In certain embodiments, the guide RNA comprises a 5' extension or overhang upstream of the guide sequence.

In certain embodiments, the guide sequence consists of nucleotides 1 through 18, counted from the 5' end of the guide sequence, and comprises a chemical modification at at least one nucleotide selected from positions 2, 3, 5, 7, 8, and 9. In certain embodiments, the chemical modification is at nucleotide 3 of the guide sequence. In certain embodiments, the chemical modification is at nucleotide 5 of the guide sequence. In certain embodiments, the chemical modification is at nucleotide 7 of the guide sequence. In certain embodiments, the chemical modification is at nucleotide 8 of the guide sequence. In certain embodiments, the chemical modification is at nucleotide 9 of the guide sequence. In certain embodiments, the chemical modification is at nucleotide 2 of the guide sequence. In certain embodiments, the guide RNA comprises at least one end modification. In certain embodiments, the guide RNA comprises a 5' extension or overhang upstream of the guide sequence.

In certain embodiments, the guide sequence consists of nucleotides 1 through 17, counted from the 5' end of the guide sequence, and comprises a chemical modification of at least one nucleotide selected from positions 1, 2, 4, 6, 7, and 8. In certain embodiments, the chemical modification is at nucleotide 2 of the guide sequence. In certain embodiments, the chemical modification is at nucleotide 4 of the guide sequence. In certain embodiments, the chemical modification is at nucleotide 6 of the guide sequence. In certain embodiments, the chemical modification is at nucleotide 7 of the guide sequence. In certain embodiments, the chemical modification is at nucleotide 8 of the guide sequence. In certain embodiments, the chemical modification is at nucleotide 1 of the guide sequence. In certain embodiments, the guide RNA comprises at least one end modification. In certain embodiments, the guide RNA comprises a 5' extension or overhang upstream of the guide sequence.

In certain embodiments, the guide sequence consists of nucleotides 1 through 16, counted from the 5' end of the guide sequence, and comprises a chemical modification of at least one nucleotide selected from positions 1, 3, 5, 6, and 7. In certain embodiments, the chemical modification is at nucleotide 1 of the guide sequence. In certain embodiments, the chemical modification is at nucleotide 3 of the guide sequence. In certain embodiments, the chemical modification is at nucleotide 5 of the guide sequence. In certain embodiments, the chemical modification is at nucleotide 6 of the guide sequence. In certain embodiments, the chemical modification is at nucleotide 7 of the guide sequence. In certain embodiments, the guide RNA comprises at least one end modification. In certain embodiments, the guide RNA comprises a 5' extension or overhang upstream of the guide sequence.

In certain embodiments, the guide sequence consists of nucleotides 1 through 15, counted from the 5' end of the guide sequence, and comprises a chemical modification at at least one nucleotide selected from positions 2, 4, 5, and 6. In certain embodiments, the chemical modification is at nucleotide 2 of the guide sequence. In certain embodiments, the chemical modification is at nucleotide 4 of the guide sequence. In certain embodiments, the chemical modification is at nucleotide 5 of the guide sequence. In certain embodiments, the chemical modification is at nucleotide 6 of the guide sequence. In certain embodiments, the guide RNA comprises at least one end modification. In certain embodiments, the guide RNA comprises a 5' extension or overhang upstream of the guide sequence.

In certain embodiments, the guide sequence consists of nucleotides 1 through 21, counted from the 5' end of the guide sequence, and comprises a chemical modification at at least one of nucleotides 5, 6, 8, 10, 11, and 12. In certain embodiments, the chemical modification is at nucleotide 12 of the guide sequence. In certain embodiments, the chemical modification is at nucleotide 6 of the guide sequence. In certain embodiments, the chemical modification is at nucleotide 8 of the guide sequence. In certain embodiments, the chemical modification is at nucleotide 11 of the guide sequence. In certain embodiments, the chemical modification is at nucleotide 10 of the guide sequence. In certain embodiments, the chemical modification is at nucleotide 5 of the guide sequence. In certain embodiments, the guide RNA comprises at least one end modification. In certain embodiments, the guide RNA comprises a 5' extension or overhang upstream of the guide sequence.

In certain embodiments, the guide sequence consists of nucleotides 1 through 22, counted from the 5' end of the guide sequence, and comprises a chemical modification at at least one of nucleotides 6, 7, 9, 11, 12, and 13. In certain embodiments, the chemical modification is at nucleotide 13 of the guide sequence. In certain embodiments, the chemical modification is at nucleotide 7 of the guide sequence. In certain embodiments, the chemical modification is at nucleotide 9 of the guide sequence. In certain embodiments, the chemical modification is at nucleotide 12 of the guide sequence. In certain embodiments, the chemical modification is at nucleotide 11 of the guide sequence. In certain embodiments, the chemical modification is at nucleotide 6 of the guide sequence. In certain embodiments, the guide RNA comprises at least one end modification. In certain embodiments, the guide RNA comprises a 5' extension or overhang upstream of the guide sequence.

In certain embodiments, the guide sequence consists of nucleotides 1 through 20-N, wherein N is a positive or negative integer between −10 and 10 (optionally between −10 and 6), counted from the 5' end of the guide sequence, and comprises at least one chemical modifications at any nucleotides from 4-N through 20-N. In certain embodiments, the guide sequence comprises modifications at at least two nucleotides selected from nucleotides 4-N through 20-N. In certain embodiments, the guide sequence comprises at least one modification at nucleotide 4-N, 5-N, 7-N, 9-N, 10-N or 11-N, as well as at least another modification at a nucleotide selected from 4-N through 20-N(but not 15-N). In certain embodiments, the nucleotide selected from 4-N through 20-N is 5-N, 6-N, 7-N, 8-N, 9-N, 10-N, 16-N, or 17-N. In certain embodiments, the guide RNA further comprises at least one end modification. In certain embodiments, the guide RNA comprises a 5' extension or overhang upstream of the guide sequence.

In certain embodiments, the guide sequence consists of nucleotides 1 through 20, counted from the 5' end of the guide sequence, and comprises at least two chemical modifications at nucleotides selected from positions 5, 6, 7, 8, 9, 10, 16, and 17. In certain embodiments, the chemical modification is at nucleotide 6 and nucleotide 10 of the guide sequence. In certain embodiments, the chemical modification is at nucleotide 5 and nucleotide 17 of the guide sequence. In certain embodiments, the chemical modification is at nucleotide 6 and nucleotide 7 of the guide sequence. In certain embodiments, the chemical modification is at nucleotide 10 and nucleotide 17 of the guide sequence. In certain embodiments, the chemical modification is at nucleotide 5 and nucleotide 16 of the guide sequence. In certain embodiments, the chemical modification is at nucleotide 10 and nucleotide 16 of the guide sequence. In certain embodiments, the chemical modification is at nucleotide 5 and nucleotide 9 of the guide sequence. In certain embodiments, the chemical modification is at nucleotide 9 and nucleotide 16 of the guide sequence. In certain embodiments, the chemical modification is at nucleotide 8 and nucleotide 17 of the guide sequence. In certain embodiments, the guide RNA comprises at least one end modification. In certain embodiments, the guide RNA comprises a 5' extension or overhang upstream of the guide sequence.

In certain embodiments, the guide sequence consists of nucleotides 1 through 19, counted from the 5' end of the guide sequence, and comprises at least two chemical modifications at nucleotides selected from positions 4, 5, 6, 7, 8, 9, 15, and 16. In certain embodiments, the chemical modification is at nucleotide 5 and nucleotide 9 of the guide sequence. In certain embodiments, the chemical modification is at nucleotide 4 and nucleotide 16 of the guide sequence. In certain embodiments, the chemical modification is at nucleotide 5 and nucleotide 6 of the guide sequence. In certain embodiments, the chemical modification is at nucleotide 9 and nucleotide 16 of the guide sequence. In certain embodiments, the chemical modification is at nucleotide 4 and nucleotide 15 of the guide sequence. In certain embodiments, the chemical modification is at nucleotide 9 and nucleotide 15 of the guide sequence. In certain embodiments, the chemical modification is at nucleotide 4 and nucleotide 8 of the guide sequence. In certain embodiments, the chemical modification is at nucleotide 8 and nucleotide 15 of the guide sequence. In certain embodiments, the chemical modification is at nucleotide 7 and nucleotide 16 of the guide sequence.

In certain embodiments, the guide sequence consists of nucleotides 1 through 18, counted from the 5' end of the guide sequence, and comprises at least two chemical modifications at nucleotides selected from positions 3, 4, 5, 6, 7, 8, 14, and 15. In certain embodiments, the chemical modification is at nucleotide 4 and nucleotide 8 of the guide sequence. In certain embodiments, the chemical modification is at nucleotide 3 and nucleotide 15 of the guide sequence. In certain embodiments, the chemical modification is at nucleotide 4 and nucleotide 5 of the guide sequence. In certain embodiments, the chemical modification is at nucleotide 8 and nucleotide 15 of the guide sequence. In certain embodiments, the chemical modification is at nucleotide 3 and nucleotide 14 of the guide sequence. In certain embodiments, the chemical modification is at nucleotide 8 and nucleotide 14 of the guide sequence. In certain embodiments, the chemical modification is at nucleotide 3 and nucleotide 7 of the guide sequence. In certain embodiments, the chemical modification is at nucleotide 7 and nucleotide 14 of the guide sequence. In certain embodiments, the chemical modification is at nucleotide 6 and nucleotide 15 of the guide sequence.

In certain embodiments, the guide sequence consists of nucleotides 1 through 17, counted from the 5' end of the guide sequence, and comprises at least two chemical modifications at nucleotides selected from positions 2, 3, 4, 5, 6, 7, 13, and 14. In certain embodiments, the chemical modification is at nucleotide 3 and nucleotide 7 of the guide sequence. In certain embodiments, the chemical modification is at nucleotide 2 and nucleotide 14 of the guide sequence. In certain embodiments, the chemical modification is at nucleotide 3 and nucleotide 4 of the guide sequence. In certain embodiments, the chemical modification is at nucleotide 7 and nucleotide 14 of the guide sequence. In certain embodiments, the chemical modification is at nucleotide 2 and nucleotide 13 of the guide sequence. In certain embodiments, the chemical modification is at nucleotide 7 and nucleotide 13 of the guide sequence. In certain embodiments, the chemical modification is at nucleotide 2 and nucleotide 6 of the guide sequence. In certain embodiments, the chemical modification is at nucleotide 6 and nucleotide 13 of the guide sequence. In certain embodiments, the chemical modification is at nucleotide 5 and nucleotide 14 of the guide sequence.

In certain embodiments, the guide sequence consists of nucleotides 1 through 16, counted from the 5' end of the guide sequence, and comprises at least two chemical modifications at nucleotides selected from positions 1, 2, 3, 4, 5, 6, 12, and 13. In certain embodiments, the chemical modification is at nucleotide 2 and nucleotide 6 of the guide sequence. In certain embodiments, the chemical modification is at nucleotide 1 and nucleotide 13 of the guide sequence. In certain embodiments, the chemical modification is at nucleotide 2 and nucleotide 3 of the guide sequence. In certain embodiments, the chemical modification is at nucleotide 6 and nucleotide 13 of the guide sequence. In certain embodiments, the chemical modification is at nucleotide 1 and nucleotide 12 of the guide sequence. In certain embodiments, the chemical modification is at nucleotide 6 and nucleotide 12 of the guide sequence. In certain embodiments, the chemical modification is at nucleotide 1 and nucleotide 5 of the guide sequence. In certain embodiments, the chemical modification is at nucleotide 5 and nucleotide 12 of the guide sequence. In certain embodiments, the chemical modification is at nucleotide 4 and nucleotide 13 of the guide sequence.

In certain embodiments, the guide sequence consists of nucleotides 1 through 15, counted from the 5' end of the guide sequence, and comprises at least two chemical modifications at nucleotides selected from positions 1, 2, 3, 4, 5, 11, and 12. In certain embodiments, the chemical modification is at nucleotide 1 and nucleotide 5 of the guide sequence. In certain embodiments, the chemical modification is at nucleotide 1 and nucleotide 2 of the guide sequence. In certain embodiments, the chemical modification is at nucleotide 5 and nucleotide 12 of the guide sequence. In certain embodiments, the chemical modification is at nucleotide 5 and nucleotide 11 of the guide sequence. In certain embodiments, the chemical modification is at nucleotide 4 and nucleotide 11 of the guide sequence. In certain embodiments, the chemical modification is at nucleotide 3 and nucleotide 12 of the guide sequence.

In certain embodiments, the guide sequence consists of nucleotides 1 through 14, counted from the 5' end of the guide sequence, and comprises at least two chemical modifications at nucleotides selected from positions 1, 2, 3, 4, 10, and 11. In certain embodiments, the chemical modification is at nucleotide 4 and nucleotide 11 of the guide sequence. In certain embodiments, the chemical modification is at nucleotide 4 and nucleotide 10 of the guide sequence. In certain embodiments, the chemical modification is at nucleotide 3 and nucleotide 10 of the guide sequence. In certain embodiments, the chemical modification is at nucleotide 2 and nucleotide 11 of the guide sequence.

In certain embodiments, a chemical modification comprises an end modification, such as a 5' end modification or a 3' end modification. Examples of end modifications include, but are not limited to phosphorylation (as natural phosphate or polyphosphate or as modified phosphonate groups such as for example, alkylphosphonate, phosphonocarboxylate, phosphonoacetate, boranophosphonate, phosphorothioate, phosphorodithioate and the like), biotinylation, conjugating or conjugated molecules, linkers, dyes, labels, tags, functional groups (such as for example but not limited to 5'-amino, 5'-thio, 5'-amido, 5'carboxy and the like), inverted linkages, or hydrocarbon moieties which may comprise ether, polyethylene glycol (PEG), ester, hydroxyl, aryl, halo, phosphodiester, bicyclic, heterocyclic or other organic functional group. In certain embodiments, the end modification comprises dimethoxytrityl.

In certain embodiments, a chemical modification comprises a modified base. As used herein, "unmodified" bases include the purine bases adenine (A) and guanine (G), and the pyrimidine bases thymine (T), cytosine (C) and uracil (U). Examples of modified bases include, but are not limited to, synthetic and natural bases such as 2-thioU, 2-thioC, 4-thioU, 6-thioG, 2-aminoA, 2-aminopurine, pseudouracil, hypoxanthine, 7-deazaguanine, 7-deaza-8-azaguanine, 7-deazaadenine, 7-deaza-8-azaadenine, 5-methylC, 5-methylU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, and 5-aminoallyl-cytosine. In certain embodiments, the modification comprises an abasic nucleotide. In certain embodiments, the modification comprises a nonstandard purine or pyrimidine structure, such as Z or P, isoC or isoG, UNA, 5-methylpyrymidine, x(A,G,C,T,U) or y(A,G,C,T,U). In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified bases. In other embodiments, the modified gRNA comprises at least 55, 60, 65, 70, 75, 80, 85, 90, 95, 100, 110, 120, 130 or 140 modified bases. In certain embodiments, all bases in a gRNA are modified.

In certain embodiments, the modification comprises a modified sugar. Examples of modified sugars include, but are not limited to, sugars having modifications at the 2' position or modifications at the 4' position. For example, in certain embodiments, the sugar comprises 2'-O—$C_{1-4}$alkyl, such as 2'-O-methyl (2'-OMe). In certain embodiments, the sugar comprises 2'-O—$C_{1-3}$alkyl-O—$C_{1-3}$alkyl, such as 2'-methoxyethoxy (2'-O—$CH_2CH_2OCH_3$) also known as 2'-O-(2-methoxyethyl) or 2'-MOE. In certain embodiments, the sugar comprises 2'-halo, such as 2'-F, 2'-Br, 2'-Cl, or 2'-I. In certain embodiments, the sugar comprises 2'-$NH_2$. In certain embodiments, the sugar comprises 2'-H (e.g., a 2'-deoxynucleotide). In certain embodiments, the sugar comprises 2'-arabino or 2'-F-arabino. In certain embodiments, the sugar comprises 2'-LNA or 2'-ULNA. In certain embodiments, the sugar comprises a 4'-thioribosyl. In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified sugars. In other embodiments, the modified gRNA comprises at least 55, 60, 65, 70, 75, 80, 85, 90, 95, 100, 110, 120, 130 or 140 modified sugars. In certain embodiments, all sugars in a gRNA are modified.

In certain embodiments, the modification comprises a modified backbone (i.e., an internucleotide linkage other than a natural phosphodiester). Examples of modified internucleotide linkages include, but are not limited to, a phosphorothioate internucleotide linkage, a chiral phosphorothioate internucleotide linkage, a phosphorodithioate internucleotide linkage, a boranophosphonate internucleotide linkage, a $C_{1-4}$alkyl phosphonate internucleotide linkage such as a methylphosphonate internucleotide linkage, a boranophosphonate internucleotide linkage, a phosphonocarboxylate internucleotide linkage such as a phosphonoacetate internucleotide linkage, a phosphonocarboxylate ester internucleotide linkage such as a phosphonoacetate ester internucleotide linkage, a thiophosphonocarboxylate internucleotide linkage such as for example a thiophosphonoacetate internmucleotide linkage, a thiophosphonocarboxylate ester internucleotide linkage such as a thiophosphonoacetate ester internucleotide linkage. Various salts, mixed salts and free acid forms are also included. In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified internucleotide linkages. In other embodiments, the modified gRNA comprises at least 55, 60, 65, 70, 75, 80, 85, 90, 95, 100, 110, 120, 130 or 140 modified internucleotide linkages. In certain embodiments, all internucleotide linkages in a gRNA are modified.

In certain embodiments, the modification is or comprises a 2'-O—$C_{1-4}$alkyl, 2'-H, 2'-O—$C_{1-3}$alkyl-O—$C_{1-3}$alkyl, 2'-F, 2'-$NH_2$, 2'-arabino, 2'-F-arabino, 2'-LNA, 2'-ULNA, 4'-thioribosyl, 2-thioU, 2-thioC, 4-thioU, 6-thioG, 2-aminoA, 2-aminopurine, pseudouracil, hypoxanthine, 7-deazaguanine, 7-deaza-8-azaguanine, 7-deazaadenine, 7-deaza-8-azaadenine, 5-MeC, 5-MeU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, 5-aminoallyl-cytosine, an abasic nucleotide, Z nucleotide, P nucleotide, UNA, isoC, isoG, 5-methyl-pyrimidine, x(A,G,C,T,U) nucleotide, y(A,G,C,T,U) nucleotide, a 3'-phosphorothioate group, a 3'-phosphonoacetate group, a 3'-phosphonoacetate ester group, a 3'-thiophosphonoacetate group, a 3'-thiophosphonoacetate ester group, a 3'-methylphosphonate group, a 3'-boranophosphonate group or a 3'-phosphorodithioate group, or combinations thereof.

In certain embodiments, the modified nucleotide comprises a 2'-O-methyl-3'-phosphonoacetate. In certain embodiments, the modified nucleotide comprises a 2'-O-methyl-3'-phosphorothioate. In certain embodiments, the modified nucleotide comprises a 2'-O-methyl-3'-thiophosphonoacetate. In certain embodiments, the modified nucleotide comprises a 2'-O-methyl-3'-phosphonocarboxylate. In certain embodiments, the modified nucleotide comprises a 2'-deoxy-3'-phosphonoacetate. In certain embodiments, the modified nucleotide comprises a 2'-deoxy-3'-phosphorothioate. In certain embodiments, the modified nucleotide comprises a 2'-deoxy-3'-thiophosphonoacetate. In certain embodiments, the modified nucleotide comprises a 2'-deoxy-3'-phosphonocarboxylate. In certain embodiments, the modified nucleotide comprises a 2'-halo-3'-phosphorothioate. In certain embodiments, the modified nucleotide comprises a 2'-halo-3'-phosphonoacetate. In certain embodiments, the modified nucleotide comprises a 2'-halo-3'-thiophosphonoacetate. In certain embodiments, the modified nucleotide comprises a 2'-halo-3'-phosphonocarboxylate. In certain embodiments, the modified nucleotide comprises a 2'-fluoro-3'-phosphorothioate. In certain embodiments, the modified nucleotide comprises a 2'-fluoro-3'-phosphonoacetate. In certain embodiments, the modified nucleotide comprises a 2'-fluoro-3'-thiophosphonoacetate. In certain embodiments, the modified nucleotide comprises a 2'-fluoro-3'-phosphonocarboxylate. In certain embodiments, the modified nucleotide comprises a Z base. In certain embodiments, the modified nucleotide comprises a P base.

In certain embodiments, the guide RNA comprises an oligonucleotide represented by Formula (I):

$$W—Y \text{ or } Y—W \qquad (I)$$

wherein W represents a nucleotide or a stretch of nucleotides of the oligonucleotide comprising at least one stability-enhancing modification and Y represents an unmodified portion of the oligonucleotide.

In certain embodiments, W is within the 5' portion of the guide RNA. In certain embodiments, W is at least partially within the first five (5) nucleotides of the 5' portion of the guide RNA. In certain embodiments, W is at least partially within the first four (4) nucleotides of the 5' portion of the guide RNA. In certain embodiments, W is at least partially within the first three (3) nucleotides of the 5' portion of the guide RNA. In certain embodiments, W is at least partially within nucleotides 4 to 20, alternatively within nucleotides 5 to 20 of the guide sequence, alternatively within nucleotides 10 to 20 of the guide sequence, alternatively within nucleotides 13 to 20 of the guide sequence, alternatively within nucleotides 13-14 or 16-19 of the guide sequence, alternatively within nucleotides 13-14 or 16-18 of the guide sequence.

In certain embodiments, W comprises a 2'-O—$C_{1-4}$alkyl, 2'-H, 2'-O—$C_{1-3}$alkyl-O—$C_{1-3}$alkyl, 2'-F, 2'-NH$_2$, 2'-arabino, 2'-F-arabino, 2'-LNA, 2'-ULNA, 4'-thioribosyl, 2-thioU, 2-thioC, 4-thioU, 6-thioG, 2-aminoA, 2-aminopurine, pseudouracil, hypoxanthine, 7-deazaguanine, 7-deaza-8-azaguanine, 7-deazaadenine, 7-deaza-8-azaadenine, 5-MeC, 5-MeU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, 5-aminoallyl-cytosine, abasic nucleotides, Z nucleotide, P nucleotide, UNA, isoC, isoG, 5-methyl-pyrimidine, x(A,G,C,T,U), y(A,G,C,T,U), a phosphorothioate internucleotide linkage, a phosphonoacetate internucleotide linkage, a phosphonoacetate ester internucleotide linkage, a thiophosphonoacetate internucleotide linkage, a thiophosphonoacetate ester internucleotide linkage a methylphosphonate internucleotide linkage, a boranophosphonate internucleotide linkage, a phosphorodithioate internucleotide linkage, or combinations thereof.

In certain embodiments, W comprises a 2'-O-methyl and a 3'-phosphonoacetate group on the same nucleotide. In certain embodiments, W comprises a 2'-O-methyl and a 3'-phosphorothioate group on the same nucleotide. In certain embodiments, W comprises a 2'-O-methyl and 3'-thiophosphonoacetate group on the same nucleotide. In certain embodiments, W comprises a 2'-F and a 3'-phosphorothioate group on the same nucleotide. In certain embodiments, W comprises a 2'-F and a 3'-phosphonoacetate group on the same nucleotide. In certain embodiments, W comprises a 2'-F and 3'-thiophosphonoacetate group on the same nucleotide.

In certain embodiments, W comprises 1, 2, 3, 4, 5, 6, 7, 8, 9, 10, 11, 12, 13, 14, 15, 16, 17, 18, 19 or 20 modified nucleotides. In certain embodiments, each of the modified nucleotides comprises the same modification. In certain embodiments, W comprises a combination of variously modified nucleotides. In certain embodiments, W comprises two or more modified nucleotides. In certain embodiments, W comprises three or more modified nucleotides. In certain embodiments, the modified nucleotides are not arranged contiguously in the sequence, or at least not entirely, as one or more unmodified nucleotides may intercede. In certain embodiments, the modified nucleotides are arranged contiguously. In certain embodiments, W comprises at least one contiguous stretch of modified nucleotides. In certain embodiments, W comprises a contiguous stretch of at least three (3) modified nucleotides. In certain embodiments, W comprises a contiguous stretch of at least four (4) modified nucleotides. In certain embodiments, W comprises a contiguous stretch of at least five (5) modified nucleotides.

In certain embodiments, the modification is a stability-altering modification. Stability refers to the ability of the gRNA to resist degradation by enzymes, such as nucleases, and other substances that exist in intra-cellular and extra-cellular environments. In certain embodiments, the modification increases nuclease resistance of the guide RNA relative to a guide RNA without the modification, thus it enhances the guide RNA stability. In certain embodiments, the stability-altering modification is a stability-enhancing modification. For example, in certain embodiments, the stability-enhancing modification comprises a 2'-O-methyl or a 2'-O—$C_{1-3}$alkyl nucleotide. In certain embodiments, the stability-enhancing modification comprises a 2'-halo nucleotide, such as 2'-F, 2'-Br, 2'-Cl, or 2'-I. In certain embodiments, the stability-enhancing modification comprises a 2'-MOE or a 2'-O—$C_{1-3}$alkyl-O—$C_{1-3}$alkyl. In certain embodiments, the stability-enhancing modification comprises a 2'-NH$_2$ nucleotide. In certain embodiments, the stability-enhancing modification comprises a 2'-H (or 2'-deoxy) nucleotide. In certain embodiments, the stability-enhancing modification comprises a 2'-arabino or a 2'-F-arabino. In certain embodiments, the stability-enhancing modification comprises a 4'-thioribosyl sugar moiety. In certain embodiments, the stability-enhancing modification comprises a 3'-phosphorothioate group. In certain embodiments, the stability-enhancing modification comprises a 3'-phosphonoacetate group. In certain embodiments, the stability-enhancing modification comprises a nucleotide containing a 3'-thiophosphonoacetate group. In certain embodiments, the stability-enhancing modification comprises a nucleotide containing a 3'-methylphosphonate group. In certain embodiments, the stability-enhancing modification comprises a nucleotide containing a 3'-boranophosphate group. In certain embodiments, the stability-enhancing modification comprises a nucleotide containing a 3'-phosphorodithioate group. In certain embodiments, the stability-enhancing modification comprises an unlocked nucleic acid ("ULNA") nucleotide.

In certain embodiments, the stability-enhancing modification comprises a 2'-O-methyl and a 3'-phosphorothioate group on the same nucleotide. In certain embodiments, the stability-enhancing modification comprises a 2'-O-methyl and a 3'-phosphonoacetate group on the same nucleotide. In certain embodiments, the stability-enhancing modification comprises a 2'-O-methyl and a 3'-thiophosphonoacetate group on the same nucleotide. In certain embodiments, the stability-enhancing modification comprises a 2'-fluoro and a 3'-phosphorothioate group on the same nucleotide. In certain embodiments, the stability-enhancing modification comprises a 2'-fluoro and a 3'-phosphonoacetate group on the same nucleotide. In certain embodiments, the stability-enhancing modification comprises a 2'-fluoro and a 3'-thiophosphonoacetate group on the same nucleotide.

In certain embodiments, the modification is a specificity-altering modification. In some embodiments, specificity enhancement may be achieved by enhancing on-target binding and/or cleavage, or reducing off-target binding and/or cleavage, or a combination of both. In some other embodiments, specificity reduction may be achieved, for example, by reducing on-target binding and/or cleavage, or increasing off-target binding and/or cleavage, or a combination of both.

In certain embodiments, the specificity-altering modification comprises a 2'-O-methyl. In certain embodiments, the specificity-altering modification comprises a 2'-halo, such as 2'-fluoro.

In certain embodiments, the specificity-altering modification comprises a 2-thiouracil base (2-thioU). In certain embodiments, the specificity-altering modification comprises 2-thioC. In certain embodiments, the specificity-altering modification comprises 4-thioU. In certain embodiments, the specificity-altering modification comprises 6-thioG. In certain embodiments, the specificity-altering modification comprises 2-aminoA. In certain embodiments, the specificity-altering modification comprises a 2-aminopurine. In certain embodiments, the specificity-altering modification comprises pseudouracil. In certain embodiments, the specificity-altering modification comprises hypoxanthine. In certain embodiments, the specificity-altering modification comprises 7-deazaguanine. In certain embodiments, the specificity-altering modification comprises 7-deaza-8-azaguanine. In certain embodiments, the specificity-altering modification comprises 7-deazaadenine. In certain embodiments, the specificity-altering modification comprises 7-deaza-8-azaadenine. In certain embodiments, the specificity-altering modification comprises 5-methylC. In certain embodiments, the specificity-altering modification comprises 5-methylU. In certain embodiments, the specificity-altering modification comprises 5-hydroxymethylcytosine. In certain embodiments, the specificity-altering modification comprises 5-hydroxymethyluracil. In certain embodiments, the specificity-altering modification comprises 5,6-dehydrouracil. In certain embodiments, the specificity-altering modification comprises 5-propynylcytosine. In certain embodiments, the specificity-altering modification comprises 5-propynyluracil. In certain embodiments, the specificity-altering modification comprises 5-ethynylcytosine. In certain embodiments, the specificity-altering modification comprises 5-ethynyluracil. In certain embodiments, the specificity-altering modification comprises 5-allylU. In certain embodiments, the specificity-altering modification comprises 5-allylC. In certain embodiments, the specificity-altering modification comprises 5-aminoallylU. In certain embodiments, the specificity-altering modification comprises 5-aminoallylC. In certain embodiments, the specificity-altering modification comprises an abasic nucleotide. In certain embodiments, the specificity-altering modification comprises a Z base. In certain embodiments, the specificity-altering modification comprises P base. In certain embodiments, the specificity-altering modification comprises a UNA base. In certain embodiments, the specificity-altering modification comprises isoC. In certain embodiments, the specificity-altering modification comprises isoG. In certain embodiments, the specificity-altering modification comprises 5-methyl-pyrimidine. In certain embodiments, the specificity-altering modification comprises x(A,G,C,T,U). In certain embodiments, the specificity-altering modification comprises y(A,G,C,T,U).

In certain embodiments, the specificity-altering modification comprises a phosphorothioate internucleotide linkage. In certain embodiments, the specificity-altering modification comprises a phosphonoacetate internucleotide linkage. In certain embodiments, the specificity-altering modification comprises a thiophosphonoacetate internucleotide linkage. In certain embodiments, the specificity-altering modification comprises a methylphosphonate internucleotide linkage. In certain embodiments, the specificity-altering modification comprises a boranophosphate internucleotide linkage. In certain embodiments, the specificity-altering modification comprises a phosphorodithioate internucleotide linkage. In certain embodiments, the specificity-altering modification comprises a ULNA. In certain embodiments, the specificity-altering modification comprises an LNA.

In certain embodiments, the modification alters RNA base pairing by, for example, altering the melting temperature ($T_m$) of the guide RNA relative to a guide RNA without the modification. In certain embodiments, the modification lowers the T. of the guide RNA relative to a guide RNA without the modification. In certain embodiments, the modification raises the $T_m$ of the guide RNA relative to a guide RNA without the modification.

In certain embodiments, a gRNA comprises a guide sequence capable of hybridizing to a target polynucleotide, and the guide sequence comprises one or more modifications that alter base pairing of the guide sequence with the target polynucleotide by altering the melting temperature ($T_m$) of the gRNA:target polynucleotide duplex relative to a similar duplex without the modification. In certain embodiments, the modification lowers the $T_m$ of the gRNA:target polynucleotide duplex relative to a similar duplex without the modification.

In certain embodiments, the specificity-altering modification lowers the $T_m$ of a base pairing interaction. In certain embodiments, the specificity-enhancing modification lowers the Tm of a first DNA/RNA duplex comprising the guide RNA and target polynucleotide by at least about 1° C., alternatively at least about 2° C., at least about 3° C., at least about 4° C., at least about 5° C., and/or up to about 6° C., alternatively up to about 8° C., alternatively up to about 10° C., alternatively up to about 13° C., for example by lowering the Tm from about 1° C. to about 13° C., alternatively from about 1° C. to about 6° C. In certain embodiments, the specificity-enhancing modification lowers the Tm of a second DNA/RNA duplex comprising the guide RNA and an off-target polynucleotide by at least about 1° C., alternatively at least about 2° C., at least about 3° C., at least about 4° C., at least about 5° C., and/or up to about 6° C., alternatively up to about 8° C., alternatively up to about 10° C., alternatively up to about 13° C., for example by lowering the Tm from about 1° C. to about 13° C., alternatively from about 1° C. to about 6° C.

In certain embodiments, the synthetic guide RNA comprises a chemical modification that alters transfection efficiency of the guide RNA relative to a guide RNA without the modification. In certain embodiments, the modification increases transfection efficiency of the guide RNA relative to a guide RNA without the modification. In certain embodiments, the modification decreases transfection efficiency of the guide RNA relative to a guide RNA without the modification. In certain embodiments, the modification neutralizes the anionic charge on phosphate to allow passive diffusion into cells. In certain embodiments, the charge-neutralizing modification comprises a phosphonoacetate alkyl ester internucleotide linkage, such as a phosphonoacetate methyl ester internucleotide linkage. Further considerations relevant to developing a gRNA include transfectability and immunostimulatory properties. In certain embodiments, the synthetic guide RNA comprises a chemical modification that promotes efficient and titratable transfectability into cells, especially into the nuclei of eukaryotic cells, and reduces immunostimulatory properties in transfected cells. In certain embodiments, the synthetic guide RNA comprises a chemical modification that promotes effective delivery into and maintaining in an intended cell, tissue, bodily fluid or organism for a duration sufficient to allow the desired gRNA functionality. In certain embodiments, the synthetic guide RNA comprises a chemical modification that alters the immunostimulatory effect of the guide RNA relative to a guide RNA without the modification.

In certain embodiments, the synthetic guide RNA comprises a chemical modification that enhances both stability and specificity of the guide RNA relative to a guide RNA without the modification. In certain embodiments, the modification enhances both stability and transfection efficiency of the guide RNA relative to a guide RNA without the modification. In certain embodiments, the modification enhances both specificity and transfection efficiency of the guide RNA relative to a guide RNA without the modification. In certain embodiments, the modification enhances the overall efficacy of the guide RNA relative to a guide RNA without the modification.

In certain embodiments, a guide RNA having a chemical modification of the present application has a specificity score of greater than 1. In certain embodiments, a guide RNA having a chemical modification of the present application has a specificity score of at least about 1.1. Thus, in certain embodiments, a guide RNA having a chemical modification of the present application has a specificity score of at least about 1.1, at least about 1.5, at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 35, at least about 40, at least about 45, at least about 50, or at least about 55. In certain embodiments, a guide RNA having a chemical modification of the present application has a specificity score of from about 2 to about 60. In certain embodiments, a guide RNA having a chemical modification of the present application has a specificity score of from about 10 to about 60.

In certain embodiments, a guide RNA having a chemical modification of the present application has an ON target cleavage of at least about 1%. In certain embodiments, a guide RNA having a chemical modification of the present application has an ON target cleavage of at least about 5%. In certain embodiments, a guide RNA having a chemical modification of the present application has an ON target cleavage of at least about 10%. In certain embodiments, a gRNA:Cas protein complex comprising a guide RNA having a chemical modification of the present application has an ON target cleavage of at least about 30%. Thus, in certain embodiments, a guide RNA having a chemical modification of the present application has an ON target cleavage of at least about 30%, at least about 35%, at least about 40%, at least about 45%, at least about 50%, at least 55%, at least about 60%, at least about 65%, at least about 70%, at least about 75%, at least about 80%, at least about 85%, or at least about 90%, at least about 95%, or at least about 99%. In certain embodiments, a guide RNA having a chemical modification of the present application has an ON target cleavage of from about 25% to about 99.9%. In certain embodiments, a guide RNA having a chemical modification of the present application has an ON target cleavage of from about 50% to about 99.9%.

In certain embodiments, a guide RNA having a chemical modification of the present application has an ON:OFF ratio of greater than 1. In certain embodiments, a guide RNA having a chemical modification of the present application has an ON:OFF ratio of at least about 1.1:1. Thus, in certain embodiments, a guide RNA having a chemical modification of the present application has an ON:OFF ratio of at least about 1.1:1, at least about 0.1.5:1, at least about 2:1, at least about 3:1, at least about 4:1, at least about 5:1, at least about 6:1, at least about 7:1, at least about 8:1, at least about 9:1, at least about 10:1, at least about 15:1, at least about 20:1, at least about 25:1, at least about 30:1, at least about 35:1, at least about 40:1, at least about 45:1, at least about 50:1, at least about 60:1, at least about 70:1, at least about 80:1, at least about 90:1, at least about 95:1, or at least about 99:1. In certain embodiments, a guide RNA having a chemical modification of the present application has an ON:OFF ratio of at least about 1.5:1 to about 99.9:1. In certain embodiments, a guide RNA having a chemical modification of the present application has an ON:OFF ratio of at least about 10:1 to about 99.9:1.

C. Guide RNA with a Combination of Modifications

In one aspect, the present technology provides a guide RNA having a combination of two or more modifications. In certain embodiments, the two modifications are on the same nucleotide (for example, one nucleotide comprises a 2'-O-methyl and a 3'-phosphonoacetate moiety). In other embodiments, the two modifications are on two different nucleotides (for example, one nucleotide has a 2'-O-methyl group and another has a 3'-phosphonoacetate moiety).

In certain embodiments, each modification in the guide RNA is the same. In certain embodiments, at least one modification in the guide RNA is different from at least one other modification in the guide RNA. In certain embodiments, the guide RNA comprises a combination of different types of modifications, and at least one type in the combination exists in multiple places in the guide RNA. In certain embodiments, at least one type in the combination appears 1, 2, 3, 4, 5, 6, 7, 8, 9, 10, 11, 12, 13, 14, 15, 16, 17, 18, 19 or 20 times in the guide RNA.

In certain embodiments, at least one type of the modifications in the combination appears in two or more modified nucleotides. In certain embodiments, at least one type of the modifications in the combination appears in three or more modified nucleotides. In certain embodiments, the modified nucleotides are not arranged contiguously in the sequence, or at least not entirely, as one or more unmodified nucleotides may intercede. In certain embodiments, the modified nucleotides are arranged contiguously. In certain embodiments, the guide RNA comprises a stretch of contiguous modified nucleotides of the same type. In certain embodiments, the stretch has at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified nucleotides.

In certain embodiments, at least one of the modifications in the combination comprises a modified sugar. In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified sugars. In other embodiments, the modified gRNA comprises at least 55, 60, 65, 70, 75, 80, 85, 90, 95, 100, 110, 120, 130 or 140 modified sugars. In certain embodiments, all sugars in a gRNA are modified.

In certain embodiments, at least one of the modifications in the combination comprises a modified backbone (i.e., an internucleotide linkage other than a natural phosphodiester). In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified internucleotide linkages. In other embodiments, the modified gRNA comprises at least 55, 60, 65, 70, 75, 80, 85, 90, 95, 100, 110, 120, 130 or 140 modified internucleotide linkages. In certain embodiments, all internucleotide linkages in a gRNA are modified.

In certain embodiments, the guide RNA comprises consecutive modifications. In certain embodiments, a guide sequence comprises 1, 2, 3, 4, 5, 6, 7, 8, 9, 10, 11, 12, 13, 14, 15, 16, 17, 18, 19 or 20 consecutive chemical modifications. In certain embodiments, the chemical modifications are at nucleotides 1 and 2, 1 through 3, 1 through 4, 1 through 5, 1 through 6, 1 through 7, 1 through 8, 1 through 9, 1 through 10, 2 and 3, 2 through 4, 2 through 5, 2 through 6, 2 through 7, 2 through 8, 2 through 9, or 2 through 10.

In certain embodiments, at least one of the modifications in the combination comprises a 2'-O-methyl, a 2'-fluoro, a 2'-amino, a 2'-deoxy, a 2'-arabino, a 2'-F-arabino, a 2-thiouracil, a 2-aminoadenine, a 5-methylcytosine, a 5-aminoallyluracil, a Z base, a 3'-phosphorothioate, a 3'-phosphonoacetate, a 3'-phosphonoacetate ester, a 3'-thiophosphonoacetate, a 3'-thiophosphonoacetate ester, a 3'-methylphosphonate, a 3'-boranophosphonate, a 3'-phosphorodithioate, or combinations thereof. In certain embodiments, at least one of the modifications in the combination comprises a 2'-O-methyl, a 2'-deoxy, a Z base, a phosphorothioate internucleotide linkage, a phosphonoacetate internucleotide linkage, a thiophosphonoacetate internucleotide linkage, or combinations thereof. In certain embodiments, at least one of the modifications in the combination comprises a 2'-F, a 2-thioU, a 4-thioU, a 2-aminoA, a 5-methylC, a 5-methylU, a 5-aminoallylU, or combinations thereof. In certain embodiments, at least one of the modifications in the combination is an "end" modification such as terminal phosphate, a PEG, a terminal amine, a terminal linker such as a hydrocarbon linker, a substituted hydrocarbon linker, a squarate linker, a triazolo linker, an internal linker such as 2-(4-butylamidofluorescein)propane-1,3-diol bis(phosphodiester) linker, a linker conjugated to a dye, a linker conjugated to a non-fluorescent label, a linker conjugated to a tag or a linker conjugated to a solid support such as for example a bead or microarray. In certain embodiments, at least two of the modifications in the combination comprise a 2'-O-methyl nucleotide and phosphorothioate internucleotide linkage, a 2'-O-methyl nucleotide and phosphonoacetate internucleotide linkage, or a 2'-O-methyl nucleotide and thiophosphonoacetate internucleotide linkage. In certain embodiments, at least two of the modifications in the combination comprise a 2'-O-methyl nucleotide and phosphonocarboxylate internucleotide linkage, a 2'-O-methyl nucleotide and phosphonocarboxylate ester internucleotide linkage, a 2'-O-methyl nucleotide and thiophosphonocarboxylate internucleotide linkage, a 2'-O-methyl nucleotide and thiophosphonocarboxylate ester internucleotide linkage, or combinations thereof. In other embodiments, the modifications in the combination further comprise a 2-thiouracil, 2-thiocytosine, 4-thiouracil, 6-thioguanine, 2-aminoadenine, 2-aminopurine, pseudouracil, inosine, 7-deazaguanine, 7-deaza-8-azaguanine, 7-deazaadenine, 7-deaza-8-azaadenine, 5-methylcytosine, 5-methyluracil, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil, 5-allylcytosine, 5-aminoallyluracil, 5-aminoallyl-cytosine, or an abasic nucleotide.

Figure 6A:
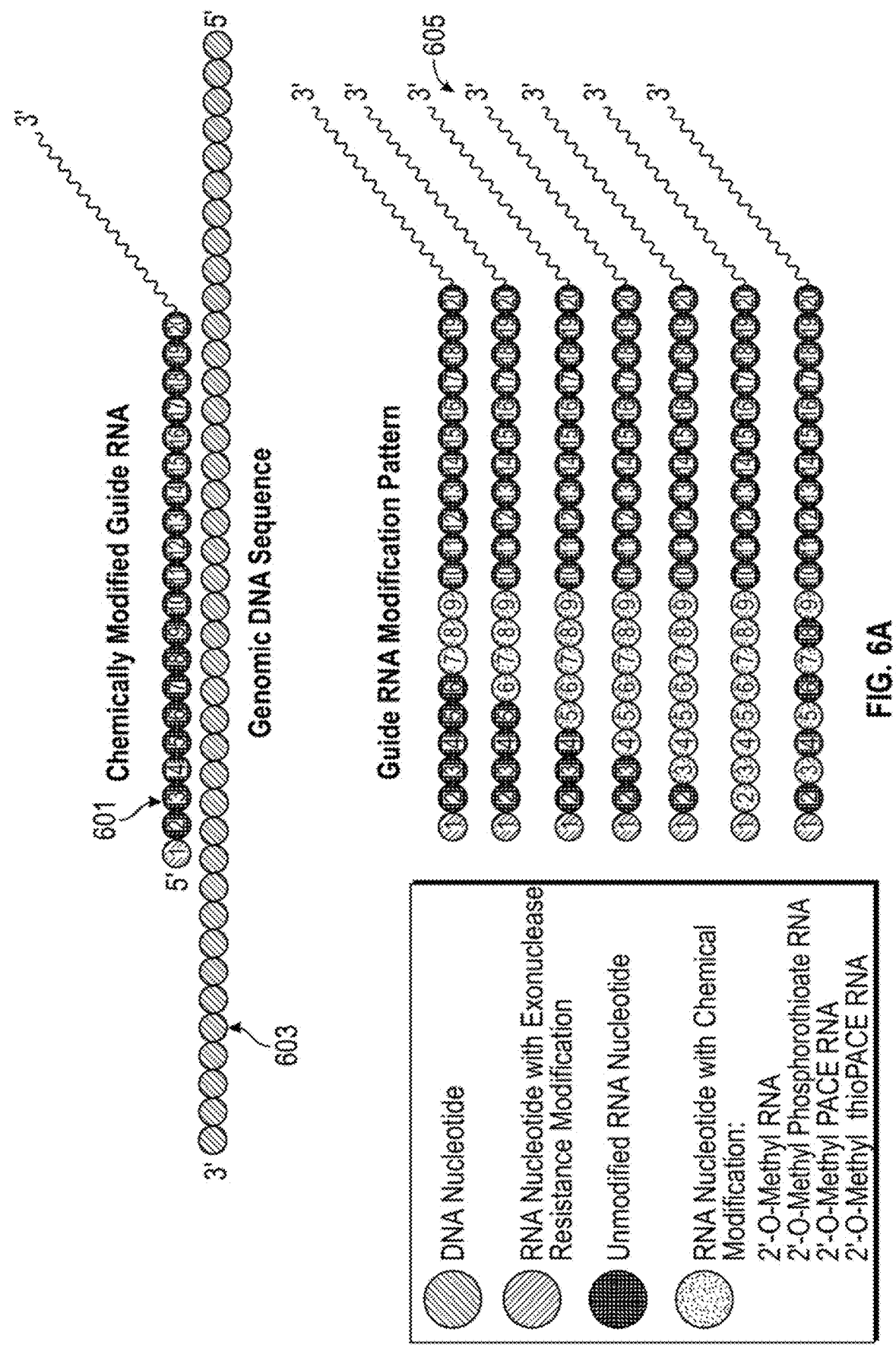
FIG. 6A illustrates experimental crRNA polynucleotides with 20-nucleotide guide sequences and modified by various types of chemical modifications incorporated at various positions in the guide sequence.
Figure 6B:
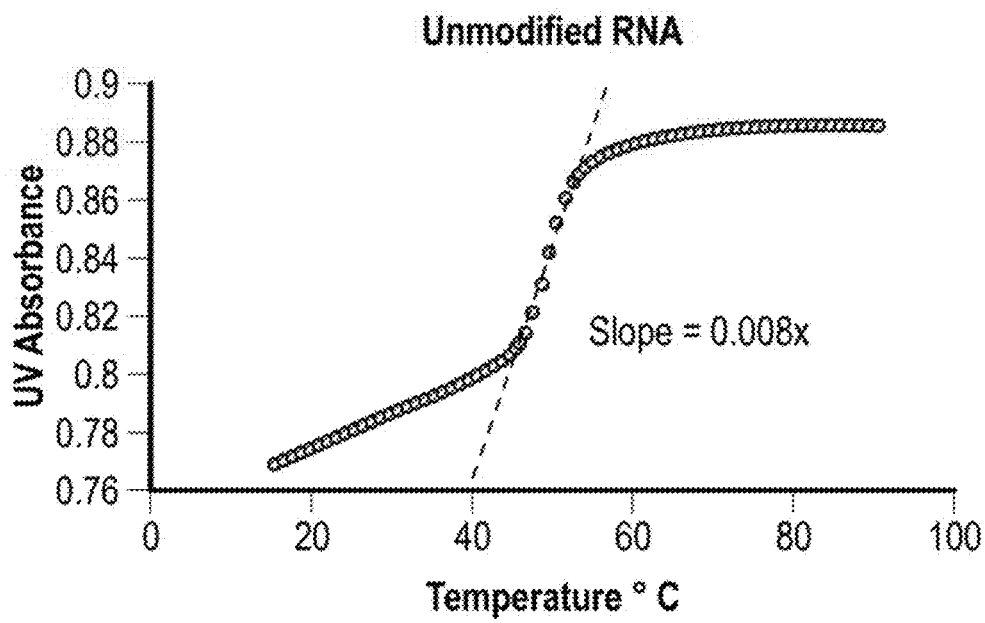
FIG. 6B shows the melting curve for an RNA/DNA duplex comprising an unmodified crRNA.
Figure 6C:
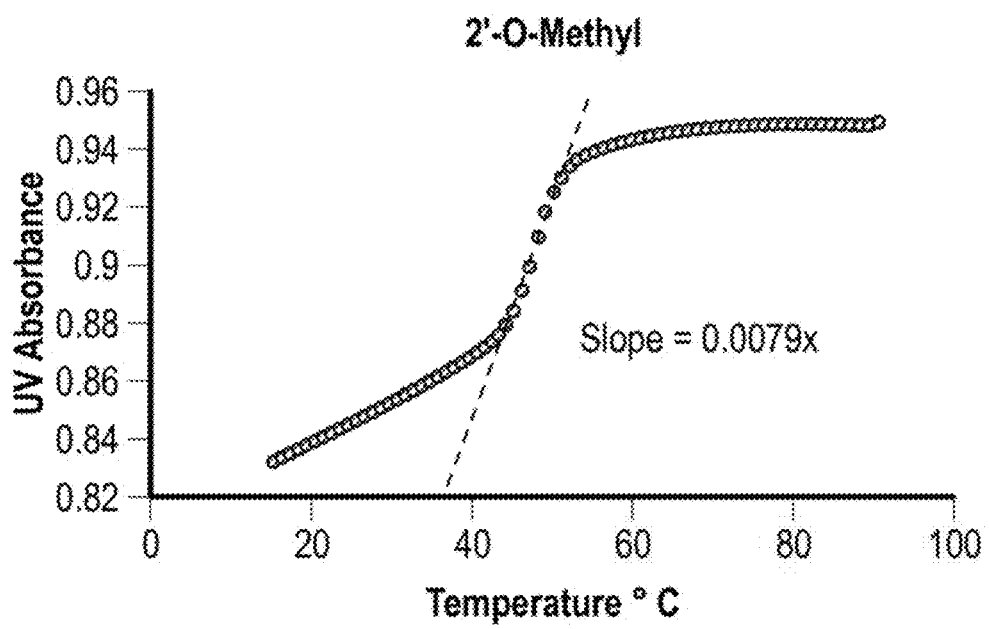
FIGS. 6C through 6F show melting curves for RNA/DNA duplexes comprising chemically modified crRNAs comprising different types of modifications at nucleotides 6 through 9 in distinct guide sequences.
Figure 6D:
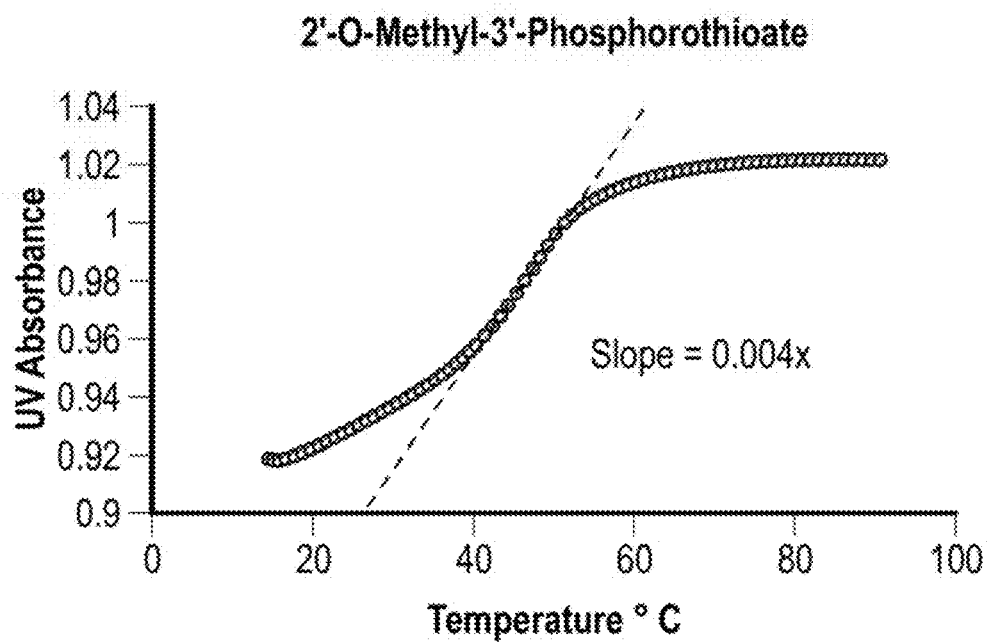
Figure 6E:
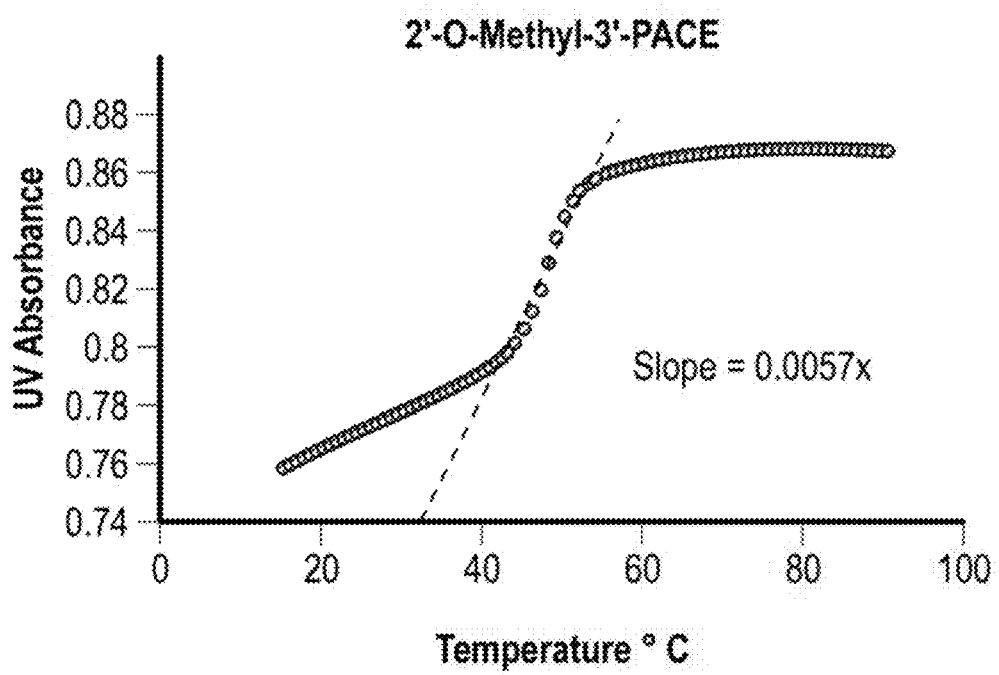
Figure 6F:
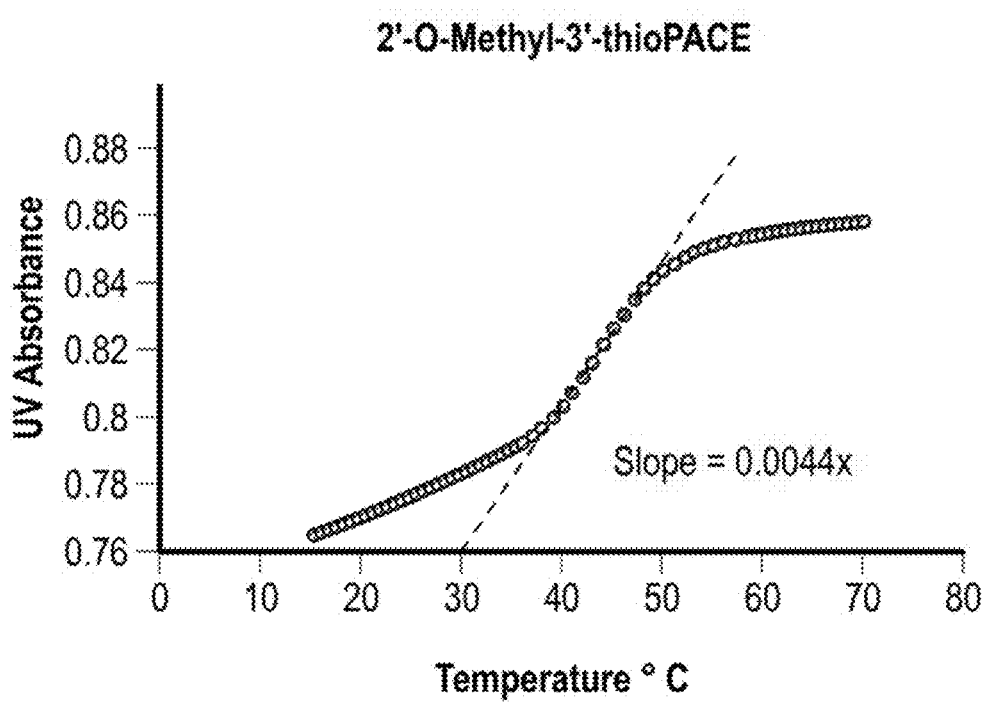
Figure 7:
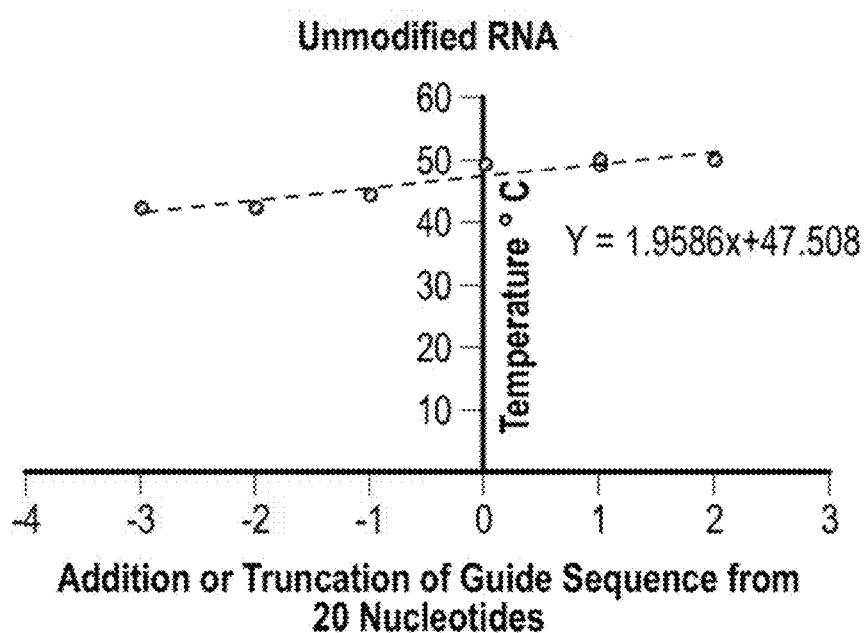
FIG. 7 is a graph showing change in melting temperature of a 20-base pair duplex of guide sequence (in a crRNA) hybridized to a complementary DNA strand after incremental 5' truncation or 5' extension of the guide sequence as indicated on the x-axis by negative or positive integers, respectively.

In certain embodiments, at least one of the modifications in the combination comprises a 2'-O-methyl-3'-phosphorothioate. In certain embodiments, at least one of the modifications in the combination comprises a 2'-O-methyl-3'-phosphonoacetate. In certain embodiments, at least one of the modifications in the combination comprises a 2'-O-methyl-3'-thiophosphonoacetate. In certain embodiments, at least one of the modifications in the combination comprises a 2'-halo-3'-phosphorothioate. In certain embodiments, at least one of the modifications in the combination comprises a 2'-halo-3'-phosphonoacetate. In certain embodiments, at least one of the modifications in the combination comprises a 2'-halo-3'-thiophosphonoacetate. In certain embodiments, at least one of the modifications in the combination comprises a 2'-fluoro-3'-phosphorothioate. In certain embodiments, at least one of the modifications in the combination comprises a 2'-fluoro-3'-phosphonoacetate. In certain embodiments, at least one of the modifications in the combination comprises a 2'-fluoro-3'-thiophosphonoacetate. Possible combinations of at least two or three modifications are represented in FIG. 6 and FIG. 7 respectively and are incorporated herein by reference.

In certain embodiments, the guide RNA comprises an oligonucleotide represented by Formula (III) or Formula (IV):

wherein Q and W each independently represent a nucleotide or a stretch of nucleotides of the oligonucleotide comprising at least one specificity-enhancing modification and Y and X each independently represent an unmodified portion of the oligonucleotide.

In certain embodiments, W is within the 5' portion of the guide RNA. In certain embodiments, W is at least partially within the first five (5) nucleotides of the 5' portion of the guide RNA. In certain embodiments, W is at least partially within the first three (3) nucleotides of the 5' portion of the guide RNA. In certain embodiments, W is within the internal region (i.e., between the 5' end and the 3' end) of the guide RNA. In certain embodiments, W is at least partially within nucleotides 4 to 20, alternatively within nucleotides 5 to 20 of the guide sequence, alternatively within nucleotides 10 to 20 of the guide sequence, alternatively within nucleotides 13 to 20 of the guide sequence, alternatively within nucleotides 13-14 or 16-19 of the guide sequence, alternatively within nucleotides 13-14 or 16-18 of the guide sequence.

In certain embodiments, at least one of the modifications in the combination enhances stability and specificity of the guide RNA relative to a guide RNA without the modification. In certain embodiments, at least one of the modifications in the combination enhances stability and transfection efficiency of the guide RNA relative to a guide RNA without the modification. In certain embodiments, at least one of the modifications in the combination enhances specificity and transfection efficiency of the guide RNA relative to a guide RNA without the modification.

In certain embodiments, at least one of the modifications in the combination alters the secondary structure of the guide RNA. This modification alters the base-pairing of any of the RNA/RNA internal duplexes in the guide RNA. Some of these modifications increase the base pairing of the RNA/RNA structure or alternatively increase the Tm of the RNA/RNA duplex, whereas other modifications decrease the base pairing (or Tm) of the RNA/RNA duplex or duplexes. Such modifications include base modified nucleotides, particularly UNA nucleotides such as the 2-thiouridine and 2-aminoadenosine pair, the Z/P nucleotide pair, the isoC/isoG pair, the 6-thioG/5-methylpyrimidine pair, and nucleotides with modifications on the sugar or the internucleotide linkages as discussed before.

In certain embodiments, the combination includes at least one modification or a set of modifications that increases nucleases resistance (i.e., stability) with at least one modification or a set of modifications that increases specificity (i.e., reduces off-target effects). In certain embodiments, the combination includes at least one modification or a set of modifications that increases nucleases resistance (i.e., stability) with at least one modification or a set of modifications that raises the Tm of some bases pairing in the guide RNA. In certain embodiments, the combination includes at least one modification or a set of modifications that increases nucleases resistance (i.e., stability) with at least one modification or a set of modifications that lowers the Tm of some bases pairing of the guide RNA. In certain embodiments, the combination includes at least one modification or a set of modifications that increases nuclease resistance (i.e., stability), at least one modification or a set of modifications that increases the Tm of some bases paring in the guide RNA, and at least one modification or a set of modifications that decreases the Tm of some base paring elsewhere in the guide RNA. In certain embodiments, the combination includes at least one modification or a set of modifications that increases nuclease resistance (i.e., stability) and at least one modification or a set of modifications that increases the binding of the guide RNA to Cas protein. In certain embodiments, the combination includes at least one modification or a set of modifications that increases nuclease resistance (i.e., stability) and at least one modification or a set of modifications that decreases the binding of the guide RNA to Cas protein. In certain embodiments, the guide RNA comprises a combination of the different types of modifications.

D. Guide RNA Structure

In certain embodiments, the guide RNA is able to form a complex with a CRISPR-associated-protein. In certain embodiments, the CRISPR-associated protein is provided by or is derived from a CRISPR-Cas type 1 system, which has an RNA-guided polynucleotide binding and/or nuclease activity. In certain embodiments, the CRISPR-associated protein is Cas9, a Cas9 mutant, or a Cas9 variant. In certain embodiments, the CRISPR-associated protein is the Cas9 nuclease from *Streptococcus pyogenes*. In certain embodiments, the CRISPR-associated protein is the Cas9 nuclease from *Streptococcus thermophilus*. In certain embodiments, the CRISPR-associated protein is the Cas9 nuclease from *Staphylococcus aureus*. In certain embodiments, the synthetic guide RNA or a synthetic guide RNA:CRISPR-associated protein complex maintains functionality of natural guide RNA or a complex that does not have modified nucleotides. In certain embodiments, the functionality includes binding a target polynucleotide. In certain embodiments, the functionality includes nicking a target polynucleotide. In certain embodiments, the functionality includes cleaving a target polynucleotide. In certain embodiments, the target polynucleotide is within a nucleic acid in vitro. In certain embodiments, the target polynucleotide is within the genome of a cell in vivo or in vitro (such as in cultured cells or cells isolated from an organism). In certain embodiments, the target polynucleotide is a protospacer in DNA.

In certain embodiments, the crRNA segment comprises from 25 to 80 nucleotides. In certain embodiments, the crRNA segment comprises a guide sequence that is capable of hybridizing to a target sequence. In certain embodiments, the guide sequence is complementary to the target sequence or a portion thereof. In certain embodiments, the guide sequence comprises from 15 to 30 nucleotides. In certain embodiments, the crRNA segment comprises a stem sequence. In certain embodiments, the stem sequence comprises from 10 to 50 nucleotides. In certain embodiments, the crRNA segment comprises a 5'-overhang sequence. In certain embodiments, the 5'-overhang sequence comprises from 1 to 10 nucleotides, alternatively 1 to 5 nucleotides, alternatively 1, 2 or 3 nucleotides. In certain embodiments, the crRNA comprises both (i) a guide sequence that is capable of hybridizing to a target sequence and (ii) a stem sequence. In certain embodiments, the crRNA comprises (i) a 5'-overhang sequence, (ii) a guide sequence that is capable of hybridizing to a target sequence, and (iii) a stem sequence. In certain embodiments wherein the crRNA segment comprises a stem sequence, the tracrRNA segment comprises a nucleotide sequence that is partially or completely complementary to the stem sequence of the crRNA segment. In certain embodiments, the tracrRNA segment comprises at least one more duplex structure.

In certain embodiments, the guide RNA is a single-guide RNA, wherein the crRNA segment and the tracrRNA segment are linked through a loop L. In certain embodiments, the loop L comprises 1, 2, 3, 4, 5, 6, 7, 8, 9, or 10 nucleotides. In certain embodiments, the loop L comprises a nucleotide sequence of GNRA, wherein N represents A, C, G, or U and R represents A or G. In certain embodiments, the loop L comprises a nucleotide sequence of GAAA. In certain embodiments, the guide RNA comprises more than one loop.

The guide RNA comprises a 5' portion (i.e., the 5' half) and a 3' portion (i.e., the 3' half). In certain embodiments, the crRNA segment is 5' (i.e., upstream) of the tracrRNA segment. In certain embodiments, the tracrRNA segment is 5' relative to the crRNA segment.

In certain embodiments, the guide RNA comprises at least two separate RNA strands, for example, a crRNA strand and a separate tracrRNA strand. See, for example, FIG. 2A. In certain embodiments, each of the strands is a synthetic strand comprising one or more modifications. In certain embodiments, at least one of the strands is a synthetic strand comprising one or more modifications. In certain embodiments, the strands function together to guide binding, nicking, or cleaving of a target polynucleotide by a Cas protein, such as Cas9. In certain embodiments, the crRNA sequence and the tracrRNA sequence are on separate stands and hybridize to each other via two complementary sequences to form a stem or duplex.

In certain embodiments, the guide RNA is a single-guide RNA comprising a crRNA sequence and a tracrRNA sequence. See, for example, FIG. 2B. In certain embodiments, the crRNA sequence and the tracrRNA sequence are connected by a loop sequence or "loop." In certain embodiments, a single-guide RNA comprises a 5' portion and a 3' portion, wherein the crRNA sequence is upstream of the tracrRNA sequence.

In certain embodiments, the total length of the two RNA pieces can be about 50-220 (e.g., about 55-200, 60-190, 60-180, 60-170, 60-160, 60-150, 60-140, 60-130, and 60-120) nucleotides in length, such as about 60, 70, 80, 90, 100, 110, 120, 130, 140, 150, 160, 170, 180, 190, 200, or 220 nucleotides in length. Similarly, the single-guide RNA (e.g., FIG. 2B) can be about 50-220 (e.g., about 55-200, 60-190, 60-180, 60-170, 60-160, 60-150, 60-140, 60-130, and 60-120) nucleotides in length, such as about 60, 70, 80, 90, 100, 110, 120, 130, 140, 150, 160, 170, 180, 190, 200, or 220 nucleotides in length.

Figure 2A:
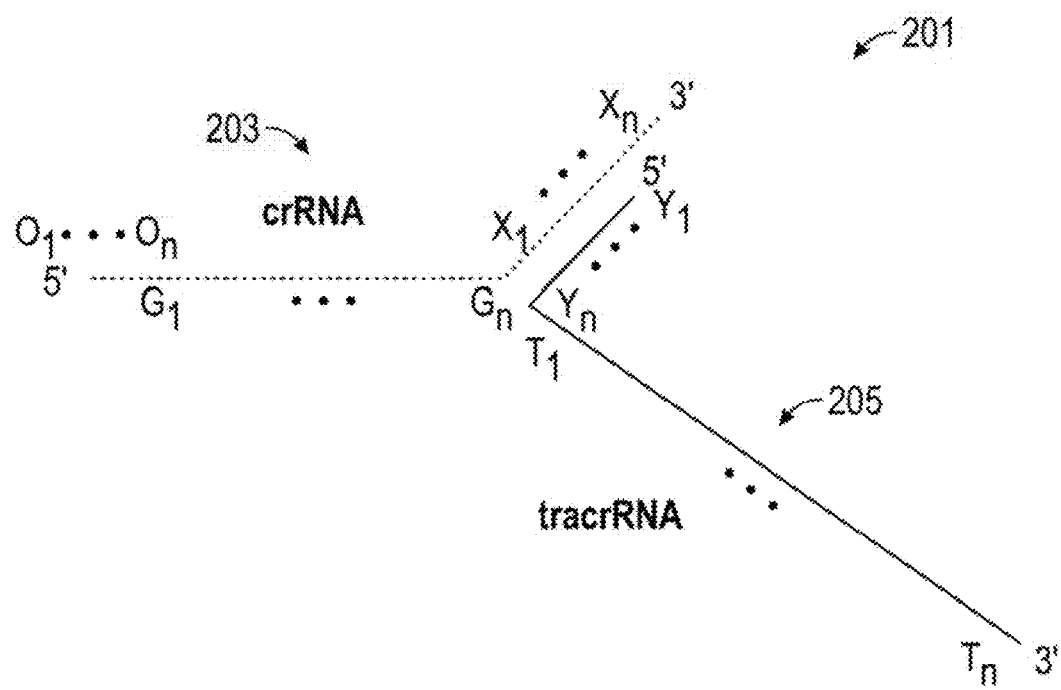
FIG. 2A shows an exemplary guide RNA 201 comprising a crRNA segment 203 and a tracrRNA segment 205.
Figure 2B:
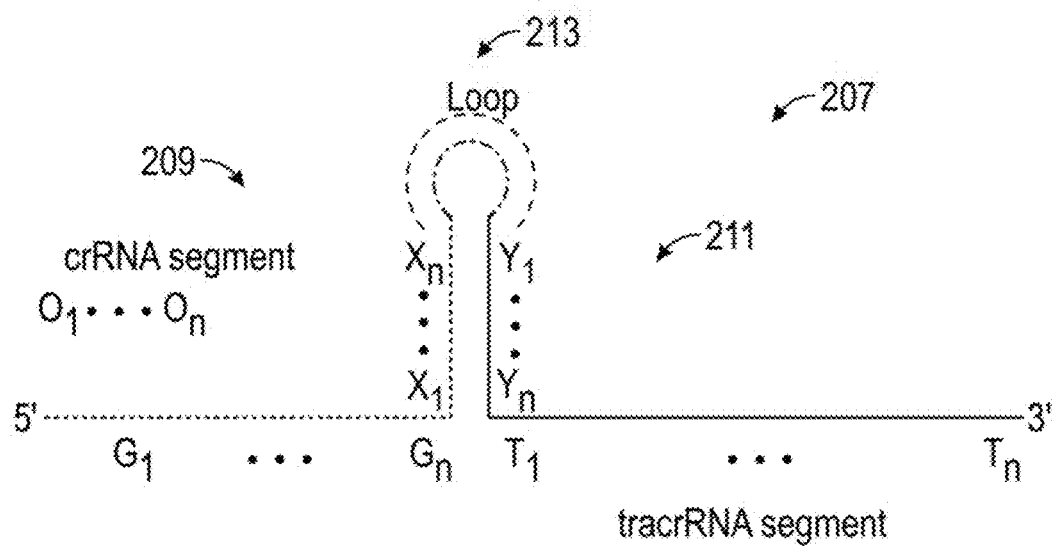
FIG. 2B shows an exemplary single-guide RNA 207 comprising a crRNA segment 209 and a tracrRNA segment 211, wherein the crRNA segment and the tracrRNA segment are linked through a loop 213.
Figure 3:
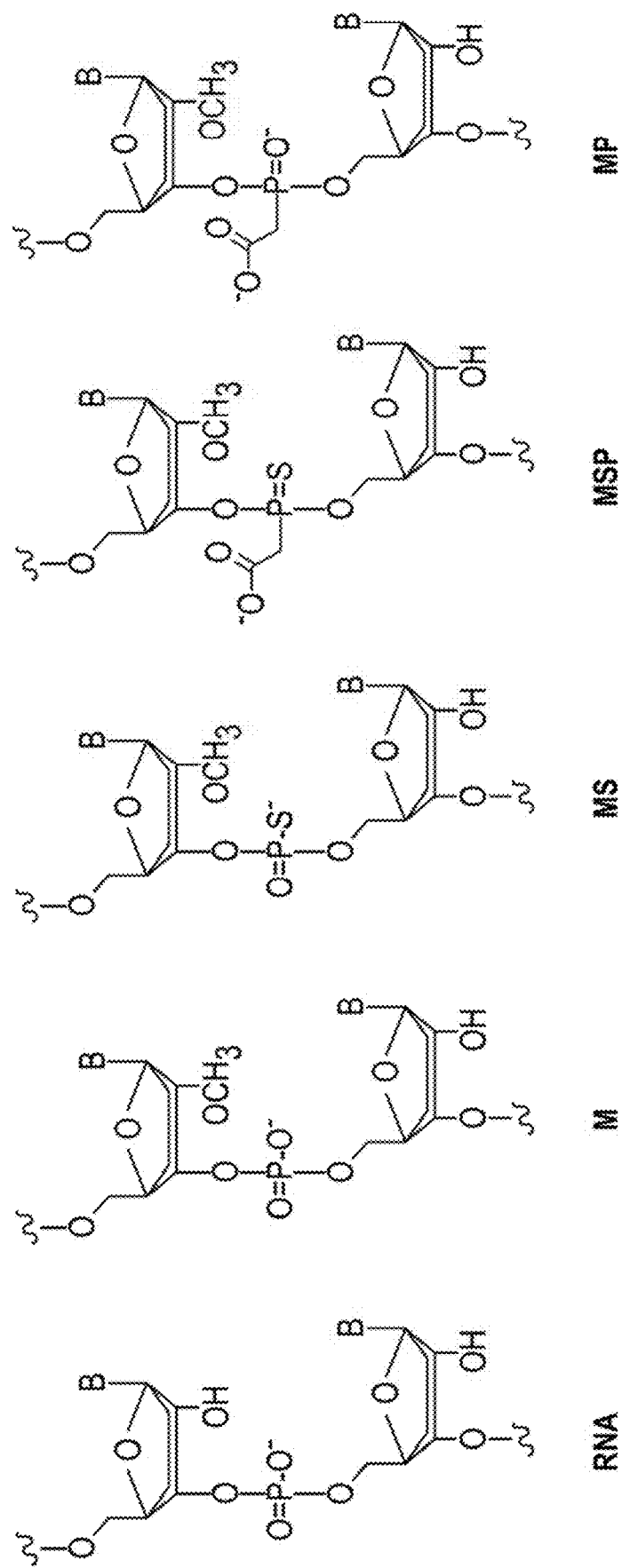
FIG. 3 shows the structures of some of the various chemical modifications that can be included in a guide RNA; of course.

As shown in FIGS. 2A and 2B, the synthetic guide RNA comprises (i) a crRNA sequence that comprises (a) a guide sequence (e.g., segment $G_1$-$G_n$, where each G represents a nucleotide in the guide sequence) capable of hybridizing to a target sequence in a nucleic acid, (b) a first stem sequence (e.g., segment $X_1$-$X_n$, where each X represents a nucleotide in the first stem sequence) capable of hybridizing partially or completely to a second stem sequence, and, optionally (c) a 5'-overhang sequence (e.g., segment $O_1$-$O_n$, where each O represents a nucleotide in the overhang sequence), and (ii) a tracrRNA sequence that comprises the second stem sequence (e.g., segment $Y_1$-$Y_n$, where each Y represents a nucleotide in the second stem sequence). The tracrRNA sequence further comprises segment $T_1$-$T_n$, where each T represents a nucleotide in the tracrRNA sequence. The synthetic guide RNA shown in FIG. 2A includes one or more modifications. Likewise, the synthetic guide RNA shown in FIG. 2B includes one or more modifications. In certain embodiments, the modification is located at any point along the length of the crRNA, the tracrRNA, or the single-guide RNA comprising a crRNA segment, a tracrRNA segment, and, optionally, a loop. In certain embodiments, any nucleotide represented by O, G, X, Y, or T in the synthetic guide RNA shown in FIGS. 2A and 2B may be a modified nucleotide. The guide RNA shown in FIG. 2B represents a single-guide RNA (sgRNA) where the crRNA segment and the tracrRNA segment are connected by a loop having the sequence GNRA, wherein N represents A, C, G, or U, and R represents A or G.

In certain embodiments, the crRNA segment of the guide RNA is 25-70 (e.g., 30-60, 35-50, or 40-45) nucleotides in length. In certain embodiments, the guide sequence is 12-30 (e.g., 16-25, 17-20, or 15-18) nucleotides in length. In some embodiments, a 5' portion of the crRNA does not hybridize or only partially hybridizes with the target sequence. For example, there can be a 5'-overhang on the crRNA segment.

In certain embodiments, the single-guide RNA comprises a central portion including the stem sequence of the crRNA segment, the stem sequence of the tracrRNA segment, and, optionally, a loop that covalently connects the crRNA segment to the tracrRNA segment. In certain embodiments, the central segment of the single-guide RNA is 8-60 (e.g., 10-55, 10-50, or 20-40) nucleotides in length.

In certain embodiments, the tracrRNA segment of the guide RNA is 10-130 (e.g., 10-125, 10-100, 10-75, 10-50, or 10-25) nucleotides in length. In certain embodiments, the tracrRNA segment includes one or more hairpin or duplex structures in addition to any hairpin or duplex structure in the central segment.

E. Synthesis of Guide RNA

In certain embodiments, guide RNAs, including single-guide RNAs are produced by chemical synthesis using the art of synthetic organic chemistry. A guide RNA that comprises any nucleotide other than the four predominant ribonucleotides, namely A, C, G, and U, whether unnatural or natural, such as a pseudouridine, inosine or a deoxynucleotide, possesses a chemical modification or substitution at the nucleotide which is chemically/structurally distinct from any of the four predominant nucleotides in RNAs.

The synthetic guide RNAs described herein can be chemically synthesized using methods well-known in the art (such as TBDMS chemistry, TOM Chemistry, ACE chemistry, etc.). For example, the synthetic guide RNAs can be synthesized using TC chemistry by the method described in Dellinger et al. (2011) *J. Am. Chem. Soc.* 133, 11540; U.S. Pat. No. 8,202,983; and US Patent Application 2010/0076183A1, the contents of which are incorporated by reference in their entireties. "TC chemistry" refers to the composition and methods of using RNA monomeric nucleotide precursors protected on the 2'-hydroxyl moiety by a thionocarbamate protecting group, to synthesize unmodified RNA or modified RNA comprising one or more modified nucleotides. The ability to chemically synthesize relatively long RNAs (as long as 200-mers or more) using TC-RNA chemistry allows one to produce guide RNAs with special features capable of outperforming those enabled by the four predominant ribonucleotides (A, C, G and U). Some synthetic guide RNAs described herein can also be made using methods known in the art that include in vitro transcription and cell-based expression. For example, 2'-fluoro NTPs can be incorporated into synthetic guide RNAs produced by cell-based expression.

Synthesis of guide RNAs can also be accomplished by chemical or enzymatic synthesis of RNA sequences that are subsequently ligated together by enzymes, or chemically ligated by chemical ligation, including but not limited to cyanogen bromide chemistry, "click" chemistry as published by R. Kumar et al. (2007) *J. Am. Chem. Soc.* 129, 6859-64, or squarate conjugation chemistry as described by K. Hill in WO2013176844 titled "Compositions and methods for conjugating oligonucleotides."

In certain embodiments, methods are provided for preparing a synthetic guide RNA. The methods comprise selecting a target polynucleotide in a genome; identifying one or more off-target polynucleotide in the genome; identifying one or more shared nucleotide residues, wherein the shared nucleotide residues are present in both the target polynucleotide and the off-target polynucleotide; and designing a synthetic guide RNA, wherein the guide sequence includes a specificity-enhancing modification. The methods can comprise synthesizing the designed guide RNA. In certain embodiments, the off-target polynucleotide is identified by an algorithm to predict off-target sites as well as their severity such as those found at http://www.rgenome.net/Cas-OFFinder; https://cm.jefferson.edu/Off-Spotter; or http://crispr.mit.edu, or other technique for identifying and quantifying the activation of off-target sites in actual cases, as disclosed in Tsai et al. (2015) *Nat. Biotechnol.* 33, 187-97; Ran et al. (2015) *Nature* 520, 186-91; Frock et al. (2015) *Nat. Biotechnol.* 33, 179-86. In certain embodiments, the method further comprises identifying at least one distinguishing position between the sequences of the target polynucleotide and the off-target polynucleotide, wherein the target polynucleotide and the off-target polynucleotide have a different nucleotide residue at the at least one distinguishing position, and including in the synthetic guide RNA a nucleotide matching (i.e., complementary to) the nucleotide at the at least one distinguishing position in the target polynucleotide.

As further described below, a guide RNA disclosed herein, including those comprising modified nucleotides and/or modified internucleotide linkages, can be used to perform various CRISPR-mediated functions (including but not limited to editing genes, regulating gene expression, cleaving target sequences, and binding to target sequences) in vitro or in vivo, such as in cell-free assays, in intact cells, or in whole organisms. For in vitro or in vivo applications, the RNA can be delivered into cells or whole organisms in any manner known in the art.

Libraries and Arrays

In one aspect, the present invention provides a set or library of multiple guide RNAs. In certain embodiments, the library contains two or more guide RNAs disclosed herein. The library can contain from about 10 to about 10' individual members, e.g., about 10 to about $10^2$, about $10^2$ to about $10^3$, about $10^3$ to about $10^5$, from about $10^5$ to about $10^7$ members. An individual member of the library differs from other members of the library at least in the guide sequence, i.e., the DNA targeting segment of the gRNA. On the other hand, in certain embodiments, each individual member of a library can contain the same or substantially the same nucleotide sequence for the tracrRNA segment as all the other members of the library. In this way, the library can comprise members that target different polynucleotides or different sequences in one or more polynucleotides.

In certain embodiments, the library comprises at least $10^2$ unique guide sequences. In certain embodiments, the library comprises at least $10^3$ unique guide sequences. In certain embodiments, the library comprises at least $10^4$ unique guide sequences. In certain embodiments, the library comprises at least $10^5$ unique guide sequences. In certain embodiments, the library comprises at least $10^6$ unique guide sequences. In certain embodiments, the library comprises at least $10^7$ unique guide sequences. In certain embodiments, the library targets at least 10 different polynucleotides. In certain embodiments, the library targets at least $10^2$ different polynucleotides. In certain embodiments, the library targets at least $10^3$ different polynucleotides. In certain embodiments, the library targets at least $10^4$ different polynucleotides. In certain embodiments, the library targets at least $10^5$ different polynucleotides. In certain embodiments, the library targets at least 10' different polynucleotides. In certain embodiments, the library targets at least $10^7$ different polynucleotides.

In certain embodiments, the library comprises a collection of guide RNAs having the same sequence and the same modifications in a progressively shifted window that moves across the sequence of the members in the library. In certain embodiments, the windows collectively cover the entire length of the RNA.

In certain embodiments, the library allows one to conduct high-throughput, multi-target genomic manipulations and analyses. In certain embodiments, only the DNA-targeting segments of the guide RNAs are varied, while the Cas protein-binding segment is the same. In certain embodiments, a first portion of the library comprises guide RNAs possessing a Cas-binding segment that recognizes, binds and directs a particular Cas protein and a second portion of the library comprises a different Cas-binding segment that recognizes, binds and directs a different Cas protein (e.g., a Cas protein from a different species), thereby allowing the library to function with two or more orthogonal Cas proteins. In certain embodiments, induced expression of a first orthogonal Cas protein utilizes the portion of the library which interacts with the first orthogonal Cas protein. In certain embodiments, induced expression of a first and second orthogonal Cas protein utilizes the portions of the library which interact with the first and second orthogonal Cas proteins, respectively. In certain embodiments, induced expression of the first and second orthogonal Cas proteins occur at different times. Accordingly, one can carry out large-scale gene editing or gene regulation by specifically manipulating or modifying multiple targets as specified in the library.

In certain embodiments, the library is an "arrayed" library, namely a collection of different features or pools of features in an addressable arrangement. For example, features of an array can be selectively cleaved and transferred to a microtiter plate such that each well in the plate contains a known feature or a known pool of features. In some other embodiments, the library is synthesized in a 48-well or in a 96-well microtiter plate format or in a 384-well plate.

In certain embodiments, synthesis of the guide RNA of this invention may be conducted on a solid support having a surface to which chemical entities may bind. In some embodiments, guide RNAs being synthesized are attached, directly or indirectly, to the same solid support and may form part of an array. An "array" is a collection of separate molecules of known monomeric sequence each arranged in a spatially defined and a physically addressable manner, such that the location of each sequence is known. An "array," or "microarray' used interchangeably herein includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. An array is "addressable" when it has multiple regions of different moieties (e.g., different polynucleotide sequences) such that a region (i.e., a "feature" of the array) at a particular predetermined location (i.e., an "address") on the array will detect a particular target or class of targets (although a feature may incidentally detect non-targets of that feature). Array features are typically, but need not be, separated by intervening spaces. The number of features that can be contained on an array will largely be determined by the surface area of the substrate, the size of a feature and the spacing between features. Arrays can have densities of up to several hundred thousand or more features per $cm^2$, such as 2,500 to 200,000 features/$cm^2$. The features may or may not be covalently bonded to the substrate.

Suitable solid supports may have a variety of forms and compositions and derive from naturally occurring materials, naturally occurring materials that have been synthetically modified, or synthetic materials. Examples of suitable support materials include, but are not limited to, silicas, silicon and silicon oxides, teflons, glasses, polysaccharides such as agarose (e.g., Sepharose® from Pharmacia) and dextran (e.g., Sephadex® and Sephacyl®, also from Pharmacia), polyacrylamides, polystyrenes, polyvinyl alcohols, copolymers of hydroxyethyl methacrylate and methyl methacrylate, and the like. In some embodiments, the solid support is a plurality of beads.

The initial monomer of the guide RNAs to be synthesized on the substrate surface can be bound to a linker which in turn is bound to a surface hydrophilic group, e.g., a surface hydroxyl moiety present on a silica substrate. In some embodiments, a universal linker is used. In some other embodiments, the initial monomer is reacted directly with a surface hydroxyl moiety, surface amine or other reactive functional group. Alternatively, guide RNAs can be synthesized first according to the present invention, and attached to a solid substrate post-synthesis by any method known in the art. Thus, the present invention can be used to prepare arrays of guide RNAs wherein the oligonucleotides are either synthesized on the array, or attached to the array substrate post-synthesis. Subsequently, the guide RNAs or a pool or a plurality of pools of guide RNAs can optionally and selectively be cleaved from the array substrate and be used as a library or libraries.

F. crRNA

The present invention also provides various crRNAs that comprise the chemical modification(s) as described for guide RNAs, as described herein. The crRNAs can function in a multi-segment guide RNA, such as a dual guide. Thus, in certain embodiments, the present invention provides a synthetic crRNA comprising (i) a guide sequence capable of hybridizing to a target polynucleotide, the target polynucleotide comprising a target sequence adjacent to a PAM site, and (ii) a stem sequence; wherein the guide sequence consists of 20-N nucleotides, where N is an integer between −10 and 10 (optionally between −10 and 6); wherein the guide sequence comprises at least one modification, and the crRNA results in higher specificity for the target polynucleotide or higher gRNA functionality than a corresponding crRNA without the modification. Here, the crRNA results in higher specificity for the target polynucleotide or higher gRNA functionality than a corresponding crRNA without the modification if, when the crRNA is included in a guide RNA or a gRNA:cas protein complex, the guide RNA or gRNA:cas protein has higher specificity for the target polynucleotide or higher gRNA functionality than a corresponding guide RNA or gRNA:cas protein complex in which the crRNA lacks the modification.

The modifications of interest are described elsewhere in this disclosure, including but not limited to at least one modification at nucleotides 4-N to 20-N, or at at least one nucleotide selected from 4-N, 5-N, 7-N, 9-N, 10-N and 11-N, of the guide sequence. Various embodiments of the particular modification(s) and target polynucleotides are also described herein.

IV. Cas Proteins

As mentioned above, a functional CRISPR-Cas system also requires a protein component (e.g., a Cas protein, which may be a Cas nuclease) that provides a desired activity, such as target binding or target nicking/cleaving. In certain embodiments, the desired activity is target binding. In certain embodiments, the desired activity is target nicking or target cleaving. In certain embodiments, the desired activity also includes a function provided by a polypeptide that is covalently fused to a Cas protein, as disclosed herein. In certain embodiments, the desired activity also includes a function provided by a polypeptide that is covalently fused to a nuclease-deficient Cas protein, as disclosed herein. Examples of such a desired activity include a transcription regulation activity (either activation or repression), an epigenetic modification activity, or a target visualization/identification activity, as described below. The Cas protein can be introduced into an in vitro or in vivo system as a purified or non-purified (i) Cas protein or (ii) mRNA encoded for expression of the Cas protein or (iii) linear or circular DNA encoded for expression of the protein. Any of these 3 methods of providing the Cas protein are well known in the art and are implied interchangeably when mention is made herein of a Cas protein or use of a Cas protein. In certain embodiments, the Cas protein is constitutively expressed from mRNA or DNA. In certain embodiments, the expression of Cas protein from mRNA or DNA is inducible or induced.

In certain embodiments, the Cas protein is chemically synthesized (see e.g., Creighton, "Proteins: Structures and Molecular Principles," W.H. Freeman & Co., NY, 1983), or produced by recombinant DNA technology as described herein. For additional guidance, skilled artisans may consult Frederick M. Ausubel et al., "Current Protocols in Molecular Biology," John Wiley & Sons, 2003; and Sambrook et al., "Molecular Cloning, A Laboratory Manual," Cold Spring Harbor Press, Cold Spring Harbor, N.Y., 2001).

In certain embodiments, the Cas protein is provided in purified or isolated form. In certain embodiments, the Cas protein is provided at about 80%, about 90%, about 95%, or about 99% purity. In certain embodiments, the Cas protein is provided as part of a composition. In certain embodiments, the Cas protein is provided in aqueous compositions suitable for use as, or inclusion in, a composition for an RNA-guided nuclease reaction. Those of skill in the art are well aware of the various substances that can be included in such nuclease reaction compositions.

In certain embodiments, a Cas protein is provided as a recombinant polypeptide. In certain examples, the recombinant polypeptide is prepared as a fusion protein. For example, in certain embodiments, a nucleic acid encoding the Cas protein is linked to another nucleic acid encoding a fusion partner, e.g., glutathione-S-transferase (GST), 6x-His epitope tag, or M13 Gene 3 protein. Suitable host cells can be used to expresses the fusion protein. In certain embodiments, the fusion protein is isolated by methods known in the art. In certain embodiments, the fusion protein can be further treated, e.g., by enzymatic digestion, to remove the fusion partner and obtain the Cas protein. Alternatively, Cas protein:gRNA complexes can be made with recombinant technology using a host cell system or an in vitro translation-transcription system known in the art. Details of such systems and technology can be found in e.g., WO2014144761 WO2014144592, WO2013176772, US20140273226, and US20140273233, the contents of which are incorporated herein by reference in their entireties.

Wild Type Cas Proteins

In certain embodiments, a Cas protein comprises a protein derived from a CRISPR-Cas type I, type II, or type III system, which has an RNA-guided polynucleotide binding and/or nuclease activity. Non-limiting examples of suitable Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cul966. See e.g., WO2014144761 WO2014144592, WO2013176772, US20140273226, and US20140273233, the contents of which are incorporated herein by reference in their entireties.

In certain embodiments, the Cas protein is derived from a type II CRISPR-Cas system. In certain embodiments, the Cas protein is or is derived from a Cas9 protein. In certain embodiments, the Cas protein is or is derived from a bacterial Cas9 protein, including those identified in WO2014144761. In certain embodiments, the Cas protein is or is derived from a *Streptococcus* sp. or *Staphylococcus* sp. Cas9 protein. In certain embodiments, the Cas protein is or is derived from the *Streptococcus thermophilus* Cas9 protein. In certain embodiments, the Cas protein is or is derived from the *Streptococcus pyogenes* Cas9 protein. In certain embodiments, the Cas protein is or is derived from the *Staphylococcus aureus* Cas9 protein. In certain embodiments, the Cas protein is or is derived from the *Streptococcus thermophilus* Cas9 protein.

In certain embodiments, the wild type Cas protein is a Cas9 protein. In certain embodiments, the wild type Cas9 protein is the Cas9 protein from *S. pyogenes* (SEQ ID NO: 115). In certain embodiments, the protein or polypeptide can comprise, consist of, or consist essentially of a fragment of SEQ ID NO: 115.

In general, a Cas protein includes at least one RNA binding domain, which interacts with the guide RNA. In certain embodiments, the Cas protein is modified to increase nucleic acid binding affinity and/or specificity, alter an enzymatic activity, and/or change another property of the protein. For example, nuclease (i.e., DNase, RNase) domains of the Cas protein can be modified, mutated, deleted, or inactivated. Alternatively, the Cas protein can be truncated to remove domains that are not essential for the function of the protein. In certain embodiments, the Cas protein is truncated or modified to optimize the activity of the effector domain. In certain embodiments, the Cas protein includes a nuclear localization sequence (NLS) that effects importation of the NLS-tagged Cas protein into the nucleus of a living cell. In certain embodiments, the Cas protein includes two or more modifications.

Mutant Cas Proteins

In some embodiments, the Cas protein can be a mutant of a wild type Cas protein (such as Cas9) or a fragment thereof. In other embodiments, the Cas protein can be derived from a mutant Cas protein. For example, the amino acid sequence of the Cas9 protein can be modified to alter one or more properties (e.g., nuclease activity, binding affinity, stability to proteases, etc.) of the protein. Alternatively, domains of the Cas9 protein not involved in RNA-guided cleavage can be eliminated from the protein such that the modified Cas9 protein is smaller than the wild type Cas9 protein. For example, reducing the size of the Cas9 coding sequence can allow it to fit within a transfection vector that otherwise cannot accommodate the wild-type sequence, such as the AAV vector among others. In some embodiments, the present system utilizes the Cas9 protein from S. pyogenes, either as encoded in bacteria or codon-optimized for expression in eukaryotic cells. Shown below is the amino acid sequence of wild type S. pyogenes Cas9 protein sequence (SEQ ID NO: 115, available at www.uniprot.org/uniprot/Q99ZW2).

MDRKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGTRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQEYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNFLALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD

A Cas9 protein generally has at least two nuclease (e.g., DNase) domains. For example, a Cas9 protein can have a RuvC-like nuclease domain and an HNH-like nuclease domain. The RuvC and HNH domains work together to cut both strands in a target site to make a double-stranded break in the target polynucleotide. (Jinek et al., Science 337: 816-21). In certain embodiments, a mutant Cas9 protein is modified to contain only one functional nuclease domain (either a RuvC-like or an HNH-like nuclease domain). For example, in certain embodiments, the mutant Cas9 protein is modified such that one of the nuclease domains is deleted or mutated such that it is no longer functional (i.e., the nuclease activity is absent). In some embodiments where one of the nuclease domains is inactive, the mutant is able to introduce a nick into a double-stranded polynucleotide (such protein is termed a "nickase") but not able to cleave the double-stranded polynucleotide. For example, an aspartate to alanine (D10A) conversion in a RuvC-like domain converts the Cas9-derived protein into a nickase. Likewise, a histidine to alanine (H840A) conversion in a HNH domain converts the Cas9-derived protein into a nickase. Likewise, an arsparagine to alanine (N863A) conversion in a HNH domain converts the Cas9-derived protein into a nickase.

In certain embodiments, both the RuvC-like nuclease domain and the HNH-like nuclease domain are modified or eliminated such that the mutant Cas9 protein is unable to nick or cleave the target polynucleotide. In certain embodiments, all nuclease domains of the Cas9-derived protein are modified or eliminated such that the Cas9-derived protein lacks all nuclease activity. In certain embodiments, a Cas9 protein that lacks some or all nuclease activity relative to a wild-type counterpart, nevertheless, maintains target recognition activity to a greater or lesser extent.

In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In certain embodiments, the "Cas mutant" or "Cas variant" is at least 50% (e.g., any number between 50% and 100%, inclusive, e.g., 50%, 60%, 70%, 80%, 90%, 95%, 98%, and 99%) identical to SEQ ID NO: 115. In certain embodiments, the "Cas mutant" or "Cas variant" binds to an RNA molecule (e.g., a sgRNA). In certain embodiments, the "Cas mutant" or "Cas variant" is targeted to a specific polynucleotide sequence via the RNA molecule.

Fusion Proteins

In certain embodiments, the Cas protein is fused to another protein or polypeptide heterologous to the Cas protein to create a fusion protein. In certain embodiments, the heterologous sequence includes one or more effector domains, such as a cleavage domain, a transcriptional activation domain, a transcriptional repressor domain, or an epigenetic modification domain. Additional examples of the effector domain include a nuclear localization signal, cell-penetrating or translocation domain, or a marker domain. In certain embodiments, the effector domain is located at the N-terminal, the C-terminal, or in an internal location of the fusion protein. In certain embodiments, the Cas protein of the fusion protein is or is derived from a Cas9 protein. In certain embodiments, the Cas protein of the fusion protein is or is derived from a modified or mutated Cas protein in which all the nuclease domains have been inactivated or deleted. In certain embodiments, the Cas protein of the fusion protein is or is derived from a modified or mutated Cas protein that lacks nuclease activity. In certain embodiments, the RuvC and/or HNH domains of the Cas protein are modified or mutated such that they no longer possess nuclease activity.

Cleavage Domains

In certain embodiments, the effector domain of the fusion protein is a cleavage domain. As used herein, a "cleavage domain" refers to a domain that cleaves DNA. The cleavage domain can be obtained from any endonuclease or exonuclease. Non-limiting examples of endonucleases from which a cleavage domain can be derived include restriction endonucleases and homing endonucleases. See, for example, New England Biolabs Catalog or Belfort et al. (1997) *Nucleic Acids Res.* 25, 3379-88. Additional enzymes that cleave DNA are known (e.g., 51 Nuclease; mung bean nuclease; pancreatic DNase I; micrococcal nuclease; yeast HO endonuclease). See also Linn et al. (eds.) "Nucleases," Cold Spring Harbor Laboratory Press, 1993. One or more of these enzymes (or functional fragments thereof) can be used as a source of cleavage domains.

In certain embodiments, the cleavage domain can be derived from a type II-S endonuclease. Type II-S endonucleases cleave DNA specifically at sites that are typically several base pairs away from the DNA recognition site of the endonuclease and, as such, have separable recognition and cleavage domains. These enzymes generally are monomers that transiently associate to form dimers to cleave each strand of DNA at staggered locations. Non-limiting examples of suitable type II-S endonucleases include BfiI, BpmI, BsaI, BsgI, BsmBI, BsmI, BspMI, FokI, MboII, and SapI. In certain embodiments, the cleavage domain of the fusion protein is a FokI cleavage domain or a fragment or derivative thereof. See Miller et al. (2007) *Nat. Biotechnol.* 25, 778-85; Szczpek et al. (2007) *Nat. Biotechnol.* 25, 786-93; Doyon et al. (2011) *Nat. Methods,* 8, 74-81.

Transcriptional Activation Domains

In certain embodiments, the effector domain of the fusion protein is a transcriptional activation domain. In general, a transcriptional activation domain interacts with transcriptional control elements and/or transcriptional regulatory proteins (i.e., transcription factors, RNA polymerases, etc.) to increase and/or activate transcription of a gene. In certain embodiments, the transcriptional activation domain is a herpes simplex virus VP16 activation domain, VP64 (which is a tetrameric derivative of VP16), a NFκB p65 activation domain, p53 activation domains 1 and 2, a CREB (cAMP response element binding protein) activation domain, an E2A activation domain, or an NFAT (nuclear factor of activated T-cells) activation domain. In certain embodiments, the transcriptional activation domain is Gal4, Gcn4, MLL, Rtg3, Gln3, Oaf1, Pip2, Pdr1, Pdr3, Pho4, or Leu3. The transcriptional activation domain may be wild type, or it may be a modified or truncated version of the original transcriptional activation domain.

Transcriptional Repressor Domains

In certain embodiments, the effector domain of the fusion protein is a transcriptional repressor domain. In general, a transcriptional repressor domain interacts with transcriptional control elements and/or transcriptional regulatory proteins (i.e., transcription factors, RNA polymerases, etc.) to decrease and/or prohibit transcription of a gene. In certain embodiments, the transcriptional repressor domains is inducible cAMP early repressor (ICER) domains, Kruppel-associated box A (KRAB-A) repressor domains, YY1 glycine rich repressor domains, Sp1-like repressors, E(spI) repressors, IκB repressor, or MeCP2.

Epigenetic Modification Domains

In certain embodiments, the effector domain of the fusion protein is an epigenetic modification domain. In general, epigenetic modification domains alter gene expression by modifying the histone structure and/or chromosomal structure. In certain embodiments, the epigenetic modification domains is a histone acetyltransferase domain, a histone deacetylase domain, a histone methyltransferase domain, a histone demethylase domain, a DNA methyltransferase domain, or a DNA demethylase domain.

Additional Domains

In certain embodiments, the fusion protein further comprises at least one additional domain. Non-limiting examples of suitable additional domains include nuclear localization signals (NLSs), cell-penetrating or translocation domains, and marker domains. An NLS generally comprises a stretch of basic amino acids. See, e.g., Lange et al. (2007) *J. Biol. Chem.* 282, 5101-5. For example, in certain embodiments, the NLS is a monopartite sequence, such as PKKKRKV (SEQ ID NO: 116) or PKKKRRV (SEQ ID NO: 117). In certain embodiments, the NLS is a bipartite sequence. In certain embodiments, the NLS is KRPAATKKAGQAKKKK (SEQ ID NO: 118).

In certain embodiments, the fusion protein comprises at least one cell-penetrating domain. In certain embodiments, the cell-penetrating domain is a cell-penetrating peptide sequence derived from the HIV-1 TAT protein. As an example, the TAT cell-penetrating sequence can be GRKKRRQRRRPPQPKKKRKV (SEQ ID NO: 119). In certain embodiments, the cell-penetrating domain is TLM (PLSSIFSRIGDPPKKKRKV; SEQ ID NO: 120), a cell-penetrating peptide sequence derived from the human hepatitis B virus. In certain embodiments, the cell-penetrating domain is MPG (GALFLGWLGAAGSTMGAPKKKRKV; SEQ ID NO: 121 or GALFLGFLGAAGSTMGAWSQPKKKRKV; SEQ ID NO: 122). In certain embodiments, the cell-penetrating domain is Pep-1 (KETWWETWWTEWSQPKKKRKV; SEQ ID NO: 123), VP22, a cell penetrating peptide from Herpes simplex virus, or a polyarginine peptide sequence.

In certain embodiments, the fusion protein comprises at least one marker domain. Non-limiting examples of marker domains include fluorescent proteins, purification tags, and epitope tags. In certain embodiments, the marker domain is a fluorescent protein. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1), blue fluorescent proteins (e.g. EBFP, EBFP2, Azurite, mKalama1, GFPuv, Sapphire, T-sapphire), cyan fluorescent proteins (e.g. ECFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), orange fluorescent proteins (mOrange, mKO, Kusabira-Orange, Monomeric Kusabira-Orange, mTangerine, tdTomato) and any other suitable fluorescent protein. In certain embodiments, the marker domain is a purification tag and/or an epitope tag. Exemplary tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, biotin carboxyl carrier protein (BCCP), and calmodulin.

V. Uses and Methods

In one aspect, the present invention provides a method for cleaving a target polynucleotide with a Cas protein. The method comprises contacting the target polynucleotide with (i) a guide RNA or a set of guide RNA molecules described herein, and (ii) a Cas protein. In certain embodiments, the method results in a double-strand break in the target polynucleotide. In certain embodiments, the Cas protein is a Cas protein having a single-strand nicking activity. In certain embodiments, the method results in a single-strand break in the target polynucleotide. In certain embodiments, a complex comprising a guide RNA and Cas protein having a single-strand nicking activity is used for sequence-targeted single-stranded DNA cleavage, i.e., nicking.

In one aspect, the present invention provides a method for cleaving two or more target polynucleotides with a Cas protein. The method comprises contacting the target polynucleotides with (i) a set of guide RNA molecules described herein, and (ii) a Cas protein. In certain embodiments, the method results in double-strand breaks in the target polynucleotides. In certain embodiments, the Cas protein is a Cas protein having a single-strand nicking activity. In certain embodiments, the method results in single-strand breaks in the target polynucleotides. In certain embodiments, a complex comprising a guide RNA and Cas protein having a single-strand nicking activity is used for sequence-targeted single-stranded DNA cleavage, i.e., nicking.

In one aspect, the present invention provides a method for binding a target polynucleotide with a Cas protein. The method comprises contacting the target polynucleotide with (i) a guide RNA or a set of guide RNA molecules described herein and (ii) a Cas protein, to result in binding of the target polynucleotide with the Cas protein. In certain embodiments, the Cas protein is a Cas variant. In certain embodiments, the Cas variant lacks some or all nuclease activity relative to a counterpart wild-type Cas protein.

In one aspect, the present invention provides a method for binding two or more target polynucleotides with a Cas protein. The method comprises contacting the target polynucleotides with (i) a set of RNA molecules described herein and (ii) a Cas protein, to result in binding of the target polynucleotides with the Cas protein. In certain embodiments, the Cas protein is a Cas variant. In certain embodiments, the Cas variant lacks some or all nuclease activity relative to a counterpart wild-type Cas protein.

In one aspect, the present invention provides a method for targeting a Cas protein to a target polynucleotide. The method comprises contacting the Cas protein with a guide RNA or a set of guide RNA molecules described herein. In certain embodiments, the method results in formation of a guide RNA:Cas protein complex. In certain embodiments, the Cas protein is a wild type Cas9 protein. In certain embodiments, the Cas protein is a mutant or variant of a Cas9 protein. In certain embodiments, the Cas protein is a Cas protein having a single-strand nicking activity. In certain embodiments, the Cas protein is a Cas protein lacking nuclease activity (e.g., a nuclease-deficient mutant of Cas protein). In certain embodiments, the Cas protein is part of a fusion protein (e.g., a fusion protein comprising (i) the Cas protein and (ii) a heterologous polypeptide).

In one aspect, the present invention provides a method for targeting a Cas protein to two or more target polynucleotides. The method comprises contacting the Cas protein with a set of guide RNA molecules described herein. In certain embodiments, the method results in formation of a guide RNA:Cas protein complex. In certain embodiments, the Cas protein is a wild type Cas9 protein. In certain embodiments, the Cas protein is a mutant or variant of a Cas9 protein. In certain embodiments, the Cas protein is a Cas protein having a single-strand nicking activity. In certain embodiments, the Cas protein is a Cas protein lacking nuclease activity (e.g., a nuclease-deficient mutant of Cas protein). In certain embodiments, the Cas protein is part of a fusion protein (e.g., a fusion protein comprising (i) the Cas protein or and (ii) a heterologous polypeptide).

In one aspect, the present invention provides a method of selecting a synthetic guide RNA. The method involves "walking" an MP modification across the guide sequence portion of a gRNA to identify which position or positions in the guide sequence enhance specificity due to the location of the MP modification. The magnitude of the specificity enhancement may be assessed for each position tested with the on-target versus off-target cleavage ratio, the cleavage percentage at the target site and the cleavage percentage at one or more off-target sites, amid/or the specificity score, thus determining which modified position or positions alters the specificity of the gRNA and to what extent. The incremental walking of a single MP across the guide sequence may also identify positions for potential synergistic improvements in specificity resulting from one or more combinations of chemical modifications among the positions tested.

In an embodiment, the method comprises providing at least a first synthetic guide RNA and a second synthetic guide RNA, both comprising the same sequences of (a) a crRNA segment comprising (i) a guide sequence capable of hybridizing to a target polynucleotide, (ii) a stem sequence; and (b) a tracrRNA segment comprising a nucleotide sequence that is partially or completely complementary to the stem sequence, wherein the first synthetic guide RNA comprises an MP modification at a first position of the guide sequence, and the second synthetic guide RNA comprises an MP modification at a second position of the guide sequence; forming a first gRNA:Cas protein complex comprising a Cas protein and the first synthetic guide RNA, contacting the target polynucleotide with the first gRNA:Cas protein complex, and cleaving, nicking or binding the target polynucleotide; forming a second gRNA:Cas protein complex comprising a Cas protein and the second synthetic guide RNA, contacting the target polynucleotide with the second gRNA:Cas protein complex, and cleaving, nicking or binding the target polynucleotide; determining the specificity of the first gRNA:Cas protein complex and the second gRNA:Cas protein complex in the cleaving, nicking or binding of the target polynucleotide; identifying which of the guide RNAs has greater specificity for the target polynucleotide. In certain embodiments, the first and second gRNA:Cas protein complexes are tested together in a competitive assay, such as by labeling of the first and second gRNAs with different fluorophores. In certain embodiments, the first and second gRNA:Cas protein complexes are tested individually in equivalent or split samples assayed in parallel or sequentially.

In certain embodiments, the specificity-enhancing modification comprises 2'-O-methyl-3'-phosphonoacetate (MP), 2'-O-methyl-3'-thiophosphonoacetate (MSP), 2'-deoxy-3'-phosphonoacetate (DP), 2'-deoxy-3'-thiophosphonoacetate (DSP), or a combination thereof. In certain embodiments, the chemical modification comprises a 2' modification that confers a C3'-endo sugar pucker and a phosphonoacetate or thiophosphonoacetate linkage modification. In certain embodiments, the 2' modification is selected from 2'-F and 2'-O-(2-methoxyethyl). In certain embodiments, the first and second synthetic guide RNAs comprise a specificity-enhancing modification at different nucleotide positions in the guide sequence portions. In certain embodiments, the specificity is determined based on ON target cleavage activity, OFF target cleavage activity, ON:OFF ratio, specificity score, or a combination thereof. In certain embodiments, the method comprises providing a first through twentieth synthetic guide RNA comprising a specificity-enhancing modification at different nucleotide positions in the guide sequence portions, forming a gRNA:Cas protein complex using each of the synthetic guide RNAs, contacting the target polynucleotide with the gRNA:Cas protein complex, cleaving, nicking or binding the target polynucleotide and measuring the specificity of each synthetic guide RNA, and identifying one or more modified positions that provide the greatest specificity enhancement. In certain embodiments, the gRNA further comprises stability-enhancing end modifications. In certain embodiments, the stability enhancing end modifications comprise 2'-O-methyl-3'-phosphonoacetate (MP), 2'-O-methyl-3'-thiophosphonoacetate (MSP), 2'-O-methyl-3'-phosphorothioate (MS), 2'-deoxy-3'-phosphonoacetate (DP), 2'-deoxy-3'-thiophosphonoacetate (DSP), 2'-fluoro-3'-phosphonoacetate (FP), 2'-fluoro-3'-thiophosphonoacetate (FSP), 2'-fluoro-3'-phosphorothioate (FS), or a combination thereof at the 5' end and/or the 3' end of the gRNA.

In certain embodiments, the guide RNA is introduced into a cell by transfection. Techniques for RNA transfection are known in the art and include electroporation and lipofection. Effective techniques for RNA transfection depend mostly on cell type. See, e.g., Lujambio et al. (Spanish National Cancer Centre) *Cancer Res. February* 2007, which describes transfection of HTC-116 colon cancer cells and uses Oligofectamine (Invitrogen) for transfection of commercially obtained, modified miRNA or precursor miRNA. See also, Cho et al. (Seoul National Univ.) *Nat. Biotechnol.* March 2013, which describes transfection of K562 cells and uses 4D Nucleofection™ (Lonza) electroporation for transfection of transcribed sgRNAs (about 60 nts long). Techniques for transfection of RNA are also known in the art. For example, therapeutic RNA has been delivered in non-pathogenic *E. coli* coated with Invasin protein (to facilitate uptake into cells expressing β-1 integrin protein) and with the *E. coli* encoded to express lysteriolysin O pore-forming protein to permit the shRNA to pass from the *E. coli* into the cytoplasm. See also Cho et al. (Seoul National Univ.) *Nat. Biotechnol.* March 2013.

In certain embodiments, the guide RNA is introduced or delivered into cells. Technologies that can be used for delivery of guide RNA include those that utilize encapsulation by biodegradable polymers, liposomes, or nanoparticles. Such polymers, liposomes, and nanoparticles can be delivered intravenously. In certain embodiments, for in vivo delivery, guide RNA can be injected into a tissue site or administered systemically. In vivo delivery can also be effected by a beta-glucan delivery system, such as those described in U.S. Pat. Nos. 5,032,401 and 5,607,677, and U.S. Publication No. 2005/0281781, which are hereby incorporated by reference in their entirety. In certain embodiments, guide RNA or a delivery vehicle containing guide RNA is targeted to a particular tissue or body compartment. For example, in certain embodiments, to target exogenous RNA to other tissues, synthetic carriers are decorated with cell-specific ligands or aptamers for receptor uptake, e.g., RNA encased in cyclodextrin nanoparticles coated with PEG and functionalized with human transferrin protein for uptake via the transferrin receptor which is highly expressed in tumor cells. Further approaches are described herein below or known in the art.

The present invention has been tested in human cells as described in Hendel et al. (2015) *Nat. Biotechnol.* 33:9, 985-9 (which is incorporated in this application in its entirety). In the cited work, modified guide RNA was introduced into K562 cells, human primary T cells, and CD34+ hematopoietic stem and progenitor cells (HSPCs). The modified guide RNA significantly enhanced genome editing efficiencies in human cells, including human primary T cells and CD34+ HSPCs as compared to unmodified guide RNA.

Examples of other uses include genomic editing and gene expression regulation as described below.

Genomic Editing

In one aspect, the present invention provides a method for genomic editing to modify a DNA sequence in vivo or in vitro ("in vitro" includes, without being limited to, a cell-free system, a cell lysate, an isolated component of a cell, and a cell outside of a living organism). The DNA sequence may comprise a chromosomal sequence, an episomal sequence, a plasmid, a mitochondrial DNA sequence, or a functional intergenic sequence, such as an enhancer sequence or a DNA sequence for a non-coding RNA. The method comprises contacting the DNA sequence with (i) a guide RNA or a set of guide RNA molecules described herein, and (ii) a Cas protein. In certain embodiments, the DNA sequence is contacted outside of a cell. In certain embodiments, the DNA sequence is located in the genome within a cell and is contacted in vitro or in vivo. In certain embodiments, the cell is within an organism or tissue. In certain embodiments, the cell is a human cell, a non-human mammalian cell, a stem cell, a non-mammalian vertebrate cell, an invertebrate cell, a plant cell, a single cell organism, or an embryo. In certain embodiments, the guide RNA aids in targeting the Cas protein to a targeted site in the DNA sequence. In certain embodiments, the Cas protein cleaves at least one strand of the DNA sequence at the targeted site. In certain embodiments, the Cas protein cleaves both strands of the DNA sequence at the targeted site.

In certain embodiments, the method further comprises introducing the Cas protein into a cell or another system. In certain embodiments, the Cas protein is introduced as a purified or non-purified protein. In certain embodiments, the Cas protein is introduced via an mRNA encoding the Cas protein. In certain embodiments, the Cas protein is introduced via a linear or circular DNA encoding the Cas protein. In certain embodiments, the cell or system comprises a Cas protein or a nucleic acid encoding a Cas protein.

In certain embodiments, a double-stranded break can be repaired via an error-prone, non-homologous end-joining ("NHEJ") repair process. In certain embodiments, a double-stranded break can be repaired by a homology-directed repair (HDR) process such that a donor sequence in a donor polynucleotide can be integrated into or exchanged with the targeted DNA sequence.

In certain embodiments, the method further comprises introducing at least one donor polynucleotide into the cell or system. In certain embodiments, the donor polynucleotide comprises at least one homologous sequence having substantial sequence identity with a sequence on either side of the targeted site in the DNA sequence. In certain embodiments, the donor polynucleotide comprises a donor sequence that can be integrated into or exchanged with the DNA sequence via homology-directed repair, such as homologous recombination.

In certain embodiments, the donor polynucleotide includes an upstream homologous sequence and a downstream homologous sequence, each of which have substantial sequence identity to sequences located upstream and downstream, respectively, of the targeted site in the DNA sequence. These sequence similarities permit, for example, homologous recombination between the donor polynucleotide and the targeted DNA sequence such that the donor sequence can be integrated into (or exchanged with) the DNA sequence targeted.

In certain embodiments, the target site(s) in the DNA sequence spans or is adjacent to a mutation, e.g., point mutation, a translocation or an inversion which may cause or be associated with a disorder. In certain embodiments, the method comprises correcting the mutation by introducing into the cell or system at least one donor polynucleotide comprising (i) a wild-type counterpart of the mutation and (ii) at least one homologous sequence having substantial sequence identity with a sequence on one side of the targeted site in the DNA sequence. In certain embodiments, the donor polynucleotide comprises a homologous sequence having substantial sequence identity with a sequence on both sides of the targeted site in the DNA sequence.

In certain embodiments, the donor polynucleotide comprises an exogenous sequence that can be integrated into or exchanged with the targeted DNA sequence via a homology-directed repair process, such as homologous recombination. In certain embodiments, the exogenous sequence comprises a protein coding gene, which, optionally, is operably linked to an exogenous promoter control sequence. Thus, in certain embodiments, upon integration of the exogenous sequence, a cell can express a protein encoded by the integrated gene. In certain embodiments, the exogenous sequence is integrated into the targeted DNA sequence such that its expression in the recipient cell or system is regulated by the exogenous promoter control sequence. Integration of an exogenous gene into the targeted DNA sequence is termed a "knock in." In other embodiments, the exogenous sequence can be a transcriptional control sequence, another expression control sequence, an RNA coding sequence, and the like.

In certain embodiments, the donor polynucleotide comprises a sequence that is essentially identical to a portion of the DNA sequence at or near the targeted site, but comprises at least one nucleotide change. For example, in certain embodiments, the donor sequence comprises a modified or mutated version of the DNA sequence at or near the targeted site such that, upon integration or exchange with the targeted site, the resulting sequence at the targeted site comprises at least one nucleotide change. In certain embodiments, the at least one nucleotide change is an insertion of one or more nucleotides, a deletion of one or more nucleotides, a substitution of one or more nucleotides, or combinations thereof. As a consequence of the integration of the modified sequence, the cell may produce a modified gene product from the targeted DNA sequence.

In certain embodiments, the methods are for multiplex applications. In certain embodiments, the methods comprise introducing a library of guide RNAs into the cell or system. In certain embodiments, the library comprises at least 10 unique guide sequences. In certain embodiments, the library comprises at least 100 unique guide sequences. In certain embodiments, the library comprises at least 1,000 unique guide sequences. In certain embodiments, the library comprises at least 10,000 unique guide sequences. In certain embodiments, the library comprises at least 100,000 unique guide sequences. In certain embodiments, the library comprises at least 1,000,000 unique guide sequences. In certain embodiments, the library targets at least 10 different polynucleotides or at least 10 different sequences within one or more polynucleotides. In certain embodiments, the library targets at least 100 different polynucleotides or at least 100 different sequences within one or more polynucleotides. In certain embodiments, the library targets at least 1,000 different polynucleotides or at least 1,000 different sequences within one or more polynucleotides. In certain embodiments, the library targets at least 10,000 different polynucleotides or at least 10,000 different sequences within one or more polynucleotides. In certain embodiments, the library targets at least 100,000 different polynucleotides or at least 100,000 different sequences within one or more polynucleotides. In certain embodiments, the library targets at least 1,000,000 different polynucleotides or at least 1,000,000 different sequences within one or more polynucleotides.

Genomic Editing in Human and Mammalian Cells

Embodiments of the present invention are useful in methods for genomic editing to modify a target polynucleotide, for example a DNA sequence, in a mammalian cell.

In certain embodiments, the DNA sequence is a chromosomal sequence. In certain embodiments, the DNA sequence is a protein-coding sequence. In certain embodiments, the DNA sequence is a functional intergenic sequence, such as an enhancer sequence or a non-coding sequence. In certain embodiments, the DNA is part of a human gene. In some such embodiments, the human gene is the clathrin light chain (CLTA1) gene, the human interleukin 2 receptor gamma (IL2RG) gene, the human cytotoxic T-lymphocyte-associated protein 4 (CLTA4) gene, the human Vascular Endothelial Growth Factor A gene (VEGFA), or the human hemoglobin beta (HBB) gene which can harbor mutations responsible for sickle cell anemia and thalassemias. Accordingly, in certain embodiments, the target polynucleotide is a HBB polynucleotide, a VEGFA polynucleotide, an IL2RG polynucleotide, a CLTA1 polynucleotide, or a CLTA4 polynucleotide. xxx In certain embodiments, a synthetic guide RNA comprises a guide sequence capable of hybridizing to an HBB, IL2RG, CLTA1, VEGFA, or CLTA4 polynucleotide. In certain embodiments, the guide sequence consists of nucleotides 1 through 20-N, counted from the 5' end of the guide sequence, N being an integer between −10 and 0, and the guide sequence comprises at least one specificity-enhancing modification at nucleotide 4-N, 5-N, 7-N, 9-N, 10-N, or 11-N. In certain embodiments, the guide sequence capable of hybridizing to one of the above target polynucleotides has a chemical modification at nucleotide 11-N. In certain embodiments, the guide sequence capable of hybridizing to one of the above target polynucleotides has a chemical modification at nucleotide 5-N. In certain embodiments, the guide sequence capable of hybridizing to one of the above target polynucleotides has a chemical modification at nucleotide 7-N. In certain embodiments, the guide sequence capable of hybridizing to one of the above target polynucleotides has a chemical modification at nucleotide 10-N. In certain embodiments, the guide sequence capable of hybridizing to one of the above target polynucleotides has a chemical modification at nucleotide 9-N. In certain embodiments, the guide sequence capable of hybridizing to one of the above target polynucleotides has a chemical modification at nucleotide 4-N. In certain embodiments, N equals zero.

In certain embodiments, the guide sequence consists of nucleotides 1 through 19, counted from the 5' end of the guide sequence, and at least one chemical modification at one of nucleotides 3, 4, 6, 8, 9, or 10. In certain embodiments, the guide sequence consists of nucleotides 1 through 18, counted from the 5' end of the guide sequence, and at least one chemical modification at one of nucleotides 2, 3, 5, 7, 8, or 9. In certain embodiments, the guide sequence consists of nucleotides 1 through 17, counted from the 5' end of the guide sequence, and at least one chemical modification at one of nucleotides 1, 2, 4, 6, 7, or 8. In certain embodiments, the guide sequence consists of nucleotides 1 through 16, counted from the 5' end of the guide sequence, and at least one chemical modification at one of nucleotides 1, 3, 5, 6, or 7. In certain embodiments, the guide sequence consists of nucleotides 1 through 15, counted from the 5' end of the guide sequence, and at least one chemical modification at one of nucleotides 2, 4, 5, or 6. In certain embodiments, the guide sequence consists of nucleotides 1 through 14, counted from the 5' end of the guide sequence, and at least one chemical modification at one of nucleotides 1, 3, 4, or 5. In certain embodiments, the chemical modification comprises 2'-O-methyl-3'-phosphonoacetate (MP), 2'-O-methyl-3'-thiophosphonoacetate (MSP), 2'-deoxy-3'-phosphonoacetate (DP), 2'-deoxy-3'-thiophosphonoacetate (DSP), or a combination thereof. In certain embodiments, the chemical modification comprises a 2'-modification that confers a C3'-endo sugar pucker and a phosphonoacetate or thiophosphonoacetate linkage modification. In certain embodiments, the 2'-modification is selected from 2'-F and 2'-O-(2-methoxyethyl).

In certain embodiments, the mammalian cell is a human cell. In some such embodiments, the human cell is a primary human cell. In further embodiments, the primary human cell is a human primary T cell. The human primary T cell may be stimulated or unstimulated. In certain embodiments, the human cell is a stem/progenitor cell, such as a CD34+ hematopoietic stem and progenitor cell (HSPC). In certain embodiments, the human cell is from a cultured cell line, for example such as can be obtained commercially. Exemplary cell lines include K562 cells, a human myelogenous leukemia line.

In certain embodiments, the cell is within a living organism. In certain other embodiments, the cell is outside of a living organism.

The method comprises contacting the DNA sequence with (i) a guide RNA or a set of guide RNA molecules described herein, and (ii) a Cas protein.

In certain embodiments, the method further comprises introducing or delivering the guide RNA into the cell. In some such embodiments, the guide RNA is introduced into a cell by transfection. Techniques for RNA transfection are known in the art and include electroporation and lipofection. In other embodiments, the guide RNA is introduced into a cell (and, more particularly, a cell nucleus) by nucleofection. Techniques for nucleofection are known in the art and may utilize nucleofection devices such as the Lonza Nucleofector 2b or the Lonza 4D-Nucleofector and associated reagents.

In certain embodiments, the method further comprises introducing or delivering the Cas protein into the cell. In some such embodiments, the Cas protein is introduced as a purified or non-purified protein. In other embodiments, the Cas protein is introduced via an mRNA encoding the Cas protein. In some such embodiments, the mRNA encoding the Cas protein is introduced into the cell by transfection. In other embodiments, the mRNA encoding the Cas protein is introduced into a cell (and, more particularly, a cell nucleus) by nucleofection.

In certain embodiments, the method employs ribonucleoprotein (RNP)-based delivery such that the Cas protein is introduced into the cell in a complex with the guide RNA. For example, a Cas9 protein may be complexed with a guide RNA in a Cas9:gRNA complex, which allows for co-delivery of the gRNA and Cas protein. For example, the Cas:gRNA complex may be nucleofected into cells.

In certain embodiments, the method employs an all-RNA delivery platform. For example, in some such embodiments, the guide RNA and the mRNA encoding the Cas protein are introduced into the cell simultaneously or substantially simultaneously (e.g., by co-transfection or co-nucleofection). In certain embodiments, co-delivery of Cas mRNA and modified gRNA results in higher editing frequencies as compared to co-delivery of Cas mRNA and unmodified gRNA. In particular, gRNA having 2'-O-methyl-3'-phosphorothioate ("MS"), 2'-O-methyl-3'-PACE ("MP"), or 2'-O-methyl-3'-thioPACE ("MSP") incorporated at three terminal nucleotides at both the 5' and 3' ends, provide higher editing frequencies as compared to unmodified gRNA.

In certain embodiments, the guide RNA and the mRNA encoding the Cas protein are introduced into the cell sequentially; that is, the guide RNA and the mRNA encoding the Cas protein are introduced into the cell at different times. The time period between the introduction of each agent may range from a few minutes (or less) to several hours or days. For example, in some such embodiments, gRNA is delivered first, followed by delivery of Cas mRNA 4, 8, 12 or 24 hours later. In other such embodiments, Cas mRNA is delivered first, followed by delivery of gRNA 4, 8, 12 or 24 hours later. In some particular embodiments, delivery of modified gRNA first, followed by delivery of Cas mRNA results in higher editing frequencies as compared to delivery of unmodified gRNA followed by delivery of Cas mRNA.

In certain embodiments, the gRNA is introduced into the cell together with a DNA plasmid encoding the Cas protein. In some such embodiments, the gRNA and the DNA plasmid encoding the Cas protein are introduced into the cell by nucleofection. In some particular embodiments, an RNP-based delivery platform or an all-RNA delivery platform provides lower cytotoxicity in primary cells than a DNA plasmid-based delivery system.

In certain embodiments, the method provides significantly enhanced genome editing efficiencies in human cells, including human primary T cells and CD34+ HSPCs.

In certain embodiments, modified gRNA increases the frequency of insertions or deletions (indels), which may be indicative of mutagenic NHEJ and gene disruption, relative to unmodified gRNA. In particular, modified gRNA having 2'-O-methyl-3'-phosphorothioate ("MS"), 2'-O-methyl-3'-PACE ("MP"), or 2'-O-methyl-3'-thioPACE ("MSP") incorporated at three terminal nucleotides at both the 5' and 3' ends, increases the frequency of indels relative to unmodified gRNA.

In certain embodiments, co-delivery of modified gRNA and Cas mRNA to human primary T cells increases the frequency of indels as compared to co-delivery of unmodified gRNA and Cas mRNA. In particular, modified gRNA having 2'-O-methyl-3'-phosphorothioate ("MS"), 2'-O-methyl-3'-PACE ("MP"), or 2'-O-methyl-3'-thioPACE ("MSP") incorporated at three terminal nucleotides at both the 5' and 3' ends, increases the frequency of indels in human primary T cells relative to unmodified gRNA.

In certain embodiments, modified gRNA improves gRNA stability relative to unmodified gRNA. As one example, gRNA having 2'-O-methyl ("M") incorporated at three terminal nucleotides at both the 5' and 3' ends modestly improves stability against nucleases and also improves base pairing thermostability over unmodified gRNA. As another example, gRNA having 2'-O-methyl-3'-phosphorothioate ("MS"), 2'-O-methyl-3'-PACE ("MP"), or 2'-O-methyl-3'-thioPACE ("MSP") incorporated at three terminal nucleotides at both the 5' and 3' ends, dramatically improves stability against nucleases relative to unmodified gRNA. It is contemplated that gRNA end modifications enhance intracellular stability against exonucleases, thus enabling increased efficacy of genome editing when Cas mRNA and gRNA are co-delivered or sequentially delivered into cells or cell lysates. In certain embodiments, a stability-enhancing modification at an end may also serve as a specificity-enhancing modification if a guide sequence comprises the same end. In certain embodiments, end modifications comprising 2'-O-methyl-3'-phosphonoacetate (MP), 2'-O-methyl-3'-thiophosphonoacetate (MSP), 2'-O-methyl-3'-phosphorothioate (MS), 2'-deoxy-3'-phosphonoacetate (DP), 2'-deoxy-3'-thiophosphonoacetate (DSP), 2'-fluoro-3'-phosphonoacetate (FP), 2'-fluoro-3'-thiophosphonoacetate (FSP), 2'-fluoro-3'-phosphorothioate (FS), 2'-O-(2-methoxyethyl)-3'-phosphonoacetate, 2'-O-(2-methoxyethyl)-thiophosphonoacetate, 2'-O-(2-methoxyethyl)-3'-phosphorothioate, or a combination thereof increases stability and specificity of a method of the present invention. In certain embodiments, modified gRNA stimulates gene targeting, which, in turn, allows for gene editing by, for example, homologous recombination or NHEJ. In particular, gRNA having 2'-O-methyl-3'-phosphorothioate ("MS"), 2'-O-methyl-3'-PACE ("MP"), or 2'-O-methyl-3'-thioPACE ("MSP") incorporated at three terminal nucleotides at both the 5' and 3' ends, stimulates higher levels of homologous recombination than unmodified gRNA.

In certain embodiments, modified gRNA retains high specificity. In certain embodiments, the ratio of on-target to off-target indel frequencies is improved with modified gRNA as compared to unmodified gRNA. In certain embodiments, modified gRNA delivered in an RNP complex with a Cas protein provides significantly better on-target versus off-target ratios compared to a DNA plasmid-based delivery system.

Gene Expression Regulation

In certain embodiments, the guide RNA described herein is used for regulating transcription or expression of a gene of interest. For example, in certain embodiments, a fusion protein comprising a Cas protein (e.g., a nuclease-deficient Cas9) and a transcription activator polypeptide is used to increase transcription of a gene. Similarly, in certain embodiments, a fusion protein comprising a Cas protein (e.g., a nuclease-deficient Cas9) and a repressor polypeptide is used to knock-down gene expression by interfering with transcription of the gene.

In at least one aspect, the present invention provides a method for regulating the expression of a gene of interest in vivo or in vitro. The method comprises introducing into a cell or another system (i) a synthetic guide RNA described herein, and (ii) a fusion protein. In certain embodiments, the fusion protein comprises a Cas protein and an effector domain, such as a transcriptional activation domain, a transcriptional repressor domain, or an epigenetic modification domain. In certain embodiments, the fusion protein comprises a mutated Cas protein, such as a Cas9 protein that is a null nuclease. In certain embodiments, the Cas protein comprises one or more mutations, such as D10A, H840A and/or N863A.

In certain embodiments, the fusion protein is introduced into the cell or system as a purified or non-purified protein. In certain embodiments, the fusion protein is introduced into the cell or system via an mRNA encoding the fusion protein. In certain embodiments, the fusion protein is introduced into the cell or system via a linear or circular DNA encoding the fusion protein.

In certain embodiments, the guide RNA aids in directing the fusion protein to a specific target polynucleotide comprising a chromosomal sequence, an episomal sequence, a plasmid, a mitochondrial DNA sequence, or a functional intergenic sequence, such as an enhancer or the DNA sequence for a non-coding RNA. In certain embodiments, the effector domain regulates expression of a sequence in the target polynucleotide. A guide RNA for modulating gene expression can be designed to target any desired endogenous gene or sequence encoding a functional RNA. A genomic target sequence can be selected in proximity of the transcription start site of the endogenous gene, or alternatively, in proximity of the translation initiation site of the endogenous gene. In certain embodiments, the target sequence is in a region of the DNA that is traditionally termed the "promoter proximal" region of a gene. In certain embodiments, the target sequence lies in a region from about 1,000 base pairs upstream of the transcription start site to about 1,000 base pairs downstream of the transcription start site. In certain embodiments, the target sequence is remote from the start site for transcription of the gene (e.g., on another chromosome).

In certain embodiments, the methods are for multiplex applications. In certain embodiments, the methods comprise introducing a library of guide RNAs into the cell or system. In certain embodiments, the library comprises at least 10, at least 100, at least 1,000, at least 10,000, at least 100,000, or at least 1,000,000 unique guide sequences. In certain embodiments, the library targets at least 10 different polynucleotides or at least 10 different sequences within one or more polynucleotides. In certain embodiments, the library targets at least 100 different polynucleotides or at least 100 different sequences within one or more polynucleotides. In certain embodiments, the library targets at least 1,000 different polynucleotides or at least 1,000 different sequences within one or more polynucleotides. In certain embodiments, the library targets at least 10,000 different polynucleotides or at least 10,000 different sequences within one or more polynucleotides. In certain embodiments, the library targets at least 100,000 different polynucleotides or at least 100,000 different sequences within one or more polynucleotides. In certain embodiments, the library targets at least 1,000,000 different polynucleotides or at least 1,000,000 different sequences within one or more polynucleotides.

Kits

In one aspect, the present invention provides kits containing reagents for performing the above-described methods, including producing gRNA:Cas protein complex and/or supporting its activity for binding, nicking or cleaving a target polynucleotide. In certain embodiments, one or more of the reaction components, e.g., one or more guide RNAs and Cas proteins, for the methods disclosed herein, can be supplied in the form of a kit for use. In certain embodiments, the kit comprises a Cas protein or a nucleic acid encoding the Cas protein, and one or more guide RNAs described herein or a set or library of guide RNAs. In certain embodiments, the kit includes one or more other reaction components. In certain embodiments, an appropriate amount of one or more reaction components is provided in one or more containers or held on a substrate.

In certain embodiments, the present invention provides a kit for selecting a synthetic guide RNA comprising at least two synthetic guide RNAs which are identical except for different modifications or modifications at different positions in the guide sequence. Each guide RNA comprises (a) a crRNA segment comprising (i) a guide sequence capable of hybridizing to a target polynucleotide, (ii) a stem sequence; and (b) a tracrRNA segment comprising a nucleotide sequence that is partially or completely complementary to the stem sequence, wherein the guide sequence comprises nucleotides 1 through 20-N (N is an integer between −10 and 10, optionally between −10 and 6), counted from the 5' end of the guide sequence, and at least one specificity-enhancing modification at a nucleotide in the guide sequence; wherein the at least two synthetic guide RNAs differ from each other by having at least one different specificity-enhancing modification or by having the specificity-enhancing modification at least one different position in the guide sequence. The kit also comprises a Cas protein or a polynucleotide coding for a Cas protein. In certain embodiments, each synthetic guide RNA in the kit comprises a specificity-enhancing modification at a different nucleotide. In certain embodiments, the kit comprises a series of synthetic guide RNAs, each one having a modification at a different nucleotide position in the guide sequence. In certain embodiments, the kit has the same number of different guide RNAs as the number of nucleotides in the guide sequence. In certain embodiments, the Cas protein is Cas9. In certain embodiments, the specificity-enhancing modification comprises 2'-O-methyl-3'-phosphonoacetate (MP), 2'-O-methyl-3'-thiophosphonoacetate (MSP), 2'-deoxy-3'-phosphonoacetate (DP), or 2'-deoxy-3'-thiophosphonoacetate (DSP), or a combination thereof. In certain embodiments, the specificity-enhancing modifications comprise a 2'-modification that confers a C3'-endo sugar pucker and a phosphonoacetate or thiophosphonoacetate linkage modification. In certain embodiments, the 2'-modification is selected from 2'-F and 2'-O-(2-methoxyethyl). In certain embodiments, the guide RNAs are synthetic single guide RNAs.

Examples of additional components of the kits include, but are not limited to, one or more different polymerases, one or more host cells, one or more reagents for introducing foreign nucleic acid into host cells, one or more reagents (e.g., probes or PCR primers) for detecting expression of the guide RNA and/or the Cas mRNA or protein or for verifying the status of the target nucleic acid, and buffers, transfection reagents or culture media for the reactions (in 1× or more concentrated forms). In certain embodiments, the kit includes one or more of the following components: biochemical and physical supports; terminating, modifying and/or digesting reagents; osmolytes; and apparati for reaction, transfection and/or detection.

The reaction components used can be provided in a variety of forms. For example, the components (e.g., enzymes, RNAs, probes and/or primers) can be suspended in an aqueous solution or bound to a bead or as a freeze-dried or lyophilized powder or pellet. In the latter case, the components, when reconstituted, form a complete mixture of components for use in an assay. The kits of the invention can be provided at any suitable temperature. For example, for storage of kits containing protein components or complexes thereof in a liquid, it is preferred that they are provided and maintained below 0° C., preferably at about −20° C., possibly in a freeze-resistant solution containing glycerol or other suitable antifreeze.

A kit or system may contain, in an amount sufficient for at least one assay, any combination of the components described herein. In some applications, one or more reaction components may be provided in pre-measured single use amounts in individual, typically disposable, tubes or equivalent containers. With such an arrangement, a RNA-guided nuclease reaction can be performed by adding a target nucleic acid, or a sample or cell containing the target nucleic acid, to the individual tubes directly. The amount of a component supplied in the kit can be any appropriate amount and may depend on the market to which the product is directed. The container(s) in which the components are supplied can be any conventional container that is capable of holding the supplied form, for instance, microfuge tubes, microtiter plates, ampoules, bottles, or integral testing devices, such as fluidic devices, cartridges, lateral flow, or other similar devices.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like). The kits may further include instructions recorded in a tangible form for use of the components.

EXAMPLES

Example 1

To evaluate the effect of chemical modification on the binding energy at physiological salt conditions, a 43-nucleotide crRNA with a 20-nucleotide guide sequence was made. A duplex was formed by mixing the crRNA with a complementary 40-nucleotide DNA oligonucleotide that comprised a 10 nucleotides overhanging on each end of the DNA oligonucleotide. The melting temperature ("Tm") of the duplex was measured. Seven additional 43-nt crRNAs were made, with several sequential modifications in the sampling and locking region and an intervening or "spacer" nucleotide at position 10 in the 20-nt guide sequence. FIG. 6A shows the type and placement of the modifications. The exonuclease resistance modification was 2'-O-methyl-3'-PACE ("MP"), and the spacer was an unmodified RNA nucleotide. Duplexes were formed individually by mixing each modified crRNA 601 with the complementary 40-nt DNA oligonucleotide 603, and the melting temperature of each RNA/DNA duplex 605 containing modifications in the RNA strand was measured to quantify the effect that the various modifications had on the binding energy under physiological salt conditions.

The effect that modifications have on the cooperativity of the duplex melting can be evaluated qualitatively by measuring the slope of the melting curve: a larger slope indicates greater cooperativity in the unbinding (and therefore in the binding during a reverse process as well, according to well-established principles of equilibrium reversibility). FIG. 6B shows the melting curve for unmodified gRNA, and FIGS. 6C through 6G show melting curves for various types of modifications at nucleotides 6 through 9 in the 20-nt guide sequence portions. The addition of 2'-O-methyl ("M") and 2'-O-methyl phosphorothioate ("MS") increased the binding energy by about 0.2° C. per modification, whereas 2'-O-methyl-3'-PACE ("MP") decreased the Tm or binding energy by 1° C. per modification and 2'-O-methyl-3'-thio-PACE ("MSP") decreased the Tm by 1.4° C. per modification. FIG. 7 is a graph showing change in melting temperature of a 20-base pair gRNA/DNA duplex as the gRNA was truncated to 17, 18 or 19 nucleotides or extended to 21 or 22 nucleotides in length. The measurements were performed in physiological salt concentrations. The measurements indicated a change in melting temperature of about 2° C. per base pair for the extension or truncation of the 20-nucleotide guide sequence.

Example 2

Further melting temperature measurements were performed using experimental crRNAs containing a linker or linker-like modification at nucleotide 9 in the guide sequences of crRNAs. The linker or linker-like modifications comprised a ULNA (unlocked nucleic acid), an abasic spacer, an alkylene spacer comprising —PO$_4$Y—(CR$^3{}_2$)$_m$—PO$_4$Y—, or an ethylene glycol spacer comprising (—PO$_4$Y—(CR$^3{}_2$CR$^3{}_2$O)$_n$—PO$_3$Y—), where m is 2, 3 or 4, n is 1, 2 or 3, each R$^3$ is independently selected from the group consisting of H, an alkyl and substituted alkyl, and each Y is H or a negative charge. For example, in certain embodiments, the alkylene spacer is a "C3 spacer" in which m is 3. In other embodiments, the ethylene glycol spacer is a "Tri-PEG spacer" in which n is 3. These modifications also decrease the binding energy by giving more flexibility to the strand which decreases the cooperativity of hybridization.

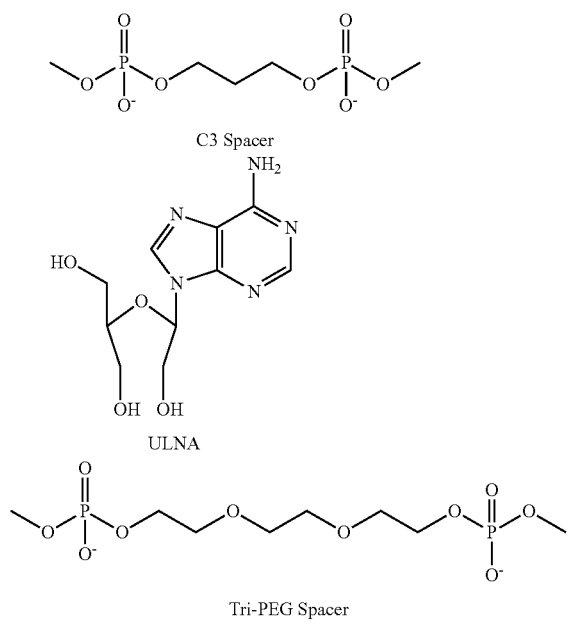

The results of these melting temperature measurements are shown in Table 1:

TABLE 1

| Entry | crRNA Name | T$_m$ |
|---|---|---|
| 1 | Control_1XMP | 50.2 |
| 2 | rA-ULNA_9_1XMP | 44.8 |
| 3 | C3-Spacer_9_1XMP | 40.9 |
| 4 | Tri-PEG-Spacer_9_1XMP | 38.3 |

Examples 3-7

To evaluate the ability of the chemically synthesized guide RNAs to bind and cleave a DNA target sequence and to evaluate the effect of various modifications on Cas9-mediated cleavage, an in vitro cleavage assay was used. Briefly, PAM-addressable DNA constructs comprising target polynucleotide sequences (ON) or off-target polynucleotide sequences (OFF) set forth in Tables 2 and 7 were prepared by preparative PCR amplification of plasmid-borne human sequences of various target genes. As exemplary genes to demonstrate the ability of the present compositions and methods to selectively edit genes, the human clathrin light chain CLTA gene, the human hemoglobin beta (HBB) gene, the human interleukin 2 receptor subunit gamma (IL2RG) gene, and the human cytotoxic T-lymphocyte-associated protein 4 (CLTA4) gene were used as target genes. These are representative of the general approach disclosed herein for evaluating and editing target genes.

Tables 3 to 6 set forth synthetic guide RNAs. In most of the guide RNAs, the first 20 nucleotides at the 5' end are complementary to the target sequence in target DNA—these complementary nucleotides make up the guide sequence. In some guide RNAs, an overhang or extension was present at the 5' end of the guide sequence, which is not complementary to the target sequence. In some guide RNAs, the 5' end of the guide sequence was truncated such that nucleotides 1, or 1 and 2, or 1 and 2 and 3, are not present. On-target constructs ("ON") comprise the 20-nt target sequence. Off-target constructs ("OFF") comprise most of the same 20 nucleotides as the target DNA, with 1, 2 or 3 nucleotide differences. Accordingly, the gRNA was mostly, but not completely, complementary to the sequence of the OFF target constructs. The OFF target constructs are based on gene sequences known to occur in the human genome.

The gRNAs were synthesized on an ABI 394 Synthesizer (Life Technologies, Carlsbad, Calif., USA) using 2'-O-thionocarbamate-protected nucleoside phosphoramidites according to procedures described in Dellinger et al. (2011) J. Am. Chem. Soc., 133, 11540-56. 2'-O-methyl phosphoramidites were incorporated into RNA oligomers under the same conditions as the 2'-O-thionocarbamate protected phosphoramidites. The 2'-O-methyl-3'-O-(di-iso-propylamino)phosphinoacetic acid-1,1-dimethylcyano-ethyl ester-5'-O-dimethoxytrityl nucleosides used for synthesis of thiophosphonoacetate (thioPACE)-modified RNAs were synthesized essentially according to published methods. See Dellinger et al. (2003) J. Am. Chem. Soc. 125, 940-50; and Threlfall et al. (2012) Org. Biomol. Chem. 10, 746-54.

All the oligonucleotides were purified using reversed-phase high-performance liquid chromatography (HPLC) and analyzed by liquid chromatography-mass spectrometry (LC-MS) using an Agilent 1290 Infinity series LC system coupled to an Agilent 6520 Q-TOF (time-of-flight) mass spectrometer (Agilent Technologies, Santa Clara, Calif., USA). The yields for the synthesis and purification of the sgRNAs were estimated using deconvolution of mass spectra obtained from LC-MS-derived total ion chromatograms. The chemical synthesis of the 100-mer sgRNAs typically yielded 25-35% full-length product from a nominal 1 micromole scale synthesis. Reversed-phase HPLC purification using ion pairing buffer conditions typically gave 20% yield from the crude product with an estimated purity of the final sgRNA in the range of 90% to 95%.

The DNA target constructs comprised the target sequences (also known as on-target sequences or identified as "ON") and off-target sequences ("OFF") set forth in Table 2, with differences in the off-target sequences from the target in bold italics, and the PAM sequences (when shown) are underlined:

TABLE 2

| On-target or Off-target Site | DNA Sequence | SEQ ID NO. |
|---|---|---|
| CLTA1 ON | AGTCCTCATCTCCCTCAAGCAGG | 1 |
| CLTA1 OFF1 | AGTCCTCAACTCCCTCAAGCAGG | 2 |
| CLTA1 OFF3 | ACTCCTCATCCCCCTCAAGCCGG | 3 |
| CLTA4 ON | GCAGATGTAGTGTTTCCACAGGG | 4 |
| CLTA4 OFF1 | GCAGATGTAGTATTTCCACAGGG | 5 |
| CLTA4 OFF2 | CCAGATGTAGCGTTTCCACAGGG | 6 |
| CLTA4 OFF3 | GCAGATGTTGTGTTTCCACAGGG | 7 |
| HBB ON | CTTGCCCCACAGGGCAGTAACGG | 8 |
| HBB OFF1 | TCAGCCCCACAGGGCAGTAAGGG | 9 |
| IL2RG ON | TGGTAATGATGGCTTCAACATGG | 10 |
| IL2RG OFF2 | TGGTGAGGATGGCTTCAACACGG | 191 |
| IL2RG OFF3 | TGGTAATGATGACTTCAACATAG | 11 |
| VEGFA ON | GGTGAGTGAGTGTGTGCGTGTGG | 192 |
| VEGFA OFF2 | TGTGGGTGAGTGTGTGCGTGAGG | 193 |

Note that HBB OFF1 differs from HBB ON in the first 3 nucleotides of the potential target sequence. Therefore, a gRNA truncated at the 5' end of its 20-nt guide sequence by 3 nucleotides to provide a 17-nt guide sequence cannot distinguish between HBB—ON and HBB—OFF1 target sequences. The full sequence of the DNA target constructs used in Examples 3-7 is set forth in Table 8 below.

Included for comparative purposes are guide RNAs having truncation of the guide sequence of a gRNA from 20 nucleotides to 18 or 17 nucleotides, with an evaluation of the ratio of cleavage of target gene sites to known off-target sites. It was seen that, in contrast to the teachings and conclusion by Yanfang et al. (2014), truncation had an effect on cleavage of specific off-target sites but did not have an effect on cleavage at other off-target sites. In spite of the teachings of Yanfang et al. (2014), the present inventors have sought and identified novel compounds and methods for CRISPR-Cas cleaving, nicking or binding a target polynucleotide with enhanced specificity and without truncation of the guide sequence.

In a 20-uL reaction volume, 2.5 nM of linearized DNA target in the presence of 50 nM sgRNA, 40 nM recombinant purified Cas9 protein (S. pyogenes; Agilent) and 0.8 mM $MgCl_2$ at pH 7.6 was incubated at 37° C. for 1 hr. Upon completion, 0.5 uL of RNace It (Agilent) was added, and incubation was continued at 37° C. for 5 min and then at 70° C. for 15 min. Crude products were loaded into a DNA 1000 or DNA 7500 LabChip for analysis on an Agilent Bioanalyzer 2200 or were loaded onto a Genomic DNA ScreenTape or a D5000 ScreenTape for analysis on an Agilent TapeStation 2200 or 4200. The workup steps serve to release Cas9 from binding of target DNA, which was assayed for cleavage.

Cleavage yields were calculated by the formula: a/(a+b)×100 where a is the sum of the band intensities of the two cleavage products and b is the remaining uncleaved DNA if present. A cleavage percentage of 100% means that all of the target DNA construct was cleaved, within the limits of detection.

Example 3

A series of 32 sgRNAs were made for targeting the "CLTA1" locus in the human CLTA gene. Briefly, individual RNA strands were synthesized and HPLC purified. All oligonucleotides were quality control approved on the basis of full-length strand purity by HPLC analysis and chemical composition by mass spectrometry analysis. Table 3 sets forth the sequences of the various CLTA1 sgRNAs. Table 3 shows the sequences of sgRNAs as Entries 1 through 31, and the table discloses certain embodiments of the present gRNAs containing one or more specificity-enhancing modifications. Entry 1 was unmodified and serves as a comparative example. Entry 2 contains MS modifications in the guide sequence at nucleotides 1, 2 and 3. Entry 3 contains MSP modifications in the guide sequence at nucleotides 1, 2 and 3. Entry 4 contains an MSP modification at nucleotide 1 of the guide sequence. Entries 5 and 6 are comparable examples having a gRNA truncated at the 5' end of its 20-nt guide sequence to an 18-nucleotide guide sequence or a 17-nucleotide guide sequence, respectively. Entries 7 and 8 are comparable examples having unmodified gRNA with one- or two-nucleotide overhangs, respectively, at the 5' end of the 20-nt guide sequence. Entries 9, 10, 11, 12, and 13 contain MP modifications in the guide sequence at nucleotide 1, nucleotides 1-2, nucleotides 1-3, nucleotides 1-4, and nucleotides 1-5, respectively. Entries 14 and 15 contain MP modifications in the tracrRNA region of the gRNA at nucleotides 2-5 counted from the 3' end of the sgRNA or nucleotides 2-6 counted from the 3' end of the sgRNA, respectively, noting that nucleotides are generally counted from 5' ends of polynucleotides. Therefore, the counting described for entries 14 and 15 is an exception to the general rule. Entries 16 and 17 contain MP modifications in the 20-nt guide sequence at nucleotides 1-2, with an MP-modified C or G nucleotide overhang, respectively. Entries 18 and 19 contain MP modifications in the 20-nt guide sequence at nucleotides 1-3, with an MP-modified UC or AG dinucleotide overhang, respectively. Entries 20 and 21 contain MP modifications in the 20-nt guide sequence at nucleotides 1-4, with an MP-modified CUC or GAG trinucleotide overhang, respectively, plus MP modifications in the tracrRNA region of the gRNA at the 3'-end of the sgRNA. Entries 22-25 contain MP modification in the guide sequence at nucleotide 20, 19, 18 or 17, respectively. Entry 26 contains MP modifications in the guide sequence at nucleotides 18 and 17. Entries 27-29 contain an M modification in the guide sequence at nucleotide 19, 18 or 17, respectively. Entry 30 contains M modifications in the guide sequence at nucleotides 18 and 17. Entry 31 contains M modifications in the guide sequence at nucleotides 1-20. Entry 32 contains M modifications in the 20-nt guide sequence at nucleotides 1-7, 9-11, 13-14 and 20, plus M modifications at several select positions across the remainder of the sgRNA sequence, specifically at nucleotides 30-31, 33, 35-36, 39, 42, 45, 47, 50, 60, 65-66, 70, 71, 76-77, 80-82, 90, 93, 95-96, 100-101, 104, and 106-112.

TABLE 3

| Entry | sgRnA Name | 5'→3' | SEQ. ID. NO. |
|---|---|---|---|
| 1 | CLTA1_unmodif | AGUCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 12 |
| 2 | CLTA1_3xMS | A<u>s</u>G<u>s</u>U<u>s</u>CCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUU<u>U</u>sU<u>s</u>U | 13 |
| 3 | CLTA1_3xMSP | <u>A</u>*s<u>G</u>*s<u>U</u>*sCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUU<u>U</u>*s<u>U</u>*sU | 14 |
| 4 | CLTA1_1xMSP | <u>A</u>*sGUCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUU<u>U</u>*sU | 15 |
| 5 | CLTA1_Truncated_18mer | UCCCUCAUCUCCCUCAAGCGUUUAAGAGCUAGUCUGGUAACAGAUAGCAAGUUUAAAUAAGGCUAGUCCGUUAUCAACUUGAAAAAGUGGCACCGAGUCGGUGCUUUUUUU | 16 |
| 6 | CLTA1_Truncated_17mer | CCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 17 |
| 7 | CLTA1_1xExtraG | G<sub>d</sub>AGUCCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 18 |
| 8 | CLTA1_2xExtraG | G<sub>d</sub>G<sub>d</sub>AGUCCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 19 |
| 9 | CLTA1_1xMP(5') | <u>A</u>*GUCCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 20 |
| 10 | CLTA1_2xMP(5') | <u>A</u>*<u>G</u>*UCCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 21 |
| 11 | CLTA1_3xMP(5') | <u>A</u>*<u>G</u>*<u>U</u>*CCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 22 |
| 12 | CLTA1_4xMP(5') | <u>A</u>*<u>G</u>*<u>U</u>*<u>C</u>*UCCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 23 |
| 13 | CLTA1_5xMP(5') | <u>A</u>*<u>G</u>*<u>U</u>*<u>C</u>*<u>C</u>*UCCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 24 |
| 14 | CLTA1_4xMP(3') | AGUCCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUU*<u>U</u>*<u>U</u>*<u>U</u>*U | 25 |
| 15 | CLTA1_5xMP(3') | AGUCCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCU*<u>U</u>*<u>U</u>*<u>U</u>*<u>U</u>*U | 26 |
| 16 | CLTA1+lover_3xMP | <u>C</u>*<u>A</u>*<u>G</u>*UCCCUCAUCUCCCUCAAGCGUUUAAGAGCUAGUCUAGCCAUAGCAAGUUUAAAUAAGGCUAGUCCGUUAUCAACUUGAAAAAGUGGCACCGAGUCGGUGCUUUUUUU | 27 |
| 17 | CLTA1+loverNC_3xMP | <u>G</u>*<u>A</u>*<u>G</u>*UCCCUCAUCUCCCUCAAGCGUUUAAGAGCUAGUCUAGCCAUAGCAAGUUUAAAUAAGGCUAGUCCGUUAUCAACUUGAAAAAGUGGCACCGAGUCGGUGCUUUUUUU | 28 |
| 18 | CLTA1+2over_5xMP | <u>U</u>*<u>C</u>*<u>A</u>*<u>G</u>*<u>U</u>*CCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 29 |
| 19 | CLTA1+2overNC_5xMP | <u>A</u>*<u>G</u>*<u>A</u>*<u>G</u>*<u>U</u>*CCCUCAUCUCCCUCAAGCGUUUAAGAGCUAGUCUGGUAACAGCAUAGCAAGUUUAAAUAAGGCUAGUCCGUUAUCAACUUGAAAAAGUGGCACCGAGUCGGUGCUUUUUUU | 30 |

TABLE 3-continued

| Entry | sgRNA Name | 5'→3' | SEQ. ID. NO. |
|---|---|---|---|
| 20 | CLTA1+3over_7xMP | C_a*U_a*C_a*A_a*G*U_a*C_a*CUCAUCUCCCCUCAAGCGUUUAAGAGCUAUGCUGGUAACAGCAAGUUAAAAUAAGGCUAGUCCGUUAUCAACUUGAAAAAGUGGCACCGAGUCGGUGCUU U_a*U_a*U*U | 31 |
| 21 | CLTA1+3overNC_7xMP | G_a*A_a*G_a*A_a*G*U_a*U_a*C*CUCAUCUCCCCUCAAGCGUUUAAGAGCUAUGCUGGUAACAGCAAGUUAAAAUAAGGCUAGUCCGUUAUCAACUUGAAAAAGUGGCACCGAGUCGGUGCUU U_a*U_a*U*U | 32 |
| 22 | CLTA1_20MP | AGUCCUCAUCUCCCCUCAAGC*GUUUAAGAGCUAUGCUGGUAACAGCAAGUUAAAAUAAGGCUAGUCCGUUAUCAACUUGAAAAAGUGGCACCGAGUCGGUGCUUUUUUU | 33 |
| 23 | CLTA1_19MP | AGUCCUCAUCUCCCCUCAAG*CGUUUAAGAGCUAUGCUGGUAACAGCAAGUUAAAAUAAGGCUAGUCCGUUAUCAACUUGAAAAAGUGGCACCGAGUCGGUGCUUUUUUU | 34 |
| 24 | CLTA1_18MP | AGUCCUCAUCUCCCCUCAA*GCGUUUAAGAGCUAUGCUGGUAACAGCAAGUUAAAAUAAGGCUAGUCCGUUAUCAACUUGAAAAAGUGGCACCGAGUCGGUGCUUUUUUU | 35 |
| 25 | CLTA1_17MP | AGUCCUCAUCUCCCCUCA*AGCGUUUAAGAGCUAUGCUGGUAACAGCAAGUUAAAAUAAGGCUAGUCCGUUAUCAACUUGAAAAAGUGGCACCGAGUCGGUGCUUUUUUU | 36 |
| 26 | CLTA1_17,18MP | AGUCCUCAUCUCCCCUCA*A*GCGUUUAAGAGCUAUGCUGGUAACAGCAAGUUAAAAUAAGGCUAGUCCGUUAUCAACUUGAAAAAGUGGCACCGAGUCGGUGCUUUUUUU | 37 |
| 27 | CLTA1_19M | AGUCCUCAUCUCCCCUCAAGCGUUUAAGAGCUAUGCUGGUAACAGCAAGUUAAAAUAAGGCUAGUCCGUUAUCAACUUGAAAAAGUGGCACCGAGUCGGUGCUUUUUUU | 38 |
| 28 | CLTA1_18M | AGUCCUCAUCUCCCCUCAAGCGUUUAAGAGCUAUGCUGGUAACAGCAAGUUAAAAUAAGGCUAGUCCGUUAUCAACUUGAAAAAGUGGCACCGAGUCGGUGCUUUUUUU | 39 |
| 29 | CLTA1_17M | AGUCCUCAUCUCCCCUCAAGCGUUUAAGAGCUAUGCUGGUAACAGCAAGUUAAAAUAAGGCUAGUCCGUUAUCAACUUGAAAAAGUGGCACCGAGUCGGUGCUUUUUUU | 40 |
| 30 | CLTA1_17,18M | AGUCCUCAUCUCCCCUCAAGCGUUUAAGAGCUAUGCUGGUAACAGCAAGUUAAAAUAAGGCUAGUCCGUUAUCAACUUGAAAAAGUGGCACCGAGUCGGUGCUUUUUUU | 41 |
| 31 | CLTA1_20xM | AGUCCUCAUCUCCCCUCAAGCGUUUAAGAGCUAUGCUGGUAACAGCAAGUUAAAAUAAGGCUAGUCCGUUAUCAACUUGAAAAAGUGGCACCGAGUCGGUGCUUUUUUU | 42 |
| 32 | CLTA1_47xM | AGUCCUCAUCUCCCCUCAAGCGUUUAAGAGCUAUGCUGGUAACAGCAAGUUAAAAUAAGGCUAGUCCGUUAUCAACUUGAAAAAGUGGCACCGAGUCGGUGCUUUUUUU | 124 |

Figure 8A:
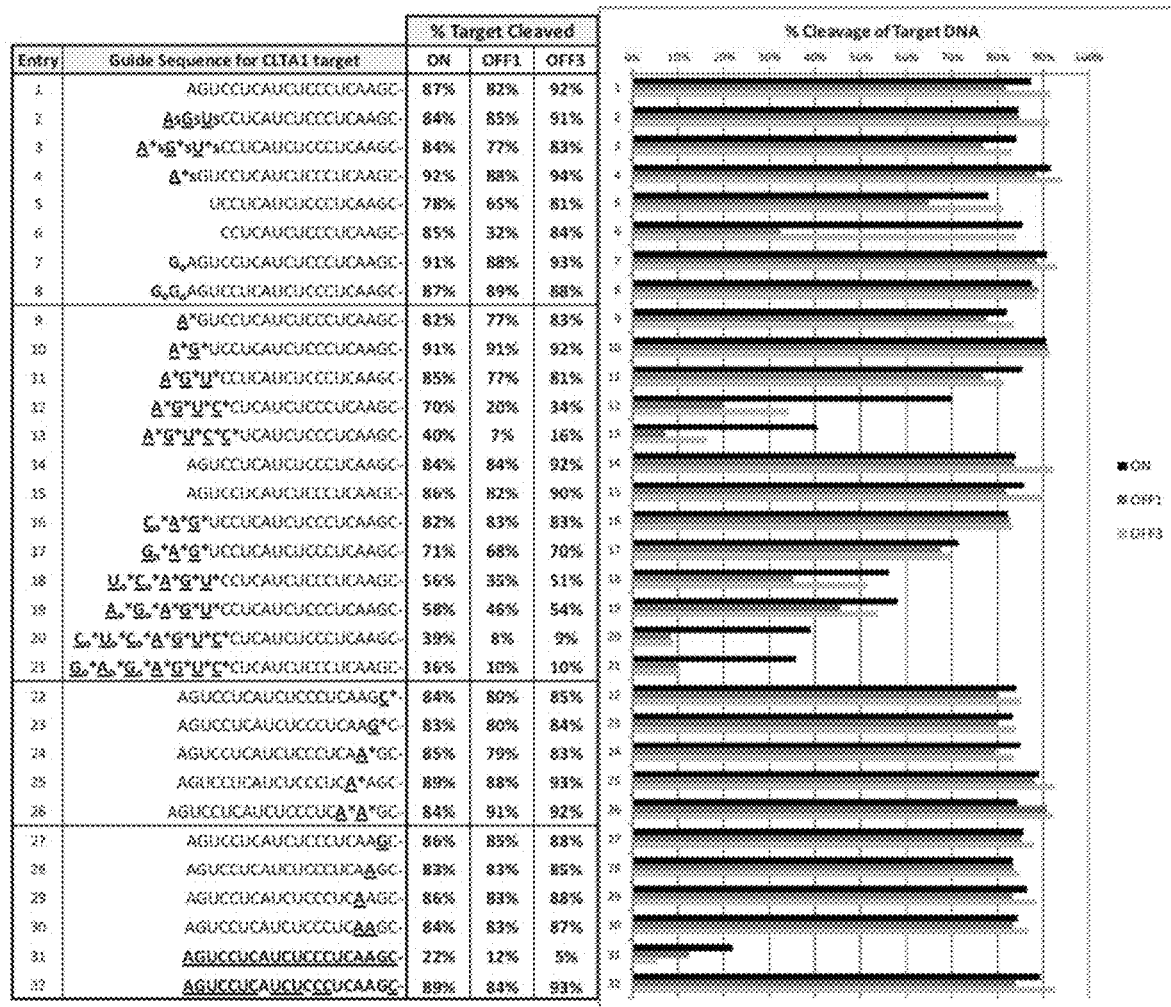
FIG. 8A shows the impact of chemical modifications in gRNAs targeted to the "CLTA1" sequence in the human CLTA gene with regard to in vitro cleavage of target polynucleotide called "ON" and separately assayed cleavage of two different off-target polynucleotides called "OFF1" and "OFF3," representing CLTA1 ON-target, CLTA1 OFF1-target, and CLTA1 OFF3-target, respectively.

LEGEND
Ns = 2'-O-methyl-3'-phosphorothioate modification of nucleotide N
N* = 2'-O-methyl-3'-PACE modification of nucleotide N
N*s = 2'-O-methyl-5'-thioPACE modification of nucleotide N
N_a* = 2'-O-methyl-3'-PACE modification of an overhanging nucleotide N (where N is located in a 5' overhang sequence covalently linked to the guide sequence of a sgRNA)
N = 2'-O-methyl modification of nucleotide N FIG. 8A shows the impact of chemical modifications in the gRNAs from Table 3 (SEQ ID NO: 12-42 and 124) with regard to Cas9-mediated target polynucleotide cleavage versus off-target polynucleotide cleavage. More particularly, the cleavage percentages of a CLTA1 target polynucleotide sequence (the on-target sequence, or "ON") and comparable off-target polynucleotide sequences (OFF1 and OFF3) are shown numerically and in bar graph form. FIG. 8B is derived from the results in FIG. 8A, with a ratio calculated for cleaved target polynucleotide versus cleaved off-target polynucleotide for each synthetic sgRNA assayed (SEQ ID NO: 12-42 and 124). Also calculated is a Specificity Score obtained by multiplying each ratio by the respective ON-target cleavage percentage per sgRNA assayed. The shaded values in entries 6, 12, 13, 20, 21, and 31 of FIG. 8B result from slightly to substantially reduced cleavage yields for the target polynucleotide sequence (ON1). Importantly, the reduction was even greater for one or both of the off-target polynucleotide sequences, yielding ON:OFF cleavage ratios greater than 2.0. The shaded values indicate that at least two-fold improvements in specificity can be obtained. Among the various chemical modifications and combinations tested in this experiment, the 2'-O-methyl-3'-PACE ("MP") modification gave the largest desired effect of decreasing off-target cleavage while retaining high levels of on-target cleavage, especially when incorporated at an optimal number of positions in the guide sequence. These examples serve as embodiments of the present teaching.

Example 4

Figure 9A:
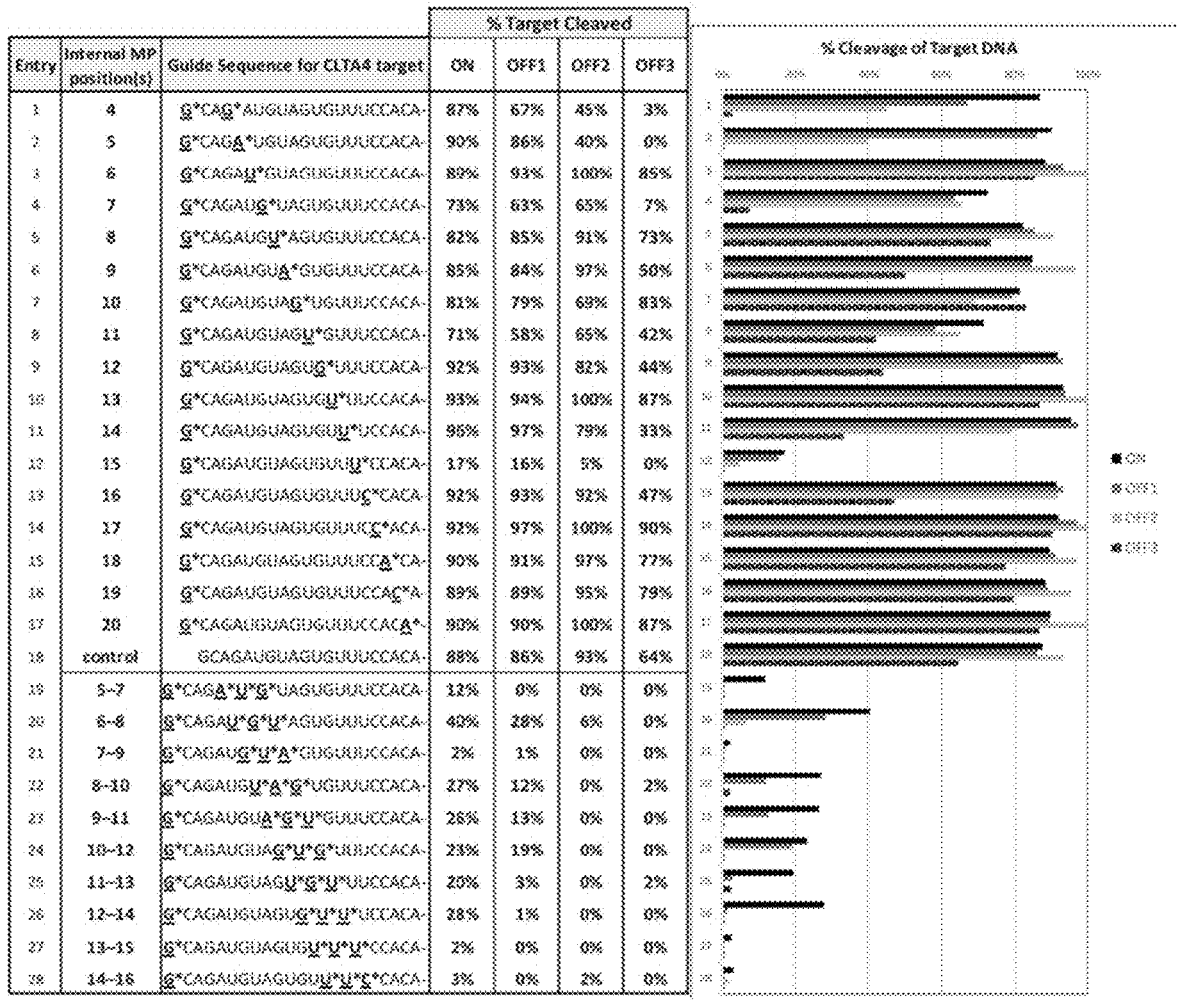
FIG. 9A shows the impact of 2'-O-methyl-3'-PACE ("MP") modifications at various locations in gRNAs targeted to the "CLTA4" sequence in the human CLTA gene with regard to in vitro cleavage of target polynucleotide called "ON" and separately assayed cleavage of three different off-target polynucleotides called "OFF1", "OFF2", and "OFF3," representing CLTA4 ON-target, CLTA4 OFF1-target, CLTA4 OFF2-target, and CLTA4 OFF3-target, respectively.

For the example represented in FIG. 9A, single or triple MP modifications were "walked" across the 20-nt guide sequence to see which modified positions could yield improvements in specificity as judged by on-target versus off-target cleavage activities. As listed in Table 4, a series of 28 sgRNAs (SEQ ID NO: 43-70) were made for targeting the "CLTA4" locus in the human CLTA gene, in which experimental sgRNAs contained a 2'-O-methyl-3'-PACE ("MP") modification at one or more positions in the guide sequence, in addition to having an MP modification at nucleotide 1 and also at the penultimate nucleotide in the tracrRNA region at the 3' end of the sgRNA which includes the last (i.e., most 3) internucleotide linkage. Thus, the modifications in the terminal internucleotide linkages were designed to protect such modified sgRNAs against degradation by exonucleases. Individual RNA strands were synthesized and HPLC purified. All oligonucleotides were quality control approved on the basis of full-length strand purity by HPLC analysis and chemical composition by mass spectrometry analysis. The cleavage percentages of a CLTA4 target polynucleotide sequence (ON) and comparable off-target polynucleotide sequences (OFF1, OFF2 and OFF3) are shown numerically and in bar graph form in FIG. 9A. FIG. 9B is derived from the results in FIG. 9A, with a ratio calculated for cleaved target polynucleotide versus cleaved off-target polynucleotide for each synthetic sgRNA (SEQ ID NO: 43-70) assayed. Ratios recorded as "large" indicate that no cleavage of off-target DNA polynucleotide was detected in those particular assays. As stated above in the description for FIG. 8B, a Specificity Score is calculated by multiplying a ratio by its respective on-target cleavage percentage. In the example represented by FIG. 9B, specificity scores ≥2.0 are shaded to indicate an improvement in specificity relative to unshaded scores. Shading indicates which MP positions in the guide sequence provided at least two-fold improvements in specificity. The results of the MP walk in entries 1-18 indicate that placement of the walked MP modification has an effect on specificity, and a trend is apparent for each set of specificity scores per off-target site assayed which shows that an MP modification near the 5' end of the guide sequence enhances specificity more so than an MP at other positions in the guide sequence, as seen in entries 1 and 2 relative to entries 3-18. This trend is consistent with a specificity enhancement trend observed for MP modifications in gRNAs targeted to the CLTA1 target sequence, in which MP modifications added to the 5' end of the CLTA sgRNA enhanced specificity, as indicated by the shaded scores in entries 12-13 and 20-21 in FIG. 8B. Although perhaps not effective in every case, a general strategy for improving specificity is to incorporate 1, 2, 3, 4 or 5 MP modifications at consecutive phosphodiester internucleotide linkages at the 5' end of a guide sequence in a gRNA.

TABLE 4

| Entry | sgRNA Name | 5'→3' | SEQ ID NO. |
|---|---|---|---|
| 1 | CLTA4_5-7MP_1xMP | G*CAGA*U*G*UAGUGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U*U | 43 |
| 2 | CLTA4_6-8MP_1xMP | G*CAGAU*G*U*AGUGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 45 |
| 3 | CLTA4_7-9MP_1xMP | G*CAGAUG*U*A*GUGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 45 |
| 4 | CLTA4_8-10MP_1xMP | G*CAGAUGU*A*G*UGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 46 |
| 5 | CLTA4_9-11MP_1xMP | G*CAGAUGUA*G*U*GUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 47 |
| 6 | CLTA4_10-12MP_1xMP | G*CAGAUGUAG*U*G*UUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 48 |
| 7 | CLTA4_11-13MP_1xMP | G*CAGAUGUAG*U*G*UUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 49 |
| 8 | CLTA4_12-14MP_1xMP | G*CAGAUGUAGUG*U*U*UCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 50 |
| 9 | CLTA4_13-15MP_1xMP | G*CAGAUGUAGUGU*U*U*CCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 51 |
| 10 | CLTA4_14-16MP_1xMP | G*CAGAUGUAGUGUU*U*C*CACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 52 |
| 11 | CLTA4_4MP_1xMP | G*CAG*AUGUAGUGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 53 |
| 12 | CLTA4_5MP_1xMP | G*CAGA*UGUAGUGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 54 |
| 13 | CLTA4_6MP_1xMP | G*CAGAU*GUAGUGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 55 |
| 14 | CLTA4_7MP_1xMP | G*CAGAUG*UAGUGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 56 |
| 15 | CLTA4_8MP_1xMP | G*CAGAUGU*AGUGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 57 |
| 16 | CLTA4_9MP_1xMP | G*CAGAUGUA*GUGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 58 |
| 17 | CLTA4_10MP_1xMP | G*CAGAUGUAG*UGUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 59 |
| 18 | CLTA4_11MP_1xMP | G*CAGAUGUAGU*GUUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 60 |
| 19 | CLTA4_12MP_1xMP | G*CAGAUGUAGUG*UUUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 61 |
| 20 | CLTA4_13MP_1xMP | G*CAGAUGUAGUGU*UUCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 62 |
| 21 | CLTA4_14MP_1xMP | G*CAGAUGUAGUGUU*UCCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 63 |
| 22 | CLTA4_15MP_1xMP | G*CAGAUGUAGUGUUU*CCACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 64 |
| 23 | CLTA4_16MP_1xMP | G*CAGAUGUAGUGUUUC*CACAGUUUAAGAGCUAUGCUGGUAACAGCAUGCAAGUUUAAAUAAGGCUAGUCCGUUAUCAACUUGAAAAAGUGGCACCGAGUCGGUGCUUUUU*U | 65 |

TABLE 4-continued

| Entry | sgRNA Name | 5'→3' | SEQ ID NO. |
|---|---|---|---|
| 24 | CLTA4_17MP_1xMP | G*CAGAUGUAGUGUUUCC*ACAGUUUAAGAGCUAUGCUGUUAACAGCAAGUUUAAAUAAGGCUAGUCCGUUAUCAACUUGAAAAAGUGGCACCGAGUCGGUGCUUUUU*U | 66 |
| 25 | CLTA4_18MP_1xMP | G*CAGAUGUAGUGUUUCCA*CAGUUUAAGAGCUAUGCUGUUAACAGCAAGUUUAAAUAAGGCUAGUCCGUUAUCAACUUGAAAAAGUGGCACCGAGUCGGUGCUUUUU*U | 67 |
| 26 | CLTA4_19MP_1xMP | G*CAGAUGUAGUGUUUCCAC*AGUUUAAGAGCUAUGCUGUUAACAGCAAGUUUAAAUAAGGCUAGUCCGUUAUCAACUUGAAAAAGUGGCACCGAGUCGGUGCUUUUU*U | 68 |
| 27 | CLTA4_20MP_1xMP | G*CAGAUGUAGUGUUUCCACA*GUUUAAGAGCUAUGCUGUUAACAGCAAGUUUAAAUAAGGCUAGUCCGUUAUCAACUUGAAAAAGUGGCACCGAGUCGGUGCUUUUU*U | 69 |
| 28 | CLTA4_unmodif | GCAGAUGUAGUGUUUCCACAGUUUAAGAGCUAUGCUGUUAACAGCAAGUUUAAAUAAGGCUAGUCCGUUAUCAACUUGAAAAAGUGGCACCGAGUCGGUGCUUUUUU | 70 |

LEGEND
Ns = 2'-O-methyl-3'-phosphorothioate modification of nucleotide N
N* = 2'-O-methyl-3'-PACE modification of nucleotide N
N*s = 2'-O-methyl-5'-thioPACE modification of nucleotide N
N_* = 2'-O-methyl-3'-PACE modification of an overhanging nucleotide N (where N is located in a 5' overhang sequence covalently linked to the guide sequence of a sgRNA)
N = 2'-O-methyl modification of nucleotide N

Example 5

In the example represented by FIG. 10, single or triple MP modifications were "walked" across the 20-nt guide sequence to see which modified positions could yield improvements in specificity as judged by on-target versus off-target cleavage activities. As listed in Table 5, a series of thirty sgRNAs (SEQ ID NO: 71-86 and 173-186) were made for targeting a locus in the human IL2RG gene. The experimental sgRNAs contained 2'-O-methyl-3'-PACE ("MP") modification at one or more positions in the guide sequence, in addition to having an MP modification at nucleotide 1 and also at the penultimate nucleotide in the tracrRNA region at the 3' end of the sgRNA which includes the last (i.e., most 3') internucleotide linkage. Thus, the modifications in the terminal internucleotide linkages were designed to protect the sgRNAs against exonucleases. Individual RNA strands were synthesized and HPLC purified. All oligonucleotides were quality control approved on the basis of full-length strand purity by HPLC analysis and chemical composition by mass spectrometry analysis. The cleavage percentages of an IL2RG target polynucleotide sequence (ON) and a comparable off-target polynucleotide sequence (OFF3) are shown numerically in FIG. 10. The figure also shows a ratio calculated for cleaved target polynucleotide versus cleaved off-target polynucleotide for each synthetic sgRNA (SEQ ID NO: 71-86 and 173-186) assayed. A Specificity Score is calculated by multiplying a ratio by its respective on-target cleavage percentage. Specificity scores ≥2.0 are shaded to indicate an improvement in specificity relative to unshaded scores, therefore the shading indicates which MP positions in the guide sequence provided at least two-fold improvements in specificity. In FIG. 10, the positions in the guide sequence which yielded the greatest improvements in specificity are indicated by darker shading. The results from MP modification of position 7, 14 or 16 are shown in entries 6, 13 and 15, respectively. Guide RNAs possessing such compositions can enhance specificity performance relative to other commonly used compositions such as gRNAs lacking MP modifications, particularly for various CRISPR-Cas applications of gRNAs targeting the clinically important IL2RG locus. The example represented by FIG. 10 also instantiates the present novel method of "walking" an MP modification across the guide sequence portion of a gRNA to identify which position or positions yield specificity enhancement due to the location of the walked MP modification. The magnitude of the specificity enhancement is assessed by the on-target versus off-target cleavage ratio for each position tested, and a practitioner can consider such values alongside the percentage of on-target cleavage measured for each design when deciding which MP-modified position or positions is likely to benefit the overall performance of the gRNA. The incremental walking of a single MP across the guide sequence may also identify positions in the sequence for potential synergistic improvements in specificity resulting from one or more combinations of MP modifications at the positions tested by the walk.

TABLE 5

| Entry | sgRNA Name | 5'→3' | SEQ ID NO |
|---|---|---|---|
| 1 | IL2RG_2MP_1xMP | U*G*GUAAUGGCUUCAACAGUUGAGAGCUAGAGCUAGAAAUAAGGCUAGUCCGUUAUCAACUUGAAAAAGUGGCACCGAGUCGGUGCUUU*U | 176 |
| 2 | IL2RG_3MP_1xMP | U*GG*UAAUGGCUUCAACAGUUGAGAGCUAGAGCUAGAAAUAAGGCUAGUCCGUUAUCAACUUGAAAAAGUGGCACCGAGUCGGUGCUUU*U | 177 |
| 3 | IL2RG_4MP_1xMP | U*GGU*AAUGGCUUCAACAGUUGAGAGCUAGAGCUAGAAAUAAGGCUAGUCCGUUAUCAACUUGAAAAAGUGGCACCGAGUCGGUGCUUU*U | 178 |
| 4 | IL2RG_5MP_1xMP | U*GGUA*AUGGCUUCAACAGUUGAGAGCUAGAGCUAGAAAUAAGGCUAGUCCGUUAUCAACUUGAAAAAGUGGCACCGAGUCGGUGCUUU*U | 179 |
| 5 | IL2RG_6MP_1xMP | U*GGUAA*UGGCUUCAACAGUUGAGAGCUAGAGCUAGAAAUAAGGCUAGUCCGUUAUCAACUUGAAAAAGUGGCACCGAGUCGGUGCUUU*U | 180 |
| 6 | IL2RG_7MP_1xMP | U*GGUAAU*GGCUUCAACAGUUGAGAGCUAGAGCUAGAAAUAAGGCUAGUCCGUUAUCAACUUGAAAAAGUGGCACCGAGUCGGUGCUUU*U | 181 |
| 7 | IL2RG_8MP_1xMP | U*GGUAAUG*GCUUCAACAGUUGAGAGCUAGAGCUAGAAAUAAGGCUAGUCCGUUAUCAACUUGAAAAAGUGGCACCGAGUCGGUGCUUU*U | 182 |
| 8 | IL2RG_9MP_1xMP | U*GGUAAUGG*CUUCAACAGUUGAGAGCUAGAGCUAGAAAUAAGGCUAGUCCGUUAUCAACUUGAAAAAGUGGCACCGAGUCGGUGCUUU*U | 183 |
| 9 | IL2RG_10MP_1xMP | U*GGUAAUGGA*UGGCUUCAACAGUUGAGAGCUAGAGCUAGAAAUAAGGCUAGUCCGUUAUCAACUUGAAAAAGUGGCACCGAGUCGGUGCUUU*U | 184 |
| 10 | IL2RG_11MP_1xMP | U*GGUAAUGAUG*GCUUCAACAGUUGAGAGCUAGAGCUAGAAAUAAGGCUAGUCCGUUAUCAACUUGAAAAAGUGGCACCGAGUCGGUGCUUU*U | 185 |
| 11 | IL2RG_12MP_1xMP | U*GGUAAUGAUGG*CUUCAACAGUUGAGAGCUAGAGCUAGAAAUAAGGCUAGUCCGUUAUCAACUUGAAAAAGUGGCACCGAGUCGGUGCUUU*U | 186 |
| 12 | IL2RG_13MP_1xMP | U*GGUAAUGAUGGC*UUCAACAGUUGAGAGCUAGAGCUAGAAAUAAGGCUAGUCCGUUAUCAACUUGAAAAAGUGGCACCGAGUCGGUGCUUU*U | 78 |
| 13 | IL2RG_14MP_1xMP | U*GGUAAUGAUGGCU*UCAACAGUUGAGAGCUAGAGCUAGAAAUAAGGCUAGUCCGUUAUCAACUUGAAAAAGUGGCACCGAGUCGGUGCUUU*U | 79 |
| 14 | IL2RG_15MP_1xMP | U*GGUAAUGAUGGCUU*CAACAGUUGAGAGCUAGAGCUAGAAAUAAGGCUAGUCCGUUAUCAACUUGAAAAAGUGGCACCGAGUCGGUGCUUU*U | 80 |
| 15 | IL2RG_16MP_1xMP | U*GGUAAUGAUGGCUUC*AACAGUUGAGAGCUAGAGCUAGAAAUAAGGCUAGUCCGUUAUCAACUUGAAAAAGUGGCACCGAGUCGGUGCUUU*U | 81 |
| 16 | IL2RG_17MP_1xMP | U*GGUAAUGAUGGCUUCA*ACAGUUGAGAGCUAGAGCUAGAAAUAAGGCUAGUCCGUUAUCAACUUGAAAAAGUGGCACCGAGUCGGUGCUUU*U | 82 |
| 17 | IL2RG_18MP_1xMP | U*GGUAAUGAUGGCUUCAA*CAGUUGAGAGCUAGAGCUAGAAAUAAGGCUAGUCCGUUAUCAACUUGAAAAAGUGGCACCGAGUCGGUGCUUU*U | 83 |
| 18 | IL2RG_19MP_1xMP | U*GGUAAUGAUGGCUUCAAC*AGUUGAGAGCUAGAGCUAGAAAUAAGGCUAGUCCGUUAUCAACUUGAAAAAGUGGCACCGAGUCGGUGCUUU*U | 84 |
| 19 | IL2RG_20MP_1xMP | U*GGUAAUGAUGGCUUCAACA*GUUGAGAGCUAGAGCUAGAAAUAAGGCUAGUCCGUUAUCAACUUGAAAAAGUGGCACCGAGUCGGUGCUUU*U | 85 |
| 20 | IL2RG_1xMP (control) | U*GGUAAUGAUGGCUUCAACAGUUGAGAGCUAGAGCUAGAAAUAAGGCUAGUCCGUUAUCAACUUGAAAAAGUGGCACCGAGUCGGUGCUUU*U | 86 |
| 21 | IL2RG_4-6MP_1xMP | U*GGU*A*A*UGAUGGCUUCAACAGUUGAGAGCUAGAGCUAGAAAUAAGCAAGUAAAUAAGCUAGUCCGUUAUCAACUGAAAAAGUGGCACCGAGUCGGUGCUUU*U | 173 |
| 22 | IL2RG_5-7MP_1xMP | U*GGUA*A*U*GAUGGCUUCAACAGUUAAGAGCUAGAGCUAGAAAUAAGCAAGUAAAUAAGCUAGUCCGUUAUCAACUGAAAAAGUGGCACCGAGUCGGUGCUUU*U | 174 |
| 23 | IL2RG_6-8MP_1xMP | U*GGUAA*U*G*AUGGCUUCAACAGUUGAGAGCUAGAGCUAGAAAUAAGCAAGUAAAUAAGCUAGUCCGUUAUCAACUGAAAAAGUGGCACCGAGUCGGUGCUUU*U | 175 |
| 24 | IL2RG_7-9MP_1xMP | U*GGUAAU*G*A*UGGCUUCAACAGUUGAGAGCUAGAGCUAGAAAUAAGCAAGUAAAUAAGCUAGUCCGUUAUCAACUGAAAAAGUGGCACCGAGUCGGUGCUUU*U | 71 |

TABLE 5-continued

| Entry | sgRNA Name | 5'→3' | SEQ ID NO |
|---|---|---|---|
| 25 | IL2RG_8-10MP_1xMP | U*GGUAAUG*A*U*GGCUUCAACAGUUGUAGCUAGAAAUAGCAAGUUAAAAAUAAGGCUAGUCCGUUAUCAACUUGAAAAAAGUGCACCGAGUCGGUGCUUU*U | 72 |
| 26 | IL2RG_9-11MP_1xMP | U*GGUAAUGA*U*G*GCUUCAACAGUUGUAGCUAGAAAUAGCAAGUUAAAAAUAAGGCUAGUCCGUUAUCAACUUGAAAAAAGUGCACCGAGUCGGUGCUUU*U | 73 |
| 27 | IL2RG_10-12MP_1xMP | U*GGUAAUGAU*G*G*CUUCAACAGUUGUAGCUAGAAAUAGCAAGUUAAAAAUAAGGCUAGUCCGUUAUCAACUUGAAAAAAGUGCACCGAGUCGGUGCUUU*U | 74 |
| 28 | IL2RG_11-13MP_1xMP | U*GGUAAUGAUG*G*C*UUCAACAGUUGUAGCUAGAAAUAGCAAGUUAAAAAUAAGGCUAGUCCGUUAUCAACUUGAAAAAAGUGCACCGAGUCGGUGCUUU*U | 75 |
| 29 | IL2RG_12-14MP_1xMP | U*GGUAAUGAUGG*C*U*UCAACAGUUGUAGCUAGAAAUAGCAAGUUAAAAAUAAGGCUAGUCCGUUAUCAACUUGAAAAAAGUGCACCGAGUCGGUGCUUU*U | 76 |
| 30 | IL2RG_13-15MP_1xMP | U*GGUAAUGAUGGC*U*U*CAACAGUUGUAGCUAGAAAUAGCAAGUUAAAAAUAAGGCUAGUCCGUUAUCAACUUGAAAAAAGUGCACCGAGUCGGUGCUUU*U | 77 |

LEGEND
N* = 2'-O-methyl-3'-PACE modification of nucleotide N

Example 6

A modification "walk" was done with an MP modification installed at incremental positions across a guide sequence targeted to the human HBB gene as shown in FIG. 11A to see if various sites in the 20-nt guide sequence may give substantial cleavage of the on-target site and decreased cleavage of the off-target site. A series of 65 sgRNAs were made for targeting the HBB gene as listed in Table 6, in which experimental sgRNAs contained a 2'-O-methyl-3'-PACE ("MP") modification at one or more internal nucleotide positions in the guide sequence, in addition to having an MP modification at nucleotide 1 and also at the penultimate nucleotide in the tracrRNA region at the 3' end of the sgRNA which includes the last (i.e., most 3) internucleotide linkage. Thus, the modifications in the terminal internucleotide linkages were designed to protect the sgRNAs against degradation by exonucleases. Individual RNA strands were synthesized and HPLC purified. All oligonucleotides were quality control approved on the basis of full-length strand purity by HPLC analysis and chemical composition by mass spectrometry analysis. The cleavage percentages of an HBB target polynucleotide sequence (ON) and a comparable off-target polynucleotide sequence (OFF1) are shown numerically in FIG. 11A. The figure also shows a ratio calculated for cleaved target polynucleotide versus cleaved off-target polynucleotide for each synthetic sgRNA (SEQ ID NO: 87-103) assayed. A Specificity Score is calculated by multiplying a ratio by its respective on-target cleavage percentage. Specificity scores ≥2.0 are shaded to indicate an improvement in specificity relative to unshaded scores, therefore the shading indicates which MP positions in the guide sequence provided at least two-fold improvements in specificity. In FIG. 11A the positions in the guide sequence that yielded the greatest improvements in specificity are indicated by darker shading, resulting from MP modification of positions 5, 9 or 11 as shown in entries 2, 6 and 8, respectively. Guide RNAs possessing such compositions can enhance specificity relative to other commonly used compositions, such as gRNAs lacking MP modifications, particularly for various CRISPR-Cas applications of gRNAs targeting the clinically important HBB locus. The example represented by FIG. 11A also instantiates our method of "walking" an MP modification across the guide sequence portion of a gRNA to identify which position or positions yield specificity enhancement due to the location of the walked MP modification. The magnitude of the specificity enhancement is assessed by the on-target versus off-target cleavage ratio for each position tested, and a practitioner can consider such values alongside the percentage of on-target cleavage measured for each design when deciding which MP-modified position or positions is likely to benefit the overall performance of the gRNA. The incremental walking of a single MP across the guide sequence may also identify positions in the sequence for potential synergistic improvements in specificity resulting from one or more combinations of MP modifications at the positions tested by the walk.

Figure 11B:
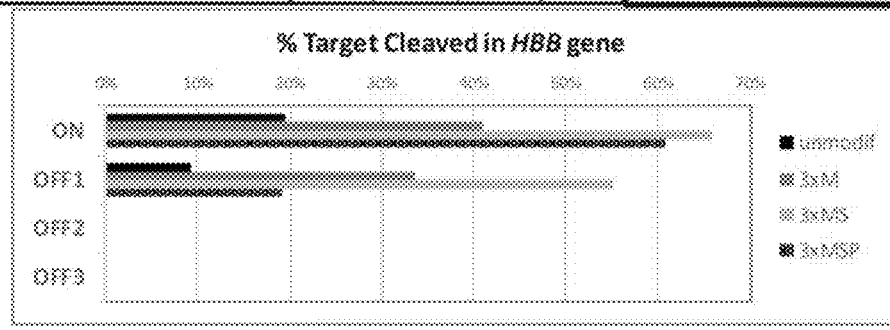
FIG. 11B shows the impact of various types of modifications in gRNAs targeted to a sequence in the human HBB gene in human K562 cells transfected with synthetic sgRNA and Cas9-expressing plasmid with regard to cleavage of a target genomic locus called "ON" versus concurrent cleavage of three different off-target genomic loci called "OFF1", "OFF2" and "OFF3" in this figure representing endogenous HBB ON-target, HBB OFF1-target, HBB OFF2-target and HBB OFF3-target sites, respectively. "Unmodif" indicates an sgRNA that was not chemically modified. "3xM" indicates that 2'-O-methyl ("M") nucleotide was incorporated at the very first three and the very last three nucleotides of an sgRNA strand, namely at its 5' and 3' termini respectively. Similarly, "3xMS" indicates that 2'-O-methyl-3'-phosphorothioate ("MS") nucleotide was incorporated likewise at the 5' and 3' termini of an sgRNA, whereas "3xMSP" indicates that 2'-O-methyl-3'-thioPACE ("MSP") nucleotide was incorporated likewise at the 5' and 3' termini of an sgRNA. All sgRNAs were assayed for editing of the indicated loci in transfected cells.

In a related experiment using HBB sgRNAs having the same 20-nt guide sequence, specificity was evaluated for editing of the genomic HBB target locus in K562 cells in which the 20-base pair target sequence in vivo was the same as was tested in polynucleotide constructs in vitro for FIG. 11A. FIG. 11B shows the impact of various types of modifications in sgRNAs targeting the human HBB gene in K562 cells by co-transfecting each synthetic sgRNA (SEQ ID NO: 187-190) with Cas9 mRNA and measuring cleavage of the target locus and three off-target loci including the same off-target sequence OFF1 as evaluated in FIG. 11A. A ratio is calculated for cleaved target (ON) versus cleaved off-target polynucleotide (OFF1) for each synthetic sgRNA assayed. A Specificity Score is calculated by multiplying a ratio by its respective on-target cleavage percentage. The results show that the PACE modifications in the guide sequence yielded a substantial improvement in specificity as evaluated by the Specificity Scores for the various types of modifications tested, especially with respect to the primary off-target activity (at OFF1).

TABLE 6

| Entry | sgRNA Name | 5'→3' | SEQ. ID. NO. |
|---|---|---|---|
| 1 | HBB_4MP_1xMP | C*UUG*CCCCACAGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 87 |
| 2 | HBB_5MP_1xMP | C*UUGC*CCCACAGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 88 |
| 3 | HBB_6MP_1xMP | C*UUGCC*CCACAGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 89 |
| 4 | HBB_7MP_1xMP | C*UUGCCC*CACAGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 90 |
| 5 | HBB_8MP_1xMP | C*UUGCCCC*ACAGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 91 |
| 6 | HBB_9MP_1xMP | C*UUGCCCCA*CAGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 92 |
| 7 | HBB_10MP_1xMP | C*UUGCCCAC*AGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 93 |
| 8 | HBB_11MP_1xMP | C*UUGCCCACA*GGGCAGUAAGUUUUAGAGCUAGAAAUAGCAAGUUAAAAUAAGGCUAGUCCGUUAUC AACUUGAAAAAGUGGCACCGAGUCGGUGCUUU*U | 94 |
| 9 | HBB_12MP_1xMP | C*UUGCCCACAG*GGCAGUAAGUUUUAGAGCUAGAAAUAGCAAGUUAAAAUAAGGCUAGUCCGUUAUC AACUUGAAAAAGUGGCACCGAGUCGGUGCUUU*U | 95 |

TABLE 6-continued

| Entry | sgRNA Name | 5'→3' | SEQ. ID. NO. |
|---|---|---|---|
| 10 | HBB_13MP_1xMP | C\*UUGCCCCACAGG\*GCAGUAAGUUUUAGAGCUAGAAAUAGCAAGUUAAAAUAAGGCUAGUCCGUUAUCAACUUGAAAAAGUGGCACCGAGUCGGUGCUU\*U | 96 |
| 11 | HBB_14MP_1xMP | C\*UUGCCCCACAGGG\*CAGUAAGUUUUAGAGCUAGAAAUAGCAAGUUAAAAUAAGGCUAGUCCGUUAUCAACUUGAAAAAGUGGCACCGAGUCGGUGCUU\*U | 97 |
| 12 | HBB_15MP_1xMP | C\*UUGCCCCACAGGGC\*AGUAAGUUUUAGAGCUAGAAAUAGCAAGUUAAAAUAAGGCUAGUCCGUUAUCAACUUGAAAAAGUGGCACCGAGUCGGUGCUU\*U | 98 |
| 13 | HBB_16MP_1xMP | C\*UUGCCCCACAGGGCA\*GUAAGUUUUAGAGCUAGAAAUAGCAAGUUAAAAUAAGGCUAGUCCGUUAUCAACUUGAAAAAGUGGCACCGAGUCGGUGCUU\*U | 99 |
| 14 | HBB_17MP_1xMP | C\*UUGCCCCACAGGGCAG\*UAAGUUUUAGAGCUAGAAAUAGCAAGUUAAAAUAAGGCUAGUCCGUUAUCAACUUGAAAAAGUGGCACCGAGUCGGUGCUU\*U | 100 |
| 15 | HBB_18MP_1xMP | C\*UUGCCCCACAGGGCAGU\*AAGUUUUAGAGCUAGAAAUAGCAAGUUAAAAUAAGGCUAGUCCGUUAUCAACUUGAAAAAGUGGCACCGAGUCGGUGCUU\*U | 101 |
| 16 | HBB_19MP_1xMP | C\*UUGCCCCACAGGGCAGUA\*AGUUUUAGAGCUAGAAAUAGCAAGUUAAAAUAAGGCUAGUCCGUUAUCAACUUGAAAAAGUGGCACCGAGUCGGUGCUU\*U | 102 |
| 17 | HBB_1xMP (control) | C\*UUGCCCCACAGGGCAGUAAGUUUUAGAGCUAGAAAUAGCAAGUUAAAAUAAGGCUAGUCCGUUAUCAACUUGAAAAAGUGGCACCGAGUCGGUGCUU\*U | 103 |
| 18 | HBB_16,17MP_1xMP | C\*UUGCCCCACAGGGCA\*G\*UAAGUUUUAGAGCUAGAAAUAGCAAGUUAAAAUAAGGCUAGUCCGUUAUCAACUUGAAAAAGUGGCACCGAGUCGGUGCUU\*U | 125 |
| 19 | HBB_14,17MP_1xMP | C\*UUGCCCCACAGG\*CAG\*UAAGUUUUAGAGCUAGAAAUAGCAAGUUAAAAUAAGGCUAGUCCGUUAUCAACUUGAAAAAGUGGCACCGAGUCGGUGCUU\*U | 126 |
| 20 | HBB_13,17MP_1xMP | C\*UUGCCCCACAGG\*GCAG\*UAAGUUUUAGAGCUAGAAAUAGCAAGUUAAAAUAAGGCUAGUCCGUUAUCAACUUGAAAAAGUGGCACCGAGUCGGUGCUU\*U | 127 |
| 21 | HBB_10,17MP_1xMP | C\*UUGCCCCAC\*AGGGCAG\*UAAGUUUUAGAGCUAGAAAUAGCAAGUUAAAAUAAGGCUAGUCCGUUAUCAACUUGAAAAAGUGGCACCGAGUCGGUGCUU\*U | 128 |
| 22 | HBB_9,17MP_1xMP | C\*UUGCCCCA\*CAGGGCAG\*UAAGUUUUAGAGCUAGAAAUAGCAAGUUAAAAUAAGGCUAGUCCGUUAUCAACUUGAAAAAGUGGCACCGAGUCGGUGCUU\*U | 129 |
| 23 | HBB_8,17MP_1xMP | C\*UUGCCCC\*ACAGGGCAG\*UAAGUUUUAGAGCUAGAAAUAGCAAGUUAAAAUAAGGCUAGUCCGUUAUCAACUUGAAAAAGUGGCACCGAGUCGGUGCUU\*U | 130 |
| 24 | HBB_7,17MP_1xMP | C\*UUGCCC\*CACAGGGCAG\*UAAGUUUUAGAGCUAGAAAUAGCAAGUUAAAAUAAGGCUAGUCCGUUAUCAACUUGAAAAAGUGGCACCGAGUCGGUGCUU\*U | 131 |
| 25 | HBB_6,17MP_1xMP | C\*UUGCC\*CCACAGGGCAG\*UAAGUUUUAGAGCUAGAAAUAGCAAGUUAAAAUAAGGCUAGUCCGUUAUCAACUUGAAAAAGUGGCACCGAGUCGGUGCUU\*U | 132 |
| 26 | HBB_5,17MP_1xMP | C\*UUGC\*CCCACAGGGCAG\*UAAGUUUUAGAGCUAGAAAUAGCAAGUUAAAAUAAGGCUAGUCCGUUAUCAACUUGAAAAAGUGGCACCGAGUCGGUGCUU\*U | 133 |
| 27 | HBB_14,16MP_1xMP | C\*UUGCCCCACAGG\*GC\*AGUAAGUUUUAGAGCUAGAAAUAGCAAGUUAAAAUAAGGCUAGUCCGUUAUCAACUUGAAAAAGUGGCACCGAGUCGGUGCUU\*U | 134 |
| 28 | HBB_13,16MP_1xMP | C\*UUGCCCCACAG\*GCA\*GUAAGUUUUAGAGCUAGAAAUAGCAAGUUAAAAUAAGGCUAGUCCGUUAUCAACUUGAAAAAGUGGCACCGAGUCGGUGCUU\*U | 135 |
| 29 | HBB_10,16MP_1xMP | C\*UUGCCCCAC\*AGGGCA\*GUAAGUUUUAGAGCUAGAAAUAGCAAGUUAAAAUAAGGCUAGUCCGUUAUCAACUUGAAAAAGUGGCACCGAGUCGGUGCUU\*U | 136 |
| 30 | HBB_9,16MP_1xMP | C\*UUGCCCCA\*CAGGGCA\*GUAAGUUUUAGAGCUAGAAAUAGCAAGUUAAAAUAAGGCUAGUCCGUUAUCAACUUGAAAAAGUGGCACCGAGUCGGUGCUU\*U | 137 |
| 31 | HBB_8,16MP_1xMP | C\*UUGCCCC\*ACAGGGCA\*GUAAGUUUUAGAGCUAGAAAUAGCAAGUUAAAAUAAGGCUAGUCCGUUAUCAACUUGAAAAAGUGGCACCGAGUCGGUGCUU\*U | 138 |
| 32 | HBB_7,16MP_1xMP | C\*UUGCCC\*CACAGGGCA\*GUAAGUUUUAGAGCUAGAAAUAGCAAGUUAAAAUAAGGCUAGUCCGUUAUCAACUUGAAAAAGUGGCACCGAGUCGGUGCUU\*U | 139 |
| 33 | HBB_6,16MP_1xMP | C\*UUGCC\*CCACAGGGCA\*GUAAGUUUUAGAGCUAGAAAUAGCAAGUUAAAAUAAGGCUAGUCCGUUAUCAACUUGAAAAAGUGGCACCGAGUCGGUGCUU\*U | 140 |
| 34 | HBB_5,16MP_1xMP | C\*UUGC\*CCCACAGGGCA\*GUAAGUUUUAGAGCUAGAAAUAGCAAGUUAAAAUAAGGCUAGUCCGUUAUCAACUUGAAAAAGUGGCACCGAGUCGGUGCUU\*U | 141 |

TABLE 6-continued

| Entry | sgRNA Name | 5'→3' | SEQ. ID. NO. |
|---|---|---|---|
| 35 | HBB_13,14MP_1xMP | <u>C</u>*UUGCCCCACAG<u>G</u>*<u>G</u>*CAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 142 |
| 36 | HBB_10,14MP_1xMP | <u>C</u>*UUGCCCA<u>C</u>*AGG<u>G</u>*CAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 143 |
| 37 | HBB_9,14MP_1xMP | <u>C</u>*UUGCCC<u>A</u>*CAGG<u>G</u>*CAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 144 |
| 38 | HBB_8,14MP_1xMP | <u>C</u>*UUGCC<u>C</u>*ACAGG<u>G</u>*CAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 145 |
| 39 | HBB_7,14MP_1xMP | <u>C</u>*UUGC<u>C</u>*CACAG<u>G</u>*CAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 146 |
| 40 | HBB_6,14MP_1xMP | <u>C</u>*UUG<u>C</u>*CCACAG<u>G</u>*CAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 147 |
| 41 | HBB_5,14MP_1xMP | <u>C</u>*UUG<u>C</u>*CCCACAG<u>G</u>*CAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 148 |
| 42 | HBB_10,13MP_1xMP | <u>C</u>*UUGCCCA<u>C</u>*AG<u>G</u>*GCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 149 |
| 43 | HBB_9,13MP_1xMP | <u>C</u>*UUGCCC<u>A</u>*CAG<u>G</u>*GCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 150 |
| 44 | HBB_8,13MP_1xMP | <u>C</u>*UUGCC<u>C</u>*ACAG<u>G</u>*GCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 151 |
| 45 | HBB_7,13MP_1xMP | <u>C</u>*UUGCC<u>C</u>*CACAG<u>G</u>*GCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 152 |
| 46 | HBB_6,13MP_1xMP | <u>C</u>*UUG<u>C</u>*CCACAG<u>G</u>*GCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 153 |
| 47 | HBB_5,13MP_1xMP | <u>C</u>*UUG<u>C</u>*CCCACAG<u>G</u>*CAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 154 |
| 48 | HBB_6,11MP_1xMP | <u>C</u>*UUG<u>C</u>*CCCACA<u>A</u>*GGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 155 |
| 49 | HBB_5,11MP_1xMP | <u>C</u>*UUG<u>C</u>*CCCAC<u>A</u>*GGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 156 |
| 50 | HBB_9,10MP_1xMP | <u>C</u>*UUGCCC<u>A</u>*<u>C</u>*AGGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 157 |
| 51 | HBB_8,10MP_1xMP | <u>C</u>*UUGCC<u>C</u>*A<u>C</u>*AGGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 158 |
| 52 | HBB_7,10MP_1xMP | <u>C</u>*UUGC<u>C</u>*CA<u>C</u>*AGGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 159 |
| 53 | HBB_6,10MP_1xMP | <u>C</u>*UUG<u>C</u>*CCA<u>C</u>*AGGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 160 |
| 54 | HBB_5,10MP_1xMP | <u>C</u>*UUG<u>C</u>*CCCA<u>C</u>*AGGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 161 |
| 55 | HBB_8,9MP_1xMP | <u>C</u>*UUGCC<u>C</u>*<u>A</u>*CAGGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 162 |
| 56 | HBB_7,9MP_1xMP | <u>C</u>*UUGC<u>C</u>*C<u>A</u>*CAGGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 163 |
| 57 | HBB_6,9MP_1xMP | <u>C</u>*UUG<u>C</u>*CC<u>A</u>*CAGGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 164 |
| 58 | HBB_5,9MP_1xMP | <u>C</u>*UUG<u>C</u>*CCC<u>A</u>*CAGGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 165 |
| 59 | HBB_6,8MP_1xMP | <u>C</u>*UUG<u>C</u>*C<u>C</u>*CACAGGGCAGUAAGUUUUAGAGCUAGAAAUAGCAAGUUAAAAUAAGGCUAGUCCGUUAUCAACUUGAAAAAGUGGCACCGAGUCGGUGCU<u>U</u>*U | 166 |

US 10,767,175 B2

TABLE 6-continued

| Entry | sgRNA Name | 5'→3' | SEQ. ID. NO. |
|---|---|---|---|
| 60 | HBB_5,8MP_1xMP | C*UUGC*CCC*ACAGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 167 |
| 61 | HBB_6,7MP_1xMP | C*UUGCC*C*CACAGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 168 |
| 62 | HBB_5,7MP_1xMP | C*UUGC*CC*CACAGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 169 |
| 63 | HBB_5,6MP_1xMP | C*UUGC*C*CCACAGGGCAGUAAGUUUUAGAGCUAGAAAUAGCAAGUUAAAAUAAGGCUAGUCCGUUAUC AACUUGAAAAAGUGGCACCGAGUCGGUGCUUU*U | 170 |
| 64 | HBB_unmodif | CUUGCCCCACAGGGCAGUAAGUUUUAGAGCUAGAAAUAGCAAGUUAAAAUAAGGCUAGUCCGUUAUC AACUUGAAAAAGUGGCACCGAGUCGGUGCUUUU | 171 |
| 65 | HBB_3xMS | CsUsUsGCCCCACAGGGCAGUAAGUUUUAGAGCUAGAAAUAGCAAGUUAAAAUAAGGCUAGUCCGUUAUC AACUUGAAAAAGUGGCACCGAGUCGGUGCUsUsUsU | 172 |

LEGEND
N* = 2'-O-methyl-3'-PACE modification of nucleotide N
Ns = 2'-O-methyl-3'-phosphorothioate modification of nucleotide N

Example 7

Further experiments for determining on-target versus off-target specificity enhancements due to MP modifications were performed either in solution using an in vitro cleavage assay or in cultured human cells of two types. The two cell types were K562 cells and induced pluripotent stem cells (also known as iPS cells or iPSCs). Cultured cells were transfected in individual wells with an MP-modified gRNA pre-complexed with recombinant Cas9 protein. Specificity was evaluated for editing of a genomic HBB target locus in which the 20-base pair target sequence in cultured cells was the same as was assayed in polynucleotide constructs in vitro as assessed in FIGS. 11A and 12A. Entries 1-17 (SEQ ID NO: 87-103) of FIG. 12A show the same results as FIG. 11A. The data in FIG. 12A are ranked according to Specificity Score from highest to lowest. Entries 18-64 (SEQ ID NO: 125-171) show the impact of additional MP modifications at various locations in gRNAs targeted to a sequence in the human HBB gene with regard to in vitro cleavage of target polynucleotide called "ON" and separately assayed cleavage of an off-target polynucleotide called "OFF1," representing HBB ON-target and HBB OFF1-target, respectively. For all entries, a ratio was calculated for cleaved target polynucleotide (ON) versus cleaved off-target polynucleotide (OFF1) for each synthetic sgRNA assayed. A Specificity Score was calculated by multiplying a ratio by its respective on-target cleavage percentage. Entries 18-64 are ranked according to Specificity Score from highest to lowest. Entries with the highest scores are shaded.

FIG. 12B shows the results of editing a genomic HBB target which has the same 20-base pair sequence as was tested in polynucleotide constructs in vitro for FIG. 12A. For FIG. 12B, the genomic HBB target site is endogenous in the human K562 cells and iPS cells tested. The results are grouped according to the number of MP modifications incorporated in the 20-nt guide sequence. Entries 1-17 in FIG. 12A and entries 1-12 and 22-33 in FIG. 12B represent testing of a single internal MP at various positions in the 20-nt guide sequence, in addition to having an MP modification at the very first internucleotide linkage at the 5' terminus and another MP at the very last internucleotide linkage at the 3' terminus of each sgRNA to protect it against exonucleolytic degradation. For entries 1-12 and 22-33 of FIG. 12B, the sgRNA tested were SEQ ID NO: 88, 90, 92-94, 96, 97, 99, 100, 103, 171 and 172. For entries 13-19 and 34-40 of FIG. 12B, the sgRNA tested were 128, 129, 133, 141, 160, 165, and 168. Included in these groupings are the results of controls lacking an internal MP modification, such as shown in entry 14 in FIG. 12A and entries 7-9 and 29-31 in FIG. 12B. Other groupings of results were made for sgRNAs having two internal MP modifications at various positions in the 20-nt guide sequence, in addition to having a single MP modification on each terminus of the sgRNAs to inhibit exonucleases, as shown for entries 18-64 in FIG. 12A and entries 13-19 and 34-40 in FIG. 12B. The various groupings are separated in the figures by heavy black lines. These figures show that the internal MP positions which give the largest specificity enhancements in vitro are the same as those which give the largest enhancements in both cell types, as shown in entries 1-2 in FIG. 12A and entries 1-2 and 22-23 in FIG. 12B. The next lower tier of specificity enhancements due to an internal MP modification is indicated by lighter shading, as shown for entries 3-5 in FIG. 12A and entries 3-5 and 24-26 in FIG. 12B. The relative ranking of specificity enhancements resulting from the position of internal MP modification in HBB sgRNAs is strikingly consistent across in vitro and in vivo assays as shown in entries 1-17 of FIG. 12A and entries 1-12 and 22-33 of FIG. 12B.

Results for a pair of internal MP modifications are grouped separately in entries 18-64 in FIG. 12A and in entries 13-19 and 34-40 in FIG. 12B, and the relative performance of these designs in vitro and in vivo as ranked by Specificity Score is remarkably consistent across the various assays and cell types. A slightly different way of evaluating specificity enhancement is simply to consider the on-target versus off-target ratio, which is ON:OFF1 for the HBB examples in FIGS. 12A and 12B. Using this alternative metric, a re-ranking of the groupings in FIG. 12B according to measured ratio, sorted from highest to lowest ratio per grouping, is shown in FIG. 12C. The various groupings in the figure are separated by heavy black lines. Comparable to our observations for Specificity Scores in FIG. 12B, the simpler assessment of specificity by ON:OFF ratio as presented in FIG. 12C shows similar outcomes across both cell types. Examples 6 and 7 demonstrate that specificity enhancements are dependent on the positions of MP modifications in the 20-nt guide sequence targeting the HBB gene.

In an experiment using some of the IL2RG sgRNAs of Table 5, specificity was evaluated for editing of the genomic IL2RG target locus in K562 cells. Also, using the VEGFA sgRNAs of Table 7 (shown below), specificity was evaluated for editing of the genomic VEGFA target locus in K562 cells.

cleavage of on-target and off-target polynucleotides in vitro as presented in Examples 4 through 7, a composite map of MP-modified positions in various guide sequences which yielded specificity enhancements is shown in FIG. 13. In particular, FIG. 13 shows a comparison of in vitro cleavage results from FIGS. 9A, 9B, 10 and 11A. FIG. 13 shows several important trends. First, as shown in Entry 12 in contrast to all other entries in FIG. 13, gRNAs having an MP modification at position 15 in their 20-nt guide sequences suffered a substantial loss of Cas9-mediated cleavage activ-

TABLE 7

| Entry | sgRNA Name | 5'→3' | SEQ. ID. NO. |
|---|---|---|---|
| 1 | VEGFA_11MP_1xMP | G*GUGAGUGAGU*GUGUGCGUGGUUUUAGAGCUAGAAAUAGCAAGUUAAAAUAAGG CUAGUCCGUUAUCAACUUGAAAAAGUGGCACCAGUCGGUGCUUU*U | 194 |
| 2 | VEGFA_10MP_1xMP | G*GUGAGUGAG*UGUGUGCGUGGUUUUAGAGCUAGAAAUAGCAAGUUAAAAUAAGG CUAGUCCGUUAUCAACUUGAAAAAGUGGCACCAGUCGGUGCUUU*U | 195 |
| 3 | VEGFA_9MP_1xMP | G*GUGAGUGA*GUGUGCGUGGUUUUAGAGCUAGAAAUAGCAAGUUAAAAUAAGG CUAGUCCGUUAUCAACUUGAAAAAGUGGCACCAGUCGGUGCUUU*U | 196 |
| 4 | VEGFA_7MP_1xMP | G*GUGAGU*GAGUGUGCGUGGUUUUAGAGCUAGAAAUAGCAAGUUAAAAUAAGG CUAGUCCGUUAUCAACUUGAAAAAGUGGCACCAGUCGGUGCUUU*U | 197 |
| 5 | VEGFA_5MP_1xMP | G*GUGA*GUGAGUGUGCGUGGUUUUAGAGCUAGAAAUAGCAAGUUAAAAUAAGG CUAGUCCGUUAUCAACUUGAAAAAGUGGCACCAGUCGGUGCUUU*U | 198 |
| 6 | VEGFA_1xMP (control) | G*GUGAGUGAG*UGUGUGCGUGGUUUUAGAGCUAGAAAUAGCAAGUUAAAAUAAGG CUAGUCCGUUAUCAACUUGAAAAAGUGGCACCAGUCGGUGCUUU*U | 199 |

In this way, the 20-nt guide sequences were tested in vivo. FIG. 14 shows the impact of various types of modifications in IL2RG sgRNAs and VEGFA sgRNAs in K562 cells. Each synthetic sgRNA was co-transfected with Cas9 mRNA, and cleavage of the target locus and of an off-target locus OFF2 were measured. A ratio is calculated for cleaved target (ON) versus cleaved off-target polynucleotide (OFF2) for each synthetic sgRNA assayed. A Specificity Score is calculated by multiplying a ratio by its respective on-target cleavage percentage.

The results in FIG. 14 show that modifications in the guide sequence of synthetic gRNAs targeting IL2RG and VEGFA yielded substantial improvements in specificity as evaluated by the Specificity Scores for the various types of modifications tested, especially with respect to the off-target activity (at OFF2). In contrast with entry 1, entry 2 shows a significant specificity enhancement resulted from MP modification at both ends of the IL2RG sgRNA, in which the 5' and 3' terminal internucleotide linkages are modified. In contrast with entries 1 & 2, entries 3 & 4 show impressive specificity enhancements for IL2RG sgRNAs having an MP modification at an internal position in the IL2RG guide sequence, namely at position 5 or 11, respectively. Furthermore, MP modification of position 5 gave the largest enhancement of specificity among entries 1 thru 4 in FIG. 14.

In contrast with entry 5, entries 6 thru 10 show significant specificity enhancements for VEGFA sgRNA having an MP modification at an internal position in the VEGFA guide sequence, namely at position 5, 7, 9, 10, or 11, respectively. When comparing the enhancements across entries 5 thru 10, it is notable for entry 6 that an MP modification at position 5 of the 20-nt guide sequence gave the largest enhancement of specificity for VEGFA.

By conducting MP walks across guide sequences in gRNAs targeting different DNA sequences and assaying ity. This suggests that position 15 was particularly intolerant of an MP modification for Cas9-mediated cleavage. Second, there is a trend for specificity enhancements throughout entries 1-2, as indicated by shaded specificity scores. This trend suggests that incorporating MP modifications at or near the 5' end of various 20-nt guide sequences can be a generally useful design strategy for enhancing the target specificity of gRNAs. Another example of the utility of this approach was discussed above in Example 3 for results presented in FIGS. 8A and 8B regarding MP modifications at the 5' end of gRNAs targeting the CLTA1 locus in vitro. A further example of the utility of the general approach was discussed above in Example 6 regarding MSP modifications at the 5' end of a gRNA targeting the HBB gene in transfected human K562 cells as shown in FIG. 11B. A third example regarding specificity effects of MP modifications is apparent in entry 3 of FIG. 13, where specificity scores resulting from MP modification of position 6 in differently targeted 20-nt guide sequences constitute the lowest scores per MP walk, disregarding the anomalous effects for position 15 mentioned above. For each series of MP walks involving CLTA4 OFF3, IL2RG OFF3 and HBB OFF1, a nadir of specificity enhancement due to MP modification of position 6 is especially noticeable in contrast to specificity scores resulting from MP modification of an adjacent position in the same guide sequence, namely position 4, 5 or 7 (shown as shaded scores throughout entries 1, 2 or 4, respectively).

Examples 3 through 7 demonstrate that gRNAs containing modifications at specific positions in guide sequences are tolerated by active Cas protein and gRNA:Cas protein complexes, as modifications at many sequence positions in gRNAs did not prevent target-specific cleavage of on-target polynucleotides. Examples 3 through 7 also demonstrate that the present gRNAs, complexes and methods can achieve on-target versus off-target ratios of at least 1.2, alternatively at least 1.5, alternatively at least 2, alternatively at least 2.5, alternatively at least 3, alternatively at least 3.5, alternatively at least 4, alternatively at least 4.5, alternatively at least 5, and/or the ratio is up to 10, 12, 15 or 20. In many instances, the 2'-O-methyl-3'-PACE ("MP") modification had a positive effect on ratios by decreasing off-target cleavage levels while retaining high levels of on-target cleavage as desired for specificity enhancements.

As a result of these experiments it is calculated that incorporation of multiple modifications that decrease binding energy at specific sites across a guide sequence will lower known and unknown off-target cleavage events.

As mentioned above, the full sequences of the DNA constructs used in Examples 3-7 are set forth in Table 8. The target polynucleotide or off-target sequence, along with PAM sequence, is shown in bold, and the PAM sequence is also underlined.

TABLE 8

```
CLTA1 ON1-target (SEQ ID NO: 104):
GCGTTTCTGGGTGAGCAAAAACAGGAAGGCAAAATGCCGCAAAAAAGGGAATAAGGGCGACACGGA
AATGTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
GCAGGCCAAAGATGTCTCCCGCATGCGCTAGTCCTCATCTCCCTCAAGCAGGCCCTGCTGGTGCAC
TGAAGAGCCACCCTGTGCGCGTGATATGCAGCTCCAGCTTTTGTTCCCTTTAGTGAGGGTTAATTGCGC
GCTTGGCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTAATTGCG
TTGCGCTCACTCCCGCTTTCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTT
GCTGGCGTTTTTCCATAGGCTCCGCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACA
TGATCCCCCATGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTTATGCGGCGACCGAGTTGC
TCTTGCCCGGCGTCAATACGGGATAATACCGCGCCACATAGC CLTA1 OFF1-target (SEQ ID NO: 105):
GCGTTTCTGGGTGAGCAAAAACAGGAAGGCAAAATGCCGCAAAAAAGGGAATAAGGGCGACACGGA
AATGTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
GCAGGGCAAAGAGGTCTCCTGTATGCACTAGTCCTCAACTCCCTCAACCAGGCGACCCTTGGTGCA
CTGACAAACCGCTCCTGCGCGTGATATGCAGCTCCAGCTTTTGTTCCCTTTAGTGAGGGTTAATTGCGC
GCTTGGCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTAATTGCG
TTGCGCTCACTGCCCGCTTTCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTT
GCTGGCGTT1TTCCATAGGCTCCGCCCCCTGACGAGCATCACAAAAATCGACGCTCAAGTCAGAGGT
```

TABLE 8-continued

```
GGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTATCAA
AAAAGGATCTTCACCTAGATCCTTTTAAATTAAAAATGAAGUTTAAATCAATCTAAAGTATATATGAGT
AAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTTTGCCATTGCTACAGGCATC
GTGGTGTCACGCTCGTCGTTTGGTATGGCTTCATTCAGCTCCGGTTCCCAACGATCAAGGCGAGTTACA
TGATCCCCCATGTTGTGCAAAAAAGCGGTTAGCTCCTTCGGTCCTCCAGATCGTTGTCAGAAGTAAGTTG
GCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGC
TCTTGCCCGGCGTCAATACGGGATAATACCGCGCCACATAGC

CLTA1 OFF3-target (SEQ ID NO: 106):
GCGTTTCTGGGTGAGCAAAAACAGGAAGGCAAATGCCGCAAAAAAGGGAATAAGGGCGACACGGA
AATGTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
AGGAGAGGGAGCCATGCTCATCTCCAGCCCACTCCTCATCCCCCTCAAGCCGGTCCCAGGCTGAGA
GGCTAAAGCTTGTCTTTGCGCGTGATATGCAGCTCCAGCTTTTGTTCCCTTTAGTGAGGGTTAATTGCG
CGCTTGGCGTAATCATGGTCATAGCTGTTTCCTGTGTGAAATTGTTATCCGCTCACAATTCCACACAAC
ATACGAGCCGGAAGCATAAAGTGTAAAGCCTGGGGTGCCTAATGAGTGAGCTAACTCACATTAATTGC
GTTGCGCTCACTGCCCGCMCCAGTCGGGAAACCTGTCGTGCCAGCTGCATTAATGAATCGGCCAAC
GCGCGGGGAGAGGCGGTTTGCGTATTGGGCGCTCTTCCCTTCCTCGCTCACTGACTCGCTGCGCTCGG
TCGTTCGGCTGCGGCGAGCGGTATCAGCTCACTCAAAGGCGGTAATACGGTTATCCACAGAATCAGGG
GATAACGCAGGAAAGAACATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCGGGAAGCGTGGCGCTTTCTC
ATAGCTCACGCTGTAGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGCTACA
GAGTTCTTGAAGTGGTGGCCTAACTACGGCTACACTAGAAGGACAGTATTTGGTATCTGCGCTCTGCT
GAAGCCAGTTACCTTCGGAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAATCTAAAGTATATAT
AGTAAACTTGGTCTGACAGTTACCAATGCTTAATCAGTGAGGCACCTATCTCAGCGATCTGTCTATTTC
GTTCATCCATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAACCAGCCA
GCCGGAAGGGCCGAGCGCAGAAGTGGTCCTGCAACTTTATCCGCCTCCATCCAGTCTATTAATTGTTG
CCGGGAAGCTAGAGTAAGTAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCCCAACGATCAAGGCGAGTTA
CATGATCCCCCATGTTGTGCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTACTGTCATGCCATCCGTAA
GATGCTTTTCTGTGACTGGTGAGTACTCAACCAAGTCATTCTGAGAATAGTGTATGCGGCGACCGAGTT
GCTCTTGCCCGGCGTCAATACGGGATAATACCGCGCCACATAGC CLTA4 ON-target (SEQ ID NO: 107):
GCGTTTCTGGGTGAGCAAAAACAGGAAGGCAAATGCCGCAAAAAAGGGAATAAGGGCGACACGGA
AATGTTGAATACTCATACTCTTCCTTTTTCAATATTATTGAAGCATTTATCAGGGTTATTGTCTCATGAG
CGGATACATATTTGAATGTATTTAGAAAAATAAACAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
AAGAGCTTCACTGAGTAGGATTAAGATATTGCAGATGTAGTGTTTCCACAGGGTGGCTCTTCAGTGC
```

TABLE 8-continued

```
ACCAGCGGAACCTGCTGCGCGTGATATGCAGCTCCAGCTTTTGTTCCCTTTAGTGAGGGTTAATTGCGC
GCTTGGCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTAATTGCG
TTGCGCTCACTGCCCGCTTTCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTT
GCTGGCGTTTTTCCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGCGCTCTGCTG
AAGCCAGTTACCTTCGGAAAAAGAGTTGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACA
TGATCCCCCATGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGC
TCTTGCCCGGCGTCAATACGGGATAATACCGCGCCACATAGC

CLTA4 OFF1-target (SEQ ID NO: 108):
GCGTTTCTGGGTGAGCAAAAACAGGAAGGCAAATGCCGCAAAAAAGGGAATAAGGGCGACACGGA
AATGTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
AAGAGCTTCACTGAGTAGGATTAAGATATTGCAGATGTAGTATTTCCACAGGGTGGCTCTTCAGTGC
ACCAGCGGAACCTGCTGCGCGTGATATGCAGCTCCAGCTTTTGTTCCCTTTAGTGAGGGTTAATTGCGC
GCTTGGCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTAATTGCG
TTGCGCTCACTGCCCGCTTTCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTT
GCTGGCGTTMCCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACA
TGATCCCCCATGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGC
TCTTGCCCGGCGTCAATACGGGATAATACCGCGCCACATAGC CLTA4 OFF2-target (SEQ ID NO: 109):
GCGTTTCTGGGTGAGCAAAAACAGGAAGGCAAATGCCGCAAAAAAGGGAATAAGGGCGACACGGA
AATGTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
```

TABLE 8-continued

```
ACCGTCTATCAGGGCGATGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTGACGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
AAGAGCTTCACTGAGTAGGATTAAGATATTCCAGATGTAGCGTTTCCACAGGGTGGCTCTTCAGTGC
ACCAGCGGAACCTGCTGCGCGTGATATGCAGCTCCAGCTTTTGTTCCCTTTAGTGAGGGTTAATTGCGC
GCTTGGCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTAATTGCG
TTGCGCTCACTGCCCGCTTTCCAGTCGGGAAACCTTCGTGCCAGCTGCATTAATGAATCGGCCAACGC
GCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTT
GCTGGCGTTTTTCCATAGGCTCCGCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACA
TGATCCCCCATGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGC
TCTTGCCCGGCGTCAATACGGGATAATACCGCGCCACATAGC

CLTA4 OFF3-target (SEQ ID NO: 110):
GCGTTTCTGGGTGAGCAAAAACAGGAAGGCAAATGCCGCAAAAAAGGGAATAAGGGCGACACGGA
AATGTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTGACGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
AAGAGCTTCACTGAGTAGGATTAAGATATTGCAGATGTTGTGTTTCCACAGGGTGGCTCTTCAGTGC
ACCAGCGGAACCTGCTGCGCGTGATATGCAGCTCCAGCTTTTGTTCCCTTTAGTGAGGGTTAATTGCGC
GCTTGGCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTAATTGCG
TTGCGCTCACTGCCCGCTTTCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTT
GCTGGCGTTTTTCCATAGGCTCCGCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACA
TGATCCCCCATGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGC
TCTTGCCCGGCGTCAATACGGGATAATACCGCGCCACATAGC
```

TABLE 8-continued

```
HBB ON-target (SEQ ID NO: 111):
GCGTTTCTGGGTGAGCAAAAACAGGAAGGCAAATGCCGCAAAAAAGGGAATAAGGGCGACACGGA
AATGTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
GGCCTCACCACCAACTTCATCCACGTTCACCTTGCCCCACAGGGCAGTAACGGCAGACTTCTCCTCA
GGAGTCAGATGCACCAGCGCGTGATATGCAGCTCCAGCTTTTGTTCCCTTTAGTGAGGGTTAATTGCGC
GCTTGGCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTAATTGCG
TTGCGCTCACTGCCCGCTTTCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTT
GCTGGCGTTTTTCCATAGGCTCCGCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCGGTAAGACACGA
CTTATCGCCACTGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACA
TGATCCCCCATGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGC
TCTTGCCCGGCGTCAATACGGGATAATACCGCGCCACATAGC HRB OFF1-target (SEQ ID NO: 112):
GCGTTTCTGGGTGAGCAAAAACAGGAAGGCAAATGCCGCAAAAAAGGGAATAAGGGCGACACGGA
AATGTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
GGATAGGAAAGGTGAAGTCAGAGCAGTGCTTCAGCCCCACAGGGCAGTAAGGGCAGCCTTCCTCTA
AATACCAGATTCCCAAAGCGCGTGATATGCAGCTCCAGCTTTTGTTCCCTTTAGTGAGGGTTAATTGCG
CGCTTGGCGTAATCATGGTCATAGCTGTTTCCTGTGTGAAATTGTTATCCGCTCACAATTCCACACAAC
ATACGAGCCGGAAGCATAAAGTGTAAAGCCTGGGGTGCCTAATGAGTGAGCTAACTCACATTAATTGC
GTTGCGCTCACTGCCCCTTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTCACTGACTCGCTGCGCTCGG
TCGTTCGGCTGCGGCGAGCGGTATCAGCTCACTCAAAGGCGGTAATACGGTTATCCACAGAATCAGGG
GATAACGCAGGAAAGAACATGTGAGCAAAAGGCCAGCAAAAGGCCAGGAACCGTAAAAAGGCCGCG
TTGCTGGCGTTTTTCCATAGGCTCCGCCCCCTGACGAGCATCACAAAAATCGACGCTCAAGTCAGAG
GTGGCGAAACCCGACAGGACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCGGGAAGCGTGGCGCTTTCTC
ATAGCTCACGCTGTAGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGCTACA
GAGTTCTTGAAGTGGTGGCCTAACTACGGCTACACTAGAAGGACAGTATTTGGTATCTGCGCTCTGCT
GAAGCCAGTTACCTTCGGAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAATCTAAAGTATATATG
AGTAAACTTGGTCTGACAGTTACCAATGCTTAATCAGTGAGGCACCTATCTCAGCGATCTGTCTATTTC
GTTCATCCATAGTTGCCTGACTCCCCGTCGTGTAGATAACTACGATACGGGAGGGCTTACCATCTGGCC
```

TABLE 8-continued

```
CCAGTGCTGCAATGATACCGCGAGACCCACGCTCACCGGCTCCAGATTTATCAGCAATAAACCAGCCA
GCCGGAAGGGCCGAGCGCAGAAGTGGTCCTGCAACTTTATCGCCTCCATCCAGTCTATTAATTGTTG
CCGGGAAGCTAGAGTAAGTAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCCCAACGATCAAGGCGAGTTA
CATGATCCCCCATGTTGTGCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTACTGTCATGCCATCCGTAA
GATGCTTTTCTGTGACTGGTGAGTACTCAACCAAGTCATTCTGAGAATAGTGTATGCGGCGACCGAGTT
GCTCTTGCCCGCGTCAATACGGGATAATACCGCGCCACATAGC

IL2RG ON-target (SEQ ID NO: 113):
GCGTTTCTGGGTGAGCAAAAACAGGAAGGCAAATGCCGCAAAAAAGGGAATAAGGGCGACACGGA
AATGTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGGGTCGAGGTG
CCGTAAAGCACTAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
GGGCAGCTCCAGGAATAAGAGGGATGTGAATGGTAATGATGGCTTCAACATGGCGCTTGCTCTTCA
TTCCCTGGGTGTAGTCTGCGCGTGATATGCAGCTCCAGCTTTTGTTCCCTTTAGTGAGGGTTAATTGCG
CGCTTGGCGTAATCATGGTCATAGCTGTTTCCTGTGTGAAATTGTTATCCGCTCACAATTCCACACAAC
ATACGAGCCGGAAGCATAAAGTGTAAAGCCTGGGGTGCCTAATGAGTGAGCTAACTCACATTAATTGC
GTTGCGCTCACTGCCCGCTTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTCACTGACTCGCTGCGCTCGG
TCGTTCGGCTGCGGCGAGCGGTATCAGCTCACTCAAAGGCGGTAATACGGTTATCCACAGAATCAGGG
GATAACGCAGGAAAGAACATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCGGGAAGCGTGGCGCTTTCTC
ATAGCTCACGCTGTAGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGCTACA
GAGTTCTTGAAGTGGTGGCCTAACTACGGCTACACTAGAAGGACAGTATTTGGTATCTGCGCTCTGCT
GAAGCCAGTTACCTTCGGAAAAAGAGTTGGTAGCTCTTGATCCGGCAAACAAACCACCGCTGGTAGCG
GTGGTTTTTTGTTTGCAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAATCTAAAGTATATATG
AGTAAACTTGGTCTGACAGTTACCAATGCTTAATCAGTGAGGCACCTATCTCAGCGATCTGTCTATTTC
GTTCATCCATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAACCAGCCA
GCCGGAAGGGCCGAGCGCAGAAGTGGTCCTGCAACTTTATCGCCTCCATCCAGTCTATTAATTGTTG
CCGGGAAGCTAGAGTAAGTAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCCCAACGATCAAGGCGAGTTA
CATGATCCCCCATGTTGTGCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTACTGTCATGCCATCCGTAA
GATGCTTTTCTGTGACTGGTGAGTACTCAACCAAGTCATTCTGAGAATAGTGTATGCGGCGACCGAGTT
GCTCTTGCCCGCGTCAATACGGGATAATACCGCGCCACATAGC IL2RG OFF3-target (SEQ ID NO: 114):
GCGTTTCTGGGTGAGCAAAAACAGGAAGGCAAATGCCGCAAAAAAGGGAATAAGGGCGACACGGA
AATaTTGAATACTCATACTCTTCCTTTTTCAATATTATTGAAGCATTTATCAGGGTTATTGTCTCATGAG
CGGATACATATTTGAATGTATTTAGAAAAATAAACAAATAGGGGTTCCGCGCACATTTCCCCGAAAAG
TGCCACCTAAATTGTAAGCGTTAATATTTTGTTAAAATTCGCGTTAAATTTTTGTTAAATCAGCTCATTT
TTTAACCAATAGGCCGAAATCGGCAAAATCCCTTATAAATCAAAAGAATAGACCGAGATAGGGTTGA
GTGTTGTTCCAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTUTTTGGGTCGAGGTG
CCGTAAAGCACTAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCCCATTCGCC
ATTCAGGCTGCGCAACTGTTGGGAAGGGCGATCGGTGCGGGCCTCTTCGCTATTACGCCAGCTGGCGA
AAGGGGGATGTGCTGCAAGGCGATTAAGTTGGGTAACGCCAGGGTTTTCCCAGTCACGACGTTGTAAA
ACGACGGCCAGTGAGCGCGCGTAATACGACTCACTATAGGGCGAATTGGGTACGATCGATGCGGCCTC
CAATATTGAGAGTGAATGAAAAGTGTCAGCTGGTAATGATGACTTCAACATAGTCAGAACTCTTTGG
GCTGTTCCAAACATCAGCGCGTGATATGCAGCTCCAGCTTTTGTTCCCTTTAGTGAGGGTTAATTGCGC
GCTTGGCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTAATTGCG
TTGCGCTCACTGCCCGCTTTCCAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCACTGACTCGCTGCGCTCGGTC
TTCGGCTGCGGCGAGCGGTATCAGCTCACTCAAAGGCGGTAATACGGTTATCCACAGAATCAGGGGA
TAACGCAGGAAAGAACATGTGAGCAAAAGGCCAGCAAAAGGCCAGGAACCGTAAAAAGGCCGCGTT
GCTGGCGTTTTTCCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCAT
AGCTCACGCTGTAGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCGGTAAGACACGA
```

TABLE 8-continued

```
CTTATCGCCACTGGCAGCAGCCACTGGTAACAGGATTAGCAGAGCGAGGTATGTAGGCGGTGCTACAG
AGTTCTTGAAGTGGTGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTGATCTT
TTCTACGGGTCTGACGCTCAGTGGAACGAAAACTCACGTTAAGGGATTTTGGTCATGAGATTATCAA
AAAGGATCTTCACCTAGATCCTTTTAAATTAAAAATGAAGTTTTAAATCAATCTAAAGTATATATGAGT
AAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAGGCGAGTTACA
TGATCCCCCATGTTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGC
TCTTGCCCGGCGTCAATACGGGATAATACCGCGCCACATAGC
```

EXEMPLARY EMBODIMENTS

Exemplary embodiments provided in accordance with the presently disclosed subject matter include, but are not limited to, the claims and the following embodiments:

A1. A synthetic guide RNA comprising:
(a) a crRNA segment comprising (i) a guide sequence capable of hybridizing to a target polynucleotide, (ii) a stem sequence; and
(b) a tracrRNA segment comprising a nucleotide sequence that is partially or completely complementary to the stem sequence,
wherein the guide sequence comprises at least one specificity-enhancing modification, wherein the synthetic guide RNA has gRNA functionality.

A2. The synthetic guide RNA of embodiment A1, wherein the at least one specificity-enhancing modification weakens hybridization between the guide sequence and the target polynucleotide.

A3. The synthetic guide RNA of embodiment A1, wherein the at least one specificity-enhancing modification weakens hybridization between the guide sequence and an off-target polynucleotide.

A4. The synthetic guide RNA of embodiment A1, wherein the at least one specificity-enhancing modification strengthens hybridization between the guide sequence and the target polynucleotide and weakens hybridization between the guide sequence and an off-target polynucleotide.

A5. The synthetic guide RNA of any of the preceding embodiments, further comprising at least one stability-enhancing modification on the 5' end or the 3' end or both ends of the guide RNA.

A6. The synthetic guide RNA of any of the preceding embodiments, wherein the guide sequence comprises a locking region, a sampling region, and a seed region, and the at least one specificity-enhancing modification is present in the sampling region and/or in the seed region.

A7. The synthetic guide RNA of embodiment A6, wherein the at least one specificity-enhancing modification is present in the seed region and/or in the sampling region and/or in the locking region.

A8. The synthetic guide RNA of any of the preceding embodiments, wherein the at least one specificity-enhancing modification comprises an internucleotide linkage modification.

A9. The synthetic guide RNA of any of the preceding embodiments, wherein the at least one specificity-enhancing modification comprises a chemically modified nucleobase.

A10. The synthetic guide RNA of any of the preceding embodiments, wherein the at least one specificity-enhancing modification is located in at least one nucleotide sugar moiety.

A11. The synthetic guide RNA of any of the preceding embodiments, wherein the at least one specificity-enhancing modification comprises a 3'-phosphonoacetate internucleotide linkage, a 3'-phosphonoacetate methyl ester internucleotide linkage, a 3'-methylphosphonate internucleotide linkage, a 3'-thiophosphonoacetate internucleotide linkage, a 3'-methylthiophosphonate internucleotide linkage, a 3'-boranophosphonate internucleotide linkage, or combinations thereof.

A12. The synthetic guide RNA of any of the preceding embodiments, comprising a 2' modification that confers a C3'-endo sugar pucker.

A13. The synthetic guide RNA of any of the preceding embodiments, wherein the at least one specificity-enhancing modification comprises:
(a) 2'-deoxyribose, 2'-deoxy-2'-fluoroarabinofuranosyl, 2'-deoxy-2'-fluororibofuranosyl, sugars such as ribose having 2'-O-phenyl, 2'-thiophenyl, 2'-S-thiophenyl, 2'-methyl, 2'-ethyl, 2'-propyl, 2'-allyl, 2'-allylphenyl, 2'-methylhydroxy, 2'-methyloxymethyl, 2'-O-carbamate, 2'-O-ethylamino, 2'-O-allylamino, 2'-O-propylamino, or 2'-O-substituted phenyl, or combinations thereof;
(b) phosphonoacetates, thiophosphonoacetates, phosphonopropionates, phosphonothiopropionates, methylphosphonates, methylphosphonothioates, or boranophosphonates; or combinations thereof; or
(c) combinations of (a) and (b).

A14. The synthetic guide RNA any of embodiments A8, A9, A11 or A13, further comprising a 2'-O-methyl modification.

A15. The synthetic guide RNA of any of the preceding embodiments, wherein the at least one specificity-enhancing modification is an unstructured nucleic acid ("UNA"), an unlocked nucleic acid ('ULNA'), an abasic nucleotide, or an alkylene spacer comprising —$PO_4Y$—$(CR^3_2)$m-$PO_4Y$—, or an ethylene glycol spacer comprising (—$PO4Y$-$(CR^3_2CR^3_2O)$n-$PO_3Y$—), where m is 2, 3 or 4, n is 1, 2 or 3, each $R^3$ is independently selected from the group consisting of H, an alkyl and a substituted alkyl, and each Y is H or a negative charge.

A16. The synthetic guide RNA of any of embodiments A1 to A9, A11 to A13, or A1 S, wherein the at least one specificity-enhancing modification does not comprise a nucleobase modification.

A17. The synthetic guide RNA of any of embodiments A1 to A15, wherein the at least one specificity-enhancing modification is a nucleobase selected from the group consisting of 2-thioU, 2-thioC, 4-thioU, 6-thioG, 2-aminopurine, hypoxanthine, 7-deazaguanine, 7-deaza-8-azaguanine, 7-deazaadenine, 7-deaza-8-azaadenine, 5-methylC, 5-methylU, 5-hydroxymethylcytosine, 5-hydroxymethyluracil, 5,6-dehydrouracil, 5-ethynylcytosine, 5-aminoallylU, 5-aminoallylC, an abasic nucleotide, a UNA base, isoC, isoG, 5-methyl-pyrimidine, x(A,G,C,T,U), y(A,G,C,T,U), and combinations thereof.

A18. The synthetic guide RNA of any of the preceding embodiments, wherein the at least one specificity-enhancing modification is a nucleotide or nucleotide analog selected from the group consisting of 5-nitroindole, nebularine, inosine, diaminopurine, an abasic linkage, and an abasic fluorophore linkage such as 3-O-yl-2-(4-butylamidofluorescein) propyl-1-O-yl-phosphodiester.

A19. The synthetic guide RNA of any of the preceding embodiments, wherein the at least one specificity-enhancing modification comprises a modification that lowers a melting temperature (Tm) of a first DNA/RNA duplex formed by the synthetic guide RNA and the target polynucleotide, relative to the Tm of a duplex without the specificity-enhancing modification.

A20. The synthetic guide RNA of embodiment A19, wherein the at least one specificity-enhancing modification lowers the Tm by about 0.5° C. per modification, alternatively by about 0.5-1.0° C. per modification, alternatively by about 1.0-2.0° C. per modification, alternatively by 2-8° C. per modification.

A21. The synthetic guide RNA of any of the preceding embodiments, wherein the guide sequence comprises 20 nucleotides and optionally comprises a 5'-overhang sequence.

A22. The synthetic guide RNA of embodiment A21, wherein the guide sequence comprises or consists of nucleotides 1 through 20, counted from the 5' end of the guide sequence, and at least one specificity-enhancing modification at nucleotide 1, alternatively at nucleotides 1 and 2, alternatively at nucleotides 1, 2, and 3, alternatively at nucleotides 1, 2, 3 and 4; alternatively at nucleotides 1, 2, 3, 4 and 5.

A23. The synthetic guide RNA of embodiment A21, wherein the guide sequence consists of nucleotides 1 through 20-N, counted from the 5' end of the guide sequence, where N is an integer between −10 and 10 (optionally between −10 and 6), and the at least one specificity-enhancing modification is within nucleotides 4-N to 20-N, alternatively within nucleotides 5-N to 20-N, alternatively within nucleotides 10-N to 20-N, alternatively within nucleotides 13-N to 20-N, alternatively within nucleotides 13-N through 14-N or 16-N through 19-N, alternatively within nucleotides 13-N through 14-N or 16-N through 18-N.

A24. The synthetic guide RNA of embodiment A21, wherein the guide sequence consists of nucleotides 1 through 20-N, wherein N is a positive or negative integer between −10 and 10 (optionally between −10 and 6), counted from the 5' end of the guide sequence, and the guide sequence comprises one specificity-enhancing modification located at nucleotide 11-N, 12-N, 13-N, 14-N, 16-N, 17-N, 18-N, 19-N or 20-N, alternatively located at nucleotide 13-N, 14-N, 16-N, 17-N, 18-N, 19-N or 20-N, alternatively located at nucleotide 13-N, 14-N, 16-N, 17-N, or 18-N.

A25. The synthetic guide RNA of any of the preceding embodiments, further comprising at least one stability-enhancing modification starting at nucleotide 1 on the 5' end and at least one stability-enhancing modification within the five terminal nucleotides on the 3' end of the guide RNA.

B1. A gRNA:Cas protein complex comprising a synthetic guide RNA of any of the preceding embodiments and a Cas protein, capable of cleaving, nicking or binding a target polynucleotide, or having cleaving activity, nicking activity and/or binding activity.

C1. A method for cleaving, nicking or binding a target polynucleotide comprising:
contacting the target polynucleotide with the gRNA:Cas protein complex of embodiment B1, and cleaving, nicking or binding the target polynucleotide.

C2. The method of embodiment C1, wherein the synthetic guide RNA comprising the at least one specificity-enhancing modification decreases the cleaving, nicking or binding of an off-target polynucleotide in comparison to an unmodified gRNA.

C3. The method of embodiment C2, wherein the at least one off-target polynucleotide is cleaved, nicked or bound by the CRISPR-associated protein, and wherein a ratio of cleaved, nicked or bound target polynucleotide to cleaved, nicked or bound off-target polynucleotide is at least 1.2, alternatively at least 1.5, alternatively at least 2, alternatively at least 2.5, alternatively at least 3, alternatively at least 3.5, alternatively at least 4, alternatively at least 4.5, alternatively at least 5 or at least 10, 12, 15 or 20.

D1. A method of preparing a synthetic guide RNA comprising:
selecting a target polynucleotide in a genome wherein the target polynucleotide comprises a respective nucleotide sequence;
identifying at least one off-target polynucleotide in the genome wherein the off-target polynucleotide comprises a respective nucleotide sequence;
aligning the sequence of the target polynucleotide with the sequence of the off-target polynucleotide to identify one or more identical portions of both sequences;
designing a synthetic guide RNA comprising;
  (a) a crRNA segment comprising (i) a guide sequence capable of hybridizing to a target polynucleotide, (ii) a stem sequence; and
  (b) a tracrRNA segment comprising a nucleotide sequence that is partially or completely complementary to the stem sequence,
wherein the guide sequence includes a specificity-enhancing modification within a portion of its sequence complementary to one of the identified identical portions.

D2. The method of embodiment D1, wherein the at least one specificity-enhancing modification weakens hybridization between the guide sequence and the target polynucleotide.

D3. The method of embodiment D1, wherein the at least one specificity-enhancing modification weakens hybridization between the guide sequence and an off-target polynucleotide.

D4. The method of embodiment D1, wherein the at least one specificity-enhancing modification strengthens hybridization between the guide sequence and the target polynucleotide and weakens hybridization between the guide sequence and an off-target polynucleotide.

D5. The method of any of the preceding embodiments, further comprising synthesizing the designed guide RNA.

D6. The method of any of the preceding embodiments, wherein the off-target polynucleotide is identified by an algorithm to predict off-target sites such as those found at http://www.rgenome.net/Cas-OFFinder, https://cm.jefferson.edu/Off-Spotter, or http://crispr.mit.edu, or other technique for identifying and quantifying the activation of off-target sites in actual cases, such as disclosed in Tsai et al. (2015) Nat. Biotechnol. 33, 187-97; Ran et al. (2015) Nature 520, 186-91; and/or Frock et al. (2015) Nat. Biotechnol. 33, 179-86.

D7. The method of any of the preceding embodiments, further comprising:
identifying at least one distinguishing nucleotide position between the target polynucleotide and the off-target polynucleotide, wherein the target polynucleotide and the off-target polynucleotide have a different nucleotide at the at least one distinguishing position, and
including in the synthetic guide RNA a nucleotide matching the nucleotide at the at least one distinguishing position in the target polynucleotide.

D8. The method of any of the preceding embodiments, wherein the specificity-enhancing modification lowers the melting temperature ("Tm") of a first DNA/RNA duplex formed by the guide sequence of the synthetic guide RNA and the target polynucleotide, relative to the Tm of a duplex without the specificity-enhancing modification.

D9. The method of embodiment D8, wherein the specificity-enhancing modification lowers the Tm of the first DNA/RNA duplex by about 0.5° C. per modification, alternatively by about 0.5-1° C. per modification, alternatively by about 1-2° C. per modification, alternatively by about 2-8° C. per modification.

D10. The method of embodiment D8, wherein the specificity-enhancing modification lowers the Tm of the first DNA/RNA duplex by at least about PC, at least about 2° C., at least about 3° C., at least about 4° C., at least about 5° C., and/or up to about 6° C., alternatively up to about 8° C., alternatively up to about 10° C., alternatively up to about 13° C., for example by lowering the Tm from about 1° C. to about 13° C., alternatively from about 1° C. to about 6° C.

D11. The method of embodiments D8, wherein the specificity-enhancing modification lowers the Tm of a second DNA/RNA duplex formed by the guide sequence of the synthetic guide RNA and the at least one off-target polynucleotide.

D12. The method of embodiments D8, wherein the Tm of the first DNA/RNA duplex is higher than the Tm of the second DNA/RNA duplex, for example at least at least about 0.5° C. higher, alternatively at least about P° C. higher.

E1. A method for cleaving, nicking or binding a target polynucleotide comprising:
selecting a target polynucleotide in a genome;
providing and/or designing a synthetic guide RNA comprising;
(a) a crRNA segment comprising (i) a guide sequence capable of hybridizing to a target polynucleotide, (ii) a stem sequence; and
(b) a tracrRNA segment comprising a nucleotide sequence that is partially or completely complementary to the stem sequence,
wherein the guide sequence includes a specificity-enhancing modification;
calculating melting temperature (Tm) of a DNA/RNA duplex of the guide sequence and the target polynucleotide; and
forming a gRNA:Cas protein complex comprising a Cas protein and the synthetic guide RNA;
contacting the target polynucleotide with a gRNA:Cas protein complex at a temperature within 10° C. of the Tm, alternatively within 5° C. of the Tm, alternatively at approximately the Tm; and
cleaving, nicking or binding the target polynucleotide by the contacting.

F1. A method for cleaving, nicking or binding a target polynucleotide comprising:
selecting a target polynucleotide in a genome;
providing and/or designing a synthetic guide RNA comprising;
(a) a crRNA segment comprising (i) a guide sequence capable of hybridizing to a target polynucleotide, (ii) a stem sequence; and
(b) a tracrRNA segment comprising a nucleotide sequence that is partially or completely complementary to the stem sequence,
wherein the guide sequence includes at least one specificity-enhancing modification; selecting said modification or combination of modifications so that melting temperature (Tm) of the DNA/RNA duplex of the guide sequence and the target polynucleotide is between 25° C. and 49° C.;
forming a gRNA:Cas protein complex comprising a Cas protein and the designed synthetic guide RNA;
contacting the target polynucleotide with a gRNA:Cas protein complex at a temperature within 12° C. of the Tm, alternatively within 8° C. of the Tm, alternatively within 5° C. of the Tm, alternatively at approximately the Tm; and
cleaving, nicking or binding the target polynucleotide.

G1. A method for cleaving, nicking or binding a target polynucleotide comprising:
selecting a target polynucleotide in a genome;
providing and/or designing a synthetic guide RNA comprising;
(a) a crRNA segment comprising (i) a guide sequence capable of hybridizing to a target polynucleotide, (ii) a stem sequence; and
(b) a tracrRNA segment comprising a nucleotide sequence that is partially or completely complementary to the stem sequence,
wherein the guide sequence includes at least one specificity-enhancing modification;
selecting or including in the guide sequence said modification or combination of modifications so that the melting temperature (Tm) of the DNA/RNA duplex of the guide sequence and the target polynucleotide is at least 0.5-1° C. lower than the Tm of the unmodified gRNA/target duplex, or at least 1-3° C. lower or at least 1-12° C. lower, and
forming a gRNA:Cas protein complex comprising a Cas protein and the designed synthetic guide RNA;
contacting the target polynucleotide with a gRNA:Cas protein complex at a temperature within 12° C. of the Tm, alternatively within 8° C. of the Tm, alternatively within 5° C. of the Tm, alternatively at approximately the Tm; and
cleaving, nicking or binding the target polynucleotide.

EFG2. The method of any of the preceding embodiments E1, F1 or G1, wherein the at least one specificity-enhancing modification weakens hybridization between the guide sequence and the target polynucleotide.

EFG3. The synthetic guide RNA of any of embodiments E1, F1 or G1, wherein the at least one specificity-enhancing modification weakens hybridization between the guide sequence and an off-target polynucleotide.

EFG4. The synthetic guide RNA of any of embodiments E1, F1 or G1, wherein the at least one specificity-enhancing modification strengthens hybridization between the guide sequence and the target polynucleotide and weakens hybridization between the guide sequence and an off-target polynucleotide.

H1. The method of any of the preceding embodiments, wherein the cleaving, nicking or binding takes place in vitro.

H2. The method of any of the preceding embodiments, wherein the cleaving, nicking or binding takes place in a cell.

H3. The method of embodiment H2, wherein the cell is isolated from a multicellular source prior to contacting the target polynucleotide with the gRNA:Cas protein complex.

H4. The method of embodiment H3, wherein the source is a plant, an animal, a multicellular protist, or a fungus.

H5. The method of any one of embodiments H2 to H4, wherein the cell, or a cell derived therefrom, is returned to the source after contacting the target polynucleotide with the gRNA:Cas protein complex.

H6. The method of any of the preceding embodiments, wherein the cleaving, nicking or binding takes place in vivo.

H7. The method of any one of embodiments any of the preceding embodiments, wherein the Cas protein is Cas9.

H8. The method of any of the preceding embodiments, wherein the cleaving or nicking results in gene editing.

H9. The method of any of the preceding embodiments, wherein the cleaving, nicking or binding results in alteration of gene expression.

H10. The method of any of the preceding embodiments, wherein the cleavage, nicking or binding results in a functional knockout of a target gene.

H11. The method of any of the preceding embodiments, further comprising repairing the cleaved target polynucleotide by homology-directed repair with an exogenous or endogenous template polynucleotide.

H12. The method of embodiment H11, wherein the exogenous or endogenous template polynucleotide comprises at least one sequence having substantial sequence identity with a sequence on either side of the cleavage site.

H13. The method of any of the preceding embodiments, further comprising repairing the cleaved target polynucleotide by non-homologous end joining.

H14. The method of any of the preceding embodiments, wherein the repairing step produces an insertion, deletion, or substitution of one or more nucleotides of the target polynucleotide.

H15. The method of embodiment H14, wherein the insertion, deletion, or substitution results in one or more amino acid changes in a protein expressed from a gene comprising the target polynucleotide.

I1. A set or library of synthetic guide RNA molecules comprising two or more synthetic guide RNAs of any of the preceding embodiments.

J1. A kit comprising a synthetic guide RNA of any of the preceding embodiments, and one or more other components.

K1. An array of RNA molecules comprising two or more synthetic guide RNAs of any of the preceding embodiments.

L1. The synthetic guide RNA, method, set or library, kit or array of any of the preceding embodiments, comprising a single RNA strand that comprises both the crRNA segment and the tracrRNA segment.

L2. The synthetic guide RNA, method, set or library, kit or array of any of the preceding embodiments, comprising two RNA strands, and the crRNA segment and the tracrRNA segment are in different RNA strands.

L3. The synthetic guide RNA, method, set or library, kit or array of any of the preceding embodiments, wherein the synthetic guide RNA is a single-guide RNA, wherein the crRNA segment and the tracrRNA segment are linked through a loop L.

L4A. The synthetic guide RNA, method, set or library, kit or array of embodiment L3, wherein the loop L comprises 1, 2, 3, 4, 5, 6, 7, 8, 9, or 10 nucleotides.

L5. The synthetic guide RNA, method, set or library, kit or array of embodiments L3 or L4, wherein the loop L comprises a nucleotide sequence of GNRA, wherein N represents A, C, G, or U and R represents A or G.

L6. The synthetic guide RNA, method, set or library, kit or array of any of embodiments L3 to L5, wherein the loop L comprises a nucleotide sequence of GAAA.

L7. The synthetic guide RNA, method, set or library, kit or array of any of embodiments L3 to L6, wherein the loop L comprises one or more modified nucleotides.

L8. The synthetic guide RNA, method, set or library, kit or array of any of embodiments L3 to L7, wherein the loop L comprises a fluorescent dye.

L9. The synthetic guide RNA, method, set or library, kit or array of any of the preceding embodiments, comprising one or more isotopic labels.

L10. The synthetic guide RNA, method, set or library, kit or array of any of the preceding embodiments, comprising one or more fluorescent labels.

L11. The synthetic guide RNA, method, set or library, kit or array of any of the preceding embodiments, wherein the synthetic guide RNA comprises at least one 2'-O-methyl-3'-phosphonoacetate (2'-O-methyl-3'-PACE) nucleotide.

L12. The synthetic guide RNA, method, set or library, kit or array of any of the preceding embodiments, wherein the synthetic guide RNA comprises at least one 2-thioU.

L13. The synthetic guide RNA, method, set or library, kit or array of any of the preceding embodiments, wherein the synthetic guide RNA comprises at least one 6-thioG.

L14. The synthetic guide RNA, method, set or library, kit or array of any of the preceding embodiments, wherein the synthetic guide RNA comprises at least one 2-thioC.

L15. The synthetic guide RNA, method, set or library, kit or array of any of the preceding embodiments, wherein the synthetic guide RNA comprises at least one 2'-deoxy-2'-fluoroarabinofuranosyl modification.

L16. The synthetic guide RNA, method, set or library, kit or array of any of the preceding embodiments, wherein the synthetic guide RNA comprises at least one 2'-deoxy-2'-fluororibofuranosyl modification.

L17. The synthetic guide RNA, method, set or library, kit or array of any of the preceding embodiments, wherein the synthetic guide RNA comprises at least one 2'-O-phenyl ribose.

L18. The synthetic guide RNA, method, set or library, kit or array of any of the preceding embodiments, wherein the synthetic guide RNA comprises at least one 2'-thiophenyl ribose.

L19. The synthetic guide RNA, method, set or library, kit or array of any of the preceding embodiments, wherein the synthetic guide RNA comprises at least one 2'-S-thiophenyl ribose.

L20. The synthetic guide RNA, method, set or library, kit or array of any of the preceding embodiments, wherein the synthetic guide RNA comprises at least one 2'-methyl ribose.

L21. The synthetic guide RNA, method, set or library, kit or array of any of the preceding embodiments, wherein the synthetic guide RNA comprises at least one 2'-ethyl ribose.

L22. The synthetic guide RNA, method, set or library, kit or array of any of the preceding embodiments, wherein the synthetic guide RNA comprises at least one 2'-propyl ribose.

L23. The synthetic guide RNA, method, set or library, kit or array of any of the preceding embodiments, wherein the synthetic guide RNA comprises at least one 2'-allyl ribose.

L24. The synthetic guide RNA, method, set or library, kit or array of any of the preceding embodiments, wherein the synthetic guide RNA comprises at least one 2'-allylphenyl ribose.

L25. The synthetic guide RNA, method, set or library, kit or array of any of the preceding embodiments, wherein the synthetic guide RNA comprises at least one 2'-methylhydroxy ribose.

L26. The synthetic guide RNA, method, set or library, kit or array of any of the preceding embodiments, wherein the synthetic guide RNA comprises at least one 2'-methyloxymethyl ribose.

L27. The synthetic guide RNA, method, set or library, kit or array of any of the preceding embodiments, wherein the synthetic guide RNA comprises at least one 2'-O-carbamate ribose.

L28. The synthetic guide RNA, method, set or library, kit or array of any of the preceding embodiments, wherein the synthetic guide RNA comprises at least one 2'-O-ethylamino ribose.

L29. The synthetic guide RNA, method, set or library, kit or array of any of the preceding embodiments, wherein the synthetic guide RNA comprises at least one 2'-O-allylamino ribose.

L30. The synthetic guide RNA, method, set or library, kit or array of any of the preceding embodiments, wherein the synthetic guide RNA comprises at least one 2'-O-propylamino ribose.

L31. The synthetic guide RNA, method, set or library, kit or array of any of the preceding embodiments, wherein the synthetic guide RNA comprises at least one 2'-O-substituted phenyl ribose.

L32. The synthetic guide RNA, method, set or library, kit or array of any of the preceding embodiments, wherein the guide sequence of the synthetic guide RNA consists of nucleotides 1 through 20-N, counted from the 5' end of the guide sequence, where N is an integer between −10 and 10 (optionally between −10 and 6), and the region of nucleotides 6-N through 14-N comprises the specificity-enhancing modification(s).

M1. A method for cleaving, nicking or binding a target HBB polynucleotide comprising:
selecting a target sequence in an HBB locus within a target polynucleotide;
providing a synthetic guide RNA comprising:
(a) a crRNA segment comprising (i) a guide sequence capable of hybridizing to a target HBB polynucleotide, (ii) a stem sequence; and
(b) a tracrRNA segment comprising a nucleotide sequence that is partially or completely complementary to the stem sequence,
wherein the guide sequence consists of 20-N nucleotides, where N is an integer between −10 and 10, and the guide sequence comprises at least one specificity-enhancing modification at a nucleotide selected from positions 4-N, 5-N, 7-N, 9-N, 10-N, and 11-N; and
forming a gRNA:Cas protein complex comprising a Cas protein and the synthetic guide RNA;
contacting the target HBB polynucleotide with the gRNA:Cas protein complex; and
cleaving, nicking or binding the target polynucleotide.

M2. The method of embodiment M1, wherein the at least one specificity-enhancing modification is at nucleotide 11-N.

M3. The method of any one of embodiments M1 or M2, wherein the at least one specificity-enhancing modification is at nucleotide 5-N.

M4. The method of any one of embodiments M1 to M3, wherein the at least one specificity-enhancing modification is at nucleotide 7-N.

M5. The method of any one of embodiments M1 to M4, wherein the at least one specificity-enhancing modification is at nucleotide 10-N.

M6. The method of any one of embodiments M1 to M5, wherein the at least one specificity-enhancing modification is at nucleotide 9-N.

M7. The method of any one of embodiments M1 to M6, wherein the at least one specificity-enhancing modification is at nucleotide 4-N.

M8. The method of any one of embodiments M1 to M7, wherein the at least one specificity-enhancing modification comprises modification with 2'-O-methyl-3'-phosphonoacetate (MP), 2'-O-methyl-3'-thiophosphonoacetate (MSP), 2'-deoxy-3'-phosphonoacetate (DP), 2'-deoxy-3'-thiophosphonoacetate (DSP), or a combination thereof.

M9. The method of any one of embodiments M1 to M7, wherein the at least one specificity-enhancing modification is selected from a 2'-modification that confers a C3'-endo sugar pucker, a phosphonoacetate or thiophosphonoacetate linkage modification, and a combination thereof.

M10. The method of embodiment M9, wherein the 2'-modification is selected from 2'-F and 2'-O-(2-methoxyethyl).

M11. The method of any one of embodiments M1 to M10, wherein the cleaving, nicking or binding takes place in vitro.

M12. The method of any one of embodiments M1 to M10, wherein the cleaving, nicking or binding takes place in a cell.

M13. The method of any one of embodiments M1 to M12, wherein the guide sequence further comprises a modification at its 5'end, 3'end, or both, optionally one or more stability-enhancing modifications selected from 2'-O-methyl-3'-phosphonoacetate (MP), 2'-O-methyl-3'-thiophosphonoacetate (MSP), 2'-O-methyl-3'-phosphorothioate (MS), 2'-deoxy-3'-phosphonoacetate (DP), 2'-deoxy-3'-thiophosphonoacetate (DSP), 2'-fluoro-3'-phosphonoacetate (FP), 2'-fluoro-3'-thiophosphonoacetate (FSP), 2'-fluoro-3'-phosphorothioate (FS), or a combination thereof.

M14. The method of any one of embodiments M1 to M13, wherein the Cas protein is Cas9 or Cpf1.

M15. The method of any one of embodiments M1 to M14, wherein the guide RNA is a synthetic single guide RNA.

M16. The method of any one of embodiments M1 to M15, wherein the method involves cleaving the target HBB polynucleotide.

M17. The method of any one of embodiments M1 to M15, wherein the method involves nicking the target HBB polynucleotide.

M18. The method of any one of embodiments M1 to M15, wherein the method involves binding the target HBB polynucleotide.

M19. The method of any of embodiments M1 to M18, wherein the at least one specificity-enhancing modification increases specificity of the method.

N1. A synthetic guide RNA comprising:
(a) a crRNA segment comprising (i) a guide sequence capable of hybridizing to a target HBB polynucleotide, (ii) a stem sequence; and
(b) a tracrRNA segment comprising a nucleotide sequence that is partially or completely complementary to the stem sequence,
wherein the guide sequence consists of 20-N nucleotides, where N is an integer between −10 and 10, and the guide sequence comprises at least one specificity-enhancing modification at a nucleotide selected from positions 4-N, 5-N, 7-N, 9-N, 10-N, and 11-N, and wherein the synthetic guide RNA has gRNA functionality.

N2. The synthetic guide RNA of embodiment N1, wherein the at least one specificity-enhancing modification is at nucleotide 11-N.

N3. The synthetic guide RNA of embodiment N1 or N2, wherein the at least one specificity-enhancing modification is at nucleotide 5-N.

N4. The synthetic guide RNA of any one of embodiments N1 to N3, wherein the at least one specificity-enhancing modification is at nucleotide 7-N.

N5. The synthetic guide RNA of any one of embodiments N1 to N4, wherein the at least one specificity-enhancing modification is at nucleotide 10-N.

N6. The synthetic guide RNA of any one of embodiments N1 to N5, wherein the at least one specificity-enhancing modification is at nucleotide 9-N.

N7. The synthetic guide RNA of any one of embodiments N1 to N6, wherein the at least one specificity-enhancing modification is at nucleotide 4-N.

N8. The synthetic guide RNA of any one of embodiments N1 to N7, wherein the at least one specificity-enhancing modification comprises 2'-O-methyl-3'-phosphonoacetate (MP), 2'-O-methyl-3'-thiophosphonoacetate (MSP), 2'-deoxy-3'-phosphonoacetate (DP), 2'-deoxy-3'-thiophosphonoacetate (DSP), or a combination thereof.

N9. The synthetic guide RNA of any one of embodiments N1 to N8, wherein the at least one specificity-enhancing modification is selected from a 2'-modification that confers a C3'-endo sugar pucker, a phosphonoacetate or thiophosphonoacetate linkage modification, and a combination thereof.

N10. The synthetic guide RNA of embodiment N9, wherein the 2'-modification is selected from 2'-F and 2'-O-(2-methoxyethyl).

N11. The synthetic guide RNA of any one of embodiments N1 to N10, wherein the at least one specificity-enhancing modification weakens hybridization between the guide sequence and the target HBB polynucleotide.

N12. The synthetic guide RNA of any one of embodiments N1 to N10, wherein the at least one specificity-enhancing modification weakens hybridization between the guide sequence and an off-target polynucleotide.

N13. The synthetic guide RNA of any one of embodiments N1 to N10, wherein the at least one specificity-enhancing modification strengthens hybridization between the guide sequence and the target HBB polynucleotide and weakens hybridization between the guide sequence and an off-target polynucleotide.

N14. The synthetic guide RNA of any one of embodiments N1 to N13, wherein the guide RNA is a synthetic single guide RNA.

N15. The method of any one of embodiments N1 to N14, wherein the guide sequence consists of nucleotides 1 through 20, counted from the 5' end of the guide sequence.

O1. A method for cleaving, nicking or binding a target polynucleotide comprising:
  selecting a target polynucleotide;
  providing a synthetic guide RNA comprising:
    (a) a crRNA segment comprising (i) a guide sequence capable of hybridizing to a target polynucleotide, (ii) a stem sequence; and
    (b) a tracrRNA segment comprising a nucleotide sequence that is partially or completely complementary to the stem sequence,
  wherein the guide sequence consists of 20-N nucleotides, where N is an integer between −10 and 10, and the guide sequence comprises at least one specificity-enhancing modification at a nucleotide selected from positions 4-N, 5-N, 7-N, 9-N, 10-N, and 11-N; and
  forming a gRNA:Cas protein complex comprising a Cas protein and the synthetic guide RNA;
  contacting the target polynucleotide with the gRNA:Cas protein complex; and
  cleaving, nicking or binding the target polynucleotide.

O2. The method of embodiment O1, wherein the target polynucleotide is selected from the group consisting of VEGFA polynucleotide, IL2RG polynucleotide, CLTA1 polynucleotide, and a CLTA4 polynucleotide.

O3. The method of embodiment O1 or O2, wherein the at least one specificity-enhancing modification at nucleotide 11-N.

O4. The method of any one of embodiments O1 to O3, wherein the at least one specificity-enhancing modification at nucleotide 5-N.

O5. The method of any one of embodiments O1 to O4, wherein the at least one specificity-enhancing modification is at nucleotide 7-N.

O6. The method of any one of embodiments O1 to O5, wherein the at least one specificity-enhancing modification is at nucleotide 10-N.

O7. The method of any one of embodiments O1 to O6, wherein the at least one specificity-enhancing modification is at nucleotide 9-N.

O8. The method of any one of embodiments O1 to O7, wherein the at least one specificity-enhancing modification is at nucleotide 4-N.

O9. The method of any of embodiments O1 to O8, wherein the at least one specificity-enhancing modification comprises modification with 2'-O-methyl-3'-phosphonoacetate (MP), 2'-O-methyl-3'-thiophosphonoacetate (MSP), 2'-deoxy-3'-phosphonoacetate (DP), 2'-deoxy-3'-thiophosphonoacetate (DSP), or a combination thereof.

O10. The method of any of embodiments 01 to 08, wherein the at least one specificity-enhancing modification comprises a 2'-modification that confers a C3'-endo sugar pucker and a phosphonoacetate or thiophosphonoacetate linkage modification.

O11. The method of embodiment O10, wherein the 2'-modification is selected from 2'-F and 2'-O-(2-methoxyethyl).

O12. The method of any of embodiments O1 to O11, wherein the at least one specificity-enhancing modification increases specificity of the method.

O13. The method of any of embodiments O1 to O12, wherein the cleaving, nicking or binding takes place in vitro.

O14. The method of any of embodiments O1 to O12, wherein the cleaving, nicking or binding takes place in a cell.

O15. The method of any of embodiments O1 to O14, wherein the Cas protein is Cas9 or Cpf1.

O16. The method of any of embodiments O1 to O15, wherein the guide RNA is a synthetic single guide RNA.

O17. The method of any of embodiments O1 to O16, wherein the method involves cleaving the target HBB polynucleotide.

O18. The method of any of embodiments O1 to O16, wherein the method involves nicking the target HBB polynucleotide.

O19. The method of any of embodiments O1 to O16, wherein the method involves binding the target HBB polynucleotide.

O20. The method of any of embodiments O1 to O19, wherein the guide sequence consists of nucleotides 1 through 20, counted from the 5' end of the guide sequence.

P1. A synthetic guide RNA comprising:
(a) a crRNA segment comprising (i) a guide sequence capable of hybridizing to a target polynucleotide, (ii) a stem sequence; and
(b) a tracrRNA segment comprising a nucleotide sequence that is partially or completely complementary to the stem sequence,
wherein the guide sequence consists of 20-N nucleotides, where N is an integer between −10 and 10, and the guide sequence comprises at least one specificity-enhancing modification at a nucleotide selected from positions 4-N, 5-N, 7-N, 9-N, 10-N, and 11-N, and wherein the synthetic guide RNA has gRNA functionality.

P2. The synthetic guide of embodiment P1, wherein the target polynucleotide is selected from the group consisting of VEGFA polynucleotide, IL2RG polynucleotide, CLTA1 polynucleotide, and a CLTA4 polynucleotide.

P3. The synthetic guide RNA of embodiment P1 or P2, wherein the at least one specificity-enhancing modification is at nucleotide 11-N.

P4. The synthetic guide RNA of any one of embodiments P1 to P3, wherein the at least one specificity-enhancing modification is at nucleotide 5-N.

P5. The synthetic guide RNA of any one of embodiments P1 to P4, wherein the at least one specificity-enhancing modification is at nucleotide 7-N.

P6. The synthetic guide RNA of any one of embodiments P1 to P5, wherein the at least one specificity-enhancing modification is at nucleotide 10-N.

P7. The synthetic guide RNA of any one of embodiments P1 to P6, wherein the at least one specificity-enhancing modification is at nucleotide 9-N.

P8. The synthetic guide RNA of any one of embodiments P1 to P7, wherein the at least one specificity-enhancing modification is at nucleotide 4-N.

P9. The synthetic guide RNA of any one of embodiments P1 to P8, wherein the specificity-enhancing modifications comprise 2'-O-methyl-3'-phosphonoacetate (MP), 2'-O-methyl-3'-thiophosphonoacetate (MSP), 2'-deoxy-3'-phosphonoacetate (DP), 2'-deoxy-3'-thiophosphonoacetate (DSP), or a combination thereof.

P10. The synthetic guide RNA of any one of embodiments P1 to P9, wherein the at least one specificity-enhancing modification comprises a 2'-modification that confers a C3'-endo sugar pucker and a phosphonoacetate or thiophosphonoacetate linkage modification.

P11. The synthetic guide RNA of embodiment P10, wherein the 2'-modification is selected from 2'-F and 2'-O-(2-methoxyethyl).

P12. The synthetic guide RNA of any one of embodiments P1 to P11, wherein the at least one specificity-enhancing modification weakens hybridization between the guide sequence and the target polynucleotide.

P13. The synthetic guide RNA of any one of embodiments P1 to P12, wherein the at least one specificity-enhancing modification weakens hybridization between the guide sequence and an off-target polynucleotide.

P14. The synthetic guide RNA of any one of embodiments P1 to P13, wherein the at least one specificity-enhancing modification strengthens hybridization between the guide sequence and the target polynucleotide and weakens hybridization between the guide sequence and an off-target polynucleotide.

P15. The synthetic guide RNA of any one of embodiments, P1 to P14, wherein the guide RNA is a synthetic single guide RNA.

P16. The synthetic guide RNA of any one of embodiments P1 to P15, wherein the guide sequence consists of nucleotides 1 through 20, counted from the 5' end of the guide sequence.

Q1. A method for cleaving, nicking or binding a target polynucleotide comprising:
selecting a target polynucleotide in a genome;
providing a synthetic guide RNA comprising:
(a) a crRNA segment comprising (i) a guide sequence capable of hybridizing to a target polynucleotide, (ii) a stem sequence; and
(b) a tracrRNA segment comprising a nucleotide sequence that is partially or completely complementary to the stem sequence,
wherein the guide sequence comprises at least two consecutive specificity-enhancing modifications; and
forming a gRNA:Cas protein complex comprising a Cas protein and the synthetic guide RNA;
contacting the target polynucleotide with a gRNA:Cas protein complex; and
cleaving, nicking or binding the target polynucleotide,
wherein the at least one specificity-enhancing modification weakens hybridization between the guide sequence and the target polynucleotide.

Q2. The method of embodiment Q1, wherein the guide sequence comprises modifications at nucleotide 1 and 2 counted from a 5'-end of the guide sequence.

Q3. The method of embodiment Q1, wherein the guide sequence comprises modifications at nucleotide 1, 2, and 3 counted from a 5'-end of the guide sequence.

Q4. The method of embodiment Q1, wherein the guide sequence comprises modifications at nucleotides 1, 2, 3, and 4 counted from a 5'-end of the guide sequence.

Q5. The method of embodiment Q1, wherein the guide sequence comprises modifications at nucleotides 1, 2, 3, 4, and 5 counted from a 5'-end of the guide sequence.

Q6. The method of embodiment Q1, wherein the guide sequence comprises consecutive specificity-enhancing modifications at a 5' end.

Q7. The method of embodiment Q1, wherein the consecutive specificity-enhancing modifications begin at nucleotide 1, 2, 3, or 4 counted from a 5'-end of the guide sequence.

Q8. The method of any one of embodiments Q1 to Q7, wherein the target polynucleotide is selected from the group consisting of a HBB polynucleotide, a VEGFA polynucleotide, an IL2RG polynucleotide, a CLTA1 polynucleotide, and a CLTA4 polynucleotide.

Q9. The method of any one of embodiments Q1 to Q8, wherein the specificity-enhancing modifications comprise 2'-O-methyl-3'-phosphonoacetate (MP), 2'-O-methyl-3'-thiophosphonoacetate (MSP), 2'-deoxy-3'-phosphonoacetate (DP), 2'-deoxy-3'-thiophosphonoacetate (DSP), or a combination thereof.

Q10. The method of any one of embodiments Q1 to Q8, wherein the at least one specificity-enhancing modification comprises a 2'-modification that confers a C3'-endo sugar pucker and a phosphonoacetate or thiophosphonoacetate linkage modification.

Q11. The method of embodiment Q10, wherein the 2'-modification is selected from 2'-F and 2'-O-(2-methoxyethyl).

Q12. The method of any one of embodiments Q1 to Q11, wherein the cleaving, nicking or binding takes place in vitro.

Q13. The method of any one of embodiments Q1 to Q11, wherein the cleaving, nicking or binding takes place in a cell.

Q14. The method of any one of embodiments Q1 to Q13, wherein the method involves cleaving the target HBB polynucleotide.

Q15. The method of any one of embodiments Q1 to Q13, wherein the method involves nicking the target HBB polynucleotide.

Q16. The method of any one of embodiments Q1 to Q13, wherein the method involves binding the target HBB polynucleotide.

Q17. The method of any one of embodiments Q1 to Q16, wherein the guide RNA is a synthetic single guide RNA.

Q18. The method of any one of embodiments Q1 to Q17, wherein the guide sequence comprises or consists of nucleotides 1 through 20, counted from the 5' end of the guide sequence.

R1. A synthetic guide RNA comprising:
(a) a crRNA segment comprising (i) a guide sequence capable of hybridizing to a target polynucleotide, (ii) a stem sequence; and
(b) a tracrRNA segment comprising a nucleotide sequence that is partially or completely complementary to the stem sequence,
wherein the guide sequence comprises at least two consecutive specificity-enhancing modifications, and wherein the synthetic guide RNA has gRNA functionality, and
wherein the at least one specificity-enhancing modification weakens hybridization between the guide sequence and the target polynucleotide.

R2. The synthetic guide RNA of embodiment R1, wherein the guide sequence comprises specificity-enhancing modifications at nucleotide 1 and 2 counted from a 5'-end of the guide sequence.

R3. The synthetic guide RNA of embodiment R1, wherein the guide sequence comprises specificity-enhancing modifications at nucleotide 1, 2, and 3 counted from a 5'-end of the guide sequence.

R4. The synthetic guide RNA of embodiment R1, wherein the guide sequence comprises specificity-enhancing modifications at nucleotides 1, 2, 3, and 4 counted from a 5'-end of the guide sequence.

R5. The synthetic guide RNA of embodiment R1, wherein the guide sequence comprises specificity-enhancing modifications at nucleotides 1, 2, 3, 4, and 5 counted from a 5'-end of the guide sequence.

R6. The synthetic guide RNA of embodiment R1, wherein the guide sequence comprises consecutive specificity-enhancing modifications at the 5' end counted from a 5'-end of the guide sequence.

R7. The synthetic guide RNA of embodiment R1, wherein the consecutive specificity-enhancing modifications begin at nucleotide 1, 2, 3, or 4 counted from a 5'-end of the guide sequence.

R8. The synthetic guide RNA of embodiment R1, wherein the guide sequence comprises three consecutive specificity-enhancing modifications.

R9. The synthetic guide RNA of embodiment R1, wherein the guide sequence comprises four consecutive specificity-enhancing modifications.

R10. The synthetic guide RNA of any one of embodiments R1 to R9, wherein the target polynucleotide is selected from the group consisting of a HBB polynucleotide, a VEGFA polynucleotide, an IL2RG polynucleotide, a CLTA1 polynucleotide, and a CLTA4 polynucleotide.

R11. The synthetic guide RNA of any one of embodiments R1 to R10, wherein the specificity-enhancing modifications comprise 2'-O-methyl-3'-phosphonoacetate (MP), 2'-O-methyl-3'-thiophosphonoacetate (MSP), 2'-deoxy-3'-phosphonoacetate (DP), 2'-deoxy-3'-thiophosphonoacetate (DSP), or a combination thereof.

R12. The synthetic guide RNA of any one of embodiments R1 to R10, wherein the at least one specificity-enhancing modification is selected from a 2'-modification that confers a C3'-endo sugar pucker, a phosphonoacetate or thiophosphonoacetate linkage modification, and a combination thereof.

R13. The synthetic guide RNA of embodiment R12, wherein the 2'-modification is selected from 2'-F and 2'-O-(2-methoxyethyl).

R14. The synthetic guide RNA of any one of embodiments R1 to R13, wherein the at least one specificity-enhancing modification weakens hybridization between the guide sequence and the target polynucleotide.

R15. The synthetic guide RNA of any one of embodiments R1 to R13, wherein the at least one specificity-enhancing modification weakens hybridization between the guide sequence and an off-target polynucleotide.

R16. The synthetic guide RNA of any one of embodiments R1 to R13, wherein the at least one specificity-enhancing modification strengthens hybridization between the guide sequence and the target polynucleotide and weakens hybridization between the guide sequence and an off-target polynucleotide.

R17. The synthetic guide RNA of any one of embodiments R1 to R16, wherein the guide RNA is a synthetic single guide RNA.

R18. The method of any one of embodiments R1 to R17, wherein the guide sequence comprises or consists of nucleotides 1 through 20, counted from the 5' end of the guide sequence.

S1. A method of selecting a synthetic guide RNA comprising:
providing at least a first synthetic guide RNA and a second synthetic guide RNA, each comprising:
(a) a crRNA segment comprising (i) a guide sequence capable of hybridizing to a target polynucleotide, (ii) a stem sequence; and
(b) a tracrRNA segment comprising a nucleotide sequence that is partially or completely complementary to the stem sequence,
wherein each of the guide sequences consists of 20-N nucleotides, where N is an integer between −10 and 10, counted from the 5' end of the guide sequence,
wherein the first synthetic guide RNA comprises a specificity-enhancing modification at a first position within the guide sequence, and the second synthetic guide RNA comprises a specificity-enhancing modification at a second position within the guide sequence;
forming a first gRNA:Cas protein complex comprising a Cas protein and the first synthetic guide RNA, contacting the target polynucleotide with the first gRNA:Cas protein complex, and cleaving, nicking or binding the target polynucleotide;
forming a second gRNA:Cas protein complex comprising a Cas protein and the second synthetic guide RNA, contacting the target polynucleotide with the second gRNA:Cas protein complex, and cleaving, nicking or binding the target polynucleotide;
determining the specificity of the first gRNA:Cas protein complex and the second gRNA:Cas protein complex in the cleaving, nicking or binding of the target polynucleotide;

identifying which of the first gRNA:Cas protein complex and the second gRNA:Cas protein complex has greater specificity for the target polynucleotide.

S2. The method of embodiment S1, wherein the specificity-enhancing modification comprises 2'-O-methyl-3'-phosphonoacetate (MP), 2'-O-methyl-3'-thiophosphonoacetate (MSP), 2'-deoxy-3'-phosphonoacetate (DP), 2'-deoxy-3'-thiophosphonoacetate (DSP), or a combination thereof.

S3. The method of embodiment S2, wherein the specificity-enhancing modification comprises 2'-O-methyl-3'-phosphonoacetate (MP) or 2'-O-methyl-3'-thiophosphonoacetate (MSP).

S4. The method of embodiment S1, wherein the at least one specificity-enhancing modification comprises a 2'-modification that confers a C3'-endo sugar pucker and a phosphonoacetate or thiophosphonoacetate linkage modification.

S5. The method of embodiment S4, wherein the 2'-modification is selected from 2'-F and 2'-O-(2-methoxyethyl).

S6. The method of any one of embodiments S1 to S5, wherein the first and second synthetic guide RNA comprise a specificity-enhancing modification at different nucleotides.

S7. The method of any one of embodiments S1 to S6, wherein the specificity is selected from ON and/or OFF target cleaving, binding, or nicking percentages, ON:OFF ratio, specificity score, or a combination thereof.

S8. The method of any one of embodiments S1 to S7, wherein the method comprises providing a first through twentieth synthetic guide RNA comprising a specificity-enhancing modification at different nucleotide positions in the guide sequence portions, forming a gRNA:Cas protein complex using each of the synthetic guide RNAs, contacting the target polynucleotide with the gRNA:Cas protein complex, cleaving, nicking or binding the target polynucleotide and measuring the specificity of each synthetic guide RNA, and identifying one or more modified positions that provide the greatest specificity enhancement.

S9. The method of any one of embodiments S1 to S8, wherein the guide sequence further comprises modification with 2'-O-methyl-3'-phosphonoacetate (MP), 2'-O-methyl-3'-thiophosphonoacetate (MSP), 2'-O-methyl-3'-phosphorothioate (MS), 2'-deoxy-3'-phosphonoacetate (DP), 2'-deoxy-3'-thiophosphonoacetate (DSP), 2'-fluoro-3'-phosphonoacetate (FP), 2'-fluoro-3'-thiophosphonoacetate (FSP), 2'-fluoro-3'-phosphorothioate (FS), or a combination thereof at the 5' end and the 3' end.

S10. The method of any one of embodiments S1 to S9, wherein the method involves cleaving a target HBB polynucleotide.

S11 The method of any one of embodiments S1 to S9, wherein the method involves nicking a target HBB polynucleotide.

S12. The method of any one of embodiments S1 to S9, wherein the method involves binding a target HBB polynucleotide.

S13. The method of any one of embodiments S1 to S12, wherein the first and second guide RNAs are a synthetic single guide RNA.

T1. A kit for selecting a synthetic guide RNA comprising:
at least two synthetic guide RNAs comprising:
(a) a crRNA segment comprising (i) a guide sequence capable of hybridizing to a target polynucleotide, (ii) a stem sequence; and
(b) a tracrRNA segment comprising a nucleotide sequence that is partially or completely complementary to the stem sequence,
wherein the guide sequence consists of 20-N nucleotides, where N is an integer between −10 and 10, counted from the 5' end of the guide sequence, and comprises at least one specificity-enhancing modification at a nucleotide in the guide sequence; and wherein the at least two synthetic guide RNAs differ from each other by having at least one different specificity-enhancing modification or by having the specificity-enhancing modification at least one different position in the guide sequence; and
a Cas protein or a polynucleotide encoding said Cas protein.

T2. The kit of embodiment T1, wherein the kit comprises at least twenty synthetic guide RNAs.

T3. The kit of embodiment T1 or T2, wherein the Cas protein is Cas9 or Cpf1.

T4. The kit of any one of embodiments T1 to T3, wherein the specificity-enhancing modification comprises 2'-O-methyl-3'-phosphonoacetate (MP), 2'-O-methyl-3'-thiophosphonoacetate (MSP), 2'-deoxy-3'-phosphonoacetate (DP), or 2'-deoxy-3'-thiophosphonoacetate (DSP).

T5. The kit of any one of embodiments T1 to T3, wherein the specificity-enhancing modification comprises a 2'-modification that confers a C3'-endo sugar pucker and a phosphonoacetate or thiophosphonoacetate linkage modification.

T6. The kit of embodiment T5, wherein the 2'-modification is selected from 2'-F and 2'-O-(2-methoxyethyl).

T7. The kit of any one of embodiments T1 to T6, wherein the guide RNAs are synthetic single guide RNAs.

U1. The synthetic guide RNA, method, or kit of any of the preceding embodiments, wherein the gRNA:Cas protein complex comprises a specificity-enhancing modification and has a specificity score of greater than 1, preferably at least 1.1, more preferably at least 1.5, even more preferably at least 2, even more preferably at least 5, even more preferably at least 10, or optimally at least 20.

U2. The synthetic guide RNA, method, or kit of any of the preceding embodiments, wherein the gRNA:Cas protein complex comprises a specificity-enhancing modification and has a specificity score of from about 2 to about 60 or preferably about 10 to about 60.

U3. The synthetic guide RNA, method, or kit of any of the preceding embodiments, wherein the gRNA:Cas protein complex comprises a specificity-enhancing modification and has an ON target cleavage of at least 30%, preferably at least 50%, more preferably at least 70%, or optimally at least 90%.

U4. The synthetic guide RNA, method, or kit of any of the preceding embodiments, wherein the gRNA:Cas protein complex comprises a specificity-enhancing modification and has an ON target cleavage of from about 25% to 99.9% or preferably from about 50% to about 99.9%.

U5. The synthetic guide RNA, method, or kit of any of the preceding embodiments, wherein the gRNA:Cas protein complex comprises a specificity-enhancing modification and has a ON:OFF ratio of greater than 1, preferably at least 1.1:1, more preferably at least 1.5:1, even more preferably at least 3:1, even more preferably at least 10:1, even more preferably at least 20:1, or optimally at least 40:1.

U6. The synthetic guide RNA, method, or kit of any of the preceding embodiments, wherein the gRNA:Cas protein complex comprises a specificity-enhancing modification and has a ON:OFF ratio of from about 1.5:1 to about 99.9:1 or preferably from about 10:1 to about 99.9:1.

W1. The synthetic guide RNA, method, or kit of any of the preceding embodiments, wherein the guide sequence consists of nucleotides 1 through 19, counted from the 5' end of the guide sequence, and comprises at least one chemical modification at one of nucleotides selected from positions 3, 4, 6, 8, 9, and 10.

W2. The synthetic guide RNA, method, or kit of any of the preceding embodiments, wherein the guide sequence consists of nucleotides 1 through 18, counted from the 5' end of the guide sequence, and comprises at least one chemical modification at one of nucleotides selected from positions 2, 3, 5, 7, 8, and 9.

W3. The synthetic guide RNA, method, or kit of any of the preceding embodiments, wherein the guide sequence consists of nucleotides 1 through 17, counted from the 5' end of the guide sequence, and comprises at least one chemical modification at one of nucleotides selected from positions 1, 2, 4, 6, 7, and 8.

W4. The synthetic guide RNA, method, or kit of any of the preceding embodiments, wherein the guide sequence consists of nucleotides 1 through 16, counted from the 5' end of the guide sequence, and comprises at least one chemical modification at one of selected from positions nucleotides 1, 3, 5, 6, and 7.

W5. The synthetic guide RNA, method, or kit any of the preceding embodiments, wherein the guide sequence consists of nucleotides 1 through 15, counted from the 5' end of the guide sequence, and comprises at least one chemical modification at one of nucleotides selected from positions 2, 4, 5, and 6.

W6. The synthetic guide RNA, method, or kit of any of the preceding embodiments, wherein the guide sequence consists of nucleotides 1 through 14, counted from the 5' end of the guide sequence, and comprises at least one chemical modification at a nucleotide selected from positions 1, 3, 4, or 5.

In the exemplary embodiments below, "X embodiments" means all the embodiments of which the numbers start with an X.

X. A synthetic guide RNA comprising:
(a) a crRNA segment comprising (i) a guide sequence capable of hybridizing to a target polynucleotide, wherein the target polynucleotide comprises a target sequence adjacent to a PAM site, (ii) a stem sequence; and
(b) a tracrRNA segment comprising a nucleotide sequence that is partially or completely complementary to the stem sequence,
wherein the guide sequence consists of 20-N nucleotides, where N is an integer between −10 and 10;
wherein the guide sequence comprises at least one modification.

X1. A synthetic crRNA comprising (i) a guide sequence capable of hybridizing to a target polynucleotide, wherein the target polynucleotide comprises a target sequence adjacent to a PAM site, and (ii) a stem sequence;
wherein the guide sequence consists of 20-N nucleotides, where N is an integer between −10 and 10;
wherein the guide sequence comprises at least one modification.

X2. The synthetic guide RNA or crRNA of embodiment X or X1, wherein the at least one modification comprises a modification at position 4-N of the guide sequence.

X3. The synthetic guide RNA or crRNA of any one of the preceding X embodiments, wherein the at least one modification comprises a modification at position 5-N of the guide sequence.

X4. The synthetic guide RNA or crRNA of any one of the preceding X embodiments, wherein the at least one modification comprises a modification at position 7-N of the guide sequence.

X5. The synthetic guide RNA or crRNA of any one of the preceding X embodiments, wherein the at least one modification comprises a modification at position 9-N of the guide sequence.

X6. The synthetic guide RNA or crRNA of any one of the preceding X embodiments, wherein the at least one modification comprises a modification at position 10-N of the guide sequence.

X7. The synthetic guide RNA or crRNA of any one of the preceding X embodiments, wherein the at least one modification comprises a modification at position 11-N of the guide sequence.

X8. The synthetic guide RNA or crRNA of any one of the preceding X embodiments, wherein the at least one modification comprises a phosphonocarboxylate internucleotide linkage, optionally a phosphonoacetate internucleotide linkage (P).

X9. The synthetic guide RNA or crRNA of any one of the preceding X embodiments, wherein the at least one modification comprises a thiophosphonocarboxylate internucleotide linkage, optionally a thiophosphonoacetate internucleotide linkage (SP).

X10. The synthetic guide RNA or crRNA of any one of the preceding X embodiments, wherein the at least one modification comprises a 2'-modification that confers a C3'-endo sugar pucker configuration.

X11. The synthetic guide RNA or crRNA of embodiment X10, wherein said 2'-modification is selected from 2'-O-methyl, 2'-fluoro, and 2'-O-(2-methoxyethyl).

X12. The synthetic guide RNA or crRNA of any one of the preceding X embodiments, wherein the at least one modification comprises a 2'-O-methyl-3'-phosphonoacetate (MP).

X13. The synthetic guide RNA or crRNA of any one of the preceding X embodiments, wherein the at least one modification comprises a 2'-O-methyl-3'-thiophosphonoacetate (MSP).

X16. The synthetic guide RNA or crRNA of embodiment X or X1, wherein the at least one modification comprises a phosphonocarboxylate or thiophosphonocarboxylate internucleotide linkage modification at any position from position 4-N to 20-N of the guide sequence, and wherein said modification is not at position 15-N of the guide sequence.

X17. The synthetic guide RNA or crRNA of embodiment X, X1 or X16, wherein the at least one modification comprises a phosphonocarboxylate or thiophosphonocarboxylate internucleotide linkage modification at position 4-N of the guide sequence.

X18. The synthetic guide RNA or crRNA of embodiment X, X1, X16 or X17, wherein the at least one modification comprises a phosphonocarboxylate or thiophosphonocarboxylate internucleotide linkage modification at position 5-N of the guide sequence.

X19. The synthetic guide RNA or crRNA of any one of embodiments X, X1 and X16-X18, wherein the at least one modification comprises a phosphonocarboxylate or thiophosphonocarboxylate internucleotide linkage modification at position 6-N of the guide sequence.

X20. The synthetic guide RNA or crRNA of any one of embodiments X, X1 and X16-X19, wherein the at least one modification comprises a phosphonocarboxylate or thiophosphonocarboxylate internucleotide linkage modification at position 7-N of the guide sequence.

X21. The synthetic guide RNA or crRNA of any one of embodiments X, X1 and X16-X20, wherein the at least one modification comprises a phosphonocarboxylate or thiophosphonocarboxylate internucleotide linkage modification at position 8-N of the guide sequence.

X22. The synthetic guide RNA or crRNA of any one of embodiments X, X1 and X16-X21, wherein the at least one modification comprises a phosphonocarboxylate or thiophosphonocarboxylate internucleotide linkage modification at position 9-N of the guide sequence.

X23. The synthetic guide RNA or crRNA of any one of embodiments X, X1 and X16-X22, wherein the at least one modification comprises a phosphonocarboxylate or thiophosphonocarboxylate internucleotide linkage modification at position 10-N of the guide sequence.

X24. The synthetic guide RNA or crRNA of any one of embodiments X, X1 and X16-X23, wherein the at least one modification comprises a phosphonocarboxylate or thiophosphonocarboxylate internucleotide linkage modification at position 11-N of the guide sequence.

X25. The synthetic guide RNA or crRNA of any one of embodiments X, X1 and X16-X24, wherein the at least one modification comprises a phosphonocarboxylate or thiophosphonocarboxylate internucleotide linkage modification at position 12-N of the guide sequence.

X26. The synthetic guide RNA or crRNA of any one of embodiments X, X1 and X16-X25, wherein the at least one modification comprises a phosphonocarboxylate or thiophosphonocarboxylate internucleotide linkage modification at position 13-N of the guide sequence.

X27. The synthetic guide RNA or crRNA of any one of embodiments X, X1 and X16-X26, wherein the at least one modification comprises a phosphonocarboxylate or thiophosphonocarboxylate internucleotide linkage modification at position 14-N of the guide sequence.

X28. The synthetic guide RNA or crRNA of any one of embodiments X, X1 and X16-X27, wherein the at least one modification comprises a phosphonocarboxylate or thiophosphonocarboxylate internucleotide linkage modification at position 16-N of the guide sequence.

X29. The synthetic guide RNA or crRNA of any one of embodiments X, X1 and X16-X28, wherein the at least one modification comprises a phosphonocarboxylate or thiophosphonocarboxylate internucleotide linkage modification at position 17-N of the guide sequence.

X30. The synthetic guide RNA or crRNA of any one of embodiments X, X1 and X16-X29, wherein the at least one modification comprises a phosphonocarboxylate or thiophosphonocarboxylate internucleotide linkage modification at position 18-N of the guide sequence.

X31. The synthetic guide RNA or crRNA of any one of embodiments X, X1 and X16-X30, wherein the at least one modification comprises a phosphonocarboxylate or thiophosphonocarboxylate internucleotide linkage modification at position 19-N of the guide sequence.

X32. The synthetic guide RNA or crRNA of any one of embodiments X, X1 and X16-X31, wherein the at least one modification comprises a phosphonocarboxylate or thiophosphonocarboxylate internucleotide linkage modification at position 20-N of the guide sequence.

X33. The synthetic guide RNA or crRNA of any one of embodiments X, X1 and X16-X32, wherein the at least one modification comprises a phosphonocarboxylate internucleotide linkage.

X34. The synthetic guide RNA or crRNA of any one of embodiments X, X1 and X16-X32, wherein the at least one modification comprises a thiophosphonocarboxylate internucleotide linkage.

X35. The synthetic guide RNA or crRNA of any one of embodiments X, X1 and X16-X33, wherein said phosphonocarboxylate internucleotide linkage is a phosphonoacetate linkage (P).

X36. The synthetic guide RNA or crRNA of any one of embodiments X, X1 and X16-X33, wherein said phosphonocarboxylate internucleotide linkage is a thiophosphonoacetate linkage (SP).

X37. The synthetic guide RNA or crRNA of any one of the preceding X embodiments, further comprising at least one modification at the 5'-end, 3'-end, or both ends of said guide RNA.

X38. The synthetic guide RNA or crRNA of embodiment X37, wherein said at least one modification at the 5'-end, the 3'-end, or both ends is independently selected from a 2'-O-methyl (M), a phosphorothioate internucleotide linkage (S), a phosphonoacetate internucleotide linkage (P), a thiophosphonoacetate internucleotide linkage (SP), a 2'-O-methyl-3'-phosphorothioate (MS), a 2'-O-methyl-3'-phosphonoacetate (MP) and a 2'-O-methyl-3'-thiophosphonoacetate (MSP) or a combination thereof.

X39. The synthetic guide RNA or crRNA of any one of embodiments X-X38, wherein said target polynucleotide is located within an HBB polynucleotide.

X40. The synthetic guide RNA or crRNA of any one of embodiments X-X38, wherein said target polynucleotide is located within an IL2RG polynucleotide.

X41. The synthetic guide RNA or crRNA of any one of embodiments X-X38, wherein said target polynucleotide is located within a VEGFA polynucleotide.

X42. The synthetic guide RNA or crRNA of any one of embodiments X-X38, wherein said target polynucleotide is located within a CL TAI polynucleotide.

X43. The synthetic guide RNA or crRNA of any one of embodiments X-X38, wherein said target polynucleotide is located within a CLTA4 polynucleotide.

X44. The synthetic guide RNA or crRNA of embodiment X39, wherein the target polynucleotide comprises GCCCCACAGGGCAGTAA (SEQ ID NO:8).

X45. The synthetic guide RNA or crRNA of embodiment X40, wherein the target polynucleotide comprises TAATGATGGCTTCAACA (SEQ ED NO:10).

X46. The synthetic guide RNA or crRNA of embodiment X41, wherein the target polynucleotide comprises GAGTGAGTGTGTGCGTG (SEQ ID NO:192).

X47, The synthetic guide RNA or crRNA of embodiment X42, wherein the target polynucleotide comprises CCTCATCTCCCTCAAGC (SEQ ID NO:1).

X48. The synthetic guide RNA or crRNA of embodiment X43, wherein the target polynucleotide comprises GATGTAGTGTTTCCACA (SEQ ID NO:4).

X49. A method for enhancing the specificity of a CRISPR function, comprising:
  selecting a target polynucleotide;
  providing at least one synthetic guide RNA of any one of the preceding X embodiments;
  forming a gRNA:Cas protein complex comprising a Cas protein and the synthetic guide RNA; and
  contacting the target polynucleotide with the gRNA:Cas protein complex.

X50. The method of embodiment X49, wherein the contacting is performed in a cell.

X51. The method of embodiment X50, wherein the cell is a primary cell.

X52. The method of any one of embodiments X49-51, wherein the Cas protein is provided as a protein or a polynucleotide expressing the Cas protein.

X53. The method of embodiment X52, wherein the polynucleotide is an mRNA.

X54. The method of any one of the preceding X embodiments, wherein said forming is performed outside of a cell.

X55. The method of any one of the preceding X embodiments, wherein the CRISPR function is gene editing.

X56. The method of any one of the preceding X embodiments, wherein the CRISPR function is CRISPRa.

X57. The method of any one of the preceding X embodiments, wherein the CRISPR function is CRISPRi.

X58. The method of any one of the preceding X embodiments, wherein the CRISPR function is regulation of gene expression.

X59. The synthetic guide RNA or crRNA or method of any one of embodiments X-X58, wherein N equals 0, and the guide sequence consists of 20 nucleotides.

X60. The synthetic guide RNA or crRNA or method of any one of embodiments X-X58, wherein N equals 1, and the guide sequence consists of 19 nucleotides.

X61. The synthetic guide RNA or crRNA or method of any one of embodiments X-X58, wherein N equals 2, and the guide sequence consists of 18 nucleotides.

X62. The synthetic guide RNA or crRNA or method of any one of embodiments X-X58, wherein N equals 3, and the guide sequence consists of 17 nucleotides.

X63. The synthetic guide RNA or crRNA or method of any one of embodiments X-X58, wherein N equals 4, and the guide sequence consists of 16 nucleotides.

X64. The synthetic guide RNA or crRNA or method of any one of embodiments X-X58, wherein N equals 5, and the guide sequence consists of 15 nucleotides.

X65. The synthetic guide RNA or crRNA or method of any one of embodiments X-X58, wherein N equals −1, and the guide sequence consists of 21 nucleotides.

X66. The synthetic guide RNA or crRNA or method of any one of embodiments X-X58, wherein N equals −2, and the guide sequence consists of 22 nucleotides.

X67. The synthetic guide RNA or crRNA or method of any one of embodiments X-X58, wherein N equals −3, and the guide sequence consists of 23 nucleotides.

X68. The synthetic guide RNA or crRNA or method of any one of embodiments X-X58, wherein N equals −4, and the guide sequence consists of 24 nucleotides.

X69. The synthetic guide RNA or crRNA or method of any one of embodiments X-X58, wherein N equals −5, and the guide sequence consists of 25 nucleotides.

X70. The synthetic guide RNA or crRNA or method of any of the preceding X embodiments, wherein no more than 10 nucleotides in the guide sequence comprise modifications.

X71. The synthetic guide RNA or crRNA or method of any of the preceding X embodiments, wherein no more than 9 nucleotides in the guide sequence comprise modifications.

X72. The synthetic guide RNA or crRNA or method of any of the preceding X embodiments, wherein no more than 8 nucleotides in the guide sequence comprise modifications.

X73. The synthetic guide RNA or crRNA or method of any of the preceding X embodiments, wherein no more than 7 nucleotides in the guide sequence comprise modifications.

X74. The synthetic guide RNA or crRNA or method of any of the preceding X embodiments, wherein no more than 6 nucleotides in the guide sequence comprise modifications.

X75. The synthetic guide RNA or crRNA or method of any of the preceding X embodiments, wherein no more than 5 nucleotides in the guide sequence comprise modifications.

X76. The synthetic guide RNA or crRNA or method of any of the preceding X embodiments, wherein no more than 4 nucleotides in the guide sequence comprise modifications.

X77. The synthetic guide RNA or crRNA or method of any of the preceding X embodiments, wherein no more than 3 nucleotides in the guide sequence comprise modifications.

X78. The synthetic guide RNA or crRNA or method of any of the preceding X embodiments, wherein no more than 2 nucleotides in the guide sequence comprise modifications.

X79. The synthetic guide RNA or crRNA or method of any of the preceding X embodiments, wherein, if the first 4 nucleotides of the guide sequence are all modified, they are not modified in an identical manner.

X80. The synthetic guide RNA or crRNA or method of any of the preceding X embodiments, wherein, if the first 5 nucleotides of the guide sequence are all modified, they are not modified in an identical manner.

X81. The synthetic guide RNA or method of any one of the preceding X embodiments, wherein the guide RNA is a single guide RNA.

X82. The synthetic guide RNA or crRNA or method of any of the preceding X embodiments, wherein the guide RNA has higher specificity for the target polynucleotide or higher gRNA functionality than a corresponding guide RNA without the modification.

X83. The method of any one of the preceding X embodiments, where at least two different synthetic guide RNAs are provided for two different target polynucleotides.

X84. The method of embodiment X83, wherein the two different target polynucleotides are located in the same gene.

X85. The synthetic guide RNA or crRNA or method of any of the preceding X embodiments, wherein N is between −10 and 6, and the guide sequence consists of 14 to 30 nucleotides.

X86. The synthetic guide RNA or crRNA or method of any of the preceding X embodiments, wherein N is between −5 and 6, and the guide sequence consists of 14 to 25 nucleotides.

X87. The synthetic guide RNA or crRNA or method of any of the preceding X embodiments, wherein N is between −4 and 3, and the guide sequence consists of 17 to 24 nucleotides.

X88. The synthetic guide RNA or crRNA or method of any of the preceding X embodiments, wherein the at least one modification comprises 2'-deoxy-3'-phosphonoacetate (DP).

X89. The synthetic guide RNA or crRNA or method of any of the preceding X embodiments, wherein the at least one modification comprises 2'-O-deoxy-3'-thiophosphonoacetate (DSP).

X90. The synthetic guide RNA or crRNA or method of any of the preceding X embodiments, comprising at least one modification at the 5'-end, the 3'-end, or both ends, which comprises 2'-deoxy-3'-phosphonoacetate (DP).

X91. The synthetic guide RNA or crRNA or method of any of the preceding X embodiments, comprising at least one modification at the 5'-end, the 3'-end, or both ends, which comprises 2'-O-deoxy-3'-thiophosphonoacetate (DSP).

Y1. A synthetic guide RNA comprising:
(a) a crRNA segment comprising (i) a guide sequence capable of hybridizing to a target polynucleotide, wherein the target polynucleotide comprises a target sequence adjacent to a PAM site, (ii) a stem sequence; and (b) a tracrRNA segment comprising a nucleotide sequence that is partially or completely complementary to the stem sequence, wherein the guide sequence consists of 20-N nucleotides, where N is an integer between −10 and 10, optionally between −10 and 6; and wherein the guide sequence further comprises at least one modification located at position 4-N, 5-N, 7-N, 9-N, 10-N or 11-N of the guide sequence, or a combination thereof.

Y2. The synthetic guide RNA of embodiment Y1 wherein said guide RNA is a single guide RNA.

Y3. The synthetic guide RNA of embodiment Y1 wherein said at least one modification is selected from a phosphonoacetate internucleotide linkage (P), a thiophosphonoacetate internucleotide linkage (SP), and a 2'-modification that confers a C3'-endo sugar pucker configuration or a combination thereof.

Y4. The synthetic guide RNA of embodiment Y3 wherein said 2'-modification is selected from 2'-O-methyl, 2'-fluoro, and 2'-O-(2-methoxyethyl).

Y5. The synthetic guide RNA of embodiment Y1 wherein said at least one modification is selected from a 2'-O-methyl-3'-phosphonoacetate (MP) and 2'-O-methyl-3'-thiophosphonoacetate (MSP).

Y6. The synthetic guide RNA of embodiment Y5 wherein said at least one modification is located at position 5-N or 11-N of the guide sequence, or a combination thereof.

Y7. The synthetic guide RNA of embodiment Y1 further comprising at least one modification at the 5'-end, 3'-end, or both ends of said guide RNA.

Y8. The synthetic guide RNA of embodiment Y7 wherein said at least one modification at the 5'-end, the 3'-end, or both ends is independently selected from a 2'-O-methyl (M), a phosphorothioate internucleotide linkage (S), a phosphonoacetate internucleotide linkage (P), a thiophosphonoacetate internucleotide linkage (SP), a 2'-O-methyl-3'-phosphorothioate (MS), a 2'-O-methyl-3'-phosphosphonoacetate (MP) and a 2'-O-methyl-3'-thiophosphosphonoacetate (MSP), or a combination thereof.

Y9. The synthetic guide RNA of embodiment Y5 further comprising at least one modification at the 5'-end, the 3'-end, or both ends independently selected from a 2'-O-methyl (M), a phosphorothioate internucleotide linkage (S), a phosphonoacetate internucleotide linkage (P), a thiophosphonoacetate internucleotide linkage (SP), a 2'-O-methyl-3'-phosphoroatioate (MS), a 2'-O-methyl-3'-phosphosphonoacetate (MP) and a 2'-O-methyl-3'-thiophosphosphonoacetate (MSP), or a combination thereof.

Y10. The synthetic guide RNA of embodiment Y5 wherein said target polynucleotide is located within the HBB gene, the IL2RG gene, or the VEGFA gene.

Y11. The synthetic guide RNA of embodiment Y10, wherein the target polynucleotide comprises GCCCCACAGGGCAGTAA of the HBB gene, TAATGATGGCTTCAACA of the IL2RG gene, or GAGTGAGTGTGTGCGTG of the VEGFA gene.

Y12. The synthetic guide RNA of embodiment Y10, wherein said guide RNA is a single guide RNA and wherein said at least one modification at the 5'-end, 3'-end or both ends of said guide RNA is independently selected from a 2'-O-methyl (M), a phosphorothioate internucleotide linkage (S), a phosphonoacetate internucleotide linkage (P), a thiophosphonoacetate internucleotide linkage (SP), a 2'-O-methyl-3'-phosphoroatioate (MS), a 2'-O-methyl-3'-phosphosphonoacetate (MP) and a 2'-O-methyl-3'-thiophosphosphonoacetate (MSP), or a combination thereof.

Y13. A synthetic guide RNA comprising:
(a) a crRNA segment comprising (i) a guide sequence capable of hybridizing to a target polynucleotide, wherein the target polynucleotide comprises a target sequence adjacent to a PAM sequence, (ii) a stem sequence; and
(b) a tracrRNA segment comprising a nucleotide sequence that is partially or completely complementary to the stem sequence, wherein the guide sequence consists of 20-N nucleotides, where N is an integer between −10 and 10, optionally between −10 and 6;

wherein the guide sequence further comprises at least one phosphonocarboxylate or thiophosphonocarboxylate internucleotide linkage modification at any position from position 4-N to 20-N of the guide sequence, and wherein said modification is not at position 15-N of the guide sequence.

Y14. The synthetic guide RNA of embodiment Y13 wherein said phosphonocarboxylate internucleotide linkage is selected from a phosphonoacetate linkage (P) and a thiophosphonoacetate linkage (SP).

Y15. The synthetic guide RNA of embodiment Y13 further comprising at least one modification at the 5'-end, 3'-end or both ends of said guide RNA.

Y16. The synthetic guide RNA of embodiment Y13 wherein said guide RNA is a single guide RNA.

Y17. The synthetic guide RNA of embodiment Y15 wherein said at least one modification at the 5'-end, the 3'-end, or both ends is independently selected from a 2'-O-methyl (M), a phosphorothioate internucleotide linkage (S), a phosphonoacetate internucleotide linkage (P), a thiophosphonoacetate internucleotide linkage (SP), a 2'-O-methyl-3'-phosphoroatioate (MS), a 2'-O-methyl-3'-phosphonoacetate (MP) and a 2'-O-methyl-3'-thiophosphosphonoacetate (MSP), or a combination thereof.

Y18. A synthetic crRNA comprising a guide sequence capable of hybridizing to a target polynucleotide comprising a target sequence adjacent to a PAM site, wherein said guide sequence consists of 20-N nucleotides, wherein N is an integer between −10 and 10, optionally between −10 and 6; wherein the guide sequence further comprises at least one phosphonocarboxylate or thiophosphonocarboxylate internucleotide linkage modification at any position from position 4-N to 20-N of the guide sequence, and wherein said modification is not at position 15-N of the guide sequence.

Y19. The synthetic crRNA of embodiment Y18 further comprising at least one modification at the 5'-end, 3'-end or both ends of said crRNA.

Y20. A method for enhancing the specificity of a CRISPR function, comprising:
  selecting a target polynucleotide;
  providing at least one synthetic guide RNA of embodiment Y13;
  forming a gRNA:Cas protein complex comprising a Cas protein and the synthetic guide RNA; and
  contacting the target polynucleotide with the gRNA:Cas protein complex;
  wherein said Cas protein is provided as a protein or as a polynucleotide encoding said Cas protein.

Y21. The method of embodiment Y20, wherein said guide RNA is a single guide RNA.

Y22. The method of embodiment Y20, wherein said guide RNA further comprises at least one modification at the 5'-end, the 3'-end, or both ends of said guide RNA.

Y23. The method of embodiment Y22 wherein said at least one modification at the 5'-end, the 3'-end, or both ends is independently selected from a 2'-O-methyl (M), a phosphorothioate internucleotide linkage (S), a phosphonoacetate internucleotide linkage (P), a thiophosphonoacetate internucleotide linkage (SP), a 2'-O-methyl-3'-phosphoroatioate (MS), a 2'-O-methyl-3'-phosphonoacetate (MP) and a 2'-O-methyl-3'-thiophosphonoacetate (MSP), or a combination thereof.

Y24. The method of embodiment Y20 wherein said guide RNA comprises at least one modification selected from a phosphonoacetate internucleotide linkage and a thiophosphonoacetate internucleotide linkage or a combination thereof.

Y25. The method of embodiment Y20 wherein said guide RNA comprises at least one modification selected from a 2'-O-methyl-3'-phosphonoacetate (MP) and 2'-O-methyl-3'-thiophosphonoacetate (MSP).

Y26. The method of embodiment Y20 wherein said contacting of said polynucleotide target with said gRNA:Cas protein complex is performed in a cell.

Y27. The method of embodiment Y26 wherein said Cas protein is a Cas9 protein.

Y28. The method of embodiment Y27, wherein said target polynucleotide is located within the HBB gene, the IL2RG gene, or the VEGFA gene.

Y29, The method of embodiment Y28, wherein the target polynucleotide comprises GCCCCACAGGGCAGTAA (SEQ ID NO:8) of the HBB gene, TAATGATGGCTTCAACA (SEQ ID NO:8) of the IL2RG gene, or GAGTGAGTGTGTGCGTG (SEQ ID NO:192) of the VEGFA gene.

Y30. The method of embodiment Y20 wherein said forming is performed outside of a cell.

The foregoing description of exemplary or preferred embodiments should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

We claim:

1. A synthetic guide RNA comprising:
   (a) a crRNA segment comprising (i) a guide sequence capable of hybridizing to a target polynucleotide, wherein the target polynucleotide comprises a target sequence adjacent to a PAM site, and (ii) a stem sequence; and
   (b) a tracrRNA segment comprising a nucleotide sequence that is partially or completely complementary to the stem sequence,
   wherein the guide sequence consists of 20-N nucleotides, where N is an integer between −10 and 3; and wherein the guide sequence comprises at least one modification located at position 4-N, 5-N, 7-N, 9-N, 10-N or 11-N relative to the 5'-end of the guide sequence, or a combination thereof; wherein the synthetic guide RNA has enhanced specificity for the target sequence compared to a guide RNA without said modification, and wherein said at least one modification is 2'-deoxy-3'-phosphonoacetate (DP), a 2'-deoxy-3'-thiophosphonoacetate (DSP), a 2'-O-methyl-3'-phosphonoacetate (MP), a 2'-O-methyl-3'-thiophosphonoacetate (MSP), a 2'-O-methyl-3'-phosphorothioate (MS), a 2'-O-(2-methoxyethyl) (MOE), a 2'-O-(2-methoxyethyl)-3'-phosphorothioate (MOES), a 2'-O-(2-methoxyethyl)-3'-phosphonoacetate (MOEP), or a 2'-O-(2-methoxyethyl)-3'-thiophosphonoacetate (MOESP).

2. The synthetic guide RNA of claim 1, wherein said guide RNA is a single guide RNA.

3. The synthetic guide RNA of claim 1, wherein said at least one modification is located at position 5-N or 11-N relative to the 5'-end of the guide sequence, or a combination thereof.

4. The synthetic guide RNA of claim 1, further comprising at least one modification at the 5'-end, 3'-end, or both ends of said guide RNA.

5. The synthetic guide RNA of claim 4, wherein said at least one modification at the 5'-end, the 3'-end, or both ends is independently a 2'-O-methyl (M), a phosphorothioate internucleotide linkage (S), a phosphonoacetate internucleotide linkage (P), a thiophosphonoacetate internucleotide linkage (SP), a 2'-O-methyl-3'-phosphorothioate (MS), a 2'-O-methyl-3'-phosphonoacetate (MP), a 2'-O-methyl-3'-thiophosphonoacetate (MSP), a 2'-deoxy-3'-phosphonoacetate (DP), a 2'-deoxy-3'-thiophosphonoacetate (DSP), or a combination thereof.

6. The synthetic guide RNA of claim 1, wherein said target polynucleotide is located within the HBB gene, the IL2RG gene, the CLTA gene, or the VEGFA gene.

7. The synthetic guide RNA of claim 6, wherein the target polynucleotide comprises GCCCCACAGGGCAGTAA (SEQ ID NO:200) of the HBB gene, TAATGATGGCTTCAACA SEQ ID NO:201) of the IL2RG gene, or GAGTGAGTGTGTGCGTG (SEQ ID NO:202) of the VEGFA gene.

8. The synthetic guide RNA of claim 6, wherein said guide RNA is a single guide RNA and further comprises at least one modification at the 5'-end, 3'-end or both ends of said guide RNA is independently a 2'-O-methyl (M), a phosphorothioate internucleotide linkage (S), a phosphonoacetate internucleotide linkage (P), a thiophosphonoacetate internucleotide linkage (SP), a 2'-O-methyl-3'-phosphorothioate (MS), a 2'-O-methyl-3'-phosphonoacetate (MP), a 2'-O-methyl-3'-thiophosphonoacetate (MSP), a 2'-deoxy-3'-phosphonoacetate (DP), a 2'-deoxy-3'-thiophosphonoacetate (DSP), or a combination thereof.

9. A synthetic crRNA comprising a guide sequence capable of hybridizing to a target polynucleotide that comprises a target sequence adjacent to a PAM site, wherein said guide sequence consists of 20-N nucleotides, wherein N is an integer between −10 and 3; and wherein the guide sequence comprises at least one modification located at position 4-N, 5-N, 7-N, 9-N, 10-N or 11-N relative to the 5'-end of the guide sequence, or a combination thereof; wherein the synthetic crRNA has enhanced specificity for the target sequence compared to a crRNA without said modification, and wherein said at least one modification is a 2'-deoxy-3'-phosphonoacetate (DP), a 2'-deoxy-3'-thiophosphonoacetate (DSP), a 2'-O-methyl-3'-phosphonoacetate (MP), a 2'-O-methyl-3'-thiophosphonoacetate (MSP), a 2'-O-methyl-3'-phosphorothioate (MS), a 2'-O-(2-methoxyethyl) (MOE), a 2'-O-(2-methoxyethyl)-3'-phosphorothioate (MOES), a 2'-O-(2-methoxyethyl)-3'-phosphonoacetate (MOEP), or a 2'-O-(2-methoxyethyl)-3'-thiophosphonoacetate (MOESP).

10. The synthetic crRNA of claim 9, further comprising at least one modification at the 5'-end, 3'-end, or both ends of said crRNA.

11. A method for enhancing the specificity of a CRISPR function, comprising:
selecting a target polynucleotide;
providing at least one synthetic guide RNA of claim 1;
forming a gRNA:Cas protein complex comprising a Cas protein and the synthetic guide RNA; and
contacting the target polynucleotide with the gRNA:Cas protein complex;
wherein said Cas protein is provided as a protein or as a polynucleotide encoding said Cas protein.

12. The method of claim 11, wherein said guide RNA is a single guide RNA.

13. The method of claim 11, wherein said guide RNA further comprises at least one modification at the 5'-end, the 3'-end, or both ends of said guide RNA.

14. The method of claim 13, wherein said at least one modification at the 5'-end, the 3'-end, or both ends is independently a 2'-O-methyl (M), a phosphorothioate internucleotide linkage (S), a phosphonoacetate internucleotide linkage (P), a thiophosphonoacetate internucleotide linkage (SP), a 2'-O-methyl-3'-phosphorothioate (MS), a 2'-O-methyl-3'-phosphonoacetate (MP), a 2'-O-methyl-3'-thiophosphonoacetate (MSP), a 2'-deoxy-3'-phosphonoacetate (DP), a 2'-deoxy-3'-thiophosphonoacetate (DSP), or a combination thereof.

15. The method of claim 11, wherein said guide RNA comprises at least one modification selected from a phosphonoacetate internucleotide linkage or a thiophosphonoacetate internucleotide linkage.

16. The method of claim 11, wherein said guide RNA comprises at least one modification selected from the group consisting of a 2'-O-methyl-3'-phosphonoacetate (MP), a 2'-O-methyl-3'-thiophosphonoacetate (MSP), a 2'-O-methyl-3'-phosphorothioate (MS) and a 2'-O-(2-methoxyethyl) (MOE).

17. The method of claim 11, wherein said contacting of said polynucleotide target with said gRNA:Cas protein complex is performed in a cell and wherein said forming said complex is performed outside or inside the cell.

18. The method of claim 17, wherein said Cas protein is a Cas9 protein.

19. The method of claim 18, wherein said target polynucleotide is located within the HBB gene, the IL2RG gene, the CLTA gene, or the VEGFA gene.

20. The method of claim 19, wherein the target polynucleotide comprises GCCCCACAGGGCAGTAA (SEQ ID NO:200) of the HBB gene, TAATGATGGCTTCAACA (SEQ NO:201) of the IL2RG gene, or GAGTGAGTGTGTGCGTG (SEQ ID NO:202) of the VEGEA gene.

21. The method of claim 11, wherein said forming is performed outside of a cell.

22. The synthetic guide RNA of claim 1, Wherein said at least one modification is a 2'-O-methyl-3'-phosphonoacetate (MP), a 2'-O-methyl-3'-thiophosphonoacetate (MSP), a 2'-O-methyl-3'-phosphorothioate (MS), a 2'-O-(2-methoxyethyl) (MOE), or a 2'-O-(2-methoxyethyl)-3'-phosphorothioate (MOES).

23. The method of claim 11, wherein said guide RNA comprises at least one modification selected from the group consisting of 2'-O-methyl-3'-phosphonoacetate (MP), a 2'-O-methyl-3'-thiophosphonoacetate (MSP), a 2'-O-methyl-3'-phosphorothioate (MS), a 2'-O-(2-methoxyethyl) (MOE), and a 2'-O-(2-methoxyethyl)-3'-phosphorothioate (MOES).

* * * * *

SEQUENCE LISTING

```
<160> NUMBER OF SEQ ID NOS: 202

<210> SEQ ID NO 1
<211> LENGTH: 23
<212> TYPE: DNA
<213> ORGANISM: Artificial Sequence
<220> FEATURE:
<223> OTHER INFORMATION: Synthetic Construct

<400> SEQUENCE: 1
agtcctcatc tccctcaagc agg                                           23

<210> SEQ ID NO 2
<211> LENGTH: 23
<212> TYPE: DNA
<213> ORGANISM: Artificial Sequence
<220> FEATURE:
<223> OTHER INFORMATION: Synthetic Construct

<400> SEQUENCE: 2
agtcctcaac tccctcaagc agg                                           23

<210> SEQ ID NO 3
<211> LENGTH: 23
<212> TYPE: DNA
<213> ORGANISM: Artificial Sequence
<220> FEATURE:
<223> OTHER INFORMATION: Synthetic Construct

<400> SEQUENCE: 3
actcctcatc ccctcaagc cgg                                            23

<210> SEQ ID NO 4
<211> LENGTH: 23
<212> TYPE: DNA
<213> ORGANISM: Artificial Sequence
<220> FEATURE:
<223> OTHER INFORMATION: Synthetic Construct

<400> SEQUENCE: 4
gcagatgtag tgtttccaca ggg                                           23

<210> SEQ ID NO 5
```

```
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5
gcagatgtag tatttccaca ggg                                              23

<210> SEQ ID NO 6
<211> LENGTH: 23
<212> TYPE: DNA
<213> ORGANISM: Artificial Sequence
<220> FEATURE:
<223> OTHER INFORMATION: Synthetic Construct

<400> SEQUENCE: 6
ccagatgtag cgtttccaca ggg                                              23

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
gcagatgttg tgtttccaca ggg                                              23

<210> SEQ ID NO 8
<211> LENGTH: 23
<212> TYPE: DNA
<213> ORGANISM: Artificial Sequence
<220> FEATURE:
<223> OTHER INFORMATION: Synthetic Construct

<400> SEQUENCE: 8
cttgccccac agggcagtaa cgg                                              23

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct

<400> SEQUENCE: 9
tcagccccac agggcagtaa ggg                                              23

<210> SEQ ID NO 10
<211> LENGTH: 23
<212> TYPE: DNA
<213> ORGANISM: Artificial Sequence
<220> FEATURE:
<223> OTHER INFORMATION: Synthetic Construct

<400> SEQUENCE: 10
tggtaatgat ggcttcaaca tgg                                              23

<210> SEQ ID NO 11
<211> LENGTH: 23
<212> TYPE: DNA
<213> ORGANISM: Artificial Sequence
<220> FEATURE:
<223> OTHER INFORMATION: Synthetic Construct

<400> SEQUENCE: 11
```
tggtaatgat gacttcaaca tag                                              23

<210> SEQ ID NO 12
<211> LENGTH: 113
<212> TYPE: RNA
<213> ORGANISM: Artificial Sequence
<220> FEATURE:
<223> OTHER INFORMATION: Synthetic Construct

<400> SEQUENCE: 12
aguccucauc ucccucaagc guuuagagc uaugcuggua acagcauagc aaguuuaaau       60
aaggcuaguc cguuaucaac uugaaaaagu ggcaccgagu cggugcuuuu uuu            113

<210> SEQ ID NO 13
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-methyl-3'-phosphorothioate
<220> FEATURE:
<221> NAME/KEY: misc_feature
<222> LOCATION: (110)..(113)
<223> OTHER INFORMATION: 2'-O-methyl-3'-phosphorothioate

<400> SEQUENCE: 13
aguccucauc ucccucaagc guuuagagc uaugcuggua acagcauagc aaguuuaaau       60
aaggcuaguc cguuaucaac uugaaaaagu ggcaccgagu cggugcuuuu uuu            113

<210> SEQ ID NO 14
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-methyl-3'-thiophosphonoacetate
<220> FEATURE:
<221> NAME/KEY: misc_feature
<222> LOCATION: (110)..(113)
<223> OTHER INFORMATION: 2'-O-methyl-3'-thiophosphonoacetate

<400> SEQUENCE: 14
aguccucauc ucccucaagc guuuagagc uaugcuggua acagcauagc aaguuuaaau       60
aaggcuaguc cguuaucaac uugaaaaagu ggcaccgagu cggugcuuuu uuu            113

<210> SEQ ID NO 15
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-thiophosphonoacetate
<220> FEATURE:
<221> NAME/KEY: misc_feature
<222> LOCATION: (112)..(113)
<223> OTHER INFORMATION: 2'-O-methyl-3'-thiophosphonoacetate

<400> SEQUENCE: 15
aguccucauc ucccucaagc guuuaagagc uaugcuggua acagcauagc aaguuuaaau    60
aaggcuaguc cguuaucaac uugaaaaagu ggcaccgagu cggugcuuuu uuu    113

```
<210> SEQ ID NO 16
<211> LENGTH: 111
<212> TYPE: RNA
<213> ORGANISM: Artificial Sequence
<220> FEATURE:
<223> OTHER INFORMATION: Synthetic Construct

<400> SEQUENCE: 16
```
uccucaucuc ccucaagcgu uuaagagcua ugcugguaac agcauagcaa guuuaaauaa    60
ggcuaguccg uuaucaacuu gaaaagugg caccgagucg gugcuuuuuu u    111

```
<210> SEQ ID NO 17
<211> LENGTH: 110
<212> TYPE: RNA
<213> ORGANISM: Artificial Sequence
<220> FEATURE:
<223> OTHER INFORMATION: Synthetic Construct

<400> SEQUENCE: 17
```
ccucaucucc cucaagcguu uaagagcuau gcugguaaca gcauagcaag uuuaauaag    60 gcuaguccgu uaucaacuug aaaaguggc accgagucgg ugcuuuuuu    110

```
<210> SEQ ID NO 18
<211> LENGTH: 114
<212> TYPE: RNA
<213> ORGANISM: Artificial Sequence
<220> FEATURE:
<223> OTHER INFORMATION: Synthetic Construct

<400> SEQUENCE: 18
```
gaguccucau ucccucaag cguuuaagag cuaugcuggu aacagcauag caaguuuaaa    60
uaaggcuagu ccguuaucaa cuugaaaaag uggcaccgag ucggugcuuu uuuu    114

```
<210> SEQ ID NO 19
<211> LENGTH: 115
<212> TYPE: RNA
<213> ORGANISM: Artificial Sequence
<220> FEATURE:
<223> OTHER INFORMATION: Synthetic Construct

<400> SEQUENCE: 19
```
ggaguccuca ucccucaa gcguuuaaga gcuaugcugg uaacagcaua gcaaguuuaa    60
auaaggcuag uccguuauca acuugaaaaa guggcaccga gucggugcuu uuuuu    115

```
<210> SEQ ID NO 20
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate

<400> SEQUENCE: 20
```
aguccucauc ucccucaagc guuuaagagc uaugcuggua acagcauagc aaguuuaaau    60
aaggcuaguc cguuaucaac uugaaaaagu ggcaccgagu cggugcuuuu uuu    113

```
<210> SEQ ID NO 21
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-O-methyl-3'-phosphonoacetate

<400> SEQUENCE: 21
aguccucauc ucccucaagc guuuaagagc uaugcuggua acagcauagc aaguuuaaau      60
aaggcuaguc cguuaucaac uugaaaaagu ggcaccgagu cggugcuuuu uuu           113

<210> SEQ ID NO 22
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-methyl-3'-phosphonoacetate

<400> SEQUENCE: 22
aguccucauc ucccucaagc guuuaagagc uaugcuggua acagcauagc aaguuuaaau      60
aaggcuaguc cguuaucaac uugaaaaagu ggcaccgagu cggugcuuuu uuu           113

<210> SEQ ID NO 23
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: 2'-O-methyl-3'-phosphonoacetate

<400> SEQUENCE: 23
aguccucauc ucccucaagc guuuaagagc uaugcuggua acagcauagc aaguuuaaau      60
aaggcuaguc cguuaucaac uugaaaaagu ggcaccgagu cggugcuuuu uuu           113

<210> SEQ ID NO 24
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(6)
<223> OTHER INFORMATION: 2'-O-methyl-3'-phosphonoacetate

<400> SEQUENCE: 24
aguccucauc ucccucaagc guuuaagagc uaugcuggua acagcauagc aaguuuaaau      60
aaggcuaguc cguuaucaac uugaaaaagu ggcaccgagu cggugcuuuu uuu           113

<210> SEQ ID NO 25
<211> LENGTH: 113
<212> TYPE: RNA
<213> ORGANISM: Artificial Sequence
<220> FEATURE:
<223> OTHER INFORMATION: Synthetic Construct
<220> FEATURE:
```

<221> NAME/KEY: misc_feature
<222> LOCATION: (109)..(113)
<223> OTHER INFORMATION: 2'-O-methyl-3'-phosphonoacetate

<400> SEQUENCE: 25
aguccucauc ucccucaagc guuuagagc uaugcuggua acagcauagc aaguuuaaau      60
aaggcuaguc cguuaucaac uugaaaaagu ggcaccgagu cggugcuuuu uuu           113

<210> SEQ ID NO 26
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (108)..(113)
<223> OTHER INFORMATION: 2'-O-methyl-3'-phosphonoacetate

<400> SEQUENCE: 26
aguccucauc ucccucaagc guuuagagc uaugcuggua acagcauagc aaguuuaaau      60
aaggcuaguc cguuaucaac uugaaaaagu ggcaccgagu cggugcuuuu uuu           113

<210> SEQ ID NO 27
<211> LENGTH: 114
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate modification of
      an overhanging nucleotide N
<220> FEATURE:
<221> NAME/KEY: misc_feature
<222> LOCATION: (2)..(4)
<223> OTHER INFORMATION: 2'-O-methyl-3'-phosphonoacetate

<400> SEQUENCE: 27
caguccucau cucccucaag cguuuaagag cuaugcuggu aacagcauag caaguuuaaa     60
uaaggcuagu ccguuaucaa cuugaaaaag uggcaccgag ucggugcuuu uuuu          114

<210> SEQ ID NO 28
<211> LENGTH: 114
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate modification of
      an overhanging nucleotide N
<220> FEATURE:
<221> NAME/KEY: misc_feature
<222> LOCATION: (2)..(4)
<223> OTHER INFORMATION: 2'-O-methyl-3'-phosphonoacetate

<400> SEQUENCE: 28
gaguccucau cucccucaag cguuuaagag cuaugcuggu aacagcauag caaguuuaaa     60
uaaggcuagu ccguuaucaa cuugaaaaag uggcaccgag ucggugcuuu uuuu          114

<210> SEQ ID NO 29
<211> LENGTH: 115
<212> TYPE: RNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-O-methyl-3'-phosphonoacetate modification of
      an overhanging nucleotide N
<220> FEATURE:
<221> NAME/KEY: misc_feature
<222> LOCATION: (3)..(6)
<223> OTHER INFORMATION: 2'-O-methyl-3'-phosphonoacetate

<400> SEQUENCE: 29
ucaguccuca ucucccucaa gcguuuaaga gcuaugcugg uaacagcaua gcaaguuuaa    60
auaaggcuag uccguuauca acuugaaaaa guggcaccga gucggugcuu uuuuu       115

<210> SEQ ID NO 30
<211> LENGTH: 115
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-O-methyl-3'-phosphonoacetate modification of
      an overhanging nucleotide N
<220> FEATURE:
<221> NAME/KEY: misc_feature
<222> LOCATION: (3)..(6)
<223> OTHER INFORMATION: 2'-O-methyl-3'-phosphonoacetate

<400> SEQUENCE: 30
agaguccuca ucucccucaa gcguuuaaga gcuaugcugg uaacagcaua gcaaguuuaa    60
auaaggcuag uccguuauca acuugaaaaa guggcaccga gucggugcuu uuuuu       115

<210> SEQ ID NO 31
<211> LENGTH: 116
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-methyl-3'-phosphonoacetate modification of
      an overhanging nucleotide N
<220> FEATURE:
<221> NAME/KEY: misc_feature
<222> LOCATION: (4)..(8)
<223> OTHER INFORMATION: 2'-O-methyl-3'-phosphonoacetate
<220> FEATURE:
<221> NAME/KEY: misc_feature
<222> LOCATION: (112)..(116)
<223> OTHER INFORMATION: 2'-O-methyl-3'-phosphonoacetate

<400> SEQUENCE: 31
cucaguccuc aucucccuca agcguuuaag agcuaugcug guaacagcau agcaaguuua    60
aauaaggcua guccguuauc aacuugaaaa aguggcaccg agucggugcu uuuuuu      116

<210> SEQ ID NO 32
<211> LENGTH: 116
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-methyl-3'-phosphonoacetate modification of
```

```
       an overhanging nucleotide N
<220> FEATURE:
<221> NAME/KEY: misc_feature
<222> LOCATION: (4)..(8)
<223> OTHER INFORMATION: 2'-O-methyl-3'-phosphonoacetate
<220> FEATURE:
<221> NAME/KEY: misc_feature
<222> LOCATION: (112)..(116)
<223> OTHER INFORMATION: 2'-O-methyl-3'-phosphonoacetate

<400> SEQUENCE: 32
gagaguccuc aucucccuca agcguuuaag agcuaugcug guaacagcau agcaaguuua      60
aauaaggcua guccguuauc aacuugaaaa aguggcaccg agucggugcu uuuuuu         116

<210> SEQ ID NO 33
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: 2'-O-methyl-3'-phosphonoacetate

<400> SEQUENCE: 33
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 34
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(20)
<223> OTHER INFORMATION: 2'-O-methyl-3'-phosphonoacetate

<400> SEQUENCE: 34
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 35
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(19)
<223> OTHER INFORMATION: 2'-O-methyl-3'-phosphonoacetate

<400> SEQUENCE: 35
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 36
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
```

<222> LOCATION: (17)..(18)
<223> OTHER INFORMATION: 2'-O-methyl-3'-phosphonoacetate

<400> SEQUENCE: 36
aguccucauc ucccucaagc guuuagagc uaugcuggua acagcauagc aaguuuaaau     60
aaggcuaguc cguuaucaac uugaaaaagu ggcaccgagu cggugcuuuu uuu           113

<210> SEQ ID NO 37
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(19)
<223> OTHER INFORMATION: 2'-O-methyl-3'-phosphonoacetate

<400> SEQUENCE: 37
aguccucauc ucccucaagc guuuagagc uaugcuggua acagcauagc aaguuuaaau     60
aaggcuaguc cguuaucaac uugaaaaagu ggcaccgagu cggugcuuuu uuu           113

<210> SEQ ID NO 38
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(20)
<223> OTHER INFORMATION: 2'-O-methyl

<400> SEQUENCE: 38
aguccucauc ucccucaagc guuuagagc uaugcuggua acagcauagc aaguuuaaau     60
aaggcuaguc cguuaucaac uugaaaaagu ggcaccgagu cggugcuuuu uuu           113

<210> SEQ ID NO 39
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(19)
<223> OTHER INFORMATION: 2'-O-methyl

<400> SEQUENCE: 39
aguccucauc ucccucaagc guuuagagc uaugcuggua acagcauagc aaguuuaaau     60
aaggcuaguc cguuaucaac uugaaaaagu ggcaccgagu cggugcuuuu uuu           113

<210> SEQ ID NO 40
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(18)
<223> OTHER INFORMATION: 2'-O-methyl

<400> SEQUENCE: 40
aguccucauc ucccucaagc guuuagagc uaugcuggua acagcauagc aaguuuaaau     60
aaggcuaguc cguuaucaac uugaaaaagu ggcaccgagu cggugcuuuu uuu         113

<210> SEQ ID NO 41
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(19)
<223> OTHER INFORMATION: 2'-O-methyl

<400> SEQUENCE: 41
aguccucauc ucccucaagc guuuagagc uaugcuggua acagcauagc aaguuuaaau    60
aaggcuaguc cguuaucaac uugaaaaagu ggcaccgagu cggugcuuuu uuu         113

<210> SEQ ID NO 42
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(21)
<223> OTHER INFORMATION: 2'-O-methyl

<400> SEQUENCE: 42
aguccucauc ucccucaagc guuuagagc uaugcuggua acagcauagc aaguuuaaau    60
aaggcuaguc cguuaucaac uugaaaaagu ggcaccgagu cggugcuuuu uuu         113

<210> SEQ ID NO 43
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(8)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 43
gcagauguag uguuuccaca guuuagagc uaugcuggua acagcauagc aaguuuaaau    60
aaggcuaguc cguuaucaac uugaaaaagu ggcaccgagu cggugcuuuu uuu         113

<210> SEQ ID NO 44
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(9)
<223> OTHER INFORMATION: 2'-O-methyl-3'-phosphonoacetate

```
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 44
gcagauguag uguuccaca guuuaagagc uaugcuggua acagcauagc aaguuuaaau      60
aaggcuaguc cguuaucaac uugaaaaagu ggcaccgagu cggugcuuuu uuu           113

<210> SEQ ID NO 45
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(10)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 45
gcagauguag uguuccaca guuuaagagc uaugcuggua acagcauagc aaguuuaaau      60
aaggcuaguc cguuaucaac uugaaaaagu ggcaccgagu cggugcuuuu uuu           113

<210> SEQ ID NO 46
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (8)..(11)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 46
gcagauguag uguuccaca guuuaagagc uaugcuggua acagcauagc aaguuuaaau      60
aaggcuaguc cguuaucaac uugaaaaagu ggcaccgagu cggugcuuuu uuu           113

<210> SEQ ID NO 47
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (9)..(12)
<223> OTHER INFORMATION: 2'-O-methyl-3'-phosphonoacetate
<220> FEATURE:
```

```
<221> NAME/KEY: misc_feature
<222> LOCATION: (112)..(113)
<223> OTHER INFORMATION: 2'-O-methyl-3'-phosphonoacetate

<400> SEQUENCE: 47
gcagauguag uguuuccaca guuuaagagc uaugcuggua acagcauagc aaguuuaaau      60
aaggcuaguc cguuaucaac uugaaaaagu ggcaccgagu cggugcuuuu uuu           113

<210> SEQ ID NO 48
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (10)..(13)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 48
gcagauguag uguuuccaca guuuaagagc uaugcuggua acagcauagc aaguuuaaau      60
aaggcuaguc cguuaucaac uugaaaaagu ggcaccgagu cggugcuuuu uuu           113

<210> SEQ ID NO 49
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (11)..(14)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 49
gcagauguag uguuuccaca guuuaagagc uaugcuggua acagcauagc aaguuuaaau      60
aaggcuaguc cguuaucaac uugaaaaagu ggcaccgagu cggugcuuuu uuu           113

<210> SEQ ID NO 50
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (12)..(15)
<223> OTHER INFORMATION: 2'-O-methyl-3'-phosphonoacetate
<220> FEATURE:
<221> NAME/KEY: misc_feature
```

```
<222> LOCATION: (112)..(113)
<223> OTHER INFORMATION: 2'-O-methyl-3'-phosphonoacetate

<400> SEQUENCE: 50
gcagauguag uguuccaca guuuagagc uaugcuggua acagcauagc aaguuuaaau      60
aaggcuaguc cguuaucaac uugaaaaagu ggcaccgagu cggugcuuuu uuu          113

<210> SEQ ID NO 51
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (13)..(16)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 51
gcagauguag uguuccaca guuuagagc uaugcuggua acagcauagc aaguuuaaau      60
aaggcuaguc cguuaucaac uugaaaaagu ggcaccgagu cggugcuuuu uuu          113

<210> SEQ ID NO 52
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (14)..(17)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 52
gcagauguag uguuccaca guuuagagc uaugcuggua acagcauagc aaguuuaaau      60
aaggcuaguc cguuaucaac uugaaaaagu ggcaccgagu cggugcuuuu uuu          113

<210> SEQ ID NO 53
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (4)..(5)
<223> OTHER INFORMATION: 2'-O-methyl-3'-phosphonoacetate
<220> FEATURE:
<221> NAME/KEY: misc_feature
<222> LOCATION: (112)..(113)
```

<223> OTHER INFORMATION: 2'-O-methyl-3'-phosphonoacetate

<400> SEQUENCE: 53
gcagauguag uguuccaca guuuaagagc uaugcuggua acagcauagc aaguuuaaau      60
aaggcuaguc cguuaucaac uugaaaaagu ggcaccgagu cggugcuuuu uuu           113

<210> SEQ ID NO 54
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 54
gcagauguag uguuccaca guuuaagagc uaugcuggua acagcauagc aaguuuaaau      60
aaggcuaguc cguuaucaac uugaaaaagu ggcaccgagu cggugcuuuu uuu           113

<210> SEQ ID NO 55
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 55
gcagauguag uguuccaca guuuaagagc uaugcuggua acagcauagc aaguuuaaau      60
aaggcuaguc cguuaucaac uugaaaaagu ggcaccgagu cggugcuuuu uuu           113

<210> SEQ ID NO 56
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 56
gcagauguag uguuuccaca guuuaagagc uaugcuggua acagcauagc aaguuuaaau        60
aaggcuaguc cguuaucaac uugaaaaagu ggcaccgagu cggugcuuuu uuu              113

<210> SEQ ID NO 57
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (8)..(9)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 57
gcagauguag uguuuccaca guuuaagagc uaugcuggua acagcauagc aaguuuaaau        60
aaggcuaguc cguuaucaac uugaaaaagu ggcaccgagu cggugcuuuu uuu              113

<210> SEQ ID NO 58
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (9)..(10)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 58
gcagauguag uguuuccaca guuuaagagc uaugcuggua acagcauagc aaguuuaaau        60
aaggcuaguc cguuaucaac uugaaaaagu ggcaccgagu cggugcuuuu uuu              113

<210> SEQ ID NO 59
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 59
gcagauguag uguuuccaca guuuaagagc uaugcuggua acagcauagc aaguuuaaau    60
aaggcuaguc cguuaucaac uugaaaaagu ggcaccgagu cggugcuuuu uuu    113

<210> SEQ ID NO 60
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (11)..(12)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 60
gcagauguag uguuuccaca guuuaagagc uaugcuggua acagcauagc aaguuuaaau    60
aaggcuaguc cguuaucaac uugaaaaagu ggcaccgagu cggugcuuuu uuu    113

<210> SEQ ID NO 61
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (12)..(13)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 61
gcagauguag uguuuccaca guuuaagagc uaugcuggua acagcauagc aaguuuaaau    60
aaggcuaguc cguuaucaac uugaaaaagu ggcaccgagu cggugcuuuu uuu    113

<210> SEQ ID NO 62
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 62
gcagauguag uguuuccaca guuuaagagc uaugcuggua acagcauagc aaguuuaaau    60
aaggcuaguc cguuaucaac uugaaaaagu ggcaccgagu cggugcuuuu uuu          113

<210> SEQ ID NO 63
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 63
gcagauguag uguuuccaca guuuaagagc uaugcuggua acagcauagc aaguuuaaau    60
aaggcuaguc cguuaucaac uugaaaaagu ggcaccgagu cggugcuuuu uuu          113

<210> SEQ ID NO 64
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (15)..(16)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 64
gcagauguag uguuuccaca guuuaagagc uaugcuggua acagcauagc aaguuuaaau    60
aaggcuaguc cguuaucaac uugaaaaagu ggcaccgagu cggugcuuuu uuu          113

<210> SEQ ID NO 65
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 65

-continued

```
gcagauguag uguuccaca guuuaagagc uaugcuggua acagcauagc aaguuuaaau          60
aaggcuaguc cguuaucaac uugaaaaagu ggcaccgagu cggugcuuuu uuu              113
```

<210> SEQ ID NO 66
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 66

```
gcagauguag uguuccaca guuuaagagc uaugcuggua acagcauagc aaguuuaaau          60
aaggcuaguc cguuaucaac uugaaaaagu ggcaccgagu cggugcuuuu uuu              113
```

<210> SEQ ID NO 67
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (18)..(19)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 67

```
gcagauguag uguuccaca guuuaagagc uaugcuggua acagcauagc aaguuuaaau          60
aaggcuaguc cguuaucaac uugaaaaagu ggcaccgagu cggugcuuuu uuu              113
```

<210> SEQ ID NO 68
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (19)..(20)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 68

```
gcagauguag uguuccaca guuuaagagc uaugcuggua acagcauagc aaguuuaaau          60
```
aaggcuaguc cguuaucaac uugaaaaagu ggcaccgagu cggugcuuuu uuu    113

<210> SEQ ID NO 69
<211> LENGTH: 113
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (20)..(21)
<223> OTHER INFORMATION: 2'-O-methyl-3'-phosphonoacetate
<220> FEATURE:
<221> NAME/KEY: misc_feature
<222> LOCATION: (112)..(113)
<223> OTHER INFORMATION: 2'-O-methyl-3'-phosphonoacetate

<400> SEQUENCE: 69
gcagauguag uguuuccaca guuuaagagc uaugcuggua acagcauagc aaguuuaaau    60
aaggcuaguc cguuaucaac uugaaaaagu ggcaccgagu cggugcuuuu uuu    113

<210> SEQ ID NO 70
<211> LENGTH: 113
<212> TYPE: RNA
<213> ORGANISM: Artificial Sequence
<220> FEATURE:
<223> OTHER INFORMATION: Synthetic Construct

<400> SEQUENCE: 70
gcagauguag uguuuccaca guuuaagagc uaugcuggua acagcauagc aaguuuaaau    60
aaggcuaguc cguuaucaac uugaaaaagu ggcaccgagu cggugcuuuu uuu    113

<210> SEQ ID NO 71
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(10)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 71
ugguaaugau ggcuucaaca guuuagagc uagaaauagc aaguuaaaau aaggcuaguc    60
cguuaucaac uugaaaaagu ggcaccgagu cggugcuuuu    100

<210> SEQ ID NO 72
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)

<223> OTHER INFORMATION: 2'-O-methyl-3'-phosphonoacetate
<220> FEATURE:
<221> NAME/KEY: misc_feature
<222> LOCATION: (8)..(11)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 72
ugguaaugau ggcuucaaca guuuuagagc uagaaauagc aaguuaaaau aaggcuaguc    60
cguuaucaac uugaaaaagu ggcaccgagu cggugcuuuu    100

<210> SEQ ID NO 73
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (9)..(12)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 73
ugguaaugau ggcuucaaca guuuuagagc uagaaauagc aaguuaaaau aaggcuaguc    60
cguuaucaac uugaaaaagu ggcaccgagu cggugcuuuu    100

<210> SEQ ID NO 74
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (10)..(13)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 74
ugguaaugau ggcuucaaca guuuuagagc uagaaauagc aaguuaaaau aaggcuaguc    60
cguuaucaac uugaaaaagu ggcaccgagu cggugcuuuu    100

<210> SEQ ID NO 75
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate

```
<220> FEATURE:
<221> NAME/KEY: misc_feature
<222> LOCATION: (11)..(14)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 75
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 76
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (12)..(15)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 76
ugguaaugau ggcuucaaca guuuuagagc uagaaauagc aaguaaaaau aaggcuaguc    60
cguuaucaac uugaaaaagu ggcaccgagu cggugcuuuu                        100

<210> SEQ ID NO 77
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (12)..(16)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 77
ugguaaugau ggcuucaaca guuuuagagc uagaaauagc aaguaaaaau aaggcuaguc    60
cguuaucaac uugaaaaagu ggcaccgagu cggugcuuuu                        100

<210> SEQ ID NO 78
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
```

```
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 78
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 79
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 79
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 80
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (15)..(16)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 80
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 81
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
```

```
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 81
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 82
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 82
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 83
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (18)..(19)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 83
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 84
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (19)..(20)
```

```
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 84
ugguaaugau ggcuucaaca guuuuagagc uagaaauagc aaguuaaaau aaggcuaguc    60
cguuaucaac uugaaaaagu ggcaccgagu cggugcuuuu                          100

<210> SEQ ID NO 85
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (20)..(21)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 85
ugguaaugau ggcuucaaca guuuuagagc uagaaauagc aaguuaaaau aaggcuaguc    60
cguuaucaac uugaaaaagu ggcaccgagu cggugcuuuu                          100

<210> SEQ ID NO 86
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 86
ugguaaugau ggcuucaaca guuuuagagc uagaaauagc aaguuaaaau aaggcuaguc    60
cguuaucaac uugaaaaagu ggcaccgagu cggugcuuuu                          100

<210> SEQ ID NO 87
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (4)..(5)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate
```

<400> SEQUENCE: 87
cuugccccac agggcaguaa guuuuagagc uagaaauagc aaguuaaaau aaggcuaguc        60
cguuaucaac uugaaaaagu ggcaccgagu cggugcuuuu                            100

<210> SEQ ID NO 88
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 88
cuugccccac agggcaguaa guuuuagagc uagaaauagc aaguuaaaau aaggcuaguc        60
cguuaucaac uugaaaaagu ggcaccgagu cggugcuuuu                            100

<210> SEQ ID NO 89
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 89
cuugccccac agggcaguaa guuuuagagc uagaaauagc aaguuaaaau aaggcuaguc        60
cguuaucaac uugaaaaagu ggcaccgagu cggugcuuuu                            100

<210> SEQ ID NO 90
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

```
<400> SEQUENCE: 90
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 91
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (8)..(9)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 91
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 92
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (9)..(10)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 92
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 93
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 93
```
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 94
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (11)..(12)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 94
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 95
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (12)..(13)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 95
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 96
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 96
cuugccccac agggcaguaa guuuuagagc uagaaauagc aaguuaaaau aaggcuaguc    60
cguuaucaac uugaaaaagu ggcaccgagu cggugcuuuu                         100

<210> SEQ ID NO 97
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 97
cuugccccac agggcaguaa guuuuagagc uagaaauagc aaguuaaaau aaggcuaguc    60
cguuaucaac uugaaaaagu ggcaccgagu cggugcuuuu                         100

<210> SEQ ID NO 98
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (15)..(16)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 98
cuugccccac agggcaguaa guuuuagagc uagaaauagc aaguuaaaau aaggcuaguc    60
cguuaucaac uugaaaaagu ggcaccgagu cggugcuuuu                         100

<210> SEQ ID NO 99
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 99
cuugccccac agggcaguaa guuuuagagc uagaaauagc aaguuaaaau aaggcuaguc    60
cguuaucaac uugaaaaagu ggcaccgagu cggugcuuuu                          100

<210> SEQ ID NO 100
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 100
cuugccccac agggcaguaa guuuuagagc uagaaauagc aaguuaaaau aaggcuaguc    60
cguuaucaac uugaaaaagu ggcaccgagu cggugcuuuu                          100

<210> SEQ ID NO 101
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (18)..(19)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 101
cuugccccac agggcaguaa guuuuagagc uagaaauagc aaguuaaaau aaggcuaguc    60
cguuaucaac uugaaaaagu ggcaccgagu cggugcuuuu                          100

<210> SEQ ID NO 102
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (19)..(20)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 102
cuugccccac agggcaguaa guuuuagagc uagaaauagc aaguuaaaau aaggcuaguc    60

| cguuaucaac uugaaaaagu ggcaccgagu cggugcuuuu | 100 |

```
<210> SEQ ID NO 103
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 103
```

| cuugccccac agggcaguaa guuuuagagc uagaaauagc aaguuaaaau aaggcuaguc | 60 |
| cguuaucaac uugaaaaagu ggcaccgagu cggugcuuuu | 100 |

```
<210> SEQ ID NO 104
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 104
```

| gcgtttctgg gtgagcaaaa acaggaaggc aaaatgccgc aaaaaaggga ataagggcga | 60 |
| cacgaaaatg ttgaatactc atactcttcc tttttcaata ttattgaagc atttatcagg | 120 |
| gttattgtct catgagcgga tacatatttg aatgtattta gaaaaataaa caaatagggg | 180 |
| ttccgcgcac atttccccga aaagtgccac ctaaattgta agcgttaata ttttgttaaa | 240 |
| attcgcgtta aatttttgtt aaatcagctc attttttaac caataggccg aaatcggcaa | 300 |
| aatcccttat aaatcaaaag aatagaccga tagggttg agtgttgttc cagtttggaa | 360 |
| caagagtcca ctattaaaga acgtggactc caacgtcaaa gggcgaaaaa ccgtctatca | 420 |
| gggcgatggc ccactacgtg aaccatcacc ctaatcaagt tttttggggt cgaggtgccg | 480 |
| taaagcacta aatcggaacc ctaaagggag cccccgattt agagcttgac ggggaaagcc | 540 |
| ggcgaacgtg cgagaaagg aagggaagaa agcgaaagga gcgggcgcta gggcgctggc | 600 |
| aagtgtagcg gtcacgctgc gcgtaaccac cacacccgcc gcgcttaatg cgccgctaca | 660 |
| gggcgcgtcc cattcgccat tcaggctgcg caactgttgg gaagggcgat cggtgcgggc | 720 |
| ctcttcgcta ttacgccagc tggcgaaagg gggatgtgct gcaaggcgat taagttgggt | 780 |
| aacgccaggg ttttcccagt cacgacgttg taaaacgacg gccagtgagc gcgcgtaata | 840 |
| cgactcacta tagggcgaat tgggtacgat cgatgcggcc tcgcaggcca agatgtctc | 900 |
| ccgcatgcgc tcagtcctca tctccctcaa gcaggccctg ctggtgcact gaagagccac | 960 |
| cctgtgcgcg tgatatgcag ctccagcttt tgttcccttt agtgagggtt aattgcgcgc | 1020 |
| ttggcgtaat catggtcata gctgtttcct gtgtgaaatt gttatccgct cacaattcca | 1080 |
| cacaacatac gagccggaag cataaagtgt aaagcctggg gtgcctaatg agtgagctaa | 1140 |
| ctcacattaa ttgcgttgcg ctcactgccc gctttccagt cgggaaacct gtcgtgccag | 1200 |
| ctgcattaat gaatcggcca acgcgcgggg agaggcggtt tgcgtattgg gcgctcttcc | 1260 |
| gcttcctcgc tcactgactc gctgcgctcg gtcgttcggc tgcggcgagc ggtatcagct | 1320 |
| cactcaaagg cggtaatacg gttatccaca gaatcagggg ataacgcagg aaagaacatg | 1380 |

```
tgagcaaaag gccagcaaaa ggccaggaac cgtaaaaagg ccgcgttgct ggcgttttc      1440 cataggctcc gcccccctga cgagcatcac aaaaatcgac gctcaagtca gaggtggcga      1500
aacccgacag gactataaag ataccaggcg tttcccctg gaagctccct cgtgcgctct       1560
cctgttccga ccctgccgct taccggatac ctgtccgcct ttctcccttc gggaagcgtg      1620
gcgctttctc atagctcacg ctgtaggtat ctcagttcgg tgtaggtcgt tcgctccaag      1680
ctgggctgtg tgcacgaacc ccccgttcag cccgaccgct cgccttatc cggtaactat       1740 cgtcttgagt ccaacccggt aagacacgac ttatcgccac tggcagcagc cactggtaac      1800
aggattagca gagcgaggta tgtaggcggt gctacagagt tcttgaagtg gtggcctaac      1860
tacggctaca ctagaaggac agtatttggt atctgcgctc tgctgaagcc agttaccttc      1920
ggaaaaagag ttggtagctc ttgatccggc aaacaaacca ccgctggtag cggtggtttt      1980
tttgtttgca agcagcagat tacgcgcaga aaaaaggat ctcaagaaga tcctttgatc       2040
ttttctacgg ggtctgacgc tcagtggaac gaaaactcac gttaagggat tttggtcatg      2100
agattatcaa aaaggatctt cacctagatc cttttaaatt aaaaatgaag ttttaaatca      2160
atctaaagta tatatgagta aacttggtct gacagttacc aatgcttaat cagtgaggca      2220
cctatctcag cgatctgtct atttcgttca tccatagttg cctgactccc cgtcgtgtag      2280
ataactacga tacgggaggg cttaccatct ggccccagtg ctgcaatgat accgcgagac      2340
ccacgctcac cggctccaga tttatcagca ataaaccagc cagccggaag ggccgagcgc      2400
agaagtggtc ctgcaacttt atccgcctcc atccagtcta ttaattgttg ccgggaagct      2460
agagtaagta gttcgccagt taatagtttg cgcaacgttg ttgccattgc tacaggcatc      2520
gtggtgtcac gctcgtcgtt tggtatggct tcattcagct ccggttccca acgatcaagg      2580
cgagttacat gatcccccat gttgtgcaaa aaagcggtta gctccttcgg tcctccgatc      2640
gttgtcagaa gtaagttggc cgcagtgtta tcactcatgg ttatggcagc actgcataat      2700
tctcttactg tcatgccatc cgtaagatgc ttttctgtga ctggtgagta ctcaaccaag      2760
tcattctgag aatagtgtat gcggcgaccg agttgctctt gcccggcgtc aatacgggat      2820
aataccgcgc cacatagc                                                    2838

<210> SEQ ID NO 105
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 105
gcgtttctgg gtgagcaaaa acaggaaggc aaaatgccgc aaaaaaggga ataagggcga        60
cacggaaatg ttgaatactc atactcttcc ttttcaata ttattgaagc atttatcagg        120
gttattgtct catgagcgga tacatatttg aatgtattta gaaaaataaa caaatagggg       180
ttccgcgcac atttccccga aaagtgccac ctaaattgta agcgttaata ttttgttaaa       240
attcgcgtta aatttttgtt aaatcagctc attttttaac caataggccg aaatcggcaa       300
aatcccttat aaatcaaaag aatagaccga gatagggttg agtgttgttc agtttggaa        360 caagagtcca ctattaaaga acgtggactc caacgtcaaa gggcgaaaaa ccgtctatca       420
gggcgatggc ccactacgtg aaccatcacc taatcaagt tttttggggt cgaggtgccg        480
taaagcacta aatcggaacc ctaaagggag cccccgattt agagcttgac ggggaaagcc       540
```

```
ggcgaacgtg gcgagaaagg aagggaagaa agcgaaagga gcgggcgcta gggcgctggc    600
aagtgtagcg gtcacgctgc gcgtaaccac cacacccgcc gcgcttaatg cgccgctaca    660
gggcgcgtcc cattcgccat tcaggctgcg caactgttgg gaagggcgat cggtgcgggc    720
ctcttcgcta ttacgccagc tggcgaaagg gggatgtgct gcaaggcgat taagttgggt    780
aacgccaggg ttttcccagt cacgacgttg taaaacgacg gccagtgagc gcgcgtaata    840
cgactcacta tagggcgaat tgggtacgat cgatgcggcc tcgcagggca aagaggtctc    900
ctgtatgcac tcagtcctca actccctcaa gcaggcgacc cttggtgcac tgacaaaccg    960
ctcctgcgcg tgatatgcag ctccagcttt tgttcccttt agtgagggtt aattgcgcgc   1020
ttggcgtaat catggtcata gctgtttcct gtgtgaaatt gttatccgct cacaattcca   1080
cacaacatac gagccggaag cataaagtgt aaagcctggg gtgcctaatg agtgagctaa   1140
ctcacattaa ttgcgttgcg ctcactgccc gctttccagt cgggaaacct gtcgtgccag   1200
ctgcattaat gaatcggcca acgcgcgggg agaggcggtt tgcgtattgg gcgctcttcc   1260
gcttcctcgc tcactgactc gctgcgctcg tcgttcggc tgcggcgagc ggtatcagct   1320
cactcaaagg cggtaatacg gttatccaca gaatcagggg ataacgcagg aaagaacatg   1380
tgagcaaaag gccagcaaaa ggccaggaac cgtaaaaagg ccgcgttgct ggcgtttttc   1440
cataggctcc gccccctga cgagcatcac aaaaatcgac gctcaagtca gaggtggcga   1500
aacccgacag gactataaag ataccaggcg tttccccctg gaagctccct cgtgcgctct   1560
cctgttccga ccctgccgct taccggatac ctgtccgcct ttctcccttc gggaagcgtg   1620
gcgctttctc atagctcacg ctgtaggtat ctcagttcgg tgtaggtcgt tcgctccaag   1680
ctgggctgtg tgcacgaacc ccccgttcag cccgaccgct gcgccttatc cggtaactat   1740
cgtcttgagt ccaacccggt aagacacgac ttatcgccac tggcagcagc cactggtaac   1800
aggattagca gagcgaggta tgtaggcggt gctacagagt tcttgaagtg gtggcctaac   1860
tacggctaca ctagaaggac agtatttggt atctgcgctc tgctgaagcc agttaccttc   1920
ggaaaaagag ttggtagctc ttgatccggc aaacaaacca ccgctggtag cggtggtttt   1980
tttgtttgca agcagcagat tacgcgcaga aaaaaaggat ctcaagaaga tcctttgatc   2040
ttttctacgg ggtctgacgc tcagtggaac gaaaactcac gttaagggat tttggtcatg   2100
agattatcaa aaaggatctt cacctagatc cttttaaatt aaaaatgaag ttttaaatca   2160
atctaaagta tatatgagta aacttggtct gacagttacc aatgcttaat cagtgaggca   2220
cctatctcag cgatctgtct atttcgttca tccatagttg cctgactccc cgtcgtgtag   2280
ataactacga tacgggaggg cttaccatct ggccccagtg ctgcaatgat accgcgagac   2340
ccacgctcac cggctccaga tttatcagca ataaaccagc cagccggaag ggccgagcgc   2400
agaagtggtc ctgcaacttt atccgcctcc atccagtcta ttaattgttg ccgggaagct   2460
agagtaagta gttcgccagt taatagtttg cgcaacgttg ttgccattgc tacaggcatc   2520
gtggtgtcac gctcgtcgtt tggtatggct tcattcagct ccggttccca acgatcaagg   2580
cgagttacat gatccccat gttgtgcaaa aaagcggtta gctccttcgg tcctccgatc   2640
gttgtcagaa gtaagttggc cgcagtgtta tcactcatgg ttatggcagc actgcataat   2700
tctcttactg tcatgccatc cgtaagatgc ttttctgtga ctggtgagta ctcaaccaag   2760
tcattctgag aatagtgtat gcggcgaccg agttgctctt gcccggcgtc aatacgggat   2820
aataccgcgc cacatagc                                                 2838
```

```
<210> SEQ ID NO 106
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 106
gcgtttctgg gtgagcaaaa acaggaaggc aaaatgccgc aaaaaaggga ataagggcga      60
cacggaaatg ttgaatactc atactcttcc tttttcaata ttattgaagc atttatcagg     120
gttattgtct catgagcgga tacatatttg aatgtattta gaaaaataaa caaataggg      180
ttccgcgcac atttccccga aaagtgccac ctaaattgta agcgttaata ttttgttaaa     240
attcgcgtta aatttttgtt aaatcagctc attttttaac caataggccg aaatcggcaa     300
aatcccttat aaatcaaaag aatagaccga tagggttg agtgttgttc cagtttggaa       360
caagagtcca ctattaaaga acgtggactc caacgtcaaa gggcgaaaaa ccgtctatca     420
gggcgatggc ccactacgtg aaccatcacc ctaatcaagt tttttggggt cgaggtgccg     480
taaagcacta atcggaacc ctaaagggag cccccgattt agagcttgac ggggaaagcc      540
ggcgaacgtg gcgagaaagg aagggaagaa agcgaaagga gcgggcgcta gggcgctggc     600
aagtgtagcg gtcacgctgc gcgtaaccac cacacccgcc gcgcttaatg cgccgctaca     660
gggcgcgtcc cattcgccat tcaggctgcg caactgttgg gaaggcgat cggtgcgggc      720
ctcttcgcta ttacgccagc tggcgaaagg gggatgtgct gcaaggcgat taagttgggt    780
aacgccaggg ttttcccagt cacgacgttg taaaacgacg gccagtgagc gcgcgtaata    840
cgactcacta tagggcgaat tgggtacgat cgatgcggcc tcaggagagg gagccatgct    900
catctccagc ccactcctca tcccctcaa gccggtccca ggctgagagg ctaaagcttg      960
tctttgcgcg tgatatgcag ctccagcttt tgttccctt agtgagggtt aattgcgcgc    1020
ttggcgtaat catggtcata gctgtttcct gtgtgaaatt gttatccgct cacaattcca   1080
cacaacatac gagccggaag cataaagtgt aaagcctggg gtgcctaatg agtgagctaa   1140
ctcacattaa ttgcgttgcg ctcactgccc gctttccagt cgggaaacct gtcgtgccag   1200
ctgcattaat gaatcggcca acgcgcgggg agaggcggtt tgcgtattgg gcgctcttcc   1260
gcttcctcgc tcactgactc gctgcgctcg gtcgttcggc tgcggcgagc ggtatcagct   1320
cactcaaagg cggtaatacg gttatccaca gaatcagggg ataacgcagg aaagaacatg   1380
tgagcaaaag gccagcaaaa ggccaggaac cgtaaaaagg ccgcgttgct ggcgtttttc   1440
cataggctcc gccccctga cgagcatcac aaaaatcgac gctcaagtca gaggtggcga   1500
aacccgacag gactataaag ataccaggcg tttccccctg gaagctccct cgtgcgctct   1560
cctgttccga ccctgccgct taccggatac ctgtccgcct ttctcccttc gggaagcgtg   1620
gcgctttctc atagctcacg ctgtaggtat ctcagttcgg tgtaggtcgt tcgctccaag   1680
ctgggctgtg tgcacgaacc ccccgttcag cccgaccgct gcgccttatc cggtaactat   1740
cgtcttgagt ccaacccggt aagacacgac ttatcgccac tggcagcagc cactggtaac   1800
aggattagca gagcgaggta tgtaggcggt gctacagagt tcttgaagtg gtggcctaac   1860
tacggctaca ctagaaggac agtatttggt atctgcgctc tgctgaagcc agttaccttc   1920
ggaaaaagag ttggtagctc ttgatccggc aaacaaacca ccgctggtag cggtggtttt   1980
tttgtttgca agcagcagat tacgcgcaga aaaaaaggat ctcaagaaga tcctttgatc   2040
ttttctacgg ggtctgacgc tcagtggaac gaaaactcac gttaagggat tttggtcatg   2100
```

```
agattatcaa aaaggatctt cacctagatc cttttaaatt aaaaatgaag ttttaaatca    2160
atctaaagta tatatgagta aacttggtct gacagttacc aatgcttaat cagtgaggca    2220
cctatctcag cgatctgtct atttcgttca tccatagttg cctgactccc cgtcgtgtag    2280
ataactacga tacgggaggg cttaccatct ggccccagtg ctgcaatgat accgcgagac    2340
ccacgctcac cggctccaga tttatcagca ataaaccagc cagccggaag ggccgagcgc    2400
agaagtggtc ctgcaacttt atccgcctcc atccagtcta ttaattgttg ccgggaagct    2460
agagtaagta gttcgccagt taatagtttg cgcaacgttg ttgccattgc tacaggcatc    2520
gtggtgtcac gctcgtcgtt tggtatggct tcattcagct ccggttccca acgatcaagg    2580
cgagttacat gatcccccat gttgtgcaaa aaagcggtta gctccttcgg tcctccgatc    2640
gttgtcagaa gtaagttggc cgcagtgtta tcactcatgg ttatggcagc actgcataat    2700
tctcttactg tcatgccatc cgtaagatgc ttttctgtga ctggtgagta ctcaaccaag    2760
tcattctgag aatagtgtat gcggcgaccg agttgctctt gcccggcgtc aatacgggat    2820
aataccgcgc cacatagc                                                  2838

<210> SEQ ID NO 107
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 107
gcgtttctgg gtgagcaaaa acaggaaggc aaaatgccgc aaaaaaggga ataagggcga      60
cacggaaatg ttgaatactc atactcttcc ttttcaata ttattgaagc atttatcagg     120
gttattgtct catgagcgga tacatatttg aatgtattta gaaaaataaa caaatagggg     180
ttccgcgcac atttccccga aaagtgccac ctaaattgta agcgttaata ttttgttaaa     240 attgcgtta aattttgtt aaatcagctc attttttaac caataggccg aaatcggcaa     300
aatcccttat aaatcaaaag aatagaccga datagggttg agtgttgttc cagtttggaa     360
caagagtcca ctattaaaga acgtggactc caacgtcaaa gggcgaaaaa ccgtctatca     420
gggcgatggc ccactacgtg aaccatcacc ctaatcaagt ttttgggt cgaggtgccg     480 taaagcacta atcggaacc ctaaagggag cccccgattt agagcttgac ggggaaagcc     540
ggcgaacgtg gcgagaaagg aagggaagaa agcgaaagga gcgggcgcta gggcgctggc     600
aagtgtagcg gtcacgctgc gcgtaaccac cacacccgcc gcgcttaatg cgccgctaca     660
gggcgcgtcc cattcgccat tcaggctgcg caactgttgg gaagggcgat cggtgcgggc     720
ctcttcgcta ttacgccagc tggcgaaagg gggatgtgct gcaaggcgat taagttgggt     780
aacgccaggg ttttcccagt cacgacgttg taaaacgacg gccagtgagc gcgcgtaata     840
cgactcacta tagggcgaat tgggtacgat cgatgcggcc tcaagagctt cactgagtag     900
gattaagata ttgcagatgt agtgtttcca cagggtggct cttcagtgca ccagcggaac     960
ctgctgcgcg tgatatgcag ctccagcttt tgttcccttt agtgagggtt aattgcgcgc    1020
ttggcgtaat catggtcata gctgtttcct gtgtgaaatt gttatccgct cacaattcca    1080
cacaacatac gagccggaag cataaagtgt aaagcctggg gtgcctaatg agtgagctaa    1140
ctcacattaa ttgcgttgcg ctcactgccc gctttccagt cgggaaacct gtcgtgccag    1200
ctgcattaat gaatcggcca acgcgcgggg agaggcggtt tgcgtattgg gcgctcttcc    1260
gcttcctcgc tcactgactc gctgcgctcg gtcgttcggc tgcggcgagc ggtatcagct    1320
```

| | |
|---|---|
| cactcaaagg cggtaatacg gttatccaca gaatcagggg ataacgcagg aaagaacatg | 1380 |
| tgagcaaaag gccagcaaaa ggccaggaac cgtaaaaagg ccgcgttgct ggcgtttttc | 1440 |
| cataggctcc gcccccctga cgagcatcac aaaaatcgac gctcaagtca gaggtggcga | 1500 |
| aacccgacag gactataaag ataccaggcg tttccccctg gaagctccct cgtgcgctct | 1560 |
| cctgttccga ccctgccgct taccggatac ctgtccgcct ttctcccttc gggaagcgtg | 1620 |
| gcgctttctc atagctcacg ctgtaggtat ctcagttcgg tgtaggtcgt tcgctccaag | 1680 |
| ctgggctgtg tgcacgaacc ccccgttcag cccgaccgct gcgccttatc cggtaactat | 1740 |
| cgtcttgagt ccaacccggt aagacacgac ttatcgccac tggcagcagc cactggtaac | 1800 |
| aggattagca gagcgaggta tgtaggcggt gctacagagt tcttgaagtg gtggcctaac | 1860 |
| tacggctaca ctagaaggac agtatttggt atctgcgctc tgctgaagcc agttaccttc | 1920 |
| ggaaaaagag ttggtagctc ttgatccggc aaacaaacca ccgctggtag cggtggtttt | 1980 |
| tttgtttgca agcagcagat tacgcgcaga aaaaaaggat ctcaagaaga tcctttgatc | 2040 |
| ttttctacgg ggtctgacgc tcagtggaac gaaaactcac gttaagggat tttggtcatg | 2100 |
| agattatcaa aaaggatctt cacctagatc cttttaaatt aaaaatgaag ttttaaatca | 2160 |
| atctaaagta tatatgagta aacttggtct gacagttacc aatgcttaat cagtgaggca | 2220 |
| cctatctcag cgatctgtct atttcgttca tccatagttg cctgactccc cgtcgtgtag | 2280 |
| ataactacga tacgggaggg cttaccatct ggccccagtg ctgcaatgat accgcgagac | 2340 |
| ccacgctcac cggctccaga tttatcagca ataaaccagc cagccggaag ggccgagcgc | 2400 |
| agaagtggtc ctgcaacttt atccgcctcc atccagtcta ttaattgttg ccgggaagct | 2460 |
| agagtaagta gttcgccagt taatagtttg cgcaacgttg ttgccattgc tacaggcatc | 2520 |
| gtggtgtcac gctcgtcgtt tggtatggct tcattcagct ccggttccca acgatcaagg | 2580 |
| cgagttacat gatcccccat gttgtgcaaa aaagcggtta gctccttcgg tcctccgatc | 2640 |
| gttgtcagaa gtaagttggc cgcagtgtta tcactcatgg ttatggcagc actgcataat | 2700 |
| tctcttactg tcatgccatc cgtaagatgc ttttctgtga ctggtgagta ctcaaccaag | 2760 |
| tcattctgag aatagtgtat gcggcgaccg agttgctctt gcccggcgtc aatacgggat | 2820 |
| aataccgcgc cacatagc | 2838 |

<210> SEQ ID NO 108
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 108

| | |
|---|---|
| gcgtttctgg gtgagcaaaa acaggaaggc aaaatgccgc aaaaaaggga taagggcga | 60 |
| cacggaaatg ttgaatactc atactcttcc ttttcaata ttattgaagc atttatcagg | 120 |
| gttattgtct catgagcgga tacatatttg aatgtattta gaaaaataaa caaatagggg | 180 |
| ttccgcgcac atttccccga aaagtgccac ctaaattgta agcgttaata ttttgttaaa | 240 |
| attcgcgtta aattttttgtt aaatcagctc attttttaac caataggccg aaatcggcaa | 300 |
| aatcccttat aaatcaaaag aatagaccga gatagggttg agtgttgttc cagtttggaa | 360 |
| caagagtcca ctattaaaga acgtggactc caacgtcaaa gggcgaaaaa ccgtctatca | 420 |
| gggcgatggc ccactacgtg aaccatcacc ctaatcaagt ttttggggt cgaggtgccg | 480 |

```
taaagcacta aatcggaacc ctaaagggag cccccgattt agagcttgac ggggaaagcc    540
ggcgaacgtg gcgagaaagg aagggaagaa agcgaaagga gcgggcgcta gggcgctggc    600
aagtgtagcg gtcacgctgc gcgtaaccac cacacccgcc gcgcttaatg cgccgctaca    660
gggcgcgtcc cattcgccat tcaggctgcg caactgttgg gaagggcgat cggtgcgggc    720
ctcttcgcta ttacgccagc tggcgaaagg gggatgtgct gcaaggcgat taagttgggt    780
aacgccaggg ttttcccagt cacgacgttg taaaacgacg gccagtgagc gcgcgtaata    840
cgactcacta tagggcgaat tgggtacgat cgatgcggcc tcaagagctt cactgagtag    900
gattaagata ttgcagatgt agtatttcca cagggtggcc cttcagtgca ccagcggaac    960
ctgctgcgcg tgatatgcag ctccagcttt tgttcccttt agtgagggtt aattgcgcgc    1020
ttggcgtaat catggtcata gctgtttcct gtgtgaaatt gttatccgct cacaattcca    1080
cacaacatac gagccggaag cataaagtgt aaagcctggg gtgcctaatg agtgagctaa    1140
ctcacattaa ttgcgttgcg ctcactgccc gctttccagt cgggaaacct gtcgtgccag    1200
ctgcattaat gaatcggcca acgcgcgggg agaggcggtt tgcgtattgg gcgctcttcc    1260
gcttcctcgc tcactgactc gctgcgctcg gtcgttcggc tgcggcgagc ggtatcagct    1320
cactcaaagg cggtaatacg gttatccaca gaatcagggg ataacgcagg aaagaacatg    1380
tgagcaaaag gccagcaaaa ggccaggaac cgtaaaaagg ccgcgttgct ggcgtttttc    1440
cataggctcc gcccccctga cgagcatcac aaaaatcgac gctcaagtca gaggtggcga    1500
aacccgacag gactataaag ataccaggcg tttccccctg gaagctccct cgtgcgctct    1560
cctgttccga ccctgccgct taccggatac ctgtccgcct ttctcccttc gggaagcgtg    1620
gcgctttctc atagctcacg ctgtaggtat ctcagttcgg tgtaggtcgt tcgctccaag    1680
ctgggctgtg tgcacgaacc ccccgttcag cccgaccgct gcgccttatc cggtaactat    1740
cgtcttgagt ccaacccggt aagacacgac ttatcgccac tggcagcagc cactggtaac    1800
aggattagca gagcgaggta tgtaggcggt gctacagagt tcttgaagtg gtggcctaac    1860
tacggctaca ctagaaggac agtatttggt atctgcgctc tgctgaagcc agttaccttc    1920
ggaaaaagag ttggtagctc ttgatccggc aaacaaacca ccgctggtag cggtggtttt    1980
tttgtttgca agcagcagat tacgcgcaga aaaaaggat ctcaagaaga tcctttgatc    2040
ttttctacgg ggtctgacgc tcagtggaac gaaaactcac gttaagggat tttggtcatg    2100
agattatcaa aaaggatctt cacctagatc cttttaaatt aaaaatgaag ttttaaatca    2160
atctaaagta tatatgagta aacttggtct gacagttacc aatgcttaat cagtgaggca    2220
cctatctcag cgatctgtct atttcgttca tccatagttg cctgactccc cgtcgtgtag    2280
ataactacga tacgggaggg cttaccatct ggccccagtg ctgcaatgat accgcgagac    2340
ccacgctcac cggctccaga tttatcagca ataaccagc cagccggaag ggccgagcgc    2400
agaagtggtc ctgcaacttt atccgcctcc atccagtcta ttaattgttg ccgggaagct    2460
agagtaagta gttcgccagt taatagtttg cgcaacgttg ttgccattgc tacaggcatc    2520
gtggtgtcac gctcgtcgtt tggtatggct tcattcagct ccggttccca acgatcaagg    2580
cgagttacat gatcccccat gttgtgcaaa aaagcggtta gctccttcgg tcctccgatc    2640
gttgtcagaa gtaagttggc cgcagtgtta tcactcatgg ttatggcagc actgcataat    2700
tctcttactg tcatgccatc cgtaagatgc ttttctgtga ctggtgagta ctcaaccaag    2760
tcattctgag aatagtgtat gcggcgaccg agttgctctt gcccggcgtc aatacgggat    2820
aataccgcgc cacatagc                                                 2838
```

<210> SEQ ID NO 109
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 109

| | | | | | |
|---|---|---|---|---|---|
| gcgtttctgg | gtgagcaaaa | acaggaaggc | aaaatgccgc | aaaaaaggga | ataagggcga | 60 |
| cacggaaatg | ttgaatactc | atactcttcc | tttttcaata | ttattgaagc | atttatcagg | 120 |
| gttattgtct | catgagcgga | tacatatttg | aatgtattta | gaaaaataaa | caatagggg | 180 |
| ttccgcgcac | atttccccga | aaagtgccac | ctaaattgta | agcgttaata | ttttgttaaa | 240 |
| attcgcgtta | aatttttgtt | aaatcagctc | attttttaac | caataggccg | aaatcggcaa | 300 |
| aatcccttat | aaatcaaaag | aatagaccga | gatagggttg | agtgttgttc | cagtttggaa | 360 |
| caagagtcca | ctattaaaga | acgtggactc | caacgtcaaa | gggcgaaaaa | ccgtctatca | 420 |
| gggcgatggc | ccactacgtg | aaccatcacc | ctaatcaagt | tttttggggt | cgaggtgccg | 480 |
| taaagcacta | aatcggaacc | ctaaagggag | cccccgattt | agagcttgac | ggggaaagcc | 540 |
| ggcgaacgtg | gcgagaaagg | aagggaagaa | agcgaaagga | gcgggcgcta | gggcgctggc | 600 |
| aagtgtagcg | gtcacgctgc | gcgtaaccac | cacacccgcc | gcgcttaatg | cgccgctaca | 660 |
| gggcgcgtcc | cattcgccat | tcaggctgcg | caactgttgg | aagggcgat | cggtgcgggc | 720 |
| ctcttcgcta | ttacgccagc | tggcgaaagg | gggatgtgct | gcaaggcgat | taagttgggt | 780 |
| aacgccaggg | ttttcccagt | cacgacgttg | taaaacgacg | gccagtgagc | gcgcgtaata | 840 |
| cgactcacta | tagggcgaat | tgggtacgat | cgatgcggcc | tcaagagctt | cactgagtag | 900 |
| gattaagata | ttccagatgt | agcgtttcca | cagggtggct | cttcagtgca | ccagcggaac | 960 |
| ctgctgcgcg | tgatatgcag | ctccagcttt | tgttcccttt | agtgagggtt | aattgcgcgc | 1020 |
| ttggcgtaat | catggtcata | gctgtttcct | gtgtgaaatt | gttatccgct | cacaattcca | 1080 |
| cacaacatac | gagccggaag | cataaagtgt | aaagcctggg | gtgcctaatg | agtgagctaa | 1140 |
| ctcacattaa | ttgcgttgcg | ctcactgccc | gctttccagt | cgggaaacct | gtcgtgccag | 1200 |
| ctgcattaat | gaatcggcca | acgcgcgggg | agaggcggtt | tgcgtattgg | gcgctcttcc | 1260 |
| gcttcctcgc | tcactgactc | gctgcgctcg | gtcgttcggc | tgcggcgagc | ggtatcagct | 1320 |
| cactcaaagg | cggtaatacg | gttatccaca | gaatcagggg | ataacgcagg | aaagaacatg | 1380 |
| tgagcaaaag | gccagcaaaa | ggccaggaac | cgtaaaaagg | ccgcgttgct | ggcgtttttc | 1440 |
| cataggctcc | gcccccctga | cgagcatcac | aaaaatcgac | gctcaagtca | gaggtggcga | 1500 |
| aacccgacag | gactataaag | ataccaggcg | tttccccctg | gaagctccct | cgtgcgctct | 1560 |
| cctgttccga | ccctgccgct | taccggatac | ctgtccgcct | ttctcccttc | gggaagcgtg | 1620 |
| gcgctttctc | atagctcacg | ctgtaggtat | ctcagttcgg | tgtaggtcgt | tcgctccaag | 1680 |
| ctgggctgtg | tgcacgaacc | ccccgttcag | cccgaccgct | gcgccttatc | cggtaactat | 1740 |
| cgtcttgagt | ccaacccggt | aagacacgac | ttatcgccac | tggcagcagc | cactggtaac | 1800 |
| aggattagca | gagcgaggta | tgtaggcggt | gctacagagt | tcttgaagtg | gtggcctaac | 1860 |
| tacggctaca | ctagaaggac | agtatttggt | atctgcgctc | tgctgaagcc | agttaccttc | 1920 |
| ggaaaaagag | ttggtagctc | ttgatccggc | aaacaaacca | ccgctggtag | cggtggtttt | 1980 |
| tttgtttgca | agcagcagat | tacgcgcaga | aaaaaggat | ctcaagaaga | tcctttgatc | 2040 |

| | |
|---|---|
| ttttctacgg ggtctgacgc tcagtggaac gaaaactcac gttaagggat tttggtcatg | 2100 |
| agattatcaa aaaggatctt cacctagatc cttttaaatt aaaaatgaag ttttaaatca | 2160 |
| atctaaagta tatatgagta aacttggtct gacagttacc aatgcttaat cagtgaggca | 2220 |
| cctatctcag cgatctgtct atttcgttca tccatagttg cctgactccc cgtcgtgtag | 2280 |
| ataactacga tacgggaggg cttaccatct ggccccagtg ctgcaatgat accgcgagac | 2340 |
| ccacgctcac cggctccaga tttatcagca ataaaccagc cagccggaag ggccgagcgc | 2400 |
| agaagtggtc ctgcaacttt atccgcctcc atccagtcta ttaattgttg ccgggaagct | 2460 |
| agagtaagta gttcgccagt taatagtttg cgcaacgttg ttgccattgc tacaggcatc | 2520 |
| gtggtgtcac gctcgtcgtt tggtatggct tcattcagct ccggttccca acgatcaagg | 2580 |
| cgagttacat gatcccccat gttgtgcaaa aaagcggtta gctccttcgg tcctccgatc | 2640 |
| gttgtcagaa gtaagttggc cgcagtgtta tcactcatgg ttatggcagc actgcataat | 2700 |
| tctcttactg tcatgccatc cgtaagatgc ttttctgtga ctggtgagta ctcaaccaag | 2760 |
| tcattctgag aatagtgtat gcggcgaccg agttgctctt gcccggcgtc aatacgggat | 2820 |
| aataccgcgc cacatagc | 2838 |

<210> SEQ ID NO 110
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 110

| | |
|---|---|
| gcgtttctgg gtgagcaaaa acaggaaggc aaaatgccgc aaaaaaggga ataagggcga | 60 |
| cacggaaatg ttgaatactc atactcttcc ttttttcaata ttattgaagc atttatcagg | 120 |
| gttattgtct catgagcgga tacatatttg aatgtattta gaaaaataaa caaatagggg | 180 |
| ttccgcgcac atttccccga aaagtgccac ctaaattgta agcgttaata ttttgttaaa | 240 |
| attcgcgtta aatttttgtt aaatcagctc attttttaac caataggccg aaatcggcaa | 300 |
| aatcccttat aaatcaaaag aatagaccga tagggttg agtgttgttc cagtttggaa | 360 |
| caagagtcca ctattaaaga acgtggactc caacgtcaaa gggcgaaaaa ccgtctatca | 420 |
| gggcgatggc ccactacgtg aaccatcacc taatcaagt tttttggggt cgaggtgccg | 480 |
| taaagcacta aatcggaacc ctaaagggag cccccgattt agagcttgac ggggaaagcc | 540 |
| ggcgaacgtg gcgagaaagg aagggaagaa agcgaaagga gcgggcgcta gggcgctggc | 600 |
| aagtgtagcg gtcacgctgc gcgtaaccac cacacccgcc gcgcttaatg cgccgctaca | 660 |
| gggcgcgtcc cattcgccat tcaggctgcg caactgttgg gaagggcgat cggtgcgggc | 720 |
| ctcttcgcta ttacgccagc tggcgaaagg gggatgtgct gcaaggcgat taagttgggt | 780 |
| aacgccaggg ttttcccagt cacgacgttg taaaacgacg gccagtgagc gcgcgtaata | 840 |
| cgactcacta tagggcgaat tgggtacgat cgatgcggcc tcaagagctt cactgagtag | 900 |
| gattaagata ttgcagatgt tgtgtttcca caggtggct cttcagtgca ccagcggaac | 960 |
| ctgctgcgcg tgatatgcag ctccagcttt tgttcccttt agtgagggtt aattgcgcgc | 1020 |
| ttggcgtaat catggtcata gctgtttcct gtgtgaaatt gttatccgct cacaattcca | 1080 |
| cacaacatac gagccggaag cataaagtgt aaagcctggg gtgcctaatg agtgagctaa | 1140 |
| ctcacattaa ttgcgttgcg ctcactgccc gctttccagt cgggaaacct gtcgtgccag | 1200 |
| ctgcattaat gaatcggcca acgcgcgggg agaggcggtt tgcgtattgg gcgctcttcc | 1260 |

```
gcttcctcgc tcactgactc gctgcgctcg gtcgttcggc tgcggcgagc ggtatcagct   1320
cactcaaagg cggtaatacg gttatccaca gaatcagggg ataacgcagg aaagaacatg   1380
tgagcaaaag gccagcaaaa ggccaggaac cgtaaaaagg ccgcgttgct ggcgtttttc   1440
cataggctcc gcccccctga cgagcatcac aaaaatcgac gctcaagtca gaggtggcga   1500
aacccgacag gactataaag ataccaggcg tttccccctg gaagctccct cgtgcgctct   1560
cctgttccga cccctgccgct taccggatac ctgtccgcct ttctcccttc gggaagcgtg   1620
gcgctttctc atagctcacg ctgtaggtat ctcagttcgg tgtaggtcgt tcgctccaag   1680
ctgggctgtg tgcacgaacc ccccgttcag cccgaccgct gcgccttatc cggtaactat   1740
cgtcttgagt ccaacccggt aagacacgac ttatcgccac tggcagcagc cactggtaac   1800
aggattagca gagcgaggta tgtaggcggt gctacagagt tcttgaagtg gtggcctaac   1860
tacggctaca ctagaaggac agtatttggt atctgcgctc tgctgaagcc agttaccttc   1920
ggaaaaagag ttggtagctc ttgatccggc aaacaaacca ccgctggtag cggtggtttt   1980
tttgtttgca agcagcagat tacgcgcaga aaaaaggat ctcaagaaga tcctttgatc   2040
ttttctacgg ggtctgacgc tcagtggaac gaaaactcac gttaagggat tttggtcatg   2100
agattatcaa aaaggatctt cacctagatc cttttaaatt aaaaatgaag ttttaaatca   2160
atctaaagta tatatgagta aacttggtct gacagttacc aatgcttaat cagtgaggca   2220
cctatctcag cgatctgtct atttcgttca tccatagttg cctgactccc cgtcgtgtag   2280
ataactacga tacgggaggg cttaccatct ggccccagtg ctgcaatgat accgcgagac   2340
ccacgctcac cggctccaga tttatcagca ataaccagc cagccggaag ggccgagcgc   2400
agaagtggtc ctgcaacttt atccgcctcc atccagtcta ttaattgttg ccgggaagct   2460
agagtaagta gttcgccagt taatagtttg cgcaacgttg ttgccattgc tacaggcatc   2520
gtggtgtcac gctcgtcgtt tggtatggct tcattcagct ccggttccca acgatcaagg   2580
cgagttacat gatcccccat gttgtgcaaa aaagcggtta gctccttcgg tcctccgatc   2640
gttgtcagaa gtaagttggc cgcagtgtta tcactcatgg ttatggcagc actgcataat   2700
tctcttactg tcatgccatc cgtaagatgc ttttctgtga ctggtgagta ctcaaccaag   2760
tcattctgag aatagtgtat gcggcgaccg agttgctctt gcccggcgtc aatacgggat   2820
aataccgcgc cacatagc                                                 2838
```

<210> SEQ ID NO 111
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 111

```
gcgtttctgg gtgagcaaaa acaggaaggc aaaatgccgc aaaaaaggga taagggcga    60 cacggaaatg ttgaatactc atactcttcc ttttcaata ttattgaagc atttatcagg   120
gttattgtct catgagcgga tacatatttg aatgtattta gaaaaataaa caaatagggg   180
ttccgcgcac atttccccga aaagtgccac ctaaattgta agcgttaata ttttgttaaa   240
attcgcgtta aattttgtt aaatcagctc attttttaac cataggccg aaatcggcaa    300 aatcccttat aaatcaaaag aatagaccga gataggttg agtgttgttc agttttggaa   360
caagagtcca ctattaaaga acgtggactc caacgtcaaa gggcgaaaaa ccgtctatca   420
```

-continued

```
gggcgatggc ccactacgtg aaccatcacc ctaatcaagt tttttggggt cgaggtgccg    480
taaagcacta aatcggaacc ctaaagggag cccccgattt agagcttgac ggggaaagcc    540
ggcgaacgtg gcgagaaagg aagggaagaa agcgaaagga gcgggcgcta gggcgctggc    600
aagtgtagcg gtcacgctgc gcgtaaccac cacacccgcc gcgcttaatg cgccgctaca    660
gggcgcgtcc cattcgccat tcaggctgcg caactgttgg gaagggcgat cggtgcgggc    720
ctcttcgcta ttacgccagc tggcgaaagg gggatgtgct gcaaggcgat taagttgggt    780
aacgccaggg ttttcccagt cacgacgttg taaaacgacg ccagtgagc gcgcgtaata    840
cgactcacta tagggcgaat tgggtacgat cgatgcggcc tcggcctcac caccaacttc    900
atccacgttc accttgcccc acagggcagt aacggcagac ttctcctcag gagtcagatg    960
caccagcgcg tgatatgcag ctccagcttt tgttcccttt agtgagggtt aattgcgcgc   1020
ttggcgtaat catggtcata gctgtttcct gtgtgaaatt gttatccgct cacaattcca   1080
cacaacatac gagccggaag cataaagtgt aaagcctggg gtgcctaatg agtgagctaa   1140
ctcacattaa ttgcgttgcg ctcactgccc gctttccagt cgggaaacct gtcgtgccag   1200
ctgcattaat gaatcggcca acgcgcgggg agaggcggtt tgcgtattgg gcgctcttcc   1260
gcttcctcgc tcactgactc gctgcgctcg gtcgttcggc tgcggcgagc ggtatcagct   1320
cactcaaagg cggtaatacg gttatccaca gaatcagggg ataacgcagg aaagaacatg   1380
tgagcaaaag gccagcaaaa ggccaggaac cgtaaaaagg ccgcgttgct ggcgtttttc   1440
cataggctcc gcccccctga cgagcatcac aaaaatcgac gctcaagtca gaggtggcga   1500
aacccgacag gactataaag ataccaggcg tttccccctg gaagctccct cgtgcgctct   1560
cctgttccga ccctgccgct taccggatac ctgtccgcct ttctcccttc gggaagcgtg   1620
gcgctttctc atagctcacg ctgtaggtat ctcagttcgg tgtaggtcgt tcgctccaag   1680
ctgggctgtg tgcacgaacc ccccgttcag cccgaccgct gcgccttatc cggtaactat   1740
cgtcttgagt ccaacccggt aagacacgac ttatcgccac tggcagcagc cactggtaac   1800
aggattagca gagcgaggta tgtaggcggt gctacagagt tcttgaagtg gtggcctaac   1860
tacggctaca ctagaaggac agtatttggt atctgcgctc tgctgaagcc agttaccttc   1920
ggaaaaagag ttggtagctc ttgatccggc aaacaaacca ccgctggtag cggtggtttt   1980
tttgtttgca agcagcagat tacgcgcaga aaaaaaggat ctcaagaaga tcctttgatc   2040
ttttctacgg ggtctgacgc tcagtggaac gaaaactcac gttaagggat tttggtcatg   2100
agattatcaa aaaggatctt cacctagatc cttttaaatt aaaaatgaag ttttaaatca   2160
atctaaagta tatatgagta aacttggtct gacagttacc aatgcttaat cagtgaggca   2220
cctatctcag cgatctgtct atttcgttca tccatagttg cctgactccc cgtcgtgtag   2280
ataactacga tacgggaggg cttaccatct ggccccagtg ctgcaatgat accgcgagac   2340
ccacgctcac cggctccaga tttatcagca ataaaccagc cagccggaag ggccgagcgc   2400
agaagtggtc ctgcaacttt atccgcctcc atccagtcta ttaattgttg ccgggaagct   2460
agagtaagta gttcgccagt taatagtttg cgcaacgttg ttgccattgc tacaggcatc   2520
gtggtgtcac gctcgtcgtt tggtatggct tcattcagct ccggttccca acgatcaagg   2580
cgagttacat gatccccat gttgtgcaaa aaagcggtta gctccttcgg tcctccgatc   2640
gttgtcagaa gtaagttggc cgcagtgtta tcactcatgg ttatggcagc actgcataat   2700
tctcttactg tcatgccatc cgtaagatgc ttttctgtga ctggtgagta ctcaaccaag   2760
tcattctgag aatagtgtat gcggcgaccg agttgctctt gcccggcgtc aatacgggat   2820
```
aataccgcgc cacatagc                                              2838

<210> SEQ ID NO 112
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 112

```
gcgtttctgg gtgagcaaaa acaggaaggc aaaatgccgc aaaaaaggga ataagggcga      60
cacggaaatg ttgaatactc atactcttcc tttttcaata ttattgaagc atttatcagg     120
gttattgtct catgagcgga tacatatttg aatgtattta gaaaaataaa caatagggg      180
ttccgcgcac atttccccga aaagtgccac ctaaattgta agcgttaata tttttgttaaa    240
attcgcgtta aattttttgtt aaatcagctc atttttttaac caataggccg aaatcggcaa   300
aatcccttat aaatcaaaag aatagaccga tagggttg agtgttgttc cagtttggaa       360
caagagtcca ctattaaaga acgtggactc caacgtcaaa gggcgaaaaa ccgtctatca     420
gggcgatggc ccactacgtg aaccatcacc ctaatcaagt ttttggggt cgaggtgccg      480
taaagcacta atcggaacc ctaaagggag cccccgattt agagcttgac ggggaaagcc      540
ggcgaacgtg gcgagaaagg aagggaagaa agcgaaagga gcgggcgcta gggcgctggc    600
aagtgtagcg gtcacgctgc gcgtaaccac cacacccgcc gcgcttaatg cgccgctaca    660
gggcgcgtcc cattcgccat tcaggctgcg caactgttgg gaagggcgat cggtgcgggc    720
ctcttcgcta ttacgccagc tggcgaaagg gggatgtgct gcaaggcgat taagttgggt    780
aacgccaggg ttttcccagt cacgacgttg taaaacgacg gccagtgagc gcgcgtaata    840
cgactcacta tagggcgaat tgggtacgat cgatgcggcc tcggatagga aaggtgaagt    900
cagagcagtg cttcagcccc acagggcagt aagggcagcc ttcctctaaa taccagattc    960
ccaaagcgcg tgatatgcag ctccagcttt tgttcccttt agtgagggtt aattgcgcgc   1020
ttggcgtaat catggtcata gctgtttcct gtgtgaaatt gttatccgct cacaattcca   1080
cacaacatac gagccggaag cataaagtgt aaagcctggg gtgcctaatg agtgagctaa   1140
ctcacattaa ttgcgttgcg ctcactgccc gctttccagt cgggaaacct gtcgtgccag   1200
ctgcattaat gaatcggcca acgcgcgggg agaggcggtt tgcgtattgg gcgctcttcc   1260
gcttcctcgc tcactgactc gctgcgctcg gtcgttcggc tgcggcgagc ggtatcagct   1320
cactcaaagg cggtaatacg gttatccaca gaatcagggg ataacgcagg aaagaacatg   1380
tgagcaaaag gccagcaaaa ggccaggaac cgtaaaaagg ccgcgttgct ggcgtttttc   1440
cataggctcc gccccctga cgagcatcac aaaaatcgac gctcaagtca gaggtggcga   1500
aacccgacag gactataaag ataccaggcg tttccccctg gaagctccct cgtgcgctct   1560
cctgttccga ccctgccgct taccggatac ctgtccgcct ttctccttc gggaagcgtg   1620
gcgctttctc atagctcacg ctgtaggtat ctcagttcgg tgtaggtcgt tcgctccaag   1680
ctgggctgtg tgcacgaacc ccccgttcag cccgaccgct gcgccttatc cggtaactat   1740
cgtcttgagt ccaacccggt aagacacgac ttatcgccac tggcagcagc cactggtaac   1800
aggattagca gagcgaggta tgtaggcggt gctacagagt tcttgaagtg gtggcctaac   1860
tacggctaca ctagaaggac agtatttggt atctgcgctc tgctgaagcc agttaccttc   1920
ggaaaaagag ttggtagctc ttgatccggc aaacaaacca ccgctggtag cggtggtttt   1980
```

| | |
|---|---:|
| tttgtttgca agcagcagat tacgcgcaga aaaaaaggat ctcaagaaga tcctttgatc | 2040 |
| ttttctacgg ggtctgacgc tcagtggaac gaaaactcac gttaagggat tttggtcatg | 2100 |
| agattatcaa aaaggatctt cacctagatc cttttaaatt aaaaatgaag ttttaaatca | 2160 |
| atctaaagta tatatgagta aacttggtct gacagttacc aatgcttaat cagtgaggca | 2220 |
| cctatctcag cgatctgtct atttcgttca tccatagttg cctgactccc cgtcgtgtag | 2280 |
| ataactacga tacgggaggg cttaccatct ggccccagtg ctgcaatgat accgcgagac | 2340 |
| ccacgctcac cggctccaga tttatcagca ataaccagc cagccggaag ggccgagcgc | 2400 |
| agaagtggtc ctgcaacttt atccgcctcc atccagtcta ttaattgttg ccgggaagct | 2460 |
| agagtaagta gttcgccagt taatagtttg cgcaacgttg ttgccattgc tacaggcatc | 2520 |
| gtggtgtcac gctcgtcgtt tggtatggct tcattcagct ccggttccca acgatcaagg | 2580 |
| cgagttacat gatccccat gttgtgcaaa aaagcggtta gctccttcgg tcctccgatc | 2640 |
| gttgtcagaa gtaagttggc cgcagtgtta tcactcatgg ttatggcagc actgcataat | 2700 |
| tctcttactg tcatgccatc cgtaagatgc ttttctgtga ctggtgagta ctcaaccaag | 2760 |
| tcattctgag aatagtgtat gcggcgaccg agttgctctt gcccggcgtc aatacgggat | 2820 |
| aataccgcgc cacatagc | 2838 |

<210> SEQ ID NO 113
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 113

| | |
|---|---:|
| gcgtttctgg gtgagcaaaa acaggaaggc aaaatgccgc aaaaaaggga ataagggcga | 60 |
| cacggaaatg ttgaatactc atactcttcc tttttcaata ttattgaagc atttatcagg | 120 |
| gttattgtct catgagcgga tacatatttg aatgtatttta gaaaaataaa caaatagggg | 180 |
| ttccgcgcac atttccccga aaagtgccac ctaaattgta agcgttaata ttttgttaaa | 240 |
| attcgcgtta aatttttgtt aaatcagctc attttttaac caataggccg aaatcggcaa | 300 |
| aatcccttat aaatcaaaag aatagaccga gatagggttg agtgttgttc cagtttggaa | 360 |
| caagagtcca ctattaaaga acgtggactc caacgtcaaa gggcgaaaaa ccgtctatca | 420 |
| gggcgatggc ccactacgtg aaccatcacc ctaatcaagt ttttttgggggt cgaggtgccg | 480 |
| taaagcacta aatcggaacc ctaaagggag cccccgattt agagcttgac ggggaaagcc | 540 |
| ggcgaacgtg gcgagaaagg aagggaagaa agcgaaagga gcgggcgcta gggcgctggc | 600 |
| aagtgtagcg gtcacgctgc gcgtaaccac cacacccgcc gcgcttaatg cgccgctaca | 660 |
| gggcgcgtcc cattcgccat tcaggctgcg caactgttgg aagggcgat cggtgcgggc | 720 |
| ctcttcgcta ttacgccagc tggcgaaagg gggatgtgct gcaaggcgat taagttgggt | 780 |
| aacgccaggg ttttcccagt cacgacgttg taaaacgacg gccagtgagc gcgcgtaata | 840 |
| cgactcacta tagggcgaat tgggtacgat cgatgcggcc tcgggcagct gcaggaataa | 900 |
| gagggatgtg aatggtaatg atggcttcaa catggcgctt gctcttcatt ccctgggtgt | 960 |
| agtctgcgcg tgatatgcag ctccagcttt tgttcccttt agtgagggtt aattgcgcgc | 1020 |
| ttggcgtaat catggtcata gctgtttcct gtgtgaaatt gttatccgct cacaattcca | 1080 |
| cacaacatac gagccggaag cataaagtgt aaagcctggg gtgcctaatg agtgagctaa | 1140 |
| ctcacattaa ttgcgttgcg ctcactgccc gctttccagt cgggaaacct gtcgtgccag | 1200 |

| | |
|---|---|
| ctgcattaat gaatcggcca acgcgcgggg agaggcggtt tgcgtattgg gcgctcttcc | 1260 |
| gcttcctcgc tcactgactc gctgcgctcg gtcgttcggc tgcggcgagc ggtatcagct | 1320 |
| cactcaaagg cggtaatacg gttatccaca gaatcagggg ataacgcagg aaagaacatg | 1380 |
| tgagcaaaag gccagcaaaa ggccaggaac cgtaaaaagg ccgcgttgct ggcgtttttc | 1440 |
| cataggctcc gcccccctga cgagcatcac aaaaatcgac gctcaagtca gaggtggcga | 1500 |
| aacccgacag gactataaag ataccaggcg tttccccctg gaagctccct cgtgcgctct | 1560 |
| cctgttccga cccgccgct taccggatac ctgtccgcct ttctcccttc gggaagcgtg | 1620 |
| gcgctttctc atagctcacg ctgtaggtat ctcagttcgg tgtaggtcgt tcgctccaag | 1680 |
| ctgggctgtg tgcacgaacc ccccgttcag cccgaccgct gcgccttatc cggtaactat | 1740 |
| cgtcttgagt ccaacccggt aagacacgac ttatcgccac tggcagcagc cactggtaac | 1800 |
| aggattagca gagcgaggta tgtaggcggt gctacagagt tcttgaagtg gtggcctaac | 1860 |
| tacggctaca ctagaaggac agtatttggt atctgcgctc tgctgaagcc agttaccttc | 1920 |
| ggaaaaagag ttggtagctc ttgatccggc aaacaaacca ccgctggtag cggtggtttt | 1980 |
| tttgtttgca agcagcagat tacgcgcaga aaaaaaggat ctcaagaaga tcctttgatc | 2040 |
| ttttctacgg ggtctgacgc tcagtggaac gaaaactcac gttaagggat tttggtcatg | 2100 |
| agattatcaa aaaggatctt cacctagatc cttttaaatt aaaaatgaag ttttaaatca | 2160 |
| atctaaagta tatatgagta aacttggtct gacagttacc aatgcttaat cagtgaggca | 2220 |
| cctatctcag cgatctgtct atttcgttca tccatagttg cctgactccc cgtcgtgtag | 2280 |
| ataactacga tacgggaggg cttaccatct ggccccagtg ctgcaatgat accgcgagac | 2340 |
| ccacgctcac cggctccaga tttatcagca ataaaccagc cagccggaag ggccgagcgc | 2400 |
| agaagtggtc ctgcaacttt atccgcctcc atccagtcta ttaattgttg ccgggaagct | 2460 |
| agagtaagta gttcgccagt taatagtttg cgcaacgttg ttgccattgc tacaggcatc | 2520 |
| gtggtgtcac gctcgtcgtt tggtatggct tcattcagct ccggttccca acgatcaagg | 2580 |
| cgagttacat gatcccccat gttgtgcaaa aaagcggtta gctccttcgg tcctccgatc | 2640 |
| gttgtcagaa gtaagttggc cgcagtgtta tcactcatgg ttatgcagc actgcataat | 2700 |
| tctcttactg tcatgccatc cgtaagatgc ttttctgtga ctggtgagta ctcaaccaag | 2760 |
| tcattctgag aatagtgtat gcggcgaccg agttgctctt gcccggcgtc aatacgggat | 2820 |
| aataccgcgc cacatagc | 2838 |

<210> SEQ ID NO 114
<211> LENGTH: 2838
<212> TYPE: DNA
<213> ORGANISM: Artificial Sequence
<220> FEATURE:
<223> OTHER INFORMATION: Synthetic Construct

<400> SEQUENCE: 114

| | |
|---|---|
| gcgtttctgg gtgagcaaaa acaggaaggc aaaatgccgc aaaaaaggga ataagggcga | 60 |
| cacggaaatg ttgaatactc atactcttcc ttttcaata ttattgaagc atttatcagg | 120 |
| gttattgtct catgagcgga tacatatttg aatgtattta gaaaaataaa caaatagggg | 180 |
| ttccgcgcac atttccccga aaagtgccac ctaaattgta agcgttaata ttttgttaaa | 240 |
| attgcgtta aatttttgtt aaatcagctc attttttaac caataggccg aaatcggcaa | 300 |
| aatcccttat aaatcaaaag aatagaccga gatagggttg agtgttgttc cagtttggaa | 360 |

-continued

```
caagagtcca ctattaaaga acgtggactc caacgtcaaa gggcgaaaaa ccgtctatca    420
gggcgatggc ccactacgtg aaccatcacc ctaatcaagt tttttggggt cgaggtgccg    480
taaagcacta atcggaacc  ctaaagggag cccccgattt agagcttgac ggggaaagcc    540
ggcgaacgtg gcgagaaagg aagggaagaa agcgaaagga gcgggcgcta gggcgctggc    600
aagtgtagcg gtcacgctgc gcgtaaccac cacacccgcc gcgcttaatg cgccgctaca    660
gggcgcgtcc cattcgccat tcaggctgcg caactgttgg gaaggcgat  cggtgcgggc    720
ctcttcgcta ttacgccagc tggcgaaagg gggatgtgct gcaaggcgat taagttgggt    780
aacgccaggg ttttcccagt cacgacgttg taaaacgacg ccagtgagc  gcgcgtaata    840
cgactcacta tagggcgaat tgggtacgat cgatgcggcc tccaatattg agagtgaatg    900
aaaagtgtca gctggtaatg atgacttcaa catagtcaga actctttggg ctgttccaaa    960
catcagcgcg tgatatgcag ctccagcttt tgttcccttt agtgagggtt aattgcgcgc   1020
ttggcgtaat catggtcata gctgtttcct gtgtgaaatt gttatccgct cacaattcca   1080
cacaacatac gagccggaag cataaagtgt aaagcctggg gtgcctaatg agtgagctaa   1140
ctcacattaa ttgcgttgcg ctcactgccc gctttccagt cgggaaacct gtcgtgccag   1200
ctgcattaat gaatcggcca acgcgcgggg agaggcggtt tgcgtattgg gcgctcttcc   1260
gcttcctcgc tcactgactc gctgcgctcg gtcgttcggc tgcggcgagc ggtatcagct   1320
cactcaaagg cggtaatacg gttatccaca gaatcagggg ataacgcagg aaagaacatg   1380
tgagcaaaag gccagcaaaa ggccaggaac cgtaaaaagg ccgcgttgct ggcgtttttc   1440
cataggctcc gccccctga  cgagcatcac aaaaatcgac gctcaagtca gaggtggcga   1500
aacccgacag gactataaag ataccaggcg tttccccctg gaagctccct cgtgcgctct   1560
cctgttccga ccctgccgct taccggatac ctgtccgcct ttctcccttc gggaagcgtg   1620
gcgctttctc atagctcacg ctgtaggtat ctcagttcgg tgtaggtcgt tcgctccaag   1680
ctgggctgtg tgcacgaacc ccccgttcag cccgaccgct gcgccttatc cggtaactat   1740
cgtcttgagt ccaacccggt aagacacgac ttatcgccac tggcagcagc cactggtaac   1800
aggattagca gagcgaggta tgtaggcggt gctacagagt tcttgaagtg gtggcctaac   1860
tacggctaca ctagaaggac agtatttggt atctgcgctc tgctgaagcc agttaccttc   1920
ggaaaaagag ttggtagctc ttgatccggc aaacaaacca ccgctggtag cggtggtttt   1980
tttgtttgca agcagcagat tacgcgcaga aaaaaaggat ctcaagaaga tcctttgatc   2040
ttttctacgg ggtctgacgc tcagtggaac gaaaactcac gttaagggat tttggtcatg   2100
agattatcaa aaaggatctt cacctagatc cttttaaatt aaaaatgaag ttttaaatca   2160
atctaaagta tatatgagta aacttggtct gacagttacc aatgcttaat cagtgaggca   2220
cctatctcag cgatctgtct atttcgttca tccatagttg cctgactccc cgtcgtgtag   2280
ataactacga tacggagggg cttaccatct ggccccagtg ctgcaatgat accgcgagac   2340
ccacgctcac cggctccaga tttatcagca ataaccagc  cagccggaag ggccgagcgc   2400
agaagtggtc ctgcaacttt atccgcctcc atccagtcta ttaattgttg ccgggaagct   2460
agagtaagta gttcgccagt taatagtttg cgcaacgttg ttgccattgc tacaggcatc   2520
gtggtgtcac gctcgtcgtt tggtatggct tcattcagct ccggttccca acgatcaagg   2580
cgagttacat gatcccccat gttgtgcaaa aaagcggtta gctccttcgg tcctccgatc   2640
gttgtcagaa gtaagttggc cgcagtgtta tcactcatgg ttatggcagc actgcataat   2700
tctcttactg tcatgccatc cgtaagatgc ttttctgtga ctggtgagta ctcaaccaag   2760
```

-continued

```
tcattctgag aatagtgtat gcggcgaccg agttgctctt gcccggcgtc aatacgggat   2820 ataccgcgc cacatagc                                                   2838
```

<210> SEQ ID NO 115
<211> LENGTH: 1368
<212> TYPE: PRT
<213> ORGANISM: Artificial Sequence
<220> FEATURE:
<223> OTHER INFORMATION: Synthetic construct

<400> SEQUENCE: 115

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
```

-continued

```
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
                450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
                530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
                610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
                690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
```

```
Thr Thr Gln Lys Gly Gln Lys Asn Ser Arg Glu Arg Met Lys Arg Ile
    770             775                 780
Glu Glu Gly Ile Lys Glu Leu Gly Ser Gln Ile Leu Lys Glu His Pro
785             790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
            835                 840                 845
Asp Asp Ser Ile Asp Asn Lys Val Leu Thr Arg Ser Asp Lys Asn Arg
            850                 855                 860
Gly Lys Ser Asp Asn Val Pro Ser Glu Val Val Lys Lys Met Lys
865             870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945             950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys  Tyr Pro Lys Leu Glu  Ser Glu Phe
            995                 1000                1005
Val Tyr  Gly Asp Tyr Lys Val  Tyr Asp Val Arg Lys   Met Ile Ala
        1010                1015                1020
Lys Ser  Glu Gln Glu Ile Gly  Lys Ala Thr Ala Lys   Tyr Phe Phe
        1025                1030                1035
Tyr Ser  Asn Ile Met Asn Phe  Phe Lys Thr Glu Ile   Thr Leu Ala
        1040                1045                1050
Asn Gly  Glu Ile Arg Lys Arg  Pro Leu Ile Glu Thr   Asn Gly Glu
        1055                1060                1065
Thr Gly  Glu Ile Val Trp Asp  Lys Gly Arg Asp Phe   Ala Thr Val
        1070                1075                1080
Arg Lys  Val Leu Ser Met Pro  Gln Val Asn Ile Val   Lys Lys Thr
        1085                1090                1095
Glu Val  Gln Thr Gly Gly Phe  Ser Lys Glu Ser Ile   Leu Pro Lys
        1100                1105                1110
Arg Asn  Ser Asp Lys Leu Ile  Ala Arg Lys Lys Asp   Trp Asp Pro
        1115                1120                1125
Lys Lys  Tyr Gly Gly Phe Asp  Ser Pro Thr Val Ala   Tyr Ser Val
        1130                1135                1140
Leu Val  Val Ala Lys Val Glu  Lys Gly Lys Ser Lys   Lys Leu Lys
        1145                1150                1155
Ser Val  Lys Glu Leu Leu Gly  Ile Thr Ile Met Glu   Arg Ser Ser
        1160                1165                1170
```

```
Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 116
<211> LENGTH: 7
<212> TYPE: PRT
<213> ORGANISM: Artificial Sequence
<220> FEATURE:
<223> OTHER INFORMATION: Synthetic Construct

<400> SEQUENCE: 116

Pro Lys Lys Lys Arg Lys Val
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic Construct

<400> SEQUENCE: 117

Pro Lys Lys Lys Arg Arg Val
1               5

<210> SEQ ID NO 118
<211> LENGTH: 16
<212> TYPE: PRT
<213> ORGANISM: Artificial Sequence
<220> FEATURE:
<223> OTHER INFORMATION: Synthetic Construct

<400> SEQUENCE: 118

Lys Arg Pro Ala Ala Thr Lys Lys Ala Gly Gln Ala Lys Lys Lys Lys
1               5                   10                  15
```

```
<210> SEQ ID NO 119
<211> LENGTH: 20
<212> TYPE: PRT
<213> ORGANISM: Artificial Sequence
<220> FEATURE:
<223> OTHER INFORMATION: Synthetic Construct

<400> SEQUENCE: 119

Gly Arg Lys Lys Arg Arg Gln Arg Arg Pro Pro Gln Pro Lys Lys
1               5                   10                  15

Lys Arg Lys Val
            20

<210> SEQ ID NO 120
<211> LENGTH: 19
<212> TYPE: PRT
<213> ORGANISM: Artificial Sequence
<220> FEATURE:
<223> OTHER INFORMATION: Synthetic Construct

<400> SEQUENCE: 120

Pro Leu Ser Ser Ile Phe Ser Arg Ile Gly Asp Pro Pro Lys Lys
1               5                   10                  15

Arg Lys Val

<210> SEQ ID NO 121
<211> LENGTH: 24
<212> TYPE: PRT
<213> ORGANISM: Artificial Sequence
<220> FEATURE:
<223> OTHER INFORMATION: Synthetic Construct

<400> SEQUENCE: 121

Gly Ala Leu Phe Leu Gly Trp Leu Gly Ala Ala Gly Ser Thr Met Gly
1               5                   10                  15

Ala Pro Lys Lys Lys Arg Lys Val
            20

<210> SEQ ID NO 122
<211> LENGTH: 27
<212> TYPE: PRT
<213> ORGANISM: Artificial Sequence
<220> FEATURE:
<223> OTHER INFORMATION: Synthetic Construct

<400> SEQUENCE: 122

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 123
<211> LENGTH: 21
<212> TYPE: PRT
<213> ORGANISM: Artificial Sequence
<220> FEATURE:
<223> OTHER INFORMATION: Synthetic Construct

<400> SEQUENCE: 123

Lys Glu Thr Trp Trp Glu Thr Trp Trp Thr Glu Trp Ser Gln Pro Lys
1               5                   10                  15

Lys Lys Arg Lys Val
            20
```

-continued

```
<210> SEQ ID NO 124
<211> LENGTH: 113
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: 2'-O-methyl
<220> FEATURE:
<221> NAME/KEY: misc_feature
<222> LOCATION: (9)..(12)
<223> OTHER INFORMATION: 2'-O-methyl
<220> FEATURE:
<221> NAME/KEY: misc_feature
<222> LOCATION: (13)..(15)
<223> OTHER INFORMATION: 2'-O-methyl
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (30)..(32)
<223> OTHER INFORMATION: 2'-O-methyl
<220> FEATURE:
<221> NAME/KEY: misc_feature
<222> LOCATION: (33)..(34)
<223> OTHER INFORMATION: 2'-O-methyl
<220> FEATURE:
<221> NAME/KEY: misc_feature
<222> LOCATION: (35)..(37)
<223> OTHER INFORMATION: 2'-O-methyl
<220> FEATURE:
<221> NAME/KEY: misc_feature
<222> LOCATION: (39)..(40)
<223> OTHER INFORMATION: 2'-O-methyl
<220> FEATURE:
<221> NAME/KEY: misc_feature
<222> LOCATION: (42)..(43)
<223> OTHER INFORMATION: 2'-O-methyl
<220> FEATURE:
<221> NAME/KEY: misc_feature
<222> LOCATION: (45)..(46)
<223> OTHER INFORMATION: 2'-O-methyl
<220> FEATURE:
<221> NAME/KEY: misc_feature
<222> LOCATION: (47)..(48)
<223> OTHER INFORMATION: 2'-O-methyl
<220> FEATURE:
<221> NAME/KEY: misc_feature
<222> LOCATION: (50)..(51)
<223> OTHER INFORMATION: 2'-O-methyl
<220> FEATURE:
<221> NAME/KEY: misc_feature
<222> LOCATION: (60)..(61)
<223> OTHER INFORMATION: 2'-O-methyl
<220> FEATURE:
<221> NAME/KEY: misc_feature
<222> LOCATION: (65)..(67)
<223> OTHER INFORMATION: 2'-O-methyl
<220> FEATURE:
<221> NAME/KEY: misc_feature
<222> LOCATION: (70)..(72)
<223> OTHER INFORMATION: 2'-O-methyl
<220> FEATURE:
<221> NAME/KEY: misc_feature
<222> LOCATION: (76)..(78)
<223> OTHER INFORMATION: 2'-O-methyl
<220> FEATURE:
<221> NAME/KEY: misc_feature
<222> LOCATION: (80)..(83)
<223> OTHER INFORMATION: 2'-O-methyl
<220> FEATURE:
<221> NAME/KEY: misc_feature
<222> LOCATION: (90)..(91)
<223> OTHER INFORMATION: 2'-O-methyl
<220> FEATURE:
```

```
<221> NAME/KEY: misc_feature
<222> LOCATION: (93)..(94)
<223> OTHER INFORMATION: 2'-O-methyl
<220> FEATURE:
<221> NAME/KEY: misc_feature
<222> LOCATION: (95)..(97)
<223> OTHER INFORMATION: 2'-O-methyl
<220> FEATURE:
<221> NAME/KEY: misc_feature
<222> LOCATION: (100)..(102)
<223> OTHER INFORMATION: 2'-O-methyl
<220> FEATURE:
<221> NAME/KEY: misc_feature
<222> LOCATION: (104)..(105)
<223> OTHER INFORMATION: 2'-O-methyl
<220> FEATURE:
<221> NAME/KEY: misc_feature
<222> LOCATION: (106)..(113)
<223> OTHER INFORMATION: 2'-O-methyl

<400> SEQUENCE: 124
aguccucauc ucccucaagc guuuaagagc uaugcuggua acagcauagc aaguuuaaau    60
aaggcuaguc cguuaucaac uugaaaaagu ggcaccgagu cggugcuuuu uuu          113

<210> SEQ ID NO 125
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (16)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 125
cuugccccac agggcaguaa guuuuagagc uagaaauagc aaguuaaaau aaggcuaguc    60
cguuaucaac uugaaaaagu ggcaccgagu cggugcuuuu                         100

<210> SEQ ID NO 126
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 126
cuugccccac agggcaguaa guuuuagagc uagaaauagc aaguuaaaau aaggcuaguc    60
```
cguuaucaac uugaaaaagu ggcaccgagu cggugcuuuu                               100

<210> SEQ ID NO 127
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 127
cuugccccac agggcaguaa guuuuagagc uagaaauagc aaguuaaaau aaggcuaguc         60
cguuaucaac uugaaaaagu ggcaccgagu cggugcuuuu                              100

<210> SEQ ID NO 128
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 128
cuugccccac agggcaguaa guuuuagagc uagaaauagc aaguuaaaau aaggcuaguc         60
cguuaucaac uugaaaaagu ggcaccgagu cggugcuuuu                              100

<210> SEQ ID NO 129
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (9)..(10)
<223> OTHER INFORMATION: 2'-O-methyl-3'-phosphonoacetate
<220> FEATURE:

```
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 129
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 130
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (8)..(9)
<223> OTHER INFORMATION: 2'-O-methyl-3'-phosphonoacetate
<220> FEATURE:
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 130
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 131
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 131
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 132
<211> LENGTH: 100
<212> TYPE: RNA
<213> ORGANISM: Artificial Sequence
```

```
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 132
cuugccccac agggcaguaa guuuuagagc uagaaauagc aaguuaaaau aaggcuaguc     60
cguuaucaac uugaaaaagu ggcaccgagu cggugcuuuu                         100

<210> SEQ ID NO 133
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (17)..(18)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 133
cuugccccac agggcaguaa guuuuagagc uagaaauagc aaguuaaaau aaggcuaguc     60
cguuaucaac uugaaaaagu ggcaccgagu cggugcuuuu                         100

<210> SEQ ID NO 134
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate
```

<400> SEQUENCE: 134
cuugccccac agggcaguaa guuuuagagc uagaaauagc aaguuaaaau aaggcuaguc    60
cguuaucaac uugaaaaagu ggcaccgagu cggugcuuuu                          100

<210> SEQ ID NO 135
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 135
cuugccccac agggcaguaa guuuuagagc uagaaauagc aaguuaaaau aaggcuaguc    60
cguuaucaac uugaaaaagu ggcaccgagu cggugcuuuu                          100

<210> SEQ ID NO 136
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 136
cuugccccac agggcaguaa guuuuagagc uagaaauagc aaguuaaaau aaggcuaguc    60
cguuaucaac uugaaaaagu ggcaccgagu cggugcuuuu                          100

<210> SEQ ID NO 137
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature

```
<222> LOCATION: (9)..(10)
<223> OTHER INFORMATION: 2'-O-methyl-3'-phosphonoacetate
<220> FEATURE:
<221> NAME/KEY: misc_feature
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 137
cuugccccac agggcaguaa guuuuagagc uagaaauagc aaguuaaaau aaggcuaguc     60
cguuaucaac uugaaaaagu ggcaccgagu cggugcuuuu                         100

<210> SEQ ID NO 138
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (8)..(9)
<223> OTHER INFORMATION: 2'-O-methyl-3'-phosphonoacetate
<220> FEATURE:
<221> NAME/KEY: misc_feature
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 138
cuugccccac agggcaguaa guuuuagagc uagaaauagc aaguuaaaau aaggcuaguc     60
cguuaucaac uugaaaaagu ggcaccgagu cggugcuuuu                         100

<210> SEQ ID NO 139
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 139
cuugccccac agggcaguaa guuuuagagc uagaaauagc aaguuaaaau aaggcuaguc     60
cguuaucaac uugaaaaagu ggcaccgagu cggugcuuuu                         100

<210> SEQ ID NO 140
```

```
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 140
cuugccccac agggcaguaa guuuuagagc uagaaauagc aaguuaaaau aaggcuaguc      60
cguuaucaac uugaaaaagu ggcaccgagu cggugcuuuu                          100

<210> SEQ ID NO 141
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (16)..(17)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 141
cuugccccac agggcaguaa guuuuagagc uagaaauagc aaguuaaaau aaggcuaguc      60
cguuaucaac uugaaaaagu ggcaccgagu cggugcuuuu                          100

<210> SEQ ID NO 142
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (13)..(15)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 142
```
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 143
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 143
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 144
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (9)..(10)
<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 144
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 145
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (8)..(9)

<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 145
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 146
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 146
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 147
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 147
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 148
<211> LENGTH: 100

```
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (14)..(15)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 148
cuugccccac agggcaguaa guuuuagagc uagaaauagc aaguuaaaau aaggcuaguc      60
cguuaucaac uugaaaaagu ggcaccgagu cggugcuuuu                          100

<210> SEQ ID NO 149
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 149
cuugccccac agggcaguaa guuuuagagc uagaaauagc aaguuaaaau aaggcuaguc      60
cguuaucaac uugaaaaagu ggcaccgagu cggugcuuuu                          100

<210> SEQ ID NO 150
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (9)..(10)
<223> OTHER INFORMATION: 2'-O-methyl-3'-phosphonoacetate
<220> FEATURE:
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (99)..(100)
```

<223> OTHER INFORMATION: 2'-O-methyl-3'-phosphonoacetate

<400> SEQUENCE: 150
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 151
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (8)..(9)
<223> OTHER INFORMATION: 2'-O-methyl-3'-phosphonoacetate
<220> FEATURE:
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 151
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 152
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 152
cuugccccac agggcaguaa guuuuagagc uagaaauagc aaguuaaaau aaggcuaguc    60
cguuaucaac uugaaaaagu ggcaccgagu cggugcuuuu    100

<210> SEQ ID NO 153
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate

```
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 153
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 154
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (13)..(14)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 154
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 155
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (11)..(12)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 155
cuugccccac agggcaguaa guuuuagagc uagaaauagc aaguuaaaau aaggcuaguc    60
cguuaucaac uugaaaaagu ggcaccgagu cggugcuuuu                        100
```

```
<210> SEQ ID NO 156
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (11)..(12)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 156
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 157
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (9)..(11)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 157
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 158
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (8)..(9)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate
```

```
<400> SEQUENCE: 158
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 159
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 159
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 160
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 160
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 161
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
```

```
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 161
cuugccccac agggcaguaa guuuuagagc uagaaauagc aaguuaaaau aaggcuaguc      60
cguuaucaac uugaaaaagu ggcaccgagu cggugcuuuu                          100

<210> SEQ ID NO 162
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (8)..(10)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 162
cuugccccac agggcaguaa guuuuagagc uagaaauagc aaguuaaaau aaggcuaguc      60
cguuaucaac uugaaaaagu ggcaccgagu cggugcuuuu                          100

<210> SEQ ID NO 163
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (9)..(10)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 163
cuugccccac agggcaguaa guuuuagagc uagaaauagc aaguuaaaau aaggcuaguc      60
cguuaucaac uugaaaaagu ggcaccgagu cggugcuuuu                          100

<210> SEQ ID NO 164
<211> LENGTH: 100
<212> TYPE: RNA
<213> ORGANISM: Artificial Sequence
```

```
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (9)..(10)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 164
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 165
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (9)..(10)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 165
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 166
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (8)..(9)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate
```

-continued

<400> SEQUENCE: 166
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 167
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (8)..(9)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 167
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 168
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(8)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 168
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 169
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature

```
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 169
cuugccccac agggcaguaa guuuagagc uagaaauagc aaguuaaaau aaggcuaguc    60
cguuaucaac uugaaaaagu ggcaccgagu cggugcuuuu                       100

<210> SEQ ID NO 170
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(7)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 170
cuugccccac agggcaguaa guuuagagc uagaaauagc aaguuaaaau aaggcuaguc    60
cguuaucaac uugaaaaagu ggcaccgagu cggugcuuuu                       100

<210> SEQ ID NO 171
<211> LENGTH: 100
<212> TYPE: RNA
<213> ORGANISM: Artificial Sequence
<220> FEATURE:
<223> OTHER INFORMATION: Synthetic construct

<400> SEQUENCE: 171
cuugccccac agggcaguaa guuuagagc uagaaauagc aaguuaaaau aaggcuaguc    60
cguuaucaac uugaaaaagu ggcaccgagu cggugcuuuu                       100

<210> SEQ ID NO 172
<211> LENGTH: 100
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: 2'-O-methyl phosphorothioate
<220> FEATURE:
<221> NAME/KEY: misc_feature
<222> LOCATION: (99)..(100)
<223> OTHER INFORMATION: 2'-O-methyl phosphorothioate

<400> SEQUENCE: 172
cuugccccac agggcaguaa guuuagagc uagaaauagc aaguuaaaau aaggcuaguc    60
cguuaucaac uugaaaaagu ggcaccgagu cggugcuuuu                       100

<210> SEQ ID NO 173
<211> LENGTH: 100
<212> TYPE: RNA
```

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (4)..(7)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 173
ugguaaugau ggcuucaaca guuuuagagc uagaaauagc aaguuaaaau aaggcuaguc      60
cguuaucaac uugaaaaagu ggcaccgagu cggugcuuuu                          100

<210> SEQ ID NO 174
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(8)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 174
ugguaaugau ggcuucaaca guuuuagagc uagaaauagc aaguuaaaau aaggcuaguc      60
cguuaucaac uugaaaaagu ggcaccgagu cggugcuuuu                          100

<210> SEQ ID NO 175
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(9)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 175
ugguaaugau ggcuucaaca guuuuagagc uagaaauagc aaguuaaaau aaggcuaguc      60
cguuaucaac uugaaaaagu ggcaccgagu cggugcuuuu                          100

<210> SEQ ID NO 176
<211> LENGTH: 100
<212> TYPE: RNA
<213> ORGANISM: Artificial Sequence
```

-continued

```
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (2)..(3)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 176
ugguaaugau ggcuucaaca guuuuagagc uagaaauagc aaguuaaaau aaggcuaguc     60
cguuaucaac uugaaaaagu ggcaccgagu cggugcuuuu                         100

<210> SEQ ID NO 177
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (3)..(4)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 177
ugguaaugau ggcuucaaca guuuuagagc uagaaauagc aaguuaaaau aaggcuaguc     60
cguuaucaac uugaaaaagu ggcaccgagu cggugcuuuu                         100

<210> SEQ ID NO 178
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (4)..(5)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 178
ugguaaugau ggcuucaaca guuuuagagc uagaaauagc aaguuaaaau aaggcuaguc     60
cguuaucaac uugaaaaagu ggcaccgagu cggugcuuuu                         100

<210> SEQ ID NO 179
<211> LENGTH: 100
<212> TYPE: RNA
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 179
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 180
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (6)..(7)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 180
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 181
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 181
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 182
<211> LENGTH: 100
<212> TYPE: RNA
<213> ORGANISM: Artificial Sequence
<220> FEATURE:
<223> OTHER INFORMATION: Synthetic Construct
```

-continued

```
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (8)..(9)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 182
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 183
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (9)..(10)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 183
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 184
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 184
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 185
<211> LENGTH: 100
<212> TYPE: RNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (11)..(12)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 185
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 186
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (12)..(13)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 186
ugguaaugau ggcuucaaca guuuuagagc uagaaauagc aaguuaaaau aaggcuaguc    60
cguuaucaac uugaaaaagu ggcaccgagu cggugcuuuu                        100

<210> SEQ ID NO 187
<211> LENGTH: 100
<212> TYPE: RNA
<213> ORGANISM: Artificial Sequence
<220> FEATURE:
<223> OTHER INFORMATION: Synthetic Construct

<400> SEQUENCE: 187
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 188
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-methyl
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 188
cuugccccac agggcaguaa guuuuagagc uagaaauagc aaguuaaaau aaggcuaguc    60
cguuaucaac uugaaaaagu ggcaccgagu cggugcuuuu                        100
```

<210> SEQ ID NO 189
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-methyl-3'-phosphorothioate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 189
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 190
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2'-O-methyl-3'-thiophosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 190
cuugccccac agggcaguaa guuuuagagc uagaaauagc aaguuaaaau aaggcuaguc    60
cguuaucaac uugaaaaagu ggcaccgagu cggugcuuuu                        100

<210> SEQ ID NO 191
<211> LENGTH: 23
<212> TYPE: DNA
<213> ORGANISM: Artificial Sequence
<220> FEATURE:
<223> OTHER INFORMATION: Synthetic Construct

<400> SEQUENCE: 191
tggtgaggat ggcttcaaca cgg                                           23

<210> SEQ ID NO 192
<211> LENGTH: 23
<212> TYPE: DNA
<213> ORGANISM: Artificial Sequence
<220> FEATURE:
<223> OTHER INFORMATION: Synthetic Construct

<400> SEQUENCE: 192
ggtgagtgag tgtgtgcgtg tgg                                           23

<210> SEQ ID NO 193
<211> LENGTH: 23
<212> TYPE: DNA
<213> ORGANISM: Artificial Sequence
<220> FEATURE:
<223> OTHER INFORMATION: Synthetic Construct

<400> SEQUENCE: 193
tgtgggtgag tgtgtgcgtg agg                                             23

<210> SEQ ID NO 194
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (11)..(12)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 194
ggugagugag ugugugcgug guuuuagagc uagaaauagc aaguuaaaau aaggcuaguc      60
cguuaucaac uugaaaaagu ggcaccgagu cggugcuuuu                          100

<210> SEQ ID NO 195
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (10)..(11)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 195
ggugagugag ugugugcgug guuuuagagc uagaaauagc aaguuaaaau aaggcuaguc      60
cguuaucaac uugaaaaagu ggcaccgagu cggugcuuuu                          100

<210> SEQ ID NO 196
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (9)..(10)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 196
ggugagugag ugugugcgug guuuuagagc uagaaauagc aaguuaaaau aaggcuaguc      60
cguuaucaac uugaaaaagu ggcaccgagu cggugcuuuu                          100

<210> SEQ ID NO 197
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (7)..(8)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 197
ggugagugag ugugugcgug guuuuagagc uagaaauagc aaguuaaaau aaggcuaguc     60
cguuaucaac uugaaaaagu ggcaccgagu cggugcuuuu                         100

<210> SEQ ID NO 198
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (5)..(6)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 198
ggugagugag ugugugcgug guuuuagagc uagaaauagc aaguuaaaau aaggcuaguc     60
cguuaucaac uugaaaaagu ggcaccgagu cggugcuuuu                         100

<210> SEQ ID NO 199
<211> LENGTH: 100
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: 2'-O-methyl-3'-phosphonoacetate
<220> FEATURE:
<221> NAME/KEY: misc_feature
<222> LOCATION: (99)..(100)
<223> OTHER INFORMATION: 2'-O-methyl-3'-phosphonoacetate

<400> SEQUENCE: 199
ggugagugag ugugugcgug guuuuagagc uagaaauagc aaguuaaaau aaggcuaguc     60
cguuaucaac uugaaaaagu ggcaccgagu cggugcuuuu                         100

<210> SEQ ID NO 200
<211> LENGTH: 17
<212> TYPE: DNA

```
<213> ORGANISM: Artificial Sequence
<220> FEATURE:
<223> OTHER INFORMATION: Synthetic Construct

<400> SEQUENCE: 200
gccccacagg gcagtaa                                                17

<210> SEQ ID NO 201
<211> LENGTH: 17
<212> TYPE: DNA
<213> ORGANISM: Artificial Sequence
<220> FEATURE:
<223> OTHER INFORMATION: Synthetic Construct

<400> SEQUENCE: 201
taatgatggc ttcaaca                                                17

<210> SEQ ID NO 202
<211> LENGTH: 17
<212> TYPE: DNA
<213> ORGANISM: Artificial Sequence
<220> FEATURE:
<223> OTHER INFORMATION: Synthetic Construct

<400> SEQUENCE: 202
gagtgagtgt gtgcgtg                                                17
```